(12) United States Patent
Gelbard et al.

(10) Patent No.: US 10,485,800 B2
(45) Date of Patent: Nov. 26, 2019

(54) MIXED LINEAGE KINASE INHIBITORS FOR HIV/AIDS THERAPIES

(71) Applicants: UNIVERSITY OF ROCHESTER, Rochester, NY (US); BOARD OF REGENTS OF THE UNIVERSITY OF NEBRASKA, Omaha, NE (US)

(72) Inventors: Harris A. Gelbard, Pittsford, NY (US); Stephen Dewhurst, Rochester, NY (US); Howard E. Gendelman, Omaha, NE (US)

(73) Assignees: The University of Rochester, Rochester, NY (US); Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 14/648,404

(22) PCT Filed: Nov. 30, 2013

(86) PCT No.: PCT/US2013/072530
§ 371 (c)(1),
(2) Date: May 29, 2015

(87) PCT Pub. No.: WO2014/085795
PCT Pub. Date: Jun. 5, 2014

(65) Prior Publication Data
US 2015/0297587 A1    Oct. 22, 2015

Related U.S. Application Data

(60) Provisional application No. 61/731,925, filed on Nov. 30, 2012, provisional application No. 61/767,748, filed on Feb. 21, 2013, provisional application No. 61/768,077, filed on Feb. 22, 2013.

(51) Int. Cl.
| | | |
|---|---|---|
| *A61K 31/496* | (2006.01) | |
| *A61K 45/06* | (2006.01) | |
| *A61K 31/427* | (2006.01) | |
| *A61K 31/4418* | (2006.01) | |
| *A61K 9/48* | (2006.01) | |

(52) U.S. Cl.
CPC .......... *A61K 31/496* (2013.01); *A61K 9/4866* (2013.01); *A61K 31/427* (2013.01); *A61K 31/4418* (2013.01); *A61K 45/06* (2013.01)

(58) Field of Classification Search
CPC .. A61K 31/496; A61K 31/437; A61K 31/422; A61K 31/4418; A61K 31/444; A61K 31/506; A61K 31/536; A61K 31/553; A61K 9/4866; A61K 45/06; A61K 2300/00

See application file for complete search history.

(56) References Cited

U.S. PATENT DOCUMENTS

| | | |
|---|---|---|
| 5,296,483 A | 3/1994 | Bodor |
| 5,312,817 A | 5/1994 | Snorrason |
| 5,445,829 A | 8/1995 | Paradissis et al. |
| 5,472,704 A | 12/1995 | Santus et al. |
| 5,672,356 A | 9/1997 | Rault et al. |
| 5,767,128 A | 6/1998 | Guillaumet et al. |
| 6,080,736 A | 6/2000 | Landry et al. |
| 6,150,354 A | 11/2000 | Davis et al. |
| 6,310,177 B1 | 10/2001 | Blaschuk et al. |
| 6,312,717 B1 | 11/2001 | Molinoff et al. |
| 6,319,919 B1 | 11/2001 | Davis et al. |
| 6,350,747 B1 | 2/2002 | Glennon et al. |
| 6,379,696 B1 | 4/2002 | Asmussen et al. |
| 6,403,597 B1 | 6/2002 | Wilson et al. |
| 6,465,006 B1 | 10/2002 | Zhang et al. |

(Continued)

FOREIGN PATENT DOCUMENTS

| | | |
|---|---|---|
| CA | 2331680 A1 | 11/1999 |
| CA | 2732950 A1 | 2/2010 |

(Continued)

OTHER PUBLICATIONS

Nowacek et al., Analyses of nanoformulated antiretroviral drug, charge, size, shape and content for uptake, drug release and antiviral activities in human monocyte-derived macrophages, Nov. 23, 2010, Journal of Controlled Release, vol. 150, pp. 204-211.*

Eggert et al. (Neuroprotective Activities of CEP-1347 in Models of NeuroAIDS, Dec. 4, 2009, The Journal of Immunology, vol. 184, pp. 746-756.*

Wang et al. Mixed-Lineage Kinase Inhibitors Require the Activation of Trk Receptors to Maintain Long-Term Neuronal Trophism and Survival. The Journal of Pharmacology and Experimental Therapeutics, 2005, 312, 1007-1019.

Wong et al. Differential effect of CLK SR Kinases on HIV-1 gene expression: potential novel targets for therapy. Retrovirology, 2011, 8, 47.

(Continued)

*Primary Examiner* — Ali Soroush
(74) *Attorney, Agent, or Firm* — Meunier Carlin & Curfman LLC

(57) ABSTRACT

Disclosed are methods for treating an individual infected with a retrovirus that comprise administering to the individual effective amounts of a mixed lineage kinase inhibitor and antiretroviral drug. In further aspects, disclosed are methods for treating an individual infected with a retrovirus that comprises administering an antiretroviral drug formulated into a crystalline nanoparticle comprising a surfactant, and a MLK inhibitor. Still further disclosed are methods for treating an individual infected with a retrovirus that comprises administering a composition comprising both an antiretroviral and MLK inhibitor formulated into a crystalline nanoparticle, which comprises a surfactant. Still further disclosed are compositions that comprise an antiretroviral drug, a MLK inhibitor, and a surfactant, wherein the composition is a crystalline nanoparticle. Compostions comprising MLK inhibitors with other drugs in nanoparticulate form, and methods of there use, are also disclosed.

22 Claims, 27 Drawing Sheets

(56) References Cited

U.S. PATENT DOCUMENTS

| | | |
|---|---|---|
| 6,482,440 B2 | 11/2002 | Zemlan et al. |
| 6,498,176 B1 | 12/2002 | Lackey et al. |
| 6,512,010 B1 | 1/2003 | Gale et al. |
| 6,517,864 B1 | 2/2003 | Orup Jacobsen et al. |
| 6,524,621 B2 | 2/2003 | Adjei et al. |
| 6,528,080 B2 | 3/2003 | Dunn et al. |
| 6,537,579 B1 | 3/2003 | Desai et al. |
| 6,541,020 B1 | 4/2003 | Ding et al. |
| 6,544,548 B1 | 4/2003 | Siller-Jackson et al. |
| 6,548,084 B2 | 4/2003 | Leonard et al. |
| 6,562,375 B1 | 5/2003 | Sako et al. |
| 6,565,883 B2 | 5/2003 | Ogorka et al. |
| 6,569,463 B2 | 5/2003 | Patel et al. |
| 6,589,549 B2 | 7/2003 | Shih et al. |
| 6,589,563 B2 | 7/2003 | Prokop |
| 6,596,308 B2 | 7/2003 | Guiterrez-Rocca et al. |
| 6,599,529 B1 | 7/2003 | Skinhøj et al. |
| 6,607,751 B1 | 8/2003 | Odidi et al. |
| 6,613,358 B2 | 9/2003 | Randolph et al. |
| 6,613,361 B1 | 9/2003 | Bologna et al. |
| 6,624,171 B1 | 9/2003 | Harris et al. |
| 6,624,200 B2 | 9/2003 | Bologna et al. |
| 6,635,680 B2 | 10/2003 | Mulye |
| 6,638,521 B2 | 10/2003 | Dobrozski |
| 6,774,132 B1 | 8/2004 | Claesson et al. |
| 6,815,439 B2 | 11/2004 | Harris et al. |
| 6,818,632 B2 | 11/2004 | Glennon et al. |
| 7,129,253 B2 | 10/2006 | Glennon et al. |
| 7,361,763 B2 | 4/2008 | Arnold et al. |
| 7,361,764 B2 | 4/2008 | Arnold et al. |
| 7,662,547 B2 * | 2/2010 | Wu ............... A61K 31/553 424/208.1 |
| 2002/0099071 A1 | 7/2002 | Glennon et al. |
| 2003/0187026 A1 | 10/2003 | Li et al. |
| 2003/0199511 A1 | 10/2003 | Li et al. |
| 2004/0043388 A1 | 3/2004 | Come et al. |
| 2004/0072836 A1 | 4/2004 | Harris et al. |
| 2004/0087800 A1 | 5/2004 | Claesson et al. |
| 2004/0191210 A1 | 9/2004 | Glennon et al. |
| 2006/0011139 A1 | 1/2006 | Sterling et al. |
| 2006/0030583 A1 | 2/2006 | Arnold et al. |
| 2006/0106022 A1 | 5/2006 | Liu et al. |
| 2007/0043068 A1 | 2/2007 | Arnold et al. |
| 2007/0287711 A1 | 12/2007 | Arnold et al. |
| 2008/0064026 A1 | 3/2008 | Wu et al. |
| 2008/0119500 A1 | 5/2008 | Jiang et al. |
| 2008/0146561 A1 | 6/2008 | Muci et al. |
| 2008/0261921 A1 | 10/2008 | Chen et al. |
| 2009/0143352 A1 | 6/2009 | Arnold et al. |
| 2011/0236437 A1 | 9/2011 | Destache |

FOREIGN PATENT DOCUMENTS

| | | |
|---|---|---|
| CN | 101027302 | 8/2007 |
| CN | 101065016 | 10/2007 |
| CN | 101573360 | 11/2009 |
| CN | 101939324 | 1/2011 |
| EP | 0691339 | 1/1996 |
| EP | 2308877 | 4/2011 |
| GB | 02400101 | 10/2004 |
| JP | 2007108926 | 4/2007 |
| WO | 1999021859 | 5/1999 |
| WO | 2000055159 | 9/2000 |
| WO | 2000056710 | 9/2000 |
| WO | 2001005790 | 1/2001 |
| WO | 2003051366 | 6/2003 |
| WO | 2004078756 | 9/2004 |
| WO | 2004078756 A2 | 9/2004 |
| WO | 2004085409 | 10/2004 |
| WO | 2005028475 | 3/2005 |
| WO | 2005095400 | 10/2005 |
| WO | 2006015123 | 2/2006 |
| WO | 2006036883 | 4/2006 |
| WO | 2006049890 | 5/2006 |
| WO | 2006063167 | 6/2006 |
| WO | 2006088836 | 8/2006 |
| WO | 2007067737 A2 | 6/2007 |
| WO | 2007106236 | 9/2007 |
| WO | 2007149557 | 12/2007 |
| WO | 2008016669 | 2/2008 |
| WO | 2008051493 | 5/2008 |
| WO | 2008119713 | 10/2008 |
| WO | 2008124848 | 10/2008 |
| WO | 2008124849 | 10/2008 |
| WO | 2008129994 | 10/2008 |
| WO | 2009054941 | 4/2009 |
| WO | 2010016490 | 2/2010 |
| WO | 2010059771 | 5/2010 |
| WO | 2010068483 | 6/2010 |
| WO | WO-2010/0684483 A2 * | 6/2010 |
| WO | 2011149950 | 12/2011 |
| WO | 2012061480 | 5/2012 |

OTHER PUBLICATIONS

Yousefi et al. HIV-1 infection is facilitated in T cells by decreasing p56lck protein tyrosine kinase activity. Clinical and Experimental Immunology, 2003, 133, 78-90.
Zhang et al. Cannabinoid CB1 receptor activation stimulates neurite outgrowth and inhibits capsaicin-induced Ca2+ influx in an in vitro model of diabetic neuropathy. Neuropharmacology, 2009, 57, 88-96.
Zherebitskaya et al. Development of selective axonopathy in adult sensory neurons isolated from diabetic rats: role of glucose-induced oxidative stress. Diabetes, 2009, 58, 1356-1364.
Office Action, dated Apr. 4, 2014, received in connection with corresponding AU Application No. 2009324894.
Office Action, dated Dec. 27, 2013, received in connection with corresponding CN Application No. 200980152665.1. (English Translation).
Office Action, dated May 16, 2013, received in connection with corresponding CN Application No. 200980152665.1.
Office Action, dated Jul. 15, 2014, received in connection with corresponding CN Application No. 200980152665.1. (English Translation).
Office Action, dated Sep. 3, 2014, received in connection with related CN Application No. 201180036376.2. (English Translation).
Office Action, dated Sep. 5, 2014, received in connection with corresponding EP Application No. 09832359.5.
Office Action, dated Nov. 12, 2013, received in connection with corresponding EP Application No. 09832359.5.
Official Action, dated May 24, 2012, received in connection with corresponding EP Application No. 09832359.5.
Search Report, dated Aug. 30, 2012, received in connection with corresponding EP Application No. 09832359.5.
European Search Report, dated Nov. 19, 2013, received in connection with related EP Application No. 11787254.9.
Office Action, dated Jul. 14, 2014, received in connection with corresponding JP Application No. 2011537733. (English Translation).
Office Action, dated Feb. 5, 2014, received in connection with corresponding JP Application No. 2011537733.
Office Action, dated Apr. 13, 2015, received in connection with corresponding JP Application No. 2013512166.
Office Action, dated Jan. 16, 2015, received in connection with corresponding NZ Application No. 614904.
Office Action, dated Sep. 5, 2013, received in connection with corresponding NZ Application No. 614904.
Office Action, dated Aug. 21, 2013, received in connection with corresponding NZ Application No. 594904.
Office Action, dated Oct. 3, 2012, received in connection with corresponding NZ Application No. 594904.
Office Action, dated Feb. 3, 2012, received in connection with corresponding NZ Application No. 594904.
Office Action, dated Jul. 9, 2013, received in connection with related NZ Application No. 603644.
Notice of Allowance, dated May 16, 2014, received in connection with related U.S. Appl. No. 13/698,829.

(56) References Cited

OTHER PUBLICATIONS

Office Action, dated Jan. 28, 2014, received in connection with related U.S. Appl. No. 13/698,829.
Restriction Requirement, dated Dec. 17, 2013, received in connection with related U.S. Appl. No. 13/698,829.
Office Action, dated Mar. 10, 2015, received in connection with related U.S. Appl. No. 14/508,566.
Notice of Allowance, dated Jul. 7, 2015, received in connection with related U.S. Appl. No. 14/508,566.
International Preliminary Report on Patentability and Written Opinion, dated May 31, 2011, received in connection with corresponding International Application No. PCT/US2009/065878.
International Search Report, dated Jul. 29, 2010, received in connection with corresponding International Application No. PCT/US2009/065878.
International Preliminary Report on Patentability and Written Opinion, dated Nov. 27, 2012, received in connection with related International Application No. PCT/US2011/037758.
International Search Report and Written Opinion, dated Feb. 9, 2012, received in connection with related International Application No. PCT/US2011/037758.
International Search Report and Written Opinion, dated Mar. 14, 2014, received in connection with related International Application No. PCT/US2013/072530.
International Preliminary Report on Patentability, dated Jun. 2, 2015, received in connection with related International Application No. PCT/US2013/072530.
Office Action, dated Jul. 27, 2015, received in connection with corresponding JP Application No. 2014232195.
Office Action, dated Oct. 2, 2015, received in connection with corresponding EP Application No. 11787254.9.
Abou-Hadeed et al. Synthesis and properties of condensed lumazine-ring systems. Pteridines, 2002, 13, 65-72.
Adams et al. Mapping the Kinase Domain of Janus Kinase 3. Bioorganic & Medicinal Chemistry Letters, 2003, 13, 3105-3110.
Averill et al. Immunocytochemical localization of trkA receptors in chemically identified subgroups of adult rat sensory neurons. European Journal of Neuroscience, 1995, 7, 1484-1494.
Bodner et al. Mixed lineage kinase 3 mediates gp120IIIB-induced neurotoxicity. Journal of Neurochemistry, 2002, 82, 1424-1434.
Bol et al. Genome-wide association study identifies single nucleotide polymorphism in DYRK1A associated with replication of HIV-1 in monocyte-derived macrophages. PloS one, 2011, 6, e17190.
Bosque et al. Induction of HIV-1 latency and reactivation in primary memory CD4+ T cells. Blood, 2009, 113, 58-65.
Cetkovic-Cvljie et al. Targeting Janus kinase 3 to attenuate the severity of acute graft-versus-host disease across the major histocompatibility barrier in mice. Blood, 2001, 98, 1607-1613.
Conforti et al. Blood level of brain-derived neurotrophic factor mRNA is progressively reduced in rodent models of Huntington's disease: Restoration by the neuroprotective compound CEP-1347, Molecular and Cellular Neuroscience, 2008, 39, 1-7.
Dash et al. Long-acting NanoART ElicitsPotent antiretroviral and neuroprotective responses in HIV-1 Infected Humanized Mice. AIDS (London, England), 2012, 26, 2135-2144.
Dash et al. Loss of neuronal integrity during progressive HIV-1 infection of humanized mice. Journal of Neuroscience, 2011, 31, 3148-57.
Daviau et al. The mixed-lineage kinase DLK undergoes Src-dependent tyrosine phosphorylation and activation in cells exposed to vanadate or platelet-derived growth factor (PDGF). Cellular Signalling, 2009, 21, 577-587.
DeBoy et al. FLT-3 expression and function on microglia in multiple sclerosis. Experimental and Molecular Pathology, 2010, 89, 109-116.
Eggert et al. Neuroprotective Activities of CEP-1347 in Models of NeuroAIDS. Journal of Immunology, 2010, 184(2), 746-756.
Eto et al. Role of dual leucine zipper-bearing kinase (DLK/MUK/ZPK) in axonal growth. Neuroscience Research, 2010, 66, 37-45.
Fernyhough et al. Insulin and insulin-like growth factor I enhance regeneration in cultured adult rat sensory neurons. Brain Research, 1993, 607, 117-124.
Garaci et al. Nerve growth factor is an autocrine factor essential for the survival of macrophages infected with HIV. Proceedings of the National Academy of Sciences of the United States of America 1999, 96, 14013-14018.
Gardiner et al. alpha7 integrin mediates neurite outgrowth of distinct populations of adult sensory neurons. Molecular and Cellular Neuroscience, 2005, 28, 229-240.
Gavazzi et al. Growth responses of different subpopulations of adult sensory neurons to neurotrophic factors in vitro. European Journal of Neuroscience, 1999, 11, 3405-3414.
Gayle et al. A severe combined immunodeficiency mutation in the mouse. Nature, 1983, 301, 527-530.
Gorantla et al. CD8+ cell depletion accelerates HIV-1 immunopathology in humanized mice. Journal of Immunology, 2010, 184, 7082-7091.
Gorantla et al. Human immunodeficiency virus type 1 pathobiology studied in humanized BALB/c-Rag2-/-gammac-/- mice. Journal of Virology, 2007, 81, 2700-2712.
Hackam et al. Translation of Research Evidence From Animals to Humans. JAMA, 2006, 296, 1731-1732.
Huang et al. Effects of Manufacturing Process Variables on In Vitro Dissolution Characteristics of Extended-Release Tablets Formulated with Hydroxypropyl Methylcellulose. Drug Development and Industrial Pharmacy, 2003, 29, 79-88.
Isakov et al. Lck protein tyrosine kinase is a key regulator of T-cell activation and a target for signal intervention by Herpesvirus saimiri and other viral gene products. European Journal of Biochemistry / FEBS, 2000, 267, 3413-3421.
Jordan. Tamoxifen: A Most Unlikely Pioneering Medicine. Nature reviews: Drug Discovery, 2003, 2, 205-213.
Kanmogne et al. Mononuclear phagocyte intercellular crosstalk facilitates transmission of cell-targeted nanoformulated antiretroviral drugs to human brain endothelial cells. International Journal of Nanomedicine, 2012, 7, 2373-2388.
Karaman et al. A quantitative analysis of kinase inhibitor selectivity. Nature Biotechnology, 2008, 26, 127-132.
Khanvilkar et al. Influence of Hydroxypropyl Methylcellulose Mixture, Apparent Viscosity, and Tablet Hardness on Drug Release Using a 23 Full Factorial Design. Drug Development and Industrial Pharmacy, 2002, 28, 601-608.
Krishnan et al. The molecular neurobiology of depression. Nature, 2008, 455, 894-902.
Lelkes et al. Reactive oxygen species, apoptosis and altered NGF-induced signaling in PC12 pheochromocytoma cells cultured in elevated glucose: An in vitro cellular model for diabetic neuropathy. Neurotoxicity Research, 2001, 3, 189-203.
Ma et al. Pharmacokinetic interactions of CEP-1347 and atazanavir in HIV-infected patients. Journal of Neurovirology, 2013, 19, 254-260.
Maggi et al. Photostability of extended-release matrix formulations. European Journal of Pharmaceutics and Biopharmaceutics, 2003, 55, 99-105.
Makino et al. Breeding of a non-obese, diabetic strain of mice. Jikken Dobutsu, 1980, 29, 1-13.
Marie-Claude et al. Acylation of oxazolo[4,5-b]pyridin-2(3H)-ones, 2-phenyloxazolo[4,5-b]pyridines and pyrrolo[2,3-b]pyridin-2(2H)-ones. Tetrahedron, 1997, 53, 5159-5168.
McCune et al. The SCID-hu mouse: murine model for the analysis of human hematolymphoid differentiation and function. Science, 1988, 241, 1632-1639.
Meanwell et al. Regiospecific Functionalization of 1,3-Dihydro-2H-benzimidazol-2-one and Structurally Related Cyclic Urea Derivatives. Journal of Organic Chemistry, 1995, 60, 1565-1582.
Merritt et al. The mixed lineage kinase DLK utilizes MKK7 and not MKK4 as substrate. Journal of Biological Chemistry, 1999, 274, 10195-10202.
Miyauchi et al. HIV enters cells via endocytosis and dynamin-dependent fusion with endosomes. Cell, 2009, 137, 433-444.

(56) References Cited

OTHER PUBLICATIONS

Mosier et al. Transfer of a functional human immune system to mice with severe combined immunodeficiency. Nature, 1988, 335, 256-259.

Park et al. CP-690550, a Janus kinase inhibitor, suppresses CD4+ T-cell-mediated acute graft-versus-host disease by inhibiting the interferon-gamma pathway. Transplantation, 2010, 90, 825-835.

Pearnchob et al. Pharmaceutical Applications of Shellac: Moisture-Protective and Taste-Making Coatings and Extended-Release Matrix Tablets. Drug Development and Industrial Pharmacy, 2003, 29, 925-938.

Pratap et al. A novel synthesis of aryl tethered imidazo[4,5-b]pyrazin-2-ones through in situ ring construction and contraction. Tetrahedron Letters, 2007, 48, 1281-1285.

Robinett. The discovery of substituted 4-(3-hydroxyanilino)-quinolines as potent RET kinase inhibitors. Bioorganic & Medicinal Chemistry Letters, 2007, 17, 5886-5893.

Schmidt et al. A multiparticulate drug-delivery system based on pellets incorporated into congealable polyethylene glycol carrier materials. International Journal of Pharmaceuticals, 2001, 216, 9-16.

Souza et al. The nerve growth factor reduces APOBEC3G synthesis and enhances HIV-1 transcription and replication in human primary macrophages. Blood, 2011, 117, 2944-2952.

Strasner et al. The Src kinase Lck facilitates assembly of HIV-1 at the plasma membrane. Journal of Immunology (Baltimore, Md.: 1950) 2008, 181, 3706-3713.

Sudimack et al. Targeted drug delivery via the folate receptor. Advanced Drug Delivery Reviews, 2000, 41, 147-162.

Sui et al. Inhibition of Mixed Lineage Kinase 3 Prevents HIV-1 Tat-Mediated Neurotoxicity and Monocyte Activation. Journal of Immunology, 2006, 177, 702-711.

Uckun et al. Janus kinase 3 inhibitor WHI-P131/JANEX-1 prevents graft-versus-host disease but spares the graft-versus-leukemia function of the bone marrow allografts in a murine bone marrow transplantation model. Blood, 2002, 99, 4192-4199.

Wang et al. Glycogen synthase kinase-3beta inactivation inhibits tumor necrosis factor-alpha production in microglia by modulating nuclear factor kappaB and MLK3/JNK signaling cascades. Journal of Neuroinflammation, 2010, 7, 99.

Office Action dated Dec. 14, 2015 in related Canadian Application 2744498.

Wang et al. "Mixed-Lineage Kinases: A Target for the Prevention of Neurodegeneration." AnnuRev Pharmacol Toxicol, 2004, 44, 451-474.

Extended European Search Report dated Jul. 18, 2016 in related European Application 13857739.0.

European Examination Report dated Oct. 17, 2016, in European Application 11 787 254.9.

Extended European Search Report dated Oct. 31, 2016 in related European Application 15186751.

Gallo et al. "Mixed-Lineage Kinase Control of JNK and p38 MAPK Pathways." Nature Reviews:Molecular Cell Biology, 2002, 3, 663-672.

Communication pursuant to Article 94(3) issued in EP Application No. 15186751.2, dated Oct. 26, 2017.

Office Action, dated Mar. 13, 2017, issued connection with Canadian Application No. 2,800,176.

Office Action, dated Apr. 5, 2017, issued connection with Chinese Application No. 201380060736.1.

Office Action, dated Feb. 13, 2017, issued connection with U.S. Appl. No. 15/172,355.

Office Action, dated Feb. 13, 2017, issued connection with U.S. Appl. No. 14/876,345.

Communication pursuant to Article 94(3) issued in EP Application No. 15186751.2 dated Sep. 7, 2018.

Office Action dated Nov. 25, 2015 received in connection with corresponding AU Application No. 2011258465.

Office Action dated Nov. 21, 2016 received in connection with corresponding AU Application No. 2011258465.

* cited by examiner

| Experimental Condition | Up regulated* | Down regulated* |
|---|---|---|
| Compound AH + HIV-1 to Control | 26 | 22 |
| Compound AH + HIV-1 to HIV-1 | 152 | 4 |
| HIV-1 to Control | 2 | 163 |
| Compound AH to Control | 7 | 25 |

*Protein changes in two out of three donors

FIG. 7B

MIXED LINEAGE KINASE INHIBITORS FOR HIV/AIDS THERAPIES

CROSS REFERENCE TO RELATED APPLICATIONS

This application claims the benefit of priority to US. Provisional Applications 61/731,925, filed Nov. 30, 2012, 61/767,748, filed Feb. 21, 2013, and 61/768,077, filed Feb. 22, 2013, which are each incorporated by reference herein in their entiriees.

ACKNOWLEDGMENT OF GOVERNMENT SUPPORT

This invention was made with government support under MH064570 and MH104147 awarded by the National Institutes of Health. The government has certain rights in the invention.

BACKGROUND

Mammalian protein kinases are involved in the regulation of important cellular functions. Due to the fact that dysfunctions in protein kinase activity have been associated with several diseases and disorders, protein kinases are targets for drug development.

Mixed lineage kinases (MLKs) are MAPK kinase kinases that target JNK and p38 MAPK for activation in response to diverse stimuli that stress cells. As a result, the MLKs regulate a broad range of cellular processes. MLK3 is the most widely expressed MLK family member and is present in neurons and brain-resident mononuclear phagocytes. It is activated by GTPases of the Ras superfamily, such as Cdc42 and Rac, which trigger protein dimerization via a leucine zipper interface, resulting in auto-phosphorylation at Thr277 and Ser281 within the protein activation loop and subsequent activation of the enzyme.

Preclinical studies of the mixed lineage kinase (MLK) inhibitor CEP1347 have shown that this agent can protect neurons against a considerable range of insults, including exposure to the Alzheimer's peptide, Aβ. Studies using the 1-methyl-4-phenyl-1,2,3,6-tetrahydropyridine model of Parkinsonism have demonstrated the efficacy of CEP1347 in treating motor deficits and neuronal degeneration, and CEP1347-mediated neuroprotection has also been observed in an in vitro model for Parkinson's Disease, using methamphetamine-exposed human mesencephalic-derived neurons. CEP1347 might also be protective in the context of neurologic complications such as HIV-associated dementia (HAD). In fact, Bodner et al. have shown that CEP1347 can protect primary rat hippocampal neurons as well as dorsal root ganglion neurons from the otherwise lethal effects of exposure to HIV-1 gp120. It has been determined that CEP1347 mediates this effect by inhibiting the activity of the mixed lineage kinase (MLK) family.

Maggirwar et al. examined the effect of the HIV-1 neurotoxins Tat and gp120 on MLK3. Tat and gp120 were shown to induce autophosphorylation of MLK3 in primary rat neurons and this was abolished by the addition of CEP1347. These studies indicate that the normal function of MLK3 is compromised by these HIV-1 neurotoxins, resulting in the downstream signaling events that result in neuronal death and monocyte activation (with release of inflammatory cytokines). Eggert et al. have demonstrated that CEP1347 is neuroprotective in an in vivo model of HIV-1 infection, reversing microglial activation and restoring normal synaptic architecture, as well as restoring macrophage secretory profiles to a trophic vs. toxic phenotype in response to HIV-1 infection (J. Immunol. 184(2):746-56, 2010)

MLK3 has been shown to drive the production of the HIV virus. As a result, several lines of evidence now support that an inhibitor of MLK3 could serve as a treatment for numerous neurological conditions, including neuroAIDS. CEP1347 does not have ideal pharmacokinetic properties, which could potentially affect its ability to gain entry, or remain at therapeutic concentrations in the CNS. Other small molecule MLK3 inhibitors are needed that have improved pharmacokinetic and brain penetrating properties.

Pharmacologic blockade of mixed lineage kinase 3 (MLK3) has been shown to result in activation of neurotrophin-mediated signaling pathways, and increased expression of neurotrophin receptors—resulting in enhanced responsiveness to endogenous neurotrophins, including BDNF (Wang, et al., *J Pharmacol Exp Ther* 312:1007-19, 2005). MLK3 inhibitors have also been shown to increase production of BDNF itself (Conforti, et al. *Mol Cell Neurosci* 39:1-7, 2008).

Combined treatment with SSRIs and MLK3 inhibitors could result in the synergistic promotion of neurogenesis, due to the neurotrophin-sensitizing effects of MLK3 inhibitors and their ability to directly upregulate BDNF (Wang and Conforti, supra). Increase of the therapeutic effectiveness of SSRIs (and possibly talk therapy and exercise also) could also result if the compounds were coadministered.

Exposure to MLK3 inhibitors may also compensate for lowered BDNF levels in hippocampus of persons with depression, thereby alleviating depression (based on the "BDNF hypothesis").

What are needed are new MLK inhibitors and new delivery mechanisms, treatments, and compositions for HIV/AIDS therapies. The compositions and methods disclosed herein address these and other needs.

SUMMARY

In accordance with the purposes of the disclosed materials, compounds, compositions, articles, devices, and methods, as embodied and broadly described herein, the disclosed subject matter relates to compositions and methods of making and using the compositions. In other aspect, disclosed herein are methods for treating an individual infected with a retrovirus that comprise administering to the individual effective amounts of a mixed lineage kinase inhibitor and antiretroviral drug. In further aspects, disclosed herein are methods for treating an individual infected with a retrovirus that comprises administering an antiretroviral drug formulated into a crystalline nanoparticle comprising a surfactant, and a MLK inhibitor. Still further disclosed are methods for treating an individual infected with a retrovirus that comprises administering a composition comprising both an antiretroviral and MLK inhibitor formulated into a crystalline nanoparticle, which comprises a surfactant. Still further disclosed herein are compositions that comprise an antiretroviral drug, a MLK inhibitor, and a surfactant, wherein the composition is a crystalline nanoparticle.

Additional advantages of the disclosed subject matter will be set forth in part in the description that follows, and in part will be obvious from the description, or can be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying Figures, which are incorporated in and constitute a part of this specification, illustrate several aspects of the invention and together with the description serve to explain the principles of the invention.

DETAILED DESCRIPTION

Figure 1:
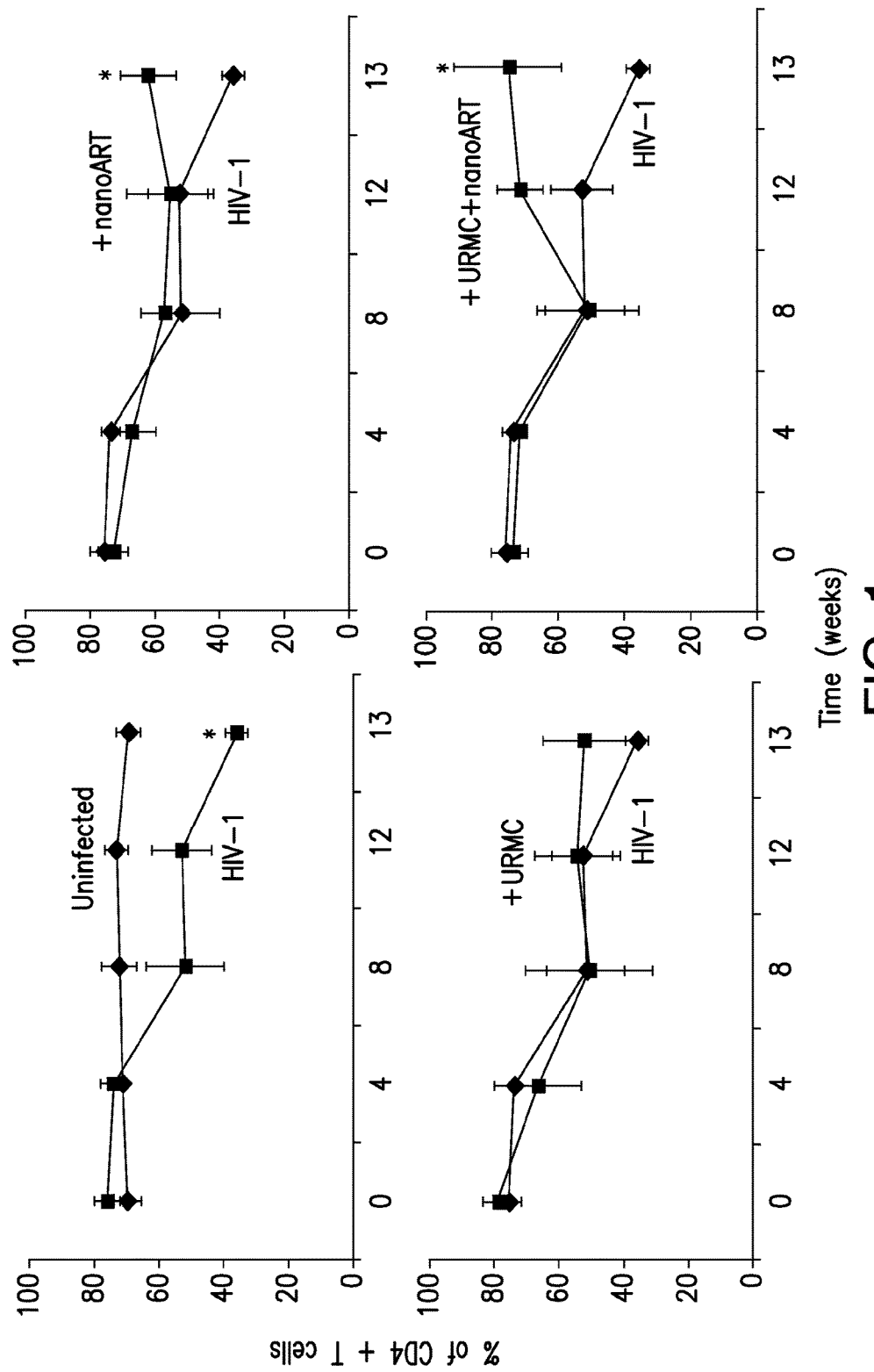
FIG. 1 is a group of graphs showing % of $CD4^+$ T Cells levels in humanized mice over thirteen weeks. The top left panel shows the controls in uninfected (diamonds) and HIV-1 infected (squares) mice. The top right panel shows mice treated with nanoparticles comprising atazanavir and ritonavir (squares) as compared to untreated HIV-1 infected mice (diamonds). The bottom left panel shows mice treated with Compound AH (squares) as compared to untreated HIV-1 infected mice (diamonds). The bottom right panel shows mice treated with both Compound AH and nanoparticles comprising atazanavir and ritonavir (squares) as compared to untreated HIV-1 infected mice (diamonds).
Figure 2:
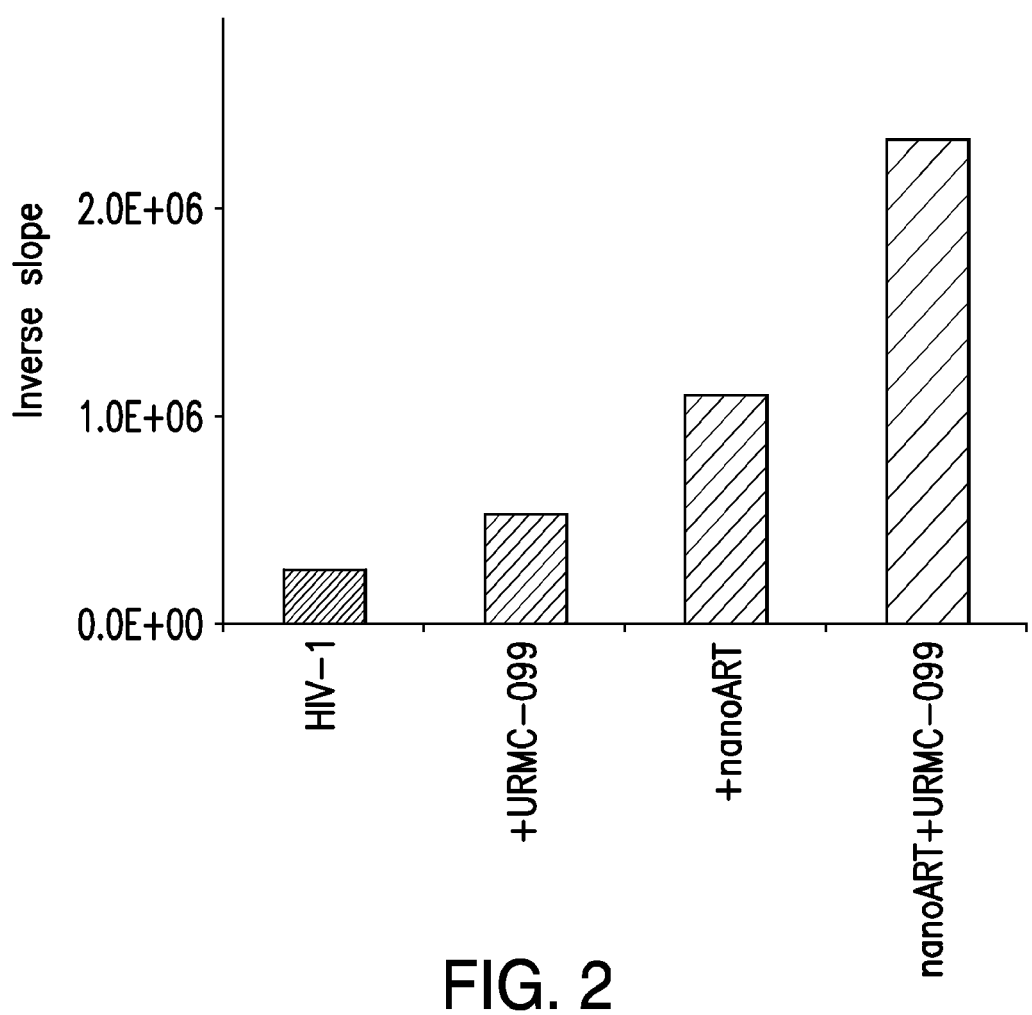
FIG. 2 is a graph showing the time course of peripheral HIV-1 viral load.
Figure 3A:
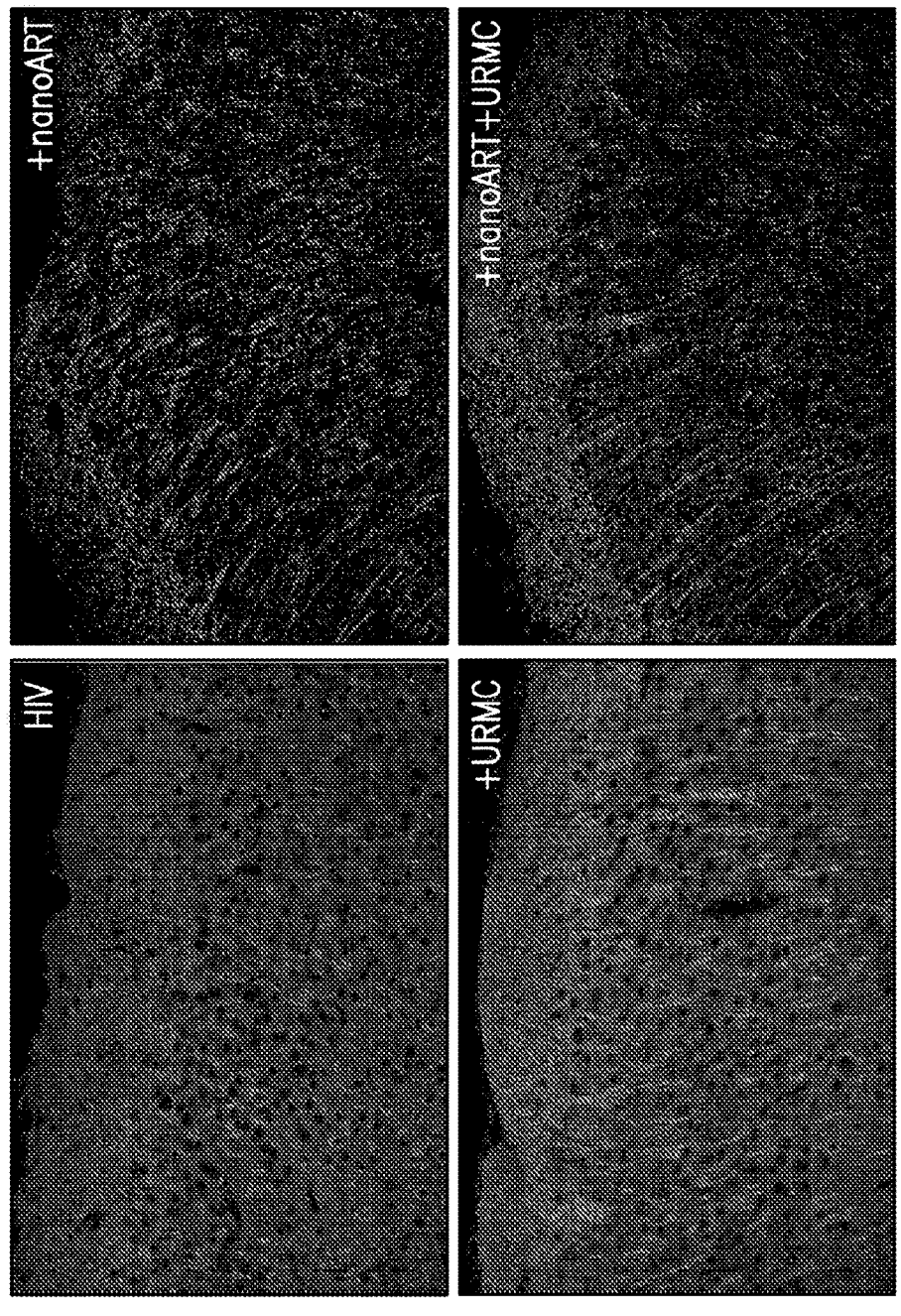
FIG. 3 is a group of photographs of samples from the cerebral cortex of untreated HIV-1 infected mice (top left), mice treated with nanoparticles comprising atazanavir and ritonavir (top right), mice treated with Compound AH (bottom left), and mice treated with both Compound AH and nanoparticles comprising atazanavir and ritonavir (bottom right). The corresponding $H^1$ MR spectroscopic analysis of the metabolites is shown in the bottom graphs.
Figure 3B:
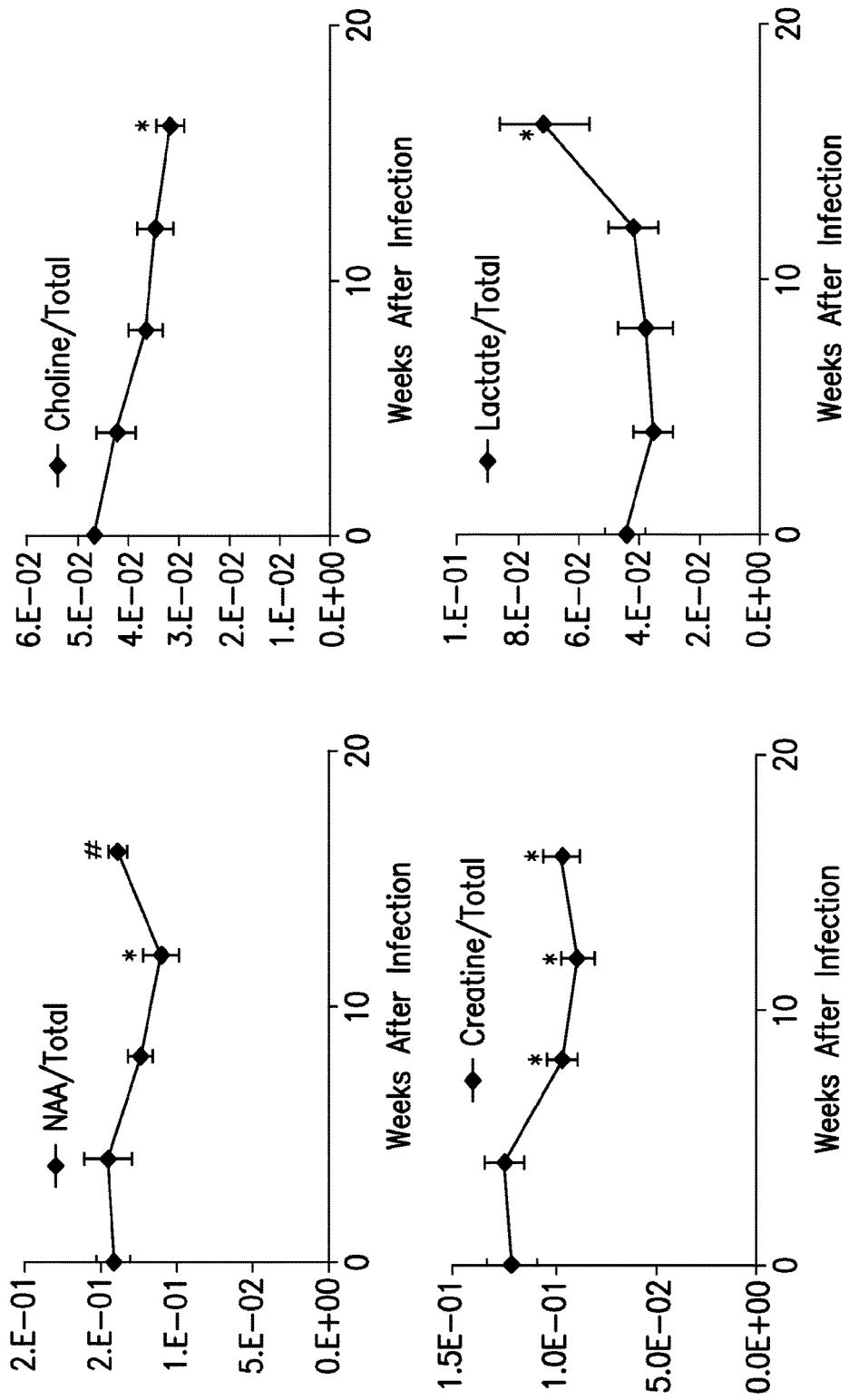

The compounds, compositions, articles, devices, and methods described herein can be understood more readily by reference to the following detailed description of specific aspects of the disclosed subject matter and the Examples and Figures.

Before the present compounds, compositions, articles, devices, and methods are disclosed and described it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Definitions

In this specification and in the claims that follow, reference will be made to a number of terms, which shall be defined to have the following meanings:

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, and the like.

"Optional" or "optionally" means that the subsequently described event or circumstance can or cannot occur, and that the description includes instances where the event or circumstance occurs and instances where it does not.

When ranges of values are disclosed, and the notation "from $n_1 \ldots$ to $n_2$" is used, where $n_1$ and $n_2$ are the numbers, then unless otherwise specified, this notation is intended to include the numbers themselves and the range between them. This range can be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

As used herein, the term "amphiphilic" means the ability to dissolve in both water and lipids/apolr environments. Typically, an amphiphilic compound comprises a hydrophilic portion and a hydrophobic portion. "Hydrophobic" designates a preference for apolar environments (e.g., a hydrophobic substance or moiety is more readily dissolved in or wetted by non-polar solvents, such as hydrocarbons, than by water). As used herein, the term "hydrophilic" means the ability to dissolve in water.

As used herein, the term "polymer" denotes molecules formed from the chemical union of two or more repeating units or monomers. The term "block copolymer" most simply refers to conjugates of at least two different polymer segments, wherein each polymer segment comprises two or more adjacent units of the same kind.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—),(—C::C—)]. Examples of suitable alkenyl radicals include ethenyl, propenyl, 2-propenyl, 2-methylpropenyl, butenyl, isobutenyl, 1,4-butadienyl, isoprenyl, vinyl, and the like. Unless otherwise specified, the term "alkenyl" can include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 6 carbon atoms. Alkyl groups can be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" can include "alkylene" groups.

The term "alkylamino," as used herein, alone or in combination, refers to an alkyl group attached to the parent molecular moiety through an amino group. Suitable alkylamino groups can be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur can be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" can include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino (CH$_3$C(O) NH—).

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which can themselves be optionally substituted. Additionally, R and R' can combine to form heterocycloalkyl, either of which can be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, naphthoyl, phenylacetyl, 3-phenylpropionyl(hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical C$_6$H$_4$=derived from benzene. Examples include benzothiophene and benzimidazole.

The term "carbamate," as used herein, alone or in combination, refers to an ester of carbamic acid (—NRC(O)O—) which can be attached to the parent molecular moiety from either the nitrogen or acid end, and which can be optionally substituted as defined herein.

The term "O-carbamyl" as used herein, alone or in combination, refers to a —OC(O)NRR' group; and the term "N-carbamyl" as used herein, alone or in combination, refers to a ROC(O)NR'— group. R and R' are as defined herein, or as defined by the specifically enumerated "R" groups designated.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which can optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronaphthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom. Haloalkoxy includes perhaloalkoxy. The term "perhaloalkoxy" refers to an alkoxy group where all of the hydrogen atoms are replaced by halogen atoms. An example of perhaloalkoxy is perfluoromethoxy.

The term "haloalkyl," as used herein, alone or in combination, refers to an alkyl radical having the meaning as defined above wherein one or more hydrogens are replaced with a halogen. Specifically embraced are monohaloalkyl, dihaloalkyl, polyhaloalkyl, and perhaloalkyl radicals. A monohaloalkyl radical, for one example, can have an iodo, bromo, chloro or fluoro atom within the radical. Dihalo and polyhaloalkyl radicals can have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like. The term "perhaloalkyl" as used herein, alone or in combination, refers to an alkyl group where all of the hydrogen atoms are replaced by halogen atoms. Examples include perfluoromethyl.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms chosen from O, N, and S, and wherein the nitrogen and sulfur atoms can optionally be oxidized and the nitrogen heteroatom can optionally be quaternized. The heteroatom(s) O, N and S can be placed at any interior position of the heteroalkyl group. Up to two heteroatoms can be consecutive, such as, for example, —CH$_2$—NH—OCH$_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom chosen from O, S, and N. Additionally, a heteroaryl can contain one or two C(O), S(O), or S(O)$_2$ groups as ring members. In certain embodiments, said heteroaryl will comprise from 5 to 10 atoms. In certain embodiments, said heteroaryl will comprise from 5 to 7 atoms. In certain embodiments, said heteroaryl will comprise from 1 to 4 heteroatoms as ring members. In further embodiments, said heteroaryl will comprise from 1 to 2 heteroatoms as ring members. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, imidazolyl, triazinyl, triazolyl, tetrazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each said heteroatom can be independently chosen from N, O, and S. Additionally, a heterocycloalkyl can contain one or two C(O), S(O), or S(O)$_2$ groups as ring members. In certain embodiments, said heterocycloalkyl will comprise from 1 to 4 heteroatoms as ring members. In further embodiments, said hetercycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups can be optionally substituted unless specifically prohibited.

The term "hydrogen," as used herein, alone or in combination, can include deuterium.

The term "hydroxy," as used herein, alone or in combination, refers to —OH.

The term "lower," as used herein, alone or in a combination, where not otherwise specifically defined, means containing from 1 to and including 6 carbon atoms.

The term "lower alkyl," as used herein, alone or in a combination, means C$_1$-C$_6$ straight or branched chain alkyl. The term "lower alkenyl" means C$_2$-C$_6$ straight or branched chain alkenyl. The term "lower alkynyl" means C$_2$-C$_6$ straight or branched chain alkynyl.

The term "lower aryl," as used herein, alone or in combination, means phenyl or naphthyl, either of which can be optionally substituted as provided.

The term "lower heteroaryl," as used herein, alone or in combination, means either 1) monocyclic heteroaryl comprising five or six ring members, of which between one and four said members can be heteroatoms chosen from O, S, and N, or 2) bicyclic heteroaryl, wherein each of the fused rings comprises five or six ring members, comprising between them one to four heteroatoms chosen from O, S, and N.

The term "lower cycloalkyl," as used herein, alone or in combination, means a monocyclic cycloalkyl having between three and six ring members. Lower cycloalkyls can be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four can be heteroatoms chosen from O, S, and N. Examples of lower heterocycloalkyls include pyrrolidinyl, imidazolidinyl, pyrazolidinyl, piperidinyl, piperazinyl, and morpholinyl. Lower heterocycloalkyls can be unsaturated.

The term "lower carboxyl," as used herein, alone or in combination, means —C(O)R, wherein R is chosen from hydrogen, lower alkyl, cycloalkyl, cycloheterolkyl, and lower heteroalkyl, any of which can be optionally substituted with hydroxyl, (0), and halogen.

The term "lower amino," as used herein, alone or in combination, refers to —NRR', wherein R and R' are independently chosen from hydrogen, lower alkyl, and lower heteroalkyl, any of which can be optionally substituted. Additionally, the R and R' of a lower amino group can combine to form a five- or six-membered heterocycloalkyl, either of which can be optionally substituted.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —SO$_3$H group and its anion as the sulfonic acid is used in salt formation.

The term "N-sulfonamido" refers to a RS(=O)$_2$NR'— group with R and R' as defined herein or as defined by the specifically enumerated "R" groups designated.

The term "S-sulfonamido" refers to a —S(=O)$_2$NRR', group, with R and R' as defined herein or as defined by the specifically enumerated "R" groups designated.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio. The term "sulfanyl," as used herein, alone or in combination, refers to —S—. The term "sulfinyl," as used herein, alone or in combination, refers to —S(O)—. The term "sulfonyl," as used herein, alone or in combination, refers to —S(O)$_2$—.

The term "thiol," as used herein, alone or in combination, refers to an —SH group.

The term "thiocarbonyl," as used herein, when alone includes thioformyl —C(S)H and in combination is a —C(S)— group.

Any definition herein can be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "optionally substituted" means the anteceding group can be substituted or unsubstituted. When substituted, the substituents of an "optionally substituted" group can include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen or deuterium, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N$_3$, SH, SCH$_3$, C(O)CH$_3$, CO$_2$CH$_3$, CO$_2$H, pyridinyl, thiophene, furanyl, lower carbamate, and lower urea. Two substituents can be joined together to form a fused five-, six-, or seven-membered carbocyclic or heterocyclic ring consisting of zero to three heteroatoms, for example forming methylenedioxy or ethylenedioxy. An optionally substituted group can be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety can be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which can be optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups can be attached to a parent molecule or can occupy a position in a chain of elements from either end as written. Thus, by way of example only, an unsymmetrical group such as —C(O)N(R)— can be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Compounds can be prepared using diastereomers, enantiomers or racemic mixtures as starting materials. Starting compounds of particular stereochemistry are either commercially available or can be made and resolved by techniques known in the art. Furthermore, diastereomer and enantiomer products can be separated by chromatography, fractional crystallization or other methods known to those of skill in the art. Additionally, the compounds disclosed herein can exist as geometric isomers. The present invention includes all cis, trans, syn, anti, entgegen (E), and zusammen (Z) isomers as well as the appropriate mixtures thereof. Additionally, compounds can exist as tautomers; all tautomeric isomers are provided by this invention. Solvates, hydrates, isomorphs, polymorphs are also provided. Additionally, the compounds disclosed herein can exist in unsolvated as well as solvated forms with pharmaceutically acceptable solvents such as water, ethanol, and the like. In general, the solvated forms are considered equivalent to the unsolvated forms.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

The term "bond" refers to a covalent linkage between two atoms, or two moieties when the atoms joined by the bond are considered to be part of larger substructure. A bond can be single, double, or triple unless otherwise specified. A dashed line between two atoms in a drawing of a molecule indicates that an additional bond can be present or absent at that position. When, for example, $Y_1$ is —$(CR_{6a}R_{6b})_m$—$Z_1$—$(CR_{7a}R_{7b})_n$—, and m and n are both 0, and $Z_1$ is a bond, then $Y_1$ collapses to a direct bond linking the parent ring system with $R_1$. This applies to all similar constructions used herein, including $Y_2$ and $Y_3$. Or, for example, when either of $R_{6a}$ and $R_{6b}$ of $(CR_{6a}R_{6b})_m$ are designated to be "a bond," and m≥1, then an additional bond forms between a C of $(CR_{6a}R_{6b})$ and an adjacent atom. When m≥2, then $(CR_{6a}R_{6b})_m$ can form an alkene (alkenylene) or alkyne (alkynylene).

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to administer a composition or to perform a method in order to reduce, prevent, inhibit, or eliminate a particular characteristic or event (e.g., tumor growth or survival). The term "control" is used synonymously with the term "treat."

As used herein, the terms "treating" and "treatment" refer to delaying the onset of, retarding or reversing the progress of, or alleviating or preventing either the disease or condition to which the term applies, or one or more symptoms of such disease or condition.

The term "individual" (and, equivalently, "subject") means all mammals including humans. Examples of individuals include humans, cows, dogs, cats, goats, sheep, pigs, and rabbits. Preferably, the individual is a human.

The term "disease" as used herein is intended to be generally synonymous, and is used interchangeably with, the terms "disorder," "syndrome," and "condition" (as in medical condition), in that all reflect an abnormal condition of the human or animal body or of one or more of its parts that impairs normal functioning, is typically manifested by distinguishing signs and symptoms, and/or causes the human or animal to have a reduced duration or quality of life.

The term "HIV associated neurocognitive disorder (HAND)" is related to, and is intended to be substantially synonymous with, the terms HIV dementia, AIDS dementia, HIV encephalopathy, and NeuroAIDS.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

As used herein, the term "administering" means oral administration, administration as a suppository, topical contact, intravenous, intraperitoneal, intramuscular, intralesional, intranasal or subcutaneous administration, or the implantation of a slow-release device, e.g., a mini-osmotic pump, to a subject. Administration is by any route including parenteral, and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, and the like.

As used herein, the term "prodrug" refers to a precursor compound that, following administration, releases the biologically active compound in vivo via some chemical or physiological process (e.g., a prodrug on reaching physiological pH or through enzyme action is converted to the biologically active compound).

The terms "controlled release," "sustained release," "extended release," and "timed release" are intended to refer interchangeably to any drug-containing formulation in which release of the drug is not immediate, i.e., with a "controlled release" formulation, oral administration does not result in immediate release of the drug into an absorption pool. The terms are used interchangeably with "nonimmediate release" as defined in *Remington: The Science and Practice of Pharmacy*, 21$^{st}$ Ed., Gennaro, Ed., Lippencott Williams & Wilkins (2003). As discussed therein, immediate and nonimmediate release can be defined kinetically by reference to the following equation:

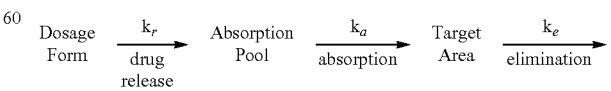

The "absorption pool" represents a solution of the drug administered at a particular absorption site, and $k_r$, $k_a$ and $k_e$ are first-order rate constants for (1) release of the drug from the formulation, (2) absorption, and (3) elimination, respectively. For immediate release dosage forms, the rate constant for drug release $k_r$ is far greater than the absorption rate constant $k_a$. For controlled release formulations, the opposite is true, i.e., $k_r<<k_a$, such that the rate of release of drug from the dosage form is the rate-limiting step in the delivery of the drug to the target area.

The terms "sustained release" and "extended release" are used in their conventional sense to refer to a drug formulation that provides for gradual release of a drug over an extended period of time, for example, 12 hours or more, and that preferably, although not necessarily, results in substantially constant blood levels of a drug over an extended time period.

As used herein, the term "delayed release" refers to a pharmaceutical preparation that passes through the stomach intact and dissolves in the small intestine.

The phrase "therapeutically effective" is intended to qualify the amount of active ingredients used in the treatment of a disease or disorder. This amount will achieve the goal of reducing or eliminating the said disease or disorder.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

When the following abbreviations and acronyms are used throughout the disclosure, they have the following meanings: $CDCl_3$, chloroform-d; $CH_2Cl_2$, methylene chloride; $CH_3CN$, acetonitrile; DIPEA, N,N-diisopropylethylamine; DMAP, 4-dimethylaminopyridine; DMF, N,N-dimethylformamide; DMSO, dimethylsulfoxide; Et, ethyl; $Et_3N$, triethylamine; EtOAc (or AcOEt), ethyl acetate; EtOH, ethanol; h, hour; HCl, hydrochloric acid; $^1H$ NMR, proton nuclear magnetic resonance; $H_2SO_4$, sulfuric acid; HPLC, high performance liquid chromatography; $K_2CO_3$, potassium carbonate; KOH, potassium hydroxide; LC-MS, liquid chromatography-mass spectroscopy; Me, methyl; MeOH, methanol; min, minute; MS ESI, mass spectroscopy with electrospray ionization; MsOH, methanesulfonic acid; NaH, sodium hydride; $NaHCO_3$, sodium bicarbonate; NaOH, sodium hydroxide; $Na_2SO_4$, sodium sulfate; NBS, N-bromosuccinimide; NCS, N-chlorosuccinimide; $NH_3$, ammonia; NIS, N-iodosuccinimide; Pd/C, palladium on carbon; $Pd(PPh_3)_4$, tetrakis(triphenylphosphine)palladium(0); $R_f$, retention factor; TBAF, tetrabutylammonium fluoride; TBAI, tetrabutylammonium iodide; TBDMS, t-butyldimethylsilyl; $Tf_2O$, trifluoromethanesulfonic anhydride; TFA, trifluoroacetic acid; THF, tetrahydrofuran; TLC, thin layer chromatography; TMS, trimethylsilyl; TMSCN, trimethylsilyl cyanide; TsOH, toluenesulfonic acid.

Methods and Compositions

It has been discovered that, unexpectedly, cellular kinase inhibition potentiates the effectiveness of conventional antiretroviral therapies (ART) for HIV/AIDS, leading to more efficient clearance of productively infected cells from the host. Thus, disclosed herein are methods for treating an individual infected with a retrovirus by administering to the individual a mixed lineage kinase (MLK) inhibitor and an antiretroviral drug. The administration of the antiretroviral drug and the MLK inhibitor can occur in any order, simultaneously, or they can be administered sequentially, wherein one is give before the other (e.g., 1 to 24 hours before, 1 to 7 days before, or 1 to 4 weeks before). Still further, disclosed herein is a regime wherein the antiretroviral drug is administered for a period of time, e.g., several weeks, without the MLK inhibitor and then the MLK inhibitor is administered along with the antiretroviral drug. In certain examples, the disclosed methods can additionally comprise the administration of a third therapeutic agent, as part of a therapeutic regimen. The compounds can be delivered in the same dosage form or separately, and further can be taken concurrently or one subsequent to the other.

If the antiretroviral drug and MKL inhibitor are administered simultaneously, they can be provided in a single, unified form, or in multiple forms (by way of example only, either as a single pill or as two separate pills). One of the compounds can be given in multiple doses, or both can be given as multiple doses. If not simultaneous, the timing between the multiple doses can be any duration of time ranging from a few minutes to four weeks.

Further disclosed herein are compositions (formulations) that comprise both MLK inhibitor(s) and antiretroviral drug(s).

MLK Inhibitors

As noted, the disclosed methods comprise, at least at some point during the treatment, the administration of an antiretroviral drug and a MLK inhibitor. "MLK inhibitor" is used herein to refer to a compound that exhibits an $IC_{50}$ with respect to an MLK activity of no more than about 100 µM and more typically not more than about 50 µM, as measured in the MLK3 assay described herein. "$IC_{50}$" is that concentration of inhibitor which reduces the activity and/or expression of an MLK enzyme (e.g., MLK3, LRRK2, DLK) to half-maximal level. Certain compounds disclosed herein have been discovered to exhibit inhibition against MLK. In certain embodiments, compounds will exhibit an $IC_{50}$ with respect to MLK3 of no more than about 10 µM; in further embodiments, compounds will exhibit an $IC_{50}$ with respect to MLK3 of no more than about 5 µM; in yet further embodiments, compounds will exhibit an $IC_{50}$ with respect to MLK3 of not more than about 1 µM; in yet further embodiments, compounds will exhibit an $IC_{50}$ with respect to MLK3 of not more than about 200 nM, as measured in the MLK3 assay described herein.

Examples of suitable MLK inhibitors that can be used in the disclosed methods include any one or more of the following compounds: CEP-1347 [3,9-bis[(ethylthio) methyl]-(8R*,9S*, 11S*)-(−)-9-hydroxy-9-methoxycarbonyl-8-methyl-2,3,9,10-tetrahydro-8,11-epoxy-1H,8H, 11H-2,7b,11a-triazadibenzo(a,g)cycloocta(cde)trinden-1-one] and CEP-11004 [3,9-bis-[(isopropylthio)methyl]-(8R*,9S*, 11S*)-(−)-9-hydroxy-9-methoxycarbonyl-8-methyl-2,3,9, 10-tetrahydro-8,11-epoxy-1H,8H, 11H-2,7b,11a-triazadibenzo(a,g)cycloocta(cde)trinden-1-one].

In further examples, the MLK inhibitor can be a compound of Formula X:

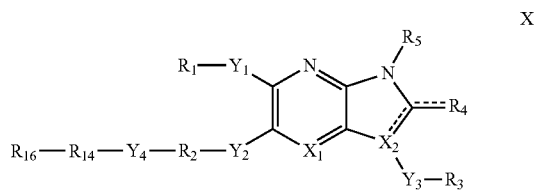

wherein:
dashed lines indicate that a second bond may alternatively be present or absent, and are absent when $X_2$ is N;
$X_1$ is chosen from CH and N;
$X_2$ is chosen from $CR_{13}$ and N;

$Y_1$ is —$(CR_{6a}R_{6b})_m$—$Z_1$—$(CR_{7a}R_{7b})_n$—;
$Y_2$ is —$(CR_{8a}R_{8b})_p$—$Z_2$—$(CR_{9a}R_{9b})_q$—;
$Y_3$ is —$(CR_{10a}R_{10b})_r$—$Z_3$—$(CR_{11a}R_{11b})_s$—;
$Y_4$ is —$(CH_2)_t$—$Z_4$—;

$Z_1$, $Z_2$, and $Z_3$, are each independently chosen from a bond, O, S, S(O), S(O)$_2$, N(R$_{12}$), C(O), C(O)N(R$_{12}$), N(R$_{12}$)C(O), S(O)$_2$N(R$_{12}$), and N(R$_{12}$)S(O)$_2$;

$Z_4$ is chosen from a bond, O, and N;

m, n, p, q, r, and s are each independently an integer from 0 to 6;

t is an integer from 0 to 2;

$R_1$, $R_2$, and $R_3$ are independently chosen from hydrogen, halo, lower alkyl, lower alkenyl, lower alkynyl, lower haloalkyl, lower cycloalkyl, heterocycloalkyl, aryl, heteroaryl, acyl, amido, amino, alkoxy, hydroxy, cyano, and nitro, any of which can be optionally substituted; or $R_1$ and $R_2$ can each additionally be heteroalkyl, and may be joined together such that $R_1$ and $R_2$ together form an alkylene, alkenylene, or heteroalkyl bridge comprising from 3 to 5 atoms, which can be optionally substituted;

$R_4$ is chosen from hydrogen, (O), (S), halogen, hydroxy, cyano, nitro, lower alkyl, lower alkenyl, lower alkynyl, lower cycloalkyl, lower cycloalkyloxy, lower thioalkoxy, lower heterocycloalkyl, aryl, lower aralkyl, lower heteroaryl, lower heteroaralkyl, amido, acyl, amino, and lower alkoxy, any of which can be optionally substituted; or $R_3$ and $R_4$ can each additionally be heteroalkyl, and can be joined together such that $R_1$ and $R_2$ together form an alkylene, alkenylene, or heteroalkyl bridge comprising from 3 to 5 atoms, which can be optionally substituted;

$R_5$ and $R_{13}$ are each independently chosen from hydrogen, halogen, hydroxy, cyano, nitro, lower alkyl, lower alkene, lower alkyne, lower aryl, lower arylalkyl, lower cycloalkyl, lower cycloalkylalkyl, lower heteroaryl, lower heteroarylalkyl, lower heterocycloalkyl, lower heterocycloalkylalkyl, and lower alkoxy, any of which can be optionally substituted; and additionally, $R_{13}$ and $R_3$ can be joined together to form a lower spiro-cycloalkyl or spiro-phenyl comprising from 3 to 6 atoms, which can be optionally substituted; and if $X_2$ is N, then $R_{13}$ is absent;

$R_{6a}$, $R_{6b}$, $R_{7a}$, $R_{7b}$, $R_{8a}$, $R_{8b}$, $R_{9a}$, $R_{9b}$, $R_{10a}$, $R_{10b}$, $R_{11a}$, $R_{11b}$, and $R_{12}$ are each independently chosen from a bond, hydrogen, halogen, hydroxy, $C_1$-$C_3$ alkoxy and $C_1$-$C_3$ alkyl;

$R_{14}$ is chosen from null, lower cycloalkyl, lower heterocycloalkyl, phenyl, and lower heteroaryl, any of which may be optionally substituted; and $R_{16}$ is chosen from lower alkyl, carboxyl, carbonyl, alkoxyethanone, carbamate, sulfonyl, heteroaryl, heteroarylalkyl, aryl, and arylalkyl.

When, for example, $Y_1$ is —$(CR_{6a}R_{6b})_m$—$Z_1$—$(CR_{7a}R_{7b})_n$—, and m and n are both 0, and $Z_1$ is a bond, then $Y_1$ collapses to a direct bond linking the parent ring system with $R_1$. This applies to all similar constructions used herein, including $Y_2$ and $Y_3$. Also, when for example $Y_1$ is —$(CR_{6a}R_{6b})_m$—$Z_1$—$(CR_{7a}R_{7b})_n$—, the rightmost portion of $Y_1$ attaches to the parent molecule.

In certain examples, $Y_1$, $Y_2$, $Y_3$, and $Y_4$ are no more than 6 atoms in length. In certain embodiments, $R_4$ is chosen from hydrogen, (O), and (S). In certain examples, $R_4$ is (O), the second bond linking $R_4$ and the fused bicyclic core is present, and the second bond in the five-membered portion of the fused bicyclic core is absent. In certain examples, $R_4$ is hydrogen, the second bond linking $R_4$ and the fused bicyclic core is absent, and the second bond in the five-membered portion of the fused bicyclic core is present.

In certain examples, $R_4$ is chosen from hydrogen, halogen, lower alkyl, and deuterium. In certain examples, $X_1$ is CH; and $X_2$ is C. In certain examples, $X_1$ is N; and $X_2$ is N. In certain examples, $X_1$ is CH; and $X_2$ is N. In certain examples, $X_1$ is N; and $X_2$ is C. In certain examples, m and n are both 0; $Z_1$ is a bond; and $R_1$ and $R_5$ are both hydrogen. In certain examples, p and r are each independently an integer from 0 to 3; q and s are each 0; and $Z_2$ and $Z_3$ are each independently chosen from a bond and O. In certain examples, $R_{6a}$, $R_{6b}$, $R_{7a}$, $R_{7b}$, $R_{8a}$, $R_{8b}$, $R_{9a}$, $R_{9b}$, $R_{10a}$, $R_{10b}$, $R_{11a}$, $R_{11b}$, and $R_{12}$ are all hydrogen.

In certain examples, compounds have structural Formula XI

XI wherein:
dashed lines indicate that a second bond may alternatively be present or absent;
$X_1$ is chosen from CH and N;
$X_2$ is chosen from C and N;
$Y_1$, $Y_2$, and $Y_3$ are independently chosen from a bond, lower alkyl, lower carboxyl, and lower heteroalkyl;
$Y_4$ is chosen from —$(CH_2)_m$, C(O), —$(CH_2)_mO$—, and —$(CH_2)_mN$—;
m is an integer from 0 to 2;
$R_1$, $R_2$, and $R_3$ are independently chosen from lower alkyl, lower alkenyl, lower alkynyl, lower haloalkyl, lower cycloalkyl, heterocycloalkyl, aryl, heteroaryl, acyl, amido, amino, alkoxy, hydroxy, cyano, and nitro, any of which can be optionally substituted; or $R_1$ and $R_2$ may each additionally be heteroalkyl, and can be joined together such that $R_1$ and $R_2$ together form an alkylene, alkenylene, or heteroalkyl bridge comprising from 3 to 5 atoms, which can be optionally substituted;
$R_4$ is chosen from hydrogen, (O), and (S);
$R_5$ is chosen from hydrogen, hydroxy, cyano, lower alkyl, lower cycloalkyl, and lower alkoxy, any of which can be optionally substituted;
$R_{13}$ is chosen from hydrogen, halogen, hydroxy, cyano, nitro, lower alkyl, lower cycloalkyl, lower cycloalkylalkyl, and lower alkoxy, any of which can be optionally substituted; and additionally, $R_{13}$ and $R_3$ can be joined together to form a lower spiro-cycloalkyl or spiro-phenyl comprising from 3 to 6 atoms, which can be optionally substituted; and
$R_{14}$ is chosen from null, lower cycloalkyl, lower heterocycloalkyl, phenyl, and lower heteroaryl, any of which can be optionally substituted.

In certain examples, compounds have structural Formula XII

XII wherein:
dashed lines indicate that a second bond may alternatively be present or absent;
$X_1$ and $X_2$ are independently chosen from CH and N;
$Y_3$ is chosen from a bond, lower alkyl, lower carboxyl, and lower heteroalkyl;
$Y_4$ is chosen from O, S, C(O), SO, $SO_2$, NH, $N(CH_3)$, $CH_2$, CHF, $CF_2$, $CH(CH_3)$, $C(CH_3)_2$, $CH_2O$—, and —$CH_2N$—; —$(CH_2)_m$—, —$(CH_2)_mO$—, and —$(CH_2)_mN$—;
m is an integer from 0 to 1;
$R_2$ is chosen from phenyl and 6-membered monocyclic heteroaryl, either of which is optionally substituted with one or more substituents chosen from deuterium, halogen, hydroxy, lower amino, lower amido, $C_1$-$C_3$ alkoxy, and $C_1$-$C_3$ alkyl;
$R_3$ is cycloalkyl, aryl, heteroaryl, bicyclic heteroaryl, any of which is optionally substituted with one or more substituents chosen from deuterium, halogen, hydroxy, lower amino, lower amido, lower carboxyl, $C_1$-$C_3$ alkoxy, $C_1$-$C_3$ alkyl, (O), (S), cyano, haloalkyl, phenyl, cycloalkyl, heteroaryl, and cycloheteroalkyl;
$R_4$ is chosen from hydrogen, $CH_3$, (O), and (S); and
$R_{14}$ is chosen from lower heteroalkyl, lower heterocycloalkyl, and lower heteroaryl, any of which is optionally substituted with one or more substituents chosen from deuterium, halogen, hydroxy, lower amino, lower amido, lower carboxyl, $C_1$-$C_3$ alkoxy, $C_1$-$C_3$ alkyl, (O), (S), haloalkyl, phenyl, benzyl, and lower cycloalkyl.

In certain examples, compounds wherein $X_1$ is N, $X_2$ is N, or both $X_1$ and $X_2$ are N. In further examples, $R_4$ is $CH_3$ In certain examples, compounds have a structural Formula chosen from Formula XII and Formula XIV:

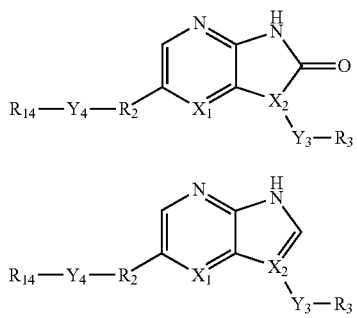

(XIII)

(XIV)

wherein:
$X_1$ and $X_2$ are independently chosen from CH and N;
$Y_3$ is chosen from a bond, lower alkyl, lower carboxyl, and lower heteroalkyl;
$Y_4$ is chosen from C(O), —$(CH_2)_m$—, —$(CH_2)_mO$—, and —$(CH_2)_mN$—;
m is an integer from 0 to 1;
$R_2$ and $R_3$ are independently chosen from lower cycloalkyl, lower heterocycloalkyl, lower aryl, and lower heteroaryl, any of which can be optionally substituted; and
$R_{14}$ is chosen from null, lower cycloalkyl, lower heterocycloalkyl, phenyl, and lower heteroaryl, any of which can be optionally substituted.

In certain examples, $R_2$ is phenyl optionally substituted with one or more substituents chosen from halogen, hydroxy, lower amino, lower amido, $C_1$-$C_3$ alkoxy, and $C_1$-$C_3$ alkyl. In certain examples, $Y_3$ is chosen from a bond or $CH_2$. In certain examples, $R_3$ is chosen from phenyl or 5/6-fused bicyclic heteroaryl, either of which is optionally substituted with one or more substituents chosen from halogen, hydroxy, cyano, lower amino, lower amido, lower phenylamido, lower phenylalkylamido, lower heterocycloalkyl, lowerheterocycloalkyl, loweralkylheterocycloalkyl, $C_1$-$C_3$ alkoxy, and $C_1$-$C_3$ alkyl.

In certain examples, $R_{14}$ is a monocyclic heterocycloalkyl optionally substituted with one or more substituents chosen from halogen, hydroxy, lower amino, lower amido, lower carboxyl, $C_1$-$C_3$ alkoxy, $C_1$-$C_3$ alkyl, (O), (S), haloalkyl, phenyl, benzyl, and lower cycloalkyl. In certain examples, $R_{14}$ is piperazinyl or morpholino, optionally substituted with one or more substituents chosen from halogen, hydroxy, lower amino, lower amido, lower carboxyl, $C_1$-$C_3$ alkoxy, $C_1$-$C_3$ alkyl, (O), (S), haloalkyl, phenyl, benzyl, and lower cycloalkyl.

In certain examples, $Y_4$ is chosen from O, S, C(O), NH, and $CH_2$,

In certain examples, compounds have a structural Formula chosen from Formula

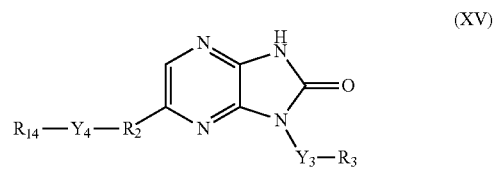

(XV)

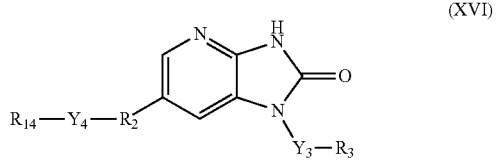

(XVI)

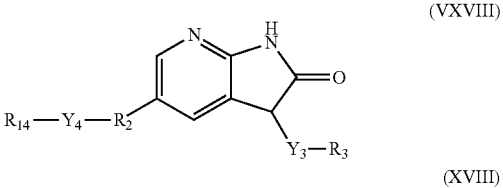

(VXVIII)

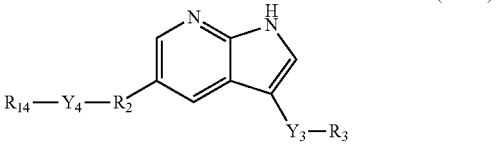

(XVIII)

wherein
$Y_3$ is chosen from a bond, lower alkyl, lower carboxyl, and lower heteroalkyl;
$Y_4$ is chosen from C(O), —$(CH_2)_m$—, —$(CH_2)_mO$—, and —$(CH_2)_mN$—;
m is an integer from 0 to 1;
$R_2$ is chosen from phenyl, 6-membered monocyclic heteroaryl, and 5/6-fused bicyclic heteroaryl, any of which may be optionally substituted;
$R_3$ is chosen from lower cycloalkyl, phenyl, and lower heteroaryl, any of which may be optionally substituted;
$R_{14}$ is chosen from null, lower cycloalkyl, lower heterocycloalkyl, phenyl, and lower heteroaryl, any of which may be optionally substituted.

In certain examples, $R_2$ and $R_3$ are each independently chosen from lower cycloalkyl, lower aryl, and monocyclic or bicyclic heteroaryl, any of which can be optionally substituted. In certain examples, $R_2$ is substituted with one or more substituents chosen from halogen, hydroxy, lower amino, $C_1$-$C_3$ alkoxy and $C_1$-$C_3$ alkyl. In further examples, $R_2$ is chosen from phenyl and lower heteroaryl, any of which can be optionally substituted. In further examples, $R_2$ is chosen from phenyl, 6-membered monocyclic heteroaryl, and 5/6-fused bicyclic heteroaryl, any of which may be optionally substituted.

In further examples, $R_2$ is chosen from phenyl, pyridinyl, pyrimidinyl, and indolyl, any of which can be optionally substituted. In further examples, $R_2$ is substituted with one or more substituents chosen from fluorine, hydroxy, $NH_2$, $NH(CH_3)$, $N(CH_3)_2$, methoxy, and methyl. In further examples, $R_2$ is optionally substituted phenyl.

In further examples, $R_2$ is chosen from

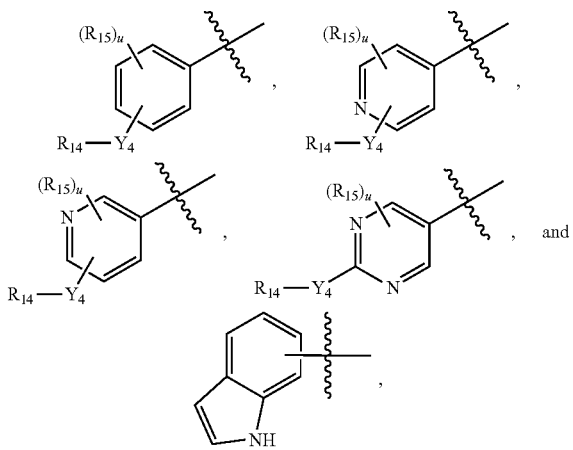

wherein
u is an integer from 0 to 3;
$Y_4$ is chosen from O, S, C(O), SO, $SO_2$, NH, $N(CH_3)$, $CH_2$, CHF, $CF_2$, $CH(CH_3)$, $C(CH_3)_2$, $CH_2O$—, and —$CH_2N$—; —$(CH_2)_m$—, —$(CH_2)_mO$—, and —$(CH_2)_m$N—;
m is an integer from 0 to 1;
$R_{14}$ is chosen from null, lower cycloalkyl, lower heterocycloalkyl, phenyl, and lower heteroaryl, any of which can be optionally substituted; and
each $R_{15}$ is independently chosen from halogen, hydroxy, $C_1$-$C_4$ alkyl, $C_2$-$C_4$ alkenyl, $C_2$-$C_4$ alkynyl, lower amino, lower amido, lower sulfonamido, and lower sulfonyl.

In certain examples, $R_{14}$ is chosen from piperazinyl, morpholinyl, pyrrolyl, and $N(CH_3)_2$.

In certain examples, each $R_{15}$ is independently chosen from $R_{15}$ is independently chosen from fluorine, hydroxy, $NH_2$, $NH(CH_3)$, $N(CH_3)_2$, $NS(O)_2CH_3$, methoxy, and methyl.

In certain examples, $Y_4$ is —$(CH_2)_m$—; m is 0; $R_{14}$ is null; u is an integer from 0 to 3; and $R_{15}$ is independently chosen from $R_{15}$ is independently chosen from fluorine, hydroxy, $NH_2$, $NH(CH_3)$, $N(CH_3)_2$, $NS(O)_2CH_3$, methoxy, and methyl. In certain examples, $Y_4$ is chosen from C(O), O, N, and —$CH_2$—. In certain examples, $Y_4$ is —$CH_2$—. In certain examples, $Y_3$ is chosen from a bond and lower alkyl. In certain examples, $Y_3$ is chosen from a bond and methyl. In certain examples, $Y_3$ is a bond.

In certain examples, $R_3$ is chosen from lower cycloalkyl, lower aryl, and monocyclic or bicyclic heteroaryl, any of which can be optionally substituted. In certain examples, $R_3$ is substituted with one or more substituents chosen from halogen, hydroxy, lower amino, lower amido, lower phenylamido, lower phenylalkylamido, lower heterocycloalkyl, lowerheterocycloalkyl, loweralkylheterocycloalkyl, $C_1$-$C_3$ alkoxy and $C_1$-$C_3$ alkyl. In certain examples, $R_3$ is chosen from benzothiazolyl, pyrrolopyridinyl, indanyl, cyclopropyl, cyclopentyl, phenyl, pyridinyl, pyrimidinyl, and indolyl, any of which can be optionally substituted. In certain examples, $R_3$ is substituted with one or more substituents chosen from fluorine, chlorine, hydroxy, $NH_2$, $NH(CH_3)$, $N(CH_3)_2$, $C(O)NH_2$, $C(O)NHCH_3$, morpholino, piperazinyl, methylpiperazinyl, acetamido, methylacetamido, methylpropionamido, phenylacetamidomethylene, benzamidomethylene, phenylpropanamidomethylene, methoxy and methyl.

In certain examples are provided a compound of structural Formula XII

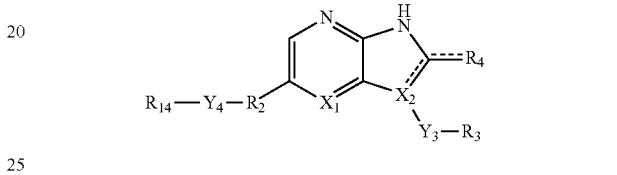

or a salt thereof, wherein:
dashed lines indicate that a second bond may alternatively be present or absent;
$X_1$ and $X_2$ are independently chosen from CH and N;
$Y_3$ is a bond;
$Y_4$ is chosen from O, S, C(O), SO, $SO_2$, NH, $N(CH_3)$, $CH_2$, CHF, $CF_2$, $CH(CH_3)$, $C(CH_3)_2$, $CH_2O$—, and —$CH_2N$—; —$(CH_2)_m$—, —$(CH_2)_mO$—, and —$(CH_2)_m$N—;
m is an integer from 0 to 1;
$R_2$ is chosen from phenyl and 6-membered monocyclic heteroaryl, either of which may be optionally substituted;
$R_3$ is optionally substituted bicyclic heteroaryl;
$R_4$ is chosen from hydrogen, $CH_3$, (O), and (S);
$R_{14}$ is optionally substituted monocyclic heterocycloalkyl.

In certain examples, $R_3$ is an optionally substituted 5/6-fused bicyclic heteroaryl.

In certain examples, wherein $Y_4$ is $CH_2$.

In certain examples, $R_{14}$ is optionally substituted piperazinyl.

In certain examples, $R_2$ is chosen from hydrogen, halo, hydroxy, $C_1$-$C_4$ alkyl, $C_3$-$C_{10}$ cycloalkyl, $C_1$-$C_4$ alkyloxy, $C_3$-$C_{10}$ cycloalkyloxy, aryl, cyano or nitro.

In certain examples, $R_1$ and $R_2$ together form a butadienylene bridge.

In certain examples, m and n are both 0; $Z_1$ is a bond; $R_1$, $R_5$, and $R_4$ are hydrogen; and $R_2$ and $R_3$ are each independently chosen from aryl and heteroaryl, either of which may be optionally substituted.

In certain examples, m and n are both 0; $Z_1$ is a bond; $R_1$, $R_5$, and $R_4$ are hydrogen; $R_2$ is selected from the group consisting of aryl and heteroaryl, either of which may be optionally substituted; and $R_3$ is chosen from 5-substituted-1H-indole, 5-substituted pyridine-2-amine, and 5-substituted pyrimidine-2-amine.

In certain examples, m is 0 or 1; n is 0; $Z_1$ is a bond; $R_1$, $R_5$, and $R_4$ are hydrogen; and $R_1$ is chosen from 5-substituted-1H-indole, 5-substituted pyridine-2-amine, and 5-substituted pyrimidine-2-amine; and $R_2$ is chosen from 5-substituted-1,2,3-trimethoxybenzene, 4-substituted-1,2- dimethoxyphenyl, 5-substituted pyridine-2-amine, and 5-substituted pyrimidine-2-amine.

In certain examples, $R_1$, $R_5$, and $R_4$ are hydrogen; and $R_2$ and $R_3$ are each independently chosen from aryl and heteroaryl, either of which can be optionally substituted.

In certain examples of Formula XII, m and n are both 0; $Z_1$ is a bond; $R_1$, $R_5$, and $R_4$ are hydrogen, $R_2$ is chosen from aryl and heteroaryl, either of which can be optionally substituted; and $R_3$ is chosen from 5-substituted-1H-indole, 5-substituted pyridine-2-amine, and 5-substituted pyrimidine-2-amine, any of which can be optionally substituted.

In certain examples of Formula XII, m and n are both 0; $Z_1$ is a bond; $R_1$, $R_5$, and $R_4$ represent hydrogen, $R_3$ is chosen from 5-substituted-1H-indole, 5-substituted pyridine-2-amine, and 5-substituted pyrimidine-2-amine; and $R_2$ is chosen from 5-substituted-1,2,3-trimethoxybenzene, 4-substituted-1,2-dimethoxybenzene, 5-substituted pyridine-2-amine, and 5-substituted pyrimidine-2-amine.

In certain examples, $R_4$ is (O), the second bond linking $R_4$ and the fused bicyclic core is present, and the second bond in the five-membered portion of the fused bicyclic core is absent; m and n are both 0; $Z_1$ is a bond; $R_1$ and $R_5$ are each hydrogen; and $R_2$ and $R_3$ are each independently chosen from aryl and heteroaryl, either of which can be optionally substituted.

In certain examples, $R_4$ is (O), the second bond linking $R_4$ and the fused bicyclic core is present, and the second bond in the five-membered portion of the fused bicyclic core is absent; m and n are both 0; $Z_1$ is a bond; $R_1$ and $R_5$ are each hydrogen; $R_2$ is chosen from aryl and heteroaryl, either of which can be optionally substituted; and $R_3$ is chosen from 5-substituted-1H-indole, 5-substituted pyridine-2-amine, and 5-substituted pyrimidine-2-amine.

In certain examples, $R_4$ is (O), the second bond linking $R_4$ and the fused bicyclic core is present, and the second bond in the five-membered portion of the fused bicyclic core is absent; m and n are both 0; $Z_1$ is a bond; $R_1$ and $R_5$ are each hydrogen; $R_3$ is chosen from 5-substituted-1H-indole, 5-substituted pyridine-2-amine, or 5-substituted pyrimidine-2-amine; and $R_2$ is chosen from 5-substituted-1,2,3-trimethoxybenzene, 4-substituted-1,2-dimethoxybenzene, 5-substituted pyridine-2-amine, and 5-substituted pyrimidine-2-amine.

In certain examples, optionally substituted groups are substituted with one or more substituent chosen from halogen, hydroxy, $C_1$-$C_3$ alkoxy and $C_1$-$C_3$ alkyl.

In certain examples, $R_4$ is mono- or poly-substituted with fluorine.

In certain examples, $R_5$ is mono- or poly-substituted with fluorine.

In certain examples, compounds have structural Formula XIX:

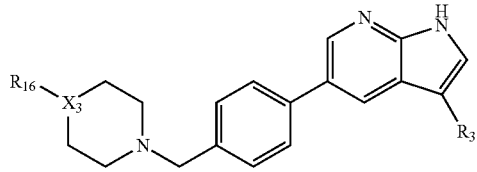

(XIX)

wherein
$X_3$ is chosen from C, N, and O;
$R_3$ is chosen from lower cycloalkyl, phenyl, and lower heteroaryl, any of which is optionally substituted with one or more substituents chosen from halogen, hydroxy, lower amino, lower amido, lower carboxyl, $C_1$-$C_3$ alkoxy, $C_1$-$C_3$ alkyl, (O), (S), cyano, haloalkyl, phenyl, cycloalkyl, heteroaryl, and cycloheteroalkyl;
$R_{16}$ is chosen from lower alkyl, lower carboxyl, carbonyl, alkoxyethanone, carbamate, sulfonyl, heteroaryl, heteroarylalkyl, aryl, arylalkyl, and heterocycloalkylcarbonyl, any of which may be optionally substituted, and when $X_3$ is O, $R_{16}$ is null, and wherein the compound of Formula XIX is optionally substituted at a carbon atom with one or more substituents chosen from deuterium, halogen, lower alkyl, lower haloalkyl, and lower haloalkoxy.

In certain examples, the compound of Formula XIX is optionally substituted at a carbon atom with one or more substituents chosen from deuterium, halogen, lower alkyl, lower haloalkyl, and lower haloalkoxy.

In certain examples, the compound of Formula XIX is optionally substituted at a carbon atom with one or more substituents chosen from deuterium, halogen, and lower alkyl.

In certain examples, the compound of Formula XIX is substituted at a carbon atom with one or more substituents chosen from deuterium, fluorine, and methyl.

In certain examples, $X_3$ is N.

In certain examples, $R_3$ is chosen from benzothiazolyl, pyrrolopyridinyl, indanyl, cyclopropyl, cyclopentyl, phenyl, pyridinyl, pyrimidinyl, and indolyl, any of which is optionally substituted with one or more substituents chosen from fluorine, chlorine, hydroxy, $NH_2$, $NH(CH_3)$, $N(CH_3)_2$, $C(O)NH_2$, $C(O)NHCH_3$, morpholino, piperazinyl, methylpiperazinyl, acetamido, methylacetamido, methylpropionamido, phenylacetamidomethylene, benzamidomethylene, phenylpropanamidomethylene, methoxy, and methyl. In certain examples, $R_3$ is phenyl optionally substituted with one or more substituents chosen from hydroxyl, lower alkyl, lower alkoxy, lower haloalkyl, lowerhaloalkoxy, halogen, lower amino, lower carboxyl, and cyano. In certain examples, $R_3$ is heteroaryl. In certain examples, $R_3$ is optionally substituted bicyclic heteroaryl. In certain examples, $R_3$ is chosen from indanyl, indolyl, indazolyl, indolinonyl, benzothiophenyl, quinolinyl, isoquinolinyl, pyrrolopyrazinyl, and pyrrolopyridinyl, any of which is optionally substituted with one or more substituents chosen from hydroxy, lower alkyl, lower alkoxy, lower haloalkyl, lowerhaloalkoxy, halogen, lower amino, and lower carboxyl. In certain examples, $R_3$ is optionally substituted at a carbon atom with one or more substituents chosen from deuterium, halogen, and lower alkyl. In certain embodiments, $R_3$ is indanyl optionally substituted at a carbon atom with one or more substituents chosen from deuterium, halogen, and lower alkyl.

In certain examples, $R_{16}$ is lower alkyl.

In certain examples $R_2$, $R_3$, or $R_{14}$ is substituted with deuterium, fluorine, or methyl.

In certain examples $X_3$ is N. In certain embodiments $X_3$ is N and $R_{16}$ is $CH_3$.

In certain examples, the compound of Formula XIX is substituted at a carbon atom on the pyrrolopyridinyl core with one or more substituents chosen from deuterium, fluorine, and methyl.

In certain examples, the compound of Formula XIX is substituted at the 2-position on the pyrrolopyridinyl core with one or more substituents chosen from deuterium, fluorine, and methyl.

In certain examples $R_3$ is indanyl or phenyl optionally substituted with with one or more substituents chosen from hydroxy, lower alkyl, lower alkoxy, lower haloalkyl, lowerhaloalkoxy, halogen, lower amino, and lower carboxyl.

In certain examples, the compounds have Structural Formula XX, wherein:

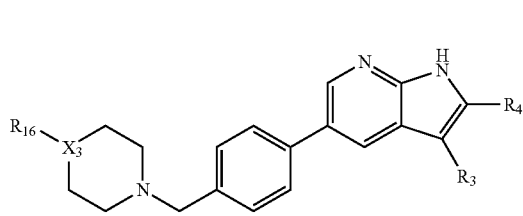

XX $X_3$ is chosen from C, N, and O;

$R_3$ is chosen from lower cycloalkyl, phenyl, and lower heteroaryl, any of which may be optionally substituted;

$R_4$ is chosen from hydrogen, halogen, lower alkyl, and deuterium; and $R_{16}$ is chosen from lower alkyl, carboxyl, carbonyl, alkoxyethanone, carbamate, sulfonyl, heteroaryl, heteroarylalkyl, aryl, arylalkyl, and heterocycloalkylcarbonyl, any of which may be optionally substituted, and when $X_3$ is O, $R_{16}$ is null.

In certain examples, the disclosed compositions and methods can use as a MLK inhibitor any compound chosen from Examples 1 to 279 (i.e., Compounds A through JD). In certain examples, the disclosed methods can comprise administration of a MLK3-inhibitor and an antiretroviral drug to an individual. In certain examples, the disclosed methods can comprise administration of a DLK-inhibitor and an antiretroviral drug to an individual. In certain examples, the disclosed methods can comprise administration of a compound of Formula X and an antiretroviral drug to an individual. In certain examples, the disclosed methods can comprise administration of any one or more of compounds A through JD and an antiretroviral drug to an individual.

Anti-Retroviral Drugs

The disclosed methods comprise the administration of an antiretroviral drug along and a MLK inhibitor to an individual. The antiretroviral drug can be effective against or specific to lentiviruses. Lentiviruses include, without limitation, human immunodeficiency virus (HIV) (e.g., HIV-1, HIV-2), bovine immunodeficiency virus (BIV), feline immunodeficiency virus (FIV), simian immunodeficiency virus (SIV), and equine infectious anemia virus (EIA). In a particular embodiment, the antiretroviral drug is an anti-HIV agent.

The antiretroviral drug can comprises one or more of an entry inhibitor, CCR5 receptor antagonist, nucleoside reverse transcriptase inhibitor, a non-nucleoside reverse transcriptase inhibitor, an integrase inhibitor, and a maturation inhibitor. Examples of these include, without limitation:

Nucleoside-analog reverse transcriptase inhibitors (NRTIs). NRTIs refer to nucleosides and nucleotides and analogues thereof that inhibit the activity of HIV-1 reverse transcriptase. An example of nucleoside-analog reverse transcriptase inhibitors is, without limitation, adefovir dipivoxil.

Non-nucleoside reverse transcriptase inhibitors (NNRTIs). NNRTIs are allosteric inhibitors which bind reversibly at a nonsubstrate-binding site on the HIV reverse transcriptase, thereby altering the shape of the active site or blocking polymerase activity. Examples of NNRTIs include, without limitation, delavirdine (BHAP, U-90152; RESCRIPTOR™), efavirenz (DMP-266, SUSTIVA™), nevirapine (VIRAMUNE™), PNU-142721, capravirine (S-1153, AG-1549), emivirine (+)-calanolide A (NSC-675451) and B, etravirine (TMC-125), rilpivi ne (T C278, EDURANT™), DAPY (TMC120), BILR-355 BS, PHI-236, and PHI-443 (TMC-278).

Protease inhibitors (PI). Protease inhibitors are inhibitors of the HIV-1 protease. Examples of protease inhibitors include, without limitation, darunavir, amprenavir (141W94, AGENERASE™), tipranivir (PNU-140690, APIVUS™), indinavir (MK-639; CRIXIVAN™), saquinavir (INVIRASE™, FORTOVASE™), fosamprenavir (LEXIVA™), lopinavir (ABT-378), ritonavir (ABT-538, NORVIR™), atazanavir (REYATAZ™), nelfinavir (AG-1343, VIRACEPT™), lasinavir (BMS-234475/CGP-61755), BMS-2322623, GW-640385X (VX-385), AG-001859, and SM-309515.

Fusion inhibitors (FI). Fusion inhibitors are compounds, such as peptides, which act by binding to HIV envelope protein and blocking the structural changes necessary for the virus to fuse with the host cell. Examples of fusion inhibitors include, without limitation, maraviroc (SELZENTRY™, Celsentri), enfuvirtide (INN, FUZEON™), T-20 (DP-178, FUZEON™) and T-1249.

Integrase inhibitors. Integrase inhibitors are a class of antiretroviral drug designed to block the action of integrase, a viral enzyme that inserts the viral genome into the DNA of the host cell. Examples of integrase inhibitors include, without limitation, raltegravir, elvitegravir, and MK-2048.

Antiretroviral drugs also include HIV vaccines such as, without limitation, ALVAC™ HIV (vCP1521), AIDS-VAX™ B/E (gp120), and combinations thereof. Anti-HIV compounds also include HIV antibodies (e.g., antibodies against gp120 or gp41), particularly broadly neutralizing antibodies.

In a particular embodiment, the antiretroviral drug used herein is a protease inhibitor, NNRTI, or NRTI. In a particular embodiment, the anti-HIV agent is selected from the group consisting of indinavir, ritonavir, atazanavir, and efavirenz. More than one anti-HIV agent may be used, particularly where the agents have different mechanisms of action (as outlined above). In a particular embodiment, the anti-HIV therapy is highly active antiretroviral therapy (HAART).

Specific examples of suitable antiretroviral drugs that can be used in the disclosed compositions and methods include one or more of the following antiretroviral compounds: lamivudine, ziduvudine, emtricitabine, abacavir, abacavir sulfate, zidovudine, tenofovir, didanosine, stavudine, delavirdine, efavirenz, nevirapine, etravirine, maraviroc, rilpivirine, and raltegravir.

In further examples, the antiretroviral drug can comprise a protease inhibitor. Further examples of suitable antiretroviral drug that can be used in the disclosed compositions and methods include one or more of the following antiretroviral compounds: atazanavir, efavirenz, indinavir, ritonavir, saquinavir, nelfinavir, amprenavir, lopinavir, fosamprenavir, tipranavir, darunavir, nelfinavir, brecanavir, boceprevir, TMC435, and declatasvir.

Salts and Prodrugs

The compounds disclosed herein, e.g., the MLK inhibitors and/or antiretroviral drugs can exist as therapeutically acceptable salts. Thus, contemplated herein are methods and compositions that have the compounds disclosed herein in the form of salts, including acid addition salts. Suitable salts include those formed with both organic and inorganic acids. Such acid addition salts will normally be pharmaceutically acceptable. However, salts of non-pharmaceutically acceptable salts can be of utility in the preparation and purification of the compound in question. Basic addition salts can also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

The term "prodrug" refers to a compound that is made more active in vivo. Certain compounds disclosed herein can also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they can be easier to administer than the compound, or parent drug. They can, for instance, be bioavailable by oral administration whereas the parent drug is not. The prodrug can also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

Prodrugs of any of the disclosed compounds include, but are not limited to, carboxylate esters, carbonate esters, hemi-esters, phosphorus esters, nitro esters, sulfate esters, sulfoxides, amides, carbamates, azo compounds, phosphamides, glycosides, ethers, acetals, and ketals. Prodrug esters and carbonates can be formed, for example, by reacting one or more hydroxyl groups of compounds of Formula X or Formula XI with alkyl, alkoxy or aryl substituted acylating reagents using methods known to those of skill in the art to produce methyl carbonates, acetates, benzoates, pivalates and the like. Illustrative examples of prodrug esters of the compounds provided herein include, but are not limited to, compounds of Formula X having a carboxyl moiety wherein the free hydrogen is replaced by $C_1$-$C_4$ alkyl, $C_1$-$C_7$ alkanoyloxymethyl, 1-(($C_1$-$C_5$)alkanoyloxy)ethyl, 1-methyl-1-(($C_1$-$C_5$)alkanoyloxy)-ethyl, $C_1$-$C_5$ alkoxycarbonyloxymethyl, 1-(($C_1$-$C_5$)alkoxycarbonyloxy)ethyl, 1-methyl-1-(($C_1$-$C_5$)alkoxycarbonyloxy)ethyl, N—(($C_1$-$C_5$)alkoxycarbonyl)aminomethyl, 1-(N—(($C_1$-$C_5$)alkoxycarbonyl)amino)ethyl, 3-phthalidyl, 4-crotonolactonyl, gamma-butyrolacton-4-yl, di-N,N—($C_1$-$C_2$)alkylamino ($C_2$-$C_3$)alkyl (e.g., beta-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl. Oligopeptide modifications and biodegradable polymer derivatives (as described, for example, in Int. *J. Pharm.* 115, 61-67, 1995) are within the scope of the present disclosure. Methods for selecting and preparing suitable prodrugs are provided, for example, in the following: T. Higuchi and V. Stella, "Prodrugs as Novel Delivery Systems," Vol. 14, ACS Symposium Series, 1975; H. Bundgaard, *Design of Prodrugs*, Elsevier, 1985; and *Bioreversible Carriers in Drug Design*, ed. Edward Roche, American Pharmaceutical Association and Pergamon Press, 1987.

Formulations

While it can be possible for compounds to be administered as the neat compound, it is also possible to present them as a pharmaceutical formulation. Accordingly, provided herein are pharmaceutical formulations which comprise one or more of the disclosed compounds (i.e., the MLK inhibitors and/or antiretrovirals disclosed herein), or one or more pharmaceutically acceptable salts, esters, prodrugs, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients can be used as suitable and as understood in the art; e.g., in *Remington: The Science and Practice of Pharmacy*, 21$^{st}$ Ed., Gennaro, Ed., Lippencott Williams & Wilkins (2003). The pharmaceutical compositions disclosed herein can be manufactured in any manner known in the art, e.g., by means of conventional mixing, dissolving, granulating, dragee-making, levigating, emulsifying, encapsulating, entrapping or compression processes.

A compound as provided herein can be incorporated into a variety of formulations for therapeutic administration, including solid, semi-solid, liquid or gaseous forms. The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route can depend upon for example the condition and disorder of the recipient. The formulations can conveniently be presented in unit dosage form and can be prepared by any of the methods well known in the art of pharmacy. Typically, these methods include the step of bringing into association a compound or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration can be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient can also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets can be made by compression or molding, optionally with one or more accessory ingredients. Compressed tablets can be prepared by compressing in a suitable machine the active ingredient in a free-flowing form such as a powder or granules, optionally mixed with binders, inert diluents, or lubricating, surface active or dispersing agents. Molded tablets can be made by molding in a suitable machine a mixture of the powdered compound moistened with an inert liquid diluent. The tablets can optionally be coated or scored and can be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses. Also provided are oral formulations in the form of powders and granules containing one or more compounds disclosed herein.

The compounds can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. The formulations can be presented in unit-dose or multi-dose containers, for example sealed ampoules and vials, and can be stored in powder form or in a freeze-dried (lyophilized) condition requiring only the addition of the sterile liquid carrier, for example, saline or sterile pyrogen-free water, immediately prior to use. Extemporaneous injection solutions and suspensions can be prepared from sterile powders, granules and tablets of the kind previously described.

Formulations for parenteral administration include aqueous and non-aqueous (oily) sterile injection solutions of the active compounds which can contain antioxidants, buffers, bacteriostats and solutes which render the formulation isotonic with the blood of the intended recipient; and aqueous and non-aqueous sterile suspensions which can include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions can take the form of tablets, lozenges, pastilles, or gels formulated in conventional manner. Such compositions can comprise the active ingredient in a flavored basis such as sucrose and *acacia* or tragacanth.

The compounds can also be formulated in rectal compositions such as suppositories or retention enemas, e.g., containing conventional suppository bases such as cocoa butter, polyethylene glycol, or other glycerides.

Certain compounds disclosed herein can be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration can comprise, for example, from 0.001% to 10% w/w (by weight) of the formulation. In certain embodiments, the active ingredient can comprise as much as 10% w/w. In other embodiments, it can comprise less than 5% w/w. In certain embodiments, the active ingredient can comprise from 2% w/w to 5% w/w. In other embodiments, it can comprise from 0.1% to 1% w/w of the formulation.

For administration by inhalation, compounds can be conveniently delivered from an insufflator, nebulizer pressurized packs or other convenient means of delivering an aerosol spray. Pressurized packs can comprise a suitable propellant such as dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Alternatively, for administration by inhalation or insufflation, the compounds can take the form of a dry powder composition, for example a powder mix of the compound and a suitable powder base such as lactose or starch. The powder composition can be presented in unit dosage form, in for example, capsules, cartridges, gelatin or blister packs from which the powder can be administered with the aid of an inhalator or insufflator.

In one example, a compound is prepared for delivery in a sustained-release, controlled release, extended-release, timed-release or delayed-release formulation, for example, in semipermeable matrices of solid hydrophobic polymers containing the therapeutic agent. Various types of sustained-release materials have been established and are well known by those skilled in the art. Current extended-release formulations include film-coated tablets, multiparticulate or pellet systems, matrix technologies using hydrophilic or lipophilic materials and wax-based tablets with pore-forming excipients (see, for example, Huang, et al. *Drug Dev. Ind. Pharm.* 29:79 (2003); Pearnchob, et al. *Drug Dev. Ind. Pharm.* 29:925 (2003); Maggi, et al. *Eur. J. Pharm. Biopharm.* 55:99 (2003); Khanvilkar, et al., *Drug Dev. Ind. Pharm.* 228:601 (2002); and Schmidt, et al., *Int. J. Pharm.* 216:9 (2001)). Sustained-release delivery systems can, depending on their design, release the compounds over the course of hours or days, for instance, over 4, 6, 8, 10, 12, 16, 20, 24 hours or more. Usually, sustained release formulations can be prepared using naturally-occurring or synthetic polymers, for instance, polymeric vinyl pyrrolidones, such as polyvinyl pyrrolidone (PVP); carboxyvinyl hydrophilic polymers; hydrophobic and/or hydrophilic hydrocolloids, such as methylcellulose, ethylcellulose, hydroxypropylcellulose, and hydroxypropylmethylcellulose; and carboxypolymethylene.

The sustained or extended-release formulations can also be prepared using natural ingredients, such as minerals, including titanium dioxide, silicon dioxide, zinc oxide, and clay (see, U.S. Pat. No. 6,638,521, herein incorporated by reference). Exemplified extended release formulations that can be used in delivering a compound include those described in U.S. Pat. Nos. 6,635,680; 6,624,200; 6,613,361; 6,613,358, 6,596,308; 6,589,563; 6,562,375; 6,548,084; 6,541,020; 6,537,579; 6,528,080 and 6,524,621, each of which is hereby incorporated herein by reference. Controlled release formulations of particular interest include those described in U.S. Pat. Nos. 6,607,751; 6,599,529; 6,569,463; 6,565,883; 6,482,440; 6,403,597; 6,319,919; 6,150,354; 6,080,736; 5,672,356; 5,472,704; 5,445,829; 5,312,817 and 5,296,483, each of which is hereby incorporated herein by reference. Those skilled in the art will readily recognize other applicable sustained release formulations.

Systemic administration can also be by transmucosal or transdermal means. For transmucosal or transdermal administration, penetrants appropriate to the barrier to be permeated are used in the formulation. For topical administration, the agents can be formulated into ointments, creams, salves, powders or gels. In one embodiment, the transdermal delivery agent can be DMSO. Transdermal delivery systems can include, e.g., patches. For transmucosal administration, penetrants appropriate to the barrier to be permeated are used in the formulation. Such penetrants are generally known in the art.

Exemplified transdermal delivery formulations that can find use with the compounds disclosed herein include those described in U.S. Pat. Nos. 6,589,549; 6,544,548; 6,517,864; 6,512,010; 6,465,006; 6,379,696; 6,312,717 and 6,310,177, each of which are hereby incorporated herein by reference.

The precise amount of compound administered to an individual will be the responsibility of the attendant physician. The specific dose level for any particular individual will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration can vary depending on the condition and its severity. The dosage can be increased or decreased over time, as required by an individual. An individual initially can be given a low dose, which is then increased to an efficacious dosage tolerable to the individual. Typically, a useful dosage for adults can be from 5 to 2000 mg, but have been known to range from 0.1 to 500 mg/kg per day. By way of example, a dose can range from 1 to 200 mg, when administered by oral route; or from 0.1 to 100 mg or, in certain embodiments, 1 to 30 mg, when administered by intravenous route; in each case administered, for example, from 1 to 4 times per day. When a compound is administered in combination with another therapeutic agent, a useful dosage of the combination partner can be from 20% to 100% of the normally recommended dose, since, as discussed below, even doses of a given drug which would be subtherapeutic if administered on its own can be therapeutic when used in combination with another agent.

Dosage amount and interval can be adjusted individually to provide plasma levels of the active compounds that are sufficient to maintain therapeutic effect. In certain examples, therapeutically effective serum levels will be achieved by administering single daily doses, but efficacious multiple daily dose schedules can be used as well. In cases of local administration or selective uptake, the effective local concentration of the drug can not be related to plasma concentration. The skilled praticioner will be able to optimize therapeutically effective local dosages without undue experimentation. Additionally, applicable methods for determining an appropriate dose and dosing schedule for administration of compounds such as those disclosed herein are described, for example, in *Goodman and Gilman's The Pharmacological Basis of Therapeutics*, 11$^{th}$ Ed., Brunton, Lazo and Parker, Eds., McGraw-Hill (2006), and in *Remington: The Science and Practice of Pharmacy*, 21$^{st}$ Ed., Gennaro, Ed., Lippencott Williams & Wilkins (2003), both of which are hereby incorporated herein by reference.

In certain instances, it can be appropriate to administer at least one of the compounds described herein (or a pharmaceutically acceptable salt, ester, or prodrug thereof) in combination with a third therapeutic agent. By way of example only, in a treatment for HIV, the individual may suffer with associated neurocognitive disease or dementia, so an increased therapeutic benefit can result by also providing the individual with another therapeutic agent for neurocognitive disease or dementia or inflammation.

Nanoparticles

In various examples of the disclosed methods, the antiretroviral drug and/or the MLK inhibitor can be formulated into a crystalline nanoparticle, wherein the nanoparticle comprises one or more surfactants. Examples of nanoparticles suitable for use herein are disclosed in WO2012/061480, which is incorporated by reference herein in its entirety for its teachings of nanoparticle formulations, as well as methods of making and using such nanoparticles.

The disclosed nanoparticles can, by following clathrin-dependent endocytosis, bypass lysosomal degradation by sorting from early endosomes to recycling endosome pathways. Particles are released intact and retained complete antiretroviral efficacy. The nanoparticles can preserve both particle integrity and antiretroviral activities, demonstrating the potent utility of this approach for targeted drug delivery. Indeed, the subcellular locale of the nanoparticles and their slow release underlie long-term antiretroviral efficacy. In addition, the data demonstrates that cells such as macrophages can act as drug transporters and, importantly, neither degrade nor modify drug-laden particles in transit. As such, the drug(s) are delivered unaltered to its intended target sites.

In one aspect, disclosed herein are nanoparticles that comprise an antiretroviral drug and/or an MLK inhibitor for the delivery of a combination antiretroviral therapy to a subject. The disclosed nanoparticles comprise at least one compound of interest and at least one surfactant. These components of the nanoparticle, along with other optional components, are described herein.

The nanoparticles suitable for use herein comprise at least one therapeutic agent, i.e., the antiretroviral drug and/or the MLK inhibitor. Thus, in one example, the nanoparticles comprise one or more antiretroviral drugs. In another example, the nanoparticles comprise one or more MLK inhibitors. In still another example, the nanoparticles comprise one or more antiretroviral drugs and one or more MLK inhibitors. The nanoparticles are generally crystalline (solids having the characteristics of crystals) nanoparticles of the therapeutic agent, wherein the nanoparticles typically comprise about 99% pure therapeutic agent. In a particular example, the nanoparticles are synthesized by adding the therapeutic agent(s), particularly the free base form of the therapeutic agent, to a surfactant (described herein) solution and then generating the nanoparticles by wet milling or high pressure homogenization. The therapeutic agent(s) and surfactant solution can be agitated prior to the wet milling or high pressure homogenization.

The therapeutic agent may be hydrophobic, a water insoluble compound, or a poorly water soluble compound. For example, the therapeutic agent may have a solubility of less than about 10 mg/mL, less than 1 mg/mL, more particularly less than about 100 g/mL, and more particularly less than about 25 g/mL in water or aqueous media in a pH range of from 0 to 14, particularly from pH 4 to 10, particularly at 20° C.

In a particular example, the resultant nanoparticle is up to 1 m in diameter. In further examples, the nanoparticle is from about 200 nm to about 500 nm in diameter, particularly from about 250 nm to about 350 nm in diameter. In a particular example, the nanoparticles are rod shaped, particularly elongated rods, rather than irregular or round shaped. The nanoparticles can be neutral or charged. The nanoparticles can be charged positively or negatively.

Surfactants

As stated hereinabove, the nanoparticles comprise at least one surfactant. A "surfactant" refers to a surface-active agent, including substances commonly referred to as wetting agents, detergents, dispersing agents, or emulsifying agents. Surfactants are usually organic compounds that are amphiphilic. In a particular example, the surfactant is an amphiphilic block copolymer. In another example, at least one surfactant of the nanoparticle is an amphiphilic block copolymer, particularly a copolymer comprising at least one block of poly (oxyethylene) and at least one block of poly (oxypropylene).

In a particular example, the surfactant is present in the nanoparticle and/or surfactant solution to synthesize the nanoparticle at a concentration ranging from about 0.0001% to about 5%. In a particular example, the concentration of the surfactant ranges from about 0.1% to about 2%. The surfactant can be charged or neutral. In a particular example, the surfactant is positively or negatively charged, particularly negatively charged.

In a particular example, the amphiphilic block copolymer is a copolymer comprising at least one block of poly (oxyethylene) and at least one block of poly (oxypropylene). Amphiphilic block copolymers are exemplified by the block copolymers having the formulas:

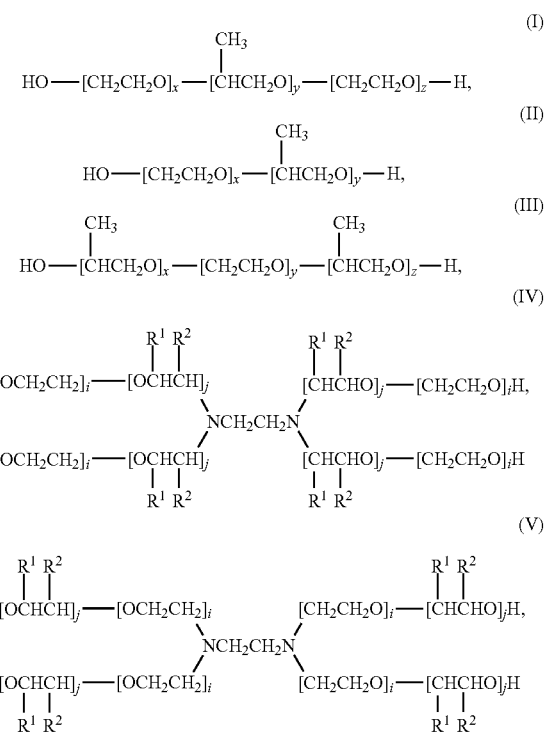

in which x, y, z, i, and j have values from about 2 to about 800, particularly from about 5 to about 200, more particularly from about 5 to about 80, and wherein for each $R^1$, $R^2$ pair, as shown in formula (IV) and (V), one is hydrogen and the other is a methyl group. The ordinarily skilled artisan will recognize that the values of x, y, and z will usually represent a statistical average and that the values of x and z are often, though not necessarily, the same. Formulas (I) through (III) are oversimplified in that, in practice, the orientation of the isopropylene radicals within the B block will be random. This random orientation is indicated in formulas (IV) and (V), which are more complete. A number of such compounds are commercially available under such generic trade names as "lipoloxamers," "PLURONICS™," "poloxamers," and "synperonics." PLURONIC™ copolymers within the B-A-B formula, as opposed to the A-B-A formula typical of PLURONICS™, are often referred to as "reversed" PLURONICS™, "PLURONIC™ R" or "meroxapol." Generally, block copolymers can be described in terms of having hydrophilic "A" and hydrophobic "B" block segments. Thus, for example, a copolymer of the formula A-B-A is a triblock copolymer consisting of a hydrophilic block connected to a hydrophobic block connected to another hydrophilic block. The "polyoxamine" polymer of formula (IV) is available from BASF under the tradename TETRONIC™. The order of the polyoxyethylene and polyoxypropylene blocks represented in formula (IV) can be reversed, creating TETRONIC R™, also available from BASF.

Polyoxypropylene-polyoxyethylene block copolymers can also be designed with hydrophilic blocks comprising a random mix of ethylene oxide and propylene oxide repeating units. To maintain the hydrophilic character of the block, ethylene oxide can predominate.

Similarly, the hydrophobic block can be a mixture of ethylene oxide and propylene oxide repeating units. Such block copolymers are available from BASF under the tradename PLURADOT™. Poly (oxyethylene)-poly (oxypropylene) block units making up the first segment need not consist solely of ethylene oxide. Nor is it necessary that all of the B-type segment contain solely of propylene oxide units. Instead, in the simplest cases, for example, at least one of the monomers in segment A can be substituted with a side chain group.

A number of poloxamer copolymers are designed to meet the following formula:

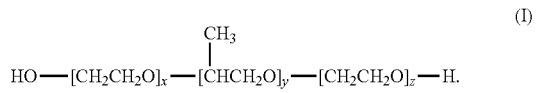

(I)

Examples of poloxamers include, without limitation, PLURONIC™ L31, L35, F38, L42, L43, L44, L61, L62, L63, L64, P65, F68, L72, P75, F77, L81, P84, P85, F87, F88, L92, F98, L101, P103, P104, P105, F108, L121, L122, L123, F127, 10R5, 10R8, 12R3, 17R1, 17R2, 17R4, 17R8, 22R4, 25R1, 25R2, 25R4, 25R5, 25R8, 31R1, 31R2, and 31R4. PLURONIC™ block copolymers are designated by a letter prefix followed by a two or a three digit number. The letter prefixes (L, P, or F) refer to the physical form of each polymer, (liquid, paste, or flakeable solid). The numeric code defines the structural parameters of the block copolymer. The last digit of this code approximates the weight content of EO block in tens of weight percent (for example, 80% weight if the digit is 8, or 10% weight if the digit is 1). The remaining first one or two digits encode the molecular mass of the central PO block. To decipher the code, one should multiply the corresponding number by 300 to obtain the approximate molecular mass in daltons (Da). Therefore Pluronic nomenclature provides a convenient approach to estimate the characteristics of the block copolymer in the absence of reference literature. For example, the code "F127" defines the block copolymer, which is a solid, has a PO block of 3600 Da (12×300) and 70% weight of EO. The precise molecular characteristics of each PLURONIC™ block copolymer can be obtained from the manufacturer.

Other biocompatible amphiphilic copolymers include those described in Gaucher et al. (*J. Control Rel.* 109:169-188, 2005). Examples of other polymers include, without limitation, poly (2-oxazoline) amphiphilic block copolymers, Polyethylene glycol-Polylactic acid (PEG-PLA), PEG-PLA-PEG, Polyethylene glycol-Poly (lactide-co-glycolide) (PEG-PLG), Polyethylene glycol-Poly (lactic-co-glycolic acid) (PEG-PLGA), Polyethylene glycol-Polycaprolactone (PEG-PCL), Polyethylene glycol-Polyaspartate (PEG-PAsp), Polyethylene glycol-Poly (glutamic acid) (PEG-PGlu), Polyethylene glycol-Poly (acrylic acid) (PEG-PAA), Polyethylene glycol-Poly (methacrylic acid) (PEG-PMA), Polyethylene glycol-poly (ethyleneimine) (PEG-PEI), Polyethylene glycol-Poly (L-lysine) (PEG-PLys), Polyethylene glycol-Poly (2-(N,N-dimethylamino) ethyl methacrylate) (PEG-PDMAEMA) and Polyethylene glycol-Chitosan derivatives.

In a particular embodiment, the surfactant comprises at least one selected from the group consisting of poloxamer 188, poloxamer 407, polyvinyl alcohol (PVA), 1,2-distearoyl-phosphatidyl ethanolamine-methyl-polyethyleneglycol conjugate-2000 (mPEG$_{2000}$DSPE), sodium dodecyl sulfate (SDS), and 1,2-dioleoyloxy-3-trimethylammoniumpropane (DOTAP).

The surfactant can be linked to a targeting ligand. A targeting ligand is a compound that will specifically bind to a specific type of tissue or cell type. In a particular example, the targeting ligand is a ligand for a cell surface marker/receptor. The targeting ligand can be an antibody or fragment thereof immunologically specific for a cell surface marker (e.g., protein or carbohydrate) preferentially or exclusively expressed on the targeted tissue or cell type. The targeting ligand can be linked directly to the surfactant or via a linker. Generally, the linker is a chemical moiety comprising a covalent bond or a chain of atoms that covalently attaches the ligand to the surfactant. The linker can be linked to any synthetically feasible position of the ligand and the surfactant. Exemplary linkers can comprise at least one optionally substituted; saturated or unsaturated; linear, branched or cyclic alkyl group or an optionally substituted aryl group. The linker can also be a polypeptide (e.g., from about 1 to about 10 amino acids, particularly about 1 to about 5). The linker can be non-degradable and can be a covalent bond or any other chemical structure, which cannot be substantially cleaved or cleaved at all under physiological environments or conditions.

In a particular embodiment, the targeting ligand is a macrophage targeting ligand. Macrophage targeting ligands include, without limitation, folate receptor ligands (e.g., folate (folic acid) and folate receptor antibodies and fragments thereof (see e.g., Sudimack et al., *Adv. Drug Del. Rev.*, 41:147-162, 2000), mannose receptor ligands (e.g., mannose), and formyl peptide receptor (FPR) ligands (e.g., N-formyl-Met-Leu-Phe (fMLF)). As demonstrated herein, the targeting of the nanoparticles to macrophage provides for central nervous system targeting (e.g., brain targeting), greater liver targeting, decreased excretion rates, decreased toxicity, and prolonged half life compared to free drug or non-targeted nanoparticles.

The disclosed nanoparticle formulations can be administered, without limitation parenterally, subcutaneously, orally, topically, pulmonarily, rectally, vaginally, intravenously, intraperitoneally, intrathecally, intracerbrally, epidurally, intramuscularly, intradermally, or intracarotidly. In a particular example, the nanoparticles are administered intravenously or intraperitoneally.

Additional Compositions and Methods

While the benefit of combining a MLK inhibitor with an antiretroviral has been demonstrated herein, especially when formulated as a crystalline nanoparticle comprising a surfactant, it has also been found herein that other drug therapies besides antivirals can be enhanced by a MLK inhibitor. Thus, disclosed herein are compositions that comprise an MLK inhibitor and a drug, wherein the drug is in a crystalline nanoparticle that further comprises one or more surfactants. The MLK inhibitor can also be in the crystalline nanoparticle with the drug or can be administered as a separate composition.

Suitable MLK inhibitors for these compositions and methods can be any one of those disclosed herein under the section "MLK inhibitors", for example Compound AH. The formulations for the crystalline nanoparticles and surfactants are also those disclosed herein under the section "nanoparticles" and "surfactants".

Suitable drugs that can be used herein in the crystalline nanoparticles are adrenocortical steroid; adrenocortical suppressant; aldosterone antagonist; amino acid; anabolic; androgen; antagonist; anthelmintic; anti-acne agent; anti-adrenergic; anti-allergic; anti-amebic; anti-androgen; anti-anemic; anti-anginal; anti-arthritic; anti-asthmatic; anti-atherosclerotic; antibacterial; anticholelithic; anticholelithogenic; anticholinergic; anticoagulant; anticoccidal; antidiabetic; antidiarrheal; antidiuretic; antidote; antiestrogen; antifibrinolytic; antifungal; antiglaucoma agent; antihemophilic; antihemorrhagic; antihistamine; antihyperlipidemia; antihyperlipoproteinemic; antihypertensive; antihypotensive; anti-infective; anti-infective, topical; anti-inflammatory; antikeratinizing agent; antimalarial; antimicrobial; antimitotic; antimycotic, antineoplastic, antineutropenic, antiparasitic; antiperistaltic, antipneumocystic; antiproliferative; antiprostatic hypertrophy; antiprotozoal; antipruritic; antipsoriatic; antirheumatic; antischistosomal; antiseborrheic; antisecretory; antispasmodic; antithrombotic; antitussive; anti-ulcerative; anti-urolithic; antiviral; appetite suppressant; benign prostatic hyperplasia therapy agent; bone resorption inhibitor; bronchodilator; carbonic anhydrase inhibitor; cardiac depressant; cardioprotectant; cardiotonic; cardiovascular agent; choleretic; cholinergic; cholinergic agonist; cholinesterase deactivator, coccidiostat; diagnostic aid; diuretic; ectoparasiticide; enzyme inhibitor; estrogen; fibrinolytic; free oxygen radical scavenger; glucocorticoid; gonad-stimulating principle; hair growth stimulant; hemostatic; hormone; hypocholesterolemic; hypoglycemic; hypolipidemic; hypotensive; immunizing agent; immunomodulator; immunoregulator; immunostimulant; immunosuppressant; impotence therapy adjunct; inhibitor; keratolytic; LHRH agonist; liver disorder treatment, luteolysin; mucolytic; mydriatic; nasal decongestant; neuromuscular blocking agent; non-hormonal sterol derivative; oxytocic; plasminogen activator; platelet activating factor antagonist; platelet aggregation inhibitor; potentiator; progestin; prostaglandin; prostate growth inhibitor; prothyrotropin; pulmonary surface; radioactive agent; regulator; relaxant; repartitioning agent; scabicide; sclerosing agent; selective adenosine A1 antagonist; steroid; suppressant; symptomatic multiple sclerosis; synergist; thyroid hormone; thyroid inhibitor; thyromimetic; amyotrophic lateral sclerosis agents; Paget's disease agents; unstable angina agents; uricosuric; vasoconstrictor; vasodilator; vulnerary; wound healing agent; or xanthine oxidase inhibitor. Any drug from this list can be formulated in a crystalline nanoparticle comprising one or more surfactants, as disclosed herein, and used with a MLK inhibitor to treat the corresponding disease.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process.

The structures of compounds synthesized in the examples below were confirmed using the following procedures. LC-MS/UV/ELS analysis was performed on instrumentation consisting of Shimadzu LC-10AD vp series HPLC pumps and dual wavelength UV detector, a Gilson 215 autosampler, a Sedex 75c evaporative light scattering (ELS) detector, and a PE/Sciex API 150EX mass spectrometer. The ELS detector was set to a temperature of 40° C., a gain setting of 7, and a $N_2$ pressure of 3.3 atm. The Turbo IonSpray source was employed on the API 150 with an ion spray voltage of 5 kV, a temperature of 300° C., and orifice and ring voltages of 5 V and 175 V respectively. Positive ions were scanned in Q1 from 160 to 650 m/z. 5.0 µL injections were performed for each sample, on a Phenomenex Gemini 5 µm C18 column. Mobile phases consisted of 0.05% formic acid in both HPLC grade water (A) and HPLC grade acetonitrile (B). 5.0 µL injections were performed for each sample, using gradient elution from 5% B to 100% B in 4 min at a flow rate of 2.0 mL/min with a final hold at 100% B of 1.8 min. UV and ELS data is collected for 4.5 min. Routine one-dimensional NMR spectroscopy was performed on a 300 MHz Varian Mercury-Plus spectrometer. The samples were dissolved in deuterated solvents obtained from Cambridge Isotope Laboratories, Inc., and transferred to 5 mm ID NMR tubes. The spectra were acquired at 293 K. The chemical shifts were recorded on the ppm scale and were referenced to the appropriate solvent signals, such as 2.49 ppm for DMSO-d6, 1.93 ppm for $CD_3CN$, 3.30 ppm for $CD_3OD$, 5.32 ppm for $CD_2Cl_2$ and 7.26 ppm for $CDCl_3$ for $^1H$ spectra.

Example 1

Scheme 1

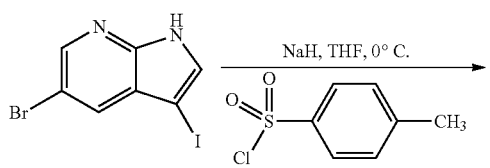

-continued

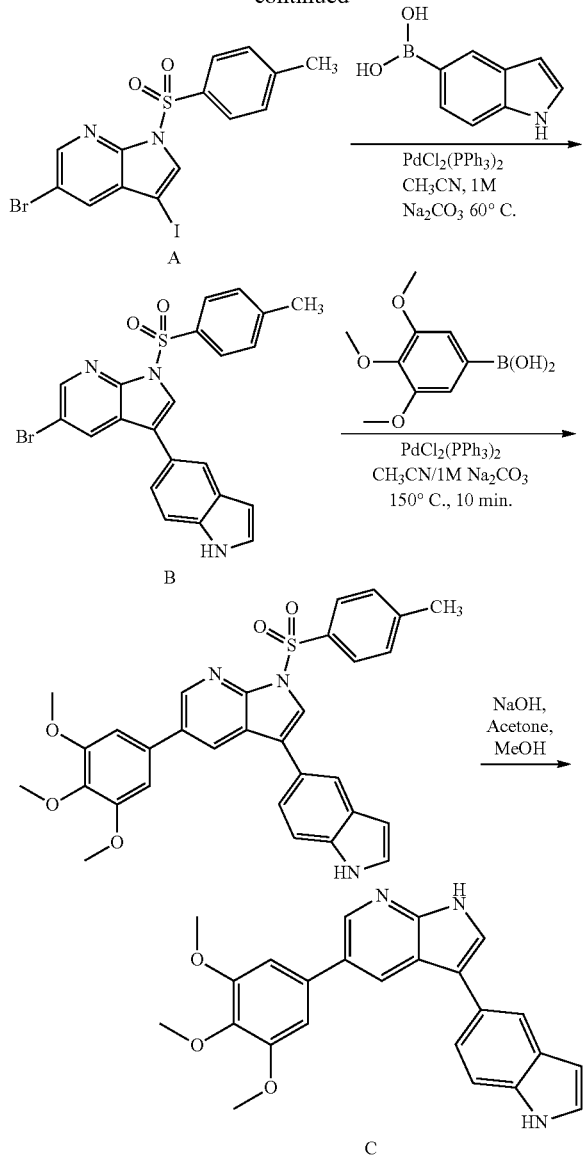

Preparation of Intermediate A: 5-bromo-3-iodo-1-tosyl-1H-pyrrolo[2,3-b]pyridine To a stirred solution of 5-bromo-3-iodo-1H-pyrrolo[2,3-b]pyridine (0.70 g, 2.2 mmol) in 15 mL of anhydrous THF cooled to 0° C. with an ice bath was added NaH [60% dispersion in mineral oil] (0.13 g, 3.3 mmol). The reaction mixture was stirred for 20 min at 0° C., after which p-toluenesulfonyl chloride (0.47 g, 2.4 mmol) was added. The resulting mixture was stirred at 0° C. for 1.5 hr, after which cold 0.5 M HCl (20 mL) was added. The mixture was partitioned between EtOAc and 0.5 M HCl, after which the organic layer was separated, dried over MgSO$_4$, filtered, and evaporated in vacuo to yield a residue that was triturated with 20% CH$_2$Cl$_2$ in hexanes to yield the title compound (0.84 g, 81%) as a light yellow powder. $^1$H NMR (DMSO-d6, 300 MHz) δ 8.51 (d, J=2.1 Hz, 1H), 8.22 (s, 1H), 8.02 (d, J=1.2 Hz, 1H), 8.00 (d, J=5.1 Hz, 2H), 7.44 (dd, J=8.7 Hz, 0.6 Hz, 2H), 2.35 (s, 3H); MS ESI (m/z): 477.0/479.0 (M+1)$^+$, calc. 476.

Preparation of Intermediate B: 5-bromo-3-(1H-indol-5-yl)-1-tosyl-1H-pyrrolo[2,3-b]pyridine To a stirred suspension of 5-bromo-3-iodo-1-tosyl-1H-pyrrolo[2,3-b]pyridine (0.35 g, 0.73 mmol) and 1H-indol-5-ylboronic acid (0.14 mg, 0.88 mmol) in CH$_3$CN (10 mL) was added 1 M Na$_2$CO$_3$ (10 mL) followed by bis(triphenylphosphine)palladium(II) dichloride (0.050 g, 0.071 mmol). The resulting mixture was stirred overnight at 60° C. After the mixture was evaporated to dryness in vacuo, it was dissolved in DMF (3 mL), absorbed onto Celite, and dried. The residue was purified via silica gel chromatography using CH$_2$Cl$_2$ as the eluent to obtain the title compound (0.26 g, 76%). $^1$H NMR (CDCl$_3$, 300 MHz): δ 8.48 (d, J=2.1 Hz, 1H), 8.27 (bs, 1H), 8.26 (d, J=2.4 Hz, 1H), 8.08 (d, J=8.1 Hz), 7.85 (s, 1H), 7.81 (m, 1H), 7.50 (d, J=8.7 Hz, 1H), 7.37 (dd, J=1.8, 8.4 Hz), 7.30 (m, 3H), 6.63 (m, 1H), 2.39 (s, 3H); MS ESI (m/z): 466.2/468.2 (M+1)$^+$, calc. 465.

Preparation of 3-(1H-indol-5-yl)-5-(3,4,5-trimethoxyphenyl)-1H-pyrrolo[2,3-b]pyridine (Compound C)

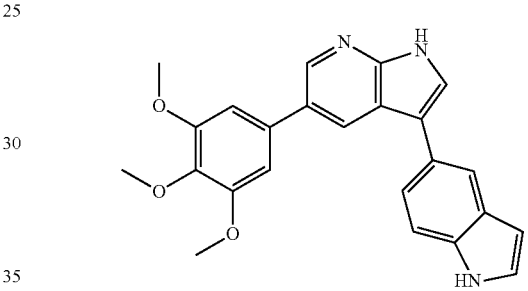

To a solution of 5-bromo-3-(1H-indol-5-yl)-1-tosyl-1H-pyrrolo[2,3-b]pyridine (65 mg, 0.14 mmol) in CH$_3$CN (1 mL) in a Personal Chemistry microwave reaction vial was added 3,4,5-trimethoxyphenylboronic acid (30 mg, 0.14 mmol), bis(triphenylphosphine)-palladium(II) dichloride (7.0 mg, 0.010 mmol), and 1 M Na$_2$CO$_3$ (1 mL). The resulting mixture was de-gassed with Ar for 10 min, after which it was heated at 150° C. for 10 min in a Personal Chemistry Optimizer. The organic layer was separated, filtered, and concentrated in vacuo. The residue was dissolved in MeOH (3 mL) and acetone (2 mL), and 2 M NaOH (1.5 mL) was added. The resulting mixture was stirred at 65° C. for 30 min, after which it was partitioned between EtOAc and 1 M NaOH. The organic layer was separated, dried over MgSO$_4$, filtered, and stripped to give a residue purified via preparatory HPLC to give the title compound as a white solid. $^1$H NMR (DMSO-d6, 300 MHz): δ 11.78 (s, 1H), 11.03 (s, 1H), 8.51 (d, J=2.1 Hz, 1H), 8.36 (d, J=1.8 Hz, 1H), 7.86 (s, 1H), 7.72 (d, J=2.4 Hz, 1H), 7.45 (s, 2H), 7.32 (m, 1H), 6.92 (s, 2H), 6.45 (m, 1H), 3.85 (s, 6H), 3.70 (s, 3H); HPLC retention time: 2.04 minutes; MS ESI (m/z): 400.4 (M+1)$^+$, calc. 399.

Example 2

Preparation of 5-(3,4-dimethoxyphenyl)-3-(1H-indol-5-yl)-1H-pyrrolo[2,3-b]pyridine (Compound D)

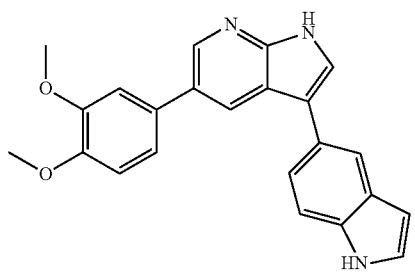 [SMILES: COc1ccc(-c2cnc3[nH]cc(-c4ccc5[nH]ccc5c4)c3c2)cc1OC]

Compound D was prepared by a method analogous to that described in Example 1 by substituting 3,4-dimethoxyphenylboronic acid for 3,4,5-trimethoxyphenylboronic acid in the reaction with intermediate B. HPLC retention time: 2.33 minutes. MS ESI (m/z): 370.2 (M+H)$^+$, calc. 369.

Example 3

Preparation of N-(4-(3-(1H-indol-5-yl)-1H-pyrrolo[2,3-b]pyridin-5-yl)phenyl)acetamide (Compound E)

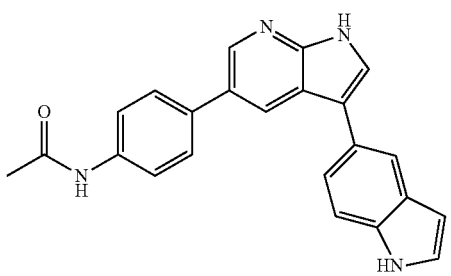 [SMILES: CC(=O)Nc1ccc(-c2cnc3[nH]cc(-c4ccc5[nH]ccc5c4)c3c2)cc1]

Compound E was prepared by a method analogous to that described in Example 1 by substituting 4-acetamidophenylboronic acid for 3,4,5-trimethoxyphenylboronic acid in the reaction with intermediate B. HPLC retention time: 1.86 minutes. MS ESI (m/z): 367.4 (M+H)$^+$, calc. 366.

Example 4

Preparation of 5-(3-(1H-indol-5-yl)-1H-pyrrolo[2,3-b]pyridin-5-yl)pyridin-2-amine (Compound F)

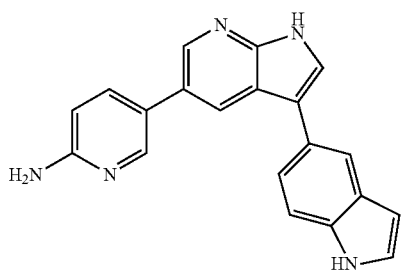 [SMILES: Nc1ccc(-c2cnc3[nH]cc(-c4ccc5[nH]ccc5c4)c3c2)cn1]

Compound F was prepared by a method analogous to that described in Example 1 by substituting 5-(4,4,5,5-tetramethyl-1,3,2-dioxaborolan-2-yl)pyridin-2-amine for 3,4,5-trimethoxyphenylboronic acid in the reaction with intermediate B. $^1$H NMR (DMSO-d6, 300 MHz): δ 11.73 (d, J=1.8 Hz, 1H), 11.05 (s, 1H), 8.43 (d, J=2.4 Hz, 1H), 8.29 (d, J=1.8 Hz, 1H), 8.27 (d, J=2.1 Hz, 1H), 7.88 (s, 1H), 7.76 (dd, J=2.4, 8.4 Hz, 1H), 7.46 (s, 2H), 7.33 (m, 1H), 6.55 (dd, J=0.6, 8.7 Hz, 1H), 6.46 (m, 1H), 5.99 (s, 2H). HPLC retention time: 1.10 minutes. MS ESI (m/z): 326.2 (M+H)$^+$, calc. 325.

Example 5

Preparation of 4-(3-(1H-indol-5-yl)-1H-pyrrolo[2,3-b]pyridin-5-yl)-2-methoxyaniline (Compound G)

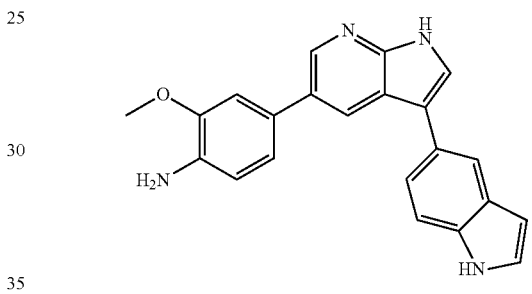

Compound G was prepared by a method analogous to that described in Example 1 by substituting 4-amino-3-methoxyphenylboronic acid for 3,4,5-trimethoxyphenylboronic acid in the reaction with intermediate B. HPLC retention time: 1.54 minutes. MS ESI (m/z): 355.4 (M+H)$^+$, calc. 354.

Example 6

Preparation of 3-(1H-indol-5-yl)-5-(6-methoxypyridin-3-yl)-1H-pyrrolo[2,3-b]pyridine (Compound H)

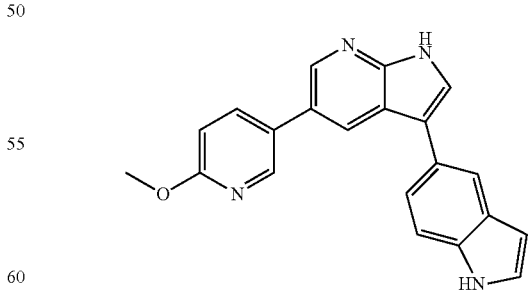

Compound H was prepared by a method analogous to that described in Example 1 by substituting 6-methoxypyridin-3-ylboronic acid for 3,4,5-trimethoxyphenylboronic acid in the reaction with intermediate B. HPLC retention time: 2.16 minutes. MS ESI (m/z): 341.4 (M+H)$^+$, calc. 340.

Example 7

Preparation of 3-(1H-indol-5-yl)-5-(2-(4-methylpiperazin-1-yl)pyridin-4-yl)-1H-pyrrolo[2,3-b]pyridine (Compound I)

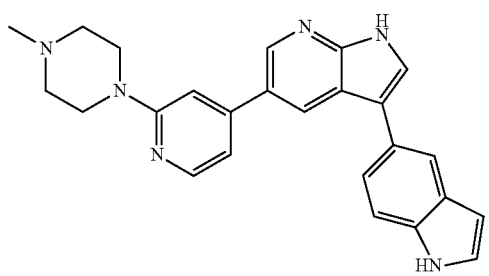 [SMILES: CN1CCN(c2cc(-c3cnc4[nH]cc(-c5ccc6[nH]ccc6c5)c4c3)ccn2)CC1]

Compound I was prepared by a method analogous to that described in Example 1 by substituting 2-(4-methylpiperazin-1-yl)pyridin-4-ylboronic acid for 3,4,5-trimethoxyphenylboronic acid in the reaction with intermediate B. HPLC retention time: 1.37 minutes. MS ESI (m/z): 409.4 (M+H)$^+$, calc. 408.

Example 8

Preparation of 4-(3-(1H-indol-5-yl)-1H-pyrrolo[2,3-b]pyridin-5-yl)aniline (Compound J)

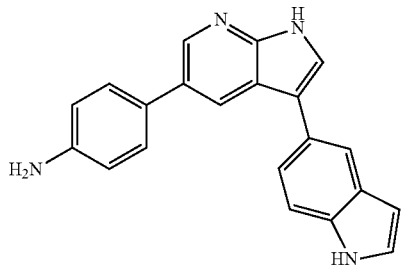 [SMILES: Nc1ccc(-c2cnc3[nH]cc(-c4ccc5[nH]ccc5c4)c3c2)cc1]

Compound J was prepared by a method analogous to that described in Example 1 by substituting 4-aminophenylboronic acid for 3,4,5-trimethoxyphenylboronic acid in the reaction with intermediate B. HPLC retention time: 1.47 minutes. MS ESI (m/z): 325.4 (M+H)$^+$, calc. 324.

Example 9

Preparation of 5-(3-(1H-indol-5-yl)-1H-pyrrolo[2,3-b]pyridin-5-yl)pyrimidin-2-amine (Compound K)

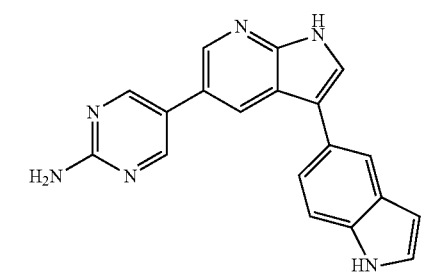 [SMILES: Nc1ncc(-c2cnc3[nH]cc(-c4ccc5[nH]ccc5c4)c3c2)cn1]

Compound K was prepared by a method analogous to that described in Example 1 by substituting 2-aminopyrimidin-5-ylboronic acid for 3,4,5-trimethoxyphenylboronic acid in the reaction with intermediate B. HPLC retention time: 1.81 minutes. MS ESI (m/z): 327.2 (M+H)$^+$, calc. 326.

Example 10

Preparation of 3-(1H-indol-5-yl)-5-(6-(piperazin-1-yl)pyridin-3-yl)-1H-pyrrolo[2,3-b]pyridine (Compound L)

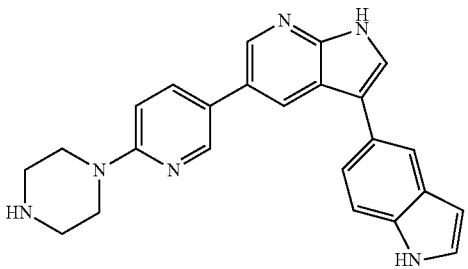 [SMILES: c1cc2cc(-c3c[nH]c4ncc(-c5ccc(N6CCNCC6)nc5)cc34)ccc2[nH]1]

Compound L was prepared by a method analogous to that described in Example 1 by substituting 6-(piperazin-1-yl)pyridin-3-ylboronic acid for 3,4,5-trimethoxyphenylboronic acid in the reaction with intermediate B. HPLC retention time: 1.15 minutes. MS ESI (m/z) 395.4 (M+H)$^+$, calc. 394.

Example 11

Preparation of N-(4-(3-(1H-indol-5-yl)-1H-pyrrolo[2,3-b]pyridin-5-yl)phenyl)methanesulfonamide (Compound M)

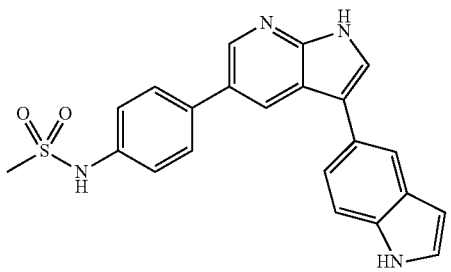 [SMILES: CS(=O)(=O)Nc1ccc(-c2cnc3[nH]cc(-c4ccc5[nH]ccc5c4)c3c2)cc1]

Compound M was prepared by a method analogous to that described in Example 1 by substituting 4-(methylsulfonamido)phenylboronic acid for 3,4,5-trimethoxyphenylboronic acid in the reaction with intermediate B. HPLC retention time: 1.99 minutes. MS ESI (m/z): 403.4 (M+H)$^+$, calc. 402.

Example 12

Preparation of 3,5-di(1H-indol-5-yl)-1H-pyrrolo[2,3-b]pyridine (Compound N)

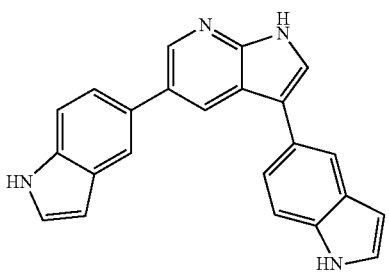 [SMILES: c1cc2cc(-c3cnc4[nH]cc(-c5ccc6[nH]ccc6c5)c4c3)ccc2[nH]1]

Compound N was prepared by a method analogous to that described in Example 1 by substituting 1H-indol-5-ylboronic acid for 3,4,5-trimethoxyphenylboronic acid in the reaction with intermediate B. HPLC retention time: 2.01 minutes. MS ESI (m/z): 349.2 (M+H)$^+$, calc. 348.

Example 13

Preparation of 5-(3-(1H-indol-5-yl)-1H-pyrrolo[2,3-b]pyridin-5-yl)-N,N-dimethylpyridin-2-amine (Compound O)

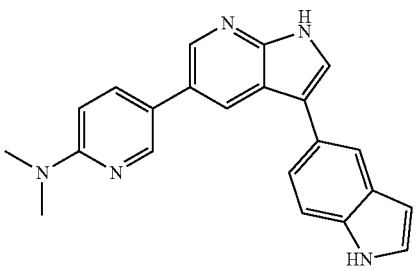 [SMILES: CN(C)c1ccc(-c2cnc3[nH]cc(-c4ccc5[nH]ccc5c4)c3c2)cn1]

Compound O was prepared by a method analogous to that described in Example 1 by substituting 6-(dimethylamino)pyridin-3-ylboronic acid for 3,4,5-trimethoxyphenylboronic acid in the reaction with intermediate B. HPLC retention time: 1.58 minutes. MS ESI (m/z): 354.4 (M+H)$^+$, calc. 353.

Example 14

Preparation of 3-(1H-indol-5-yl)-5-phenyl-1H-pyrrolo[2,3-b]pyridine (Compound P)

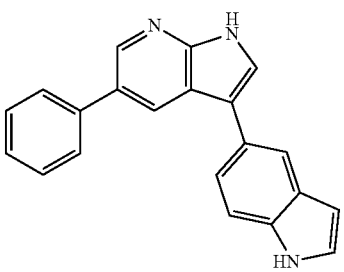 [SMILES: c1ccc(-c2cnc3[nH]cc(-c4ccc5[nH]ccc5c4)c3c2)cc1]

Compound P was prepared by a method analogous to that described in Example 1 by substituting phenylboronic acid for 3,4,5-trimethoxyphenylboronic acid in the reaction with intermediate B. HPLC retention time: 2.49 minutes. MS ESI (m/z): 310.2 (M+H)$^+$, calc. 309.

Example 15

Preparation of 4-(5-(3,4,5-trimethoxyphenyl)-1H-pyrrolo[2,3-b]pyridin-3-yl)aniline (Compound Q)

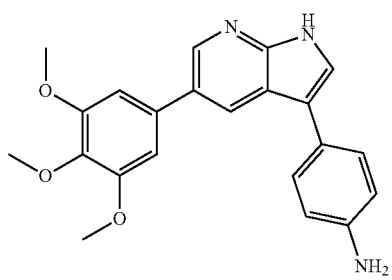 [SMILES: COc1cc(-c2cnc3[nH]cc(-c4ccc(N)cc4)c3c2)cc(OC)c1OC]

Compound Q was prepared by a method analogous to that described in Example 1 by substituting 4-aminophenylboronic acid for 1H-indol-5-ylboronic acid in the reaction with Intermediate A. HPLC retention time: 1.45 minutes. MS ESI (m/z): 376.4 (M+H), calc. 375.

Example 16

Preparation of N-(4-(5-(3,4,5-trimethoxyphenyl)-1H-pyrrolo[2,3-b]pyridin-3-yl)phenyl)acetamide (Compound R)

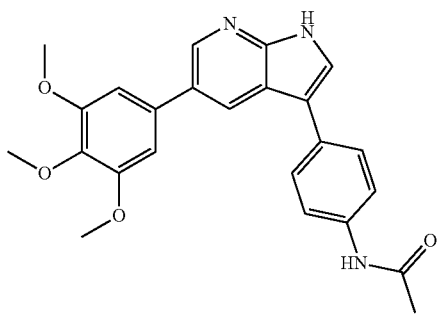 [SMILES: COc1cc(-c2cnc3[nH]cc(-c4ccc(NC(C)=O)cc4)c3c2)cc(OC)c1OC]

Compound R was prepared by a method analogous to that described in Example 1 by substituting 4-acetamidophenylboronic acid for 1H-indol-5-ylboronic acid in the reaction with Intermediate A. HPLC retention time: 1.98 minutes. MS ESI (m/z): 418.6 (M+H)+, calc. 417.

Example 17

Preparation of 5-(5-(3,4,5-trimethoxyphenyl)-1H-pyrrolo[2,3-b]pyridin-3-yl)pyrimidin-2-amine (Compound S)

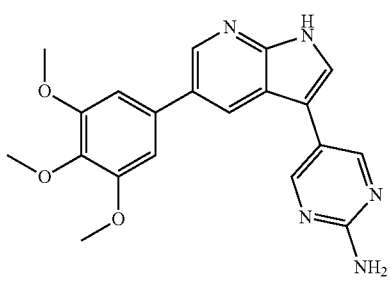 [SMILES: COc1cc(-c2cnc3[nH]cc(-c4cnc(N)nc4)c3c2)cc(OC)c1OC]

Compound S was prepared by a method analogous to that described in Example 1 by substituting 2-aminopyrimidin-5-ylboronic acid for 1H-indol-5-ylboronic acid in the reaction with Intermediate A. HPLC retention time: 1.98 minutes. MS ESI (m/z): 378.4 (M+H)+, calc. 377.

Example 18

Preparation of 5-(5-(3,4,5-trimethoxyphenyl)-1H-pyrrolo[2,3-b]pyridin-3-yl)pyridin-2-amine (Compound T)

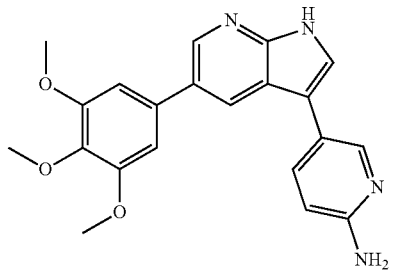

Compound T was prepared by a method analogous to that described in Example 1 by substituting 5-(4,4,5,5-tetramethyl-1,3,2-dioxaborolan-2-yl)pyridin-2-amine for 1H-indol-5-ylboronic acid in the reaction with Intermediate A. $^1$H NMR (DMSO-d6, 300 MHz): δ 11.82 (s, 1H), 8.53 (d, J=1.8 Hz, 1H), 8.31 (d, J=1.8, 1 H), 8.28 (d, J=1.5 Hz), 7.76 (dd, J=2.1, 8.4 Hz, 1H), 7.70 (d, J=2.4 Hz, 1H), 6.95 (s, 2H), 6.54 (d, J=8.4 Hz, 1 H), 5.87 (s, 2H), 3.86 (s, 6H), 3.68 (s, 3H); HPLC retention time: 1.10 minutes. MS ESI (m/z): 377.4 (M+H)+, calc. 376.

Example 19

Preparation of N,N-dimethyl-5-(5-(3,4,5-trimethoxyphenyl)-1H-pyrrolo[2,3-b]pyridin-3-yl)pyridin-2-amine (Compound U)

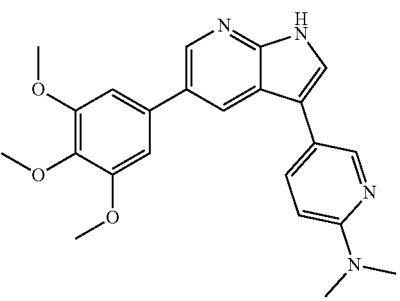

Compound U was prepared by a method analogous to that described in Example 1 by substituting 6-(dimethylamino)pyridin-3-ylboronic acid for 1H-indol-5-ylboronic acid in the reaction with Intermediate A. HPLC retention time: 1.43 minutes. MS ESI (m/z): 405.6 (M+H)+, calc. 404.

Example 20

Preparation of 5,5'-(1H-pyrrolo[2,3-b]pyridine-3,5-diyl)dipyrimidin-2-amine (Compound V)

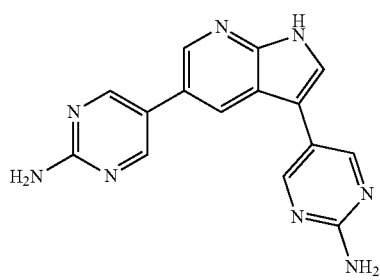 [SMILES: Nc1ncc(-c2cnc3[nH]cc(-c4cnc(N)nc4)c3c2)cn1]

Compound W was prepared by a method analogous to that described in Example 1 by substituting 2-aminopyrimidin-5-ylboronic acid for 1H-indol-5-ylboronic acid in the reaction with Intermediate A and 2-aminopyrimidin-5-ylboronic acid for 3,4,5-trimethoxyphenylboronic acid in the reaction with Intermediate B. HPLC retention time: 1.17 minutes. MS ESI (m/z): 305.2 (M+H)$^+$, calc. 304.

Example 21

Preparation of 5,5'-(1H-pyrrolo[2,3-b]pyridine-3,5-diyl)bis(N,N-dimethylpyridin-2-amine) (Compound W)

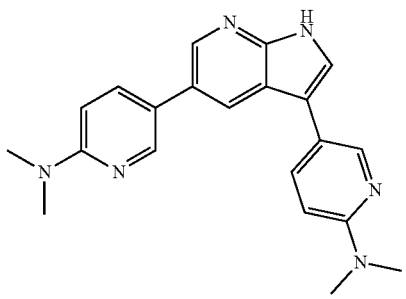

Compound X was prepared by a method analogous to that described in Example 1 by substituting 6-(dimethylamino)pyridin-3-ylboronic acid for 1H-indol-5-ylboronic acid in the reaction with Intermediate A and 6-(dimethylamino)pyridin-3-ylboronic acid for 3,4,5-trimethoxyphenylboronic acid in the reaction with Intermediate B. HPLC retention time: 1.17 minutes. MS ESI (m/z): 359.4 (M+H)$^+$, calc. 358.

Example 22

Preparation of 5-(3-(3-chloro-4-fluorophenyl)-1H-pyrrolo[2,3-b]pyridin-5-yl)-N,N-dimethylpyridin-2-amine (Compound X)

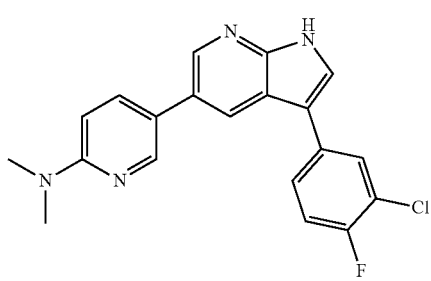 [SMILES: CN(C)c1ccc(-c2cnc3[nH]cc(-c4ccc(F)c(Cl)c4)c3c2)cn1]

Compound Y was prepared by a method analogous to that described in Example 1 by substituting 3-chloro-4-fluorophenylboronic acid for 1H-indol-5-ylboronic acid in the reaction with Intermediate A and 6-(dimethylamino)pyridin-3-ylboronic acid for 3,4,5-trimethoxyphenylboronic acid in the reaction with Intermediate B. HPLC retention time: 1.73 minutes. MS ESI (m/z): 367.2 (M+H)$^+$, calc. 366.

Example 23

Preparation of 5-(3-(4-aminophenyl)-1H-pyrrolo[2,3-b]pyridin-5-yl)pyridin-2-amine (Compound Y)

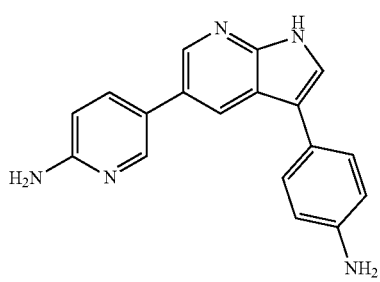 [SMILES: Nc1ccc(-c2c[nH]c3ncc(-c4ccc(N)nc4)cc23)cc1]

Compound Z was prepared by a method analogous to that described in Example 1 by substituting 4-aminophenylboronic acid for 1H-indol-5-ylboronic acid in the reaction with Intermediate A and 6-aminopyridin-3-ylboronic acid for 3,4,5-trimethoxyphenylboronic acid in the reaction with Intermediate B. HPLC retention time: 0.68 minutes. MS ESI (m/z): 302.4 (M+H)$^+$, calc. 301.

Example 24

Preparation of 3-(1-methyl-1H-indol-5-yl)-5-(3,4,5-trimethoxyphenyl)-1H-pyrrolo[2,3-b]pyridine (Compound Z)

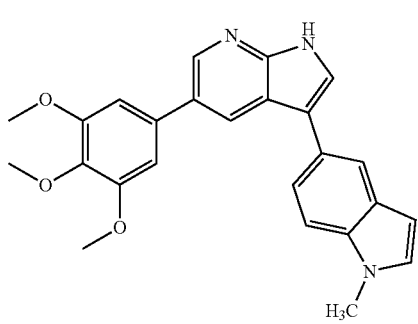 [SMILES: COc1cc(-c2cnc3[nH]cc(-c4ccc5c(ccn5C)c4)c3c2)cc(OC)c1OC]

Compound AA was prepared by a method analogous to that described in Example 1 by substituting 1-methyl-1H-indol-5-ylboronic acid for 1H-indol-5-ylboronic acid in the reaction with Intermediate A. HPLC retention time: 2.29 minutes. MS ESI (m/z): 414.4 (M+H)$^+$, calc. 413.

Example 25

Preparation of 4-(5-(3,4,5-trimethoxyphenyl)-1H-pyrrolo[2,3-b]pyridin-3-yl)benzamide (Compound AA)

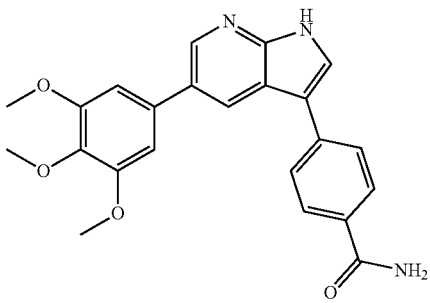 [SMILES: COc1cc(-c2cnc3[nH]cc(-c4ccc(C(N)=O)cc4)c3c2)cc(OC)c1OC]

Compound AA was prepared by a method analogous to that described in Example 1 by substituting 4-carbamoyl-phenylboronic acid for 1H-indol-5-ylboronic acid in the reaction with Intermediate A. HPLC retention time: 1.64 minutes. MS ESI (m/z): 404.6 (M+H)$^+$, calc. 403.

Example 26

Preparation of 4-(5-(3,4-dimethoxyphenyl)-1H-pyrrolo[2,3-b]pyridin-3-yl)benzamide (Compound AB)

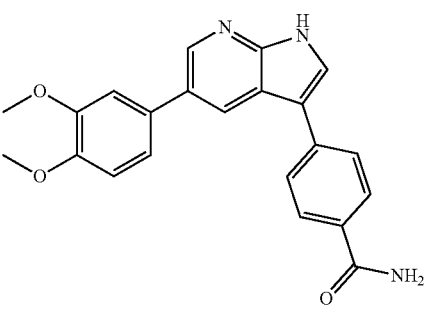 [SMILES: COc1ccc(-c2cnc3[nH]cc(-c4ccc(C(N)=O)cc4)c3c2)cc1OC]

Compound AB was prepared by a method analogous to that described in Example 1 by substituting 4-carbamoyl-phenylboronic acid for 1H-indol-5-ylboronic acid in the reaction with Intermediate A and 3,4-dimethoxyphenylboronic acid for 3,4,5-trimethoxyphenylboronic acid in the reaction with Intermediate B. HPLC retention time: 1.60 minutes. MS ESI (m/z): 374.2 (M+H)$^+$, calc. 373.

Example 27

Preparation of 4-(5-(4-amino-3-methoxyphenyl)-1H-pyrrolo[2,3-b]pyridin-3-yl)benzamide (Compound AC)

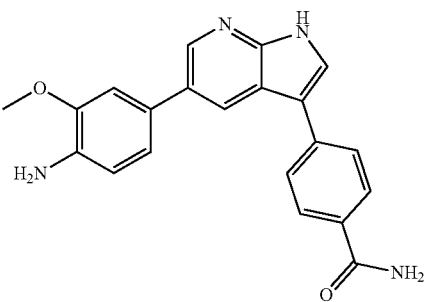 [SMILES: COc1cc(-c2cnc3[nH]cc(-c4ccc(C(N)=O)cc4)c3c2)ccc1N]

Compound AC was prepared by a method analogous to that described in Example 1 by substituting 4-carbamoyl-phenylboronic acid for 1H-indol-5-ylboronic acid in the reaction with Intermediate A and 4-amino-3-methoxyphenylboronic acid for 3,4,5-trimethoxyphenylboronic acid in the reaction with Intermediate B. HPLC retention time: 1.46 minutes. MS ESI (m/z): 359.2 (M+H)$^+$, calc. 358.

Example 28

Preparation of 4-(5-(6-aminopyridin-3-yl)-1H-pyrrolo[2,3-b]pyridin-3-yl)benzamide (Compound AD)

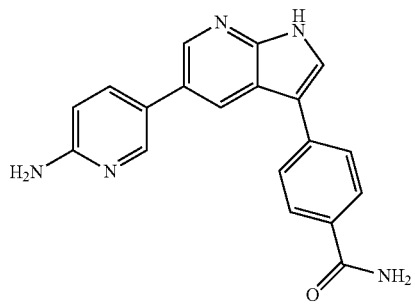 [SMILES: NC(=O)c1ccc(-c2c[nH]c3ncc(-c4ccc(N)nc4)cc23)cc1]

Compound AD was prepared by a method analogous to that described in Example 1 by substituting 4-carbamoylphenylboronic acid for 1H-indol-5-ylboronic acid in the reaction with Intermediate A and 5-(4,4,5,5-tetramethyl-1,3,2-dioxaborolan-2-yl)pyridin-2-amine for 3,4,5-trimethoxyphenylboronic acid in the reaction with Intermediate B. HPLC retention time: 1.13 minutes. MS ESI (m/z): 330.4 (M+H)$^+$, calc. 329.

Example 29

Preparation of 5-(3-(3-chloro-4-fluorophenyl)-1H-pyrrolo[2,3-b]pyridin-5-yl)pyridin-2-amine (Compound AE)

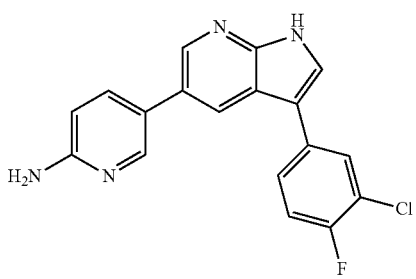 [SMILES: Nc1ccc(-c2cnc3[nH]cc(-c4ccc(F)c(Cl)c4)c3c2)cn1]

Compound AE was prepared by a method analogous to that described in Example 1 by substituting 3-chloro-4-fluorophenylboronic acid for 1H-indol-5-ylboronic acid in the reaction with Intermediate A and 5-(4,4,5,5-tetramethyl-1,3,2-dioxaborolan-2-yl)pyridin-2-amine for 3,4,5-trimethoxyphenylboronic acid in the reaction with Intermediate B. HPLC retention time: 1.47 minutes. MS ESI (m/z): 339.4 (M+H)$^+$, calc. 338.

Example 30

Scheme 2

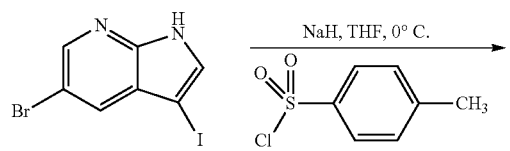

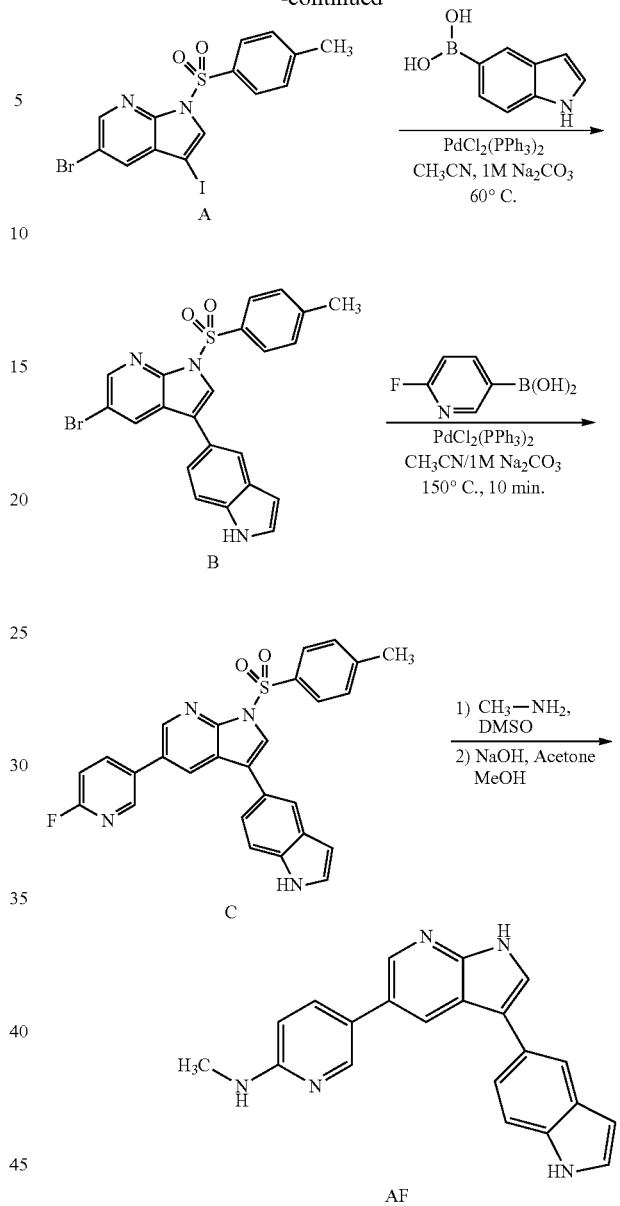

Preparation of 5-(3-(1H-indol-5-yl)-1H-pyrrolo[2,3-b]pyridin-5-yl)-N-methylpyridin-2-amine (Compound AF)

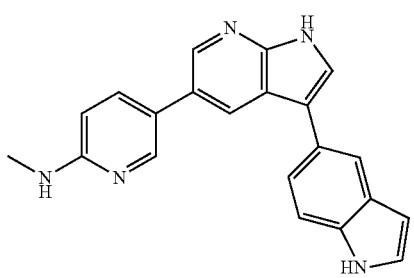 [SMILES: CNc1ccc(-c2cnc3[nH]cc(-c4ccc5[nH]ccc5c4)c3c2)cn1]

Making reference to Scheme 2, the preparation of Intermediates A and B are discussed in Example 1. To a solution of 5-bromo-3-(1H-indol-5-yl)-1-tosyl-1H-pyrrolo[2,3-b]pyridine (40 mg, 0.09 mmol)(Intermediate B) in CH$_3$CN (1 mL) in a microwave reaction vial was added 6-fluoropyridin-3-ylboronic acid (12 mg, 0.09 mmol), bis(triphenylphosphine)-palladium(II) dichloride (5.0 mg, 0.007 mmol), and 1 M Na$_2$CO$_3$ (1 mL). The resulting mixture was de-gassed with Ar for 10 min, after which it was heated at 150° C. for 10 min in a Personal Chemistry Optimizer. The organic layer was separated, filtered, and concentrated in vacuo to give intermediate AF. The residue was dissolved in DMSO (0.5 mL) and methylamine hydrochloride salt (29 mg, 0.43 mmol), and K$_2$CO$_3$ (95 mg, 0.70 mmol) were added. The resulting mixture was stirred at 80° C. for 48 hr, after which it was diluted with DMF (0.5 mL), filtered, and subjected to preparative HPLC to yield the title compound (6.0 mg, 21%). $^1$H NMR (DMSO-d6, 300 MHz): δ 11.77 (s, 1H), 11.07 (s, 1H), 8.46 (d, J=2.1 Hz, 1H), 8.34 (dd, J=2.4, 9.3 Hz, 1H), 7.90 (s, 1H), 7.86 (m, 1H), 7.74 (d, J=2.7 Hz, 1H), 7.47 (s, 2H), 7.35 (s, 1H), 6.80 (s, 1H), 6.63 (d, J=8.4 Hz, 1H), 6.48 (m, 1H), 2.84 (d, J=4.5 Hz, 1H). HPLC retention time: 1.10 minutes; HPLC retention time: 1.56 minutes; MS ESI (m/z): 340.2 (M+1)$^+$, calc. 339.

Example 31

Preparation of 5-(3-(1H-indol-5-yl)-1H-pyrrolo[2,3-b]pyridin-5-yl)-N-(2-(pyrrolidin-1-yl)ethyl)pyridin-2-amine (Compound AG)

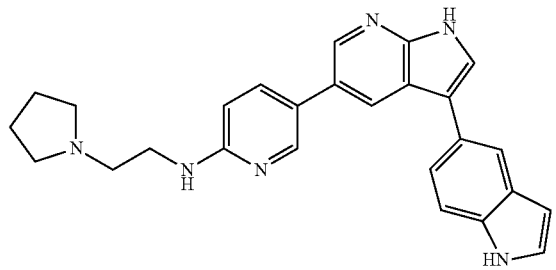 [SMILES: c1cc2cc(-c3c[nH]c4ncc(-c5ccc(NCCN6CCCC6)nc5)cc34)ccc2[nH]1]

Compound AG was prepared by a method analogous to that described in Example 30 by substituting 2-(pyrrolidin-1-yl)ethanamine for methylamine hydrochloride salt in the reaction with intermediate AF. HPLC retention time: 1.58 minutes. MS ESI (m/z): 354.4 (M+H)$^+$, calc. 353.

Example 32

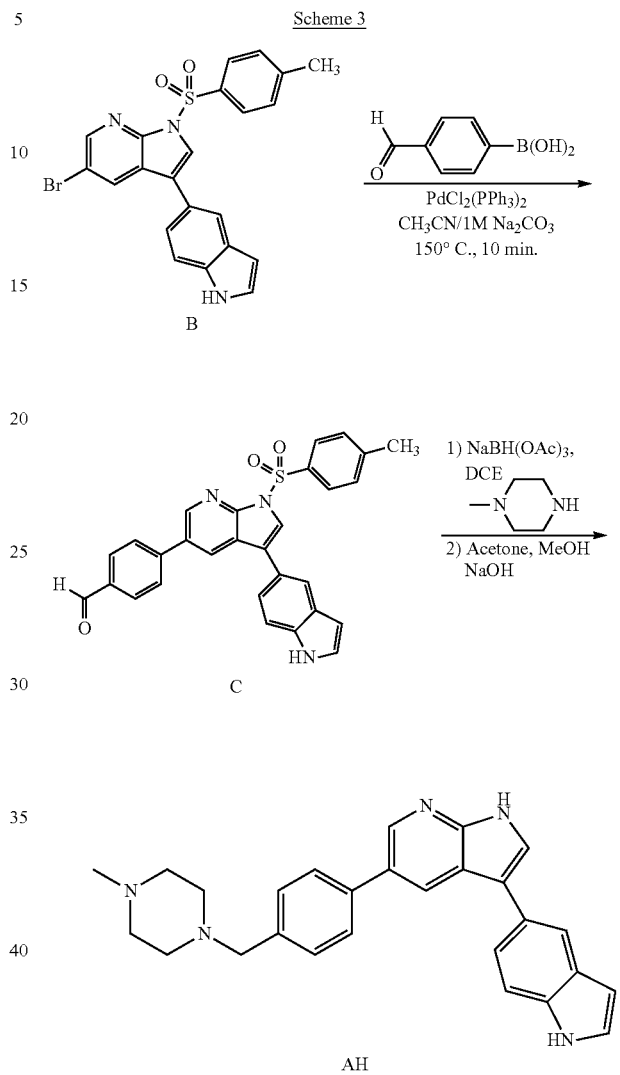

Preparation of Intermediate C: 4-(3-(1H-indol-5-yl)-1-tosyl-1H-pyrrolo[2,3-b]pyridin-5-yl)benzaldehyde Making reference to Scheme 3, to a solution of 5-bromo-3-(1H-indol-5-yl)-1-tosyl-1H-pyrrolo[2,3-b]pyridine [Intermediate B, see Example 1](0.20 g, 0.43 mmole) in CH$_3$CN (4 mL) in a Personal Chemistry microwave reaction vial was added 4-formylphenylboronic acid (64 mg, 0.43 mmol), bis(triphenylphosphine)-palladium(II) dichloride (40 mg, 0.057 mmol), and 1 M Na$_2$CO$_3$ (2 mL). The resulting mixture was de-gassed with Ar for 10 min, after which it was heated at 150° C. for 10 min in a Personal Chemistry Optimizer. The organic layer was separated, filtered, and partitioned between EtOAc and brine. The organic layer was dried over MgSO$_4$, filtered, and concentrated in vacuo to give Intermediate AJ. HPLC retention time: 3.01 minutes. MS ESI (m/z): 492.4 (M+H)$^+$, calc. 491.

Preparation of 3-(1H-indol-5-yl)-5-(4-((4-methyl-piperazin-1-yl)methyl)phenyl)-1H-pyrrolo[2,3-b]pyridine (Compound AH)

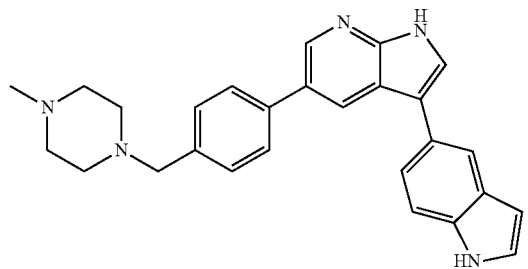 [SMILES: CN1CCN(Cc2ccc(-c3cnc4[nH]cc(-c5ccc6[nH]ccc6c5)c4c3)cc2)CC1]

To a solution of 4-(3-(1H-indol-5-yl)-1-tosyl-1H-pyrrolo[2,3-b]pyridin-5-yl)benzaldehyde [Intermediate C](0.11 g, 0.214 mmol) in $CH_2Cl_2$ (3 mL) was added 1-methylpiperazine (40 μL, 0.40 mmol) and sodium triacetoxyborohydride (68 mg, 0.32 mmol). The reaction mixture was stirred for 1 hr at room temperature, after which it was partitioned between $CH_2Cl_2$ and 1 M NaOH. The organic layer was separated, dried over $MgSO_4$, and concentrated in vacuo. The residue was dissolved in 3:2 MeOH:acetone (5 mL), and 2 M NaOH (1.5 mL) was added. The resulting mixture was stirred at 65° C. for 30 min, after which it was partitioned between EtOAc and 1 M NaOH. The organic layer was separated, dried over $MgSO_4$, filtered, and stripped to provide a residue that was subjected to preparatory HPLC to yield the title compound. HPLC retention time: 1.63 minutes; MS ESI (m/z) 422.4 $(M+1)^+$, calc. 421.

Example 33

Preparation of 1-(4-(3-(1H-indol-5-yl)-1H-pyrrolo[2,3-b]pyridin-5-yl)phenyl)-N,N-dimethylmethan-amine (Compound AI)

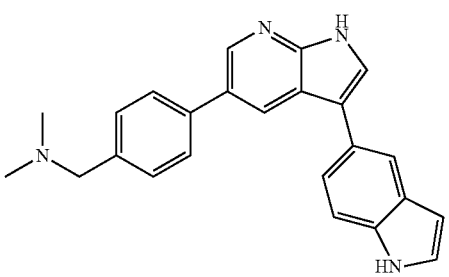 [SMILES: CN(C)Cc1ccc(-c2cnc3[nH]cc(-c4ccc5[nH]ccc5c4)c3c2)cc1]

Compound AL was prepared by a method analogous to that described in Example 32 by substituting dimethylamine (2 M solution in THF) for 1-methylpiperazine in the reaction with Intermediate AJ. HPLC retention time: 1.66 minutes. MS ESI (m/z): 367.4 $(M+H)^+$, calc. 366.

Example 34

Scheme 4

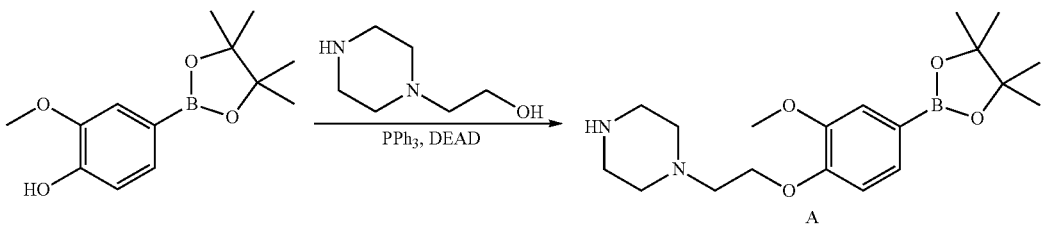

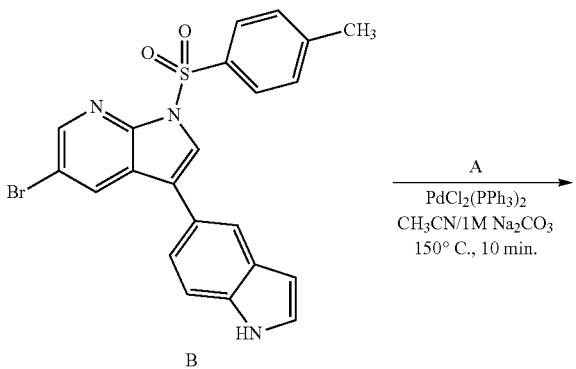

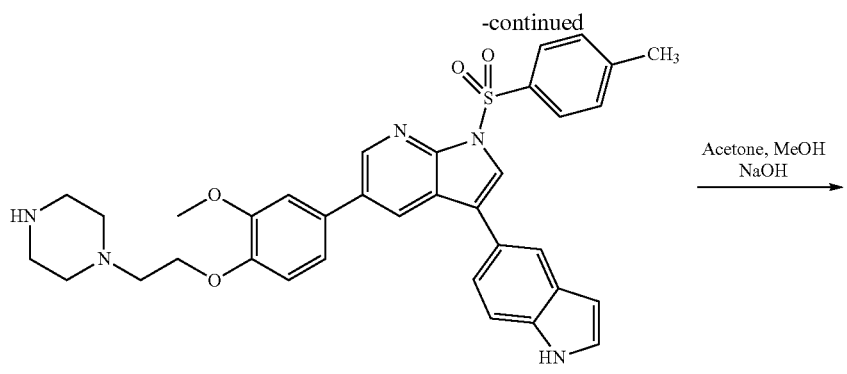

C

AJ

Preparation of Intermediate A: 1-(2-(2-methoxy-4-(4,4,5,5-tetramethyl-1,3,2-dioxaborolan-2-yl)phenoxy)ethyl)piperazine Making reference to Scheme 4, to a solution of 2-(piperazin-1-yl)ethanol (0.78 mL, 6.0 mmol) and triphenylphosphine (1.6 g, 6.0 mmol) in anhydrous THF (20 mL) at 0° C. was added diethyl azodicarboxylate (0.95 mL, 6.0 mmol), followed by 2-methoxy-4-(4,4,5,5-tetramethyl-1,3,2-dioxaborolan-2-yl)phenol (1.0 g, 4.0 mmol). After stirring for 4 h at rt, additional triphenylphosphine (1.6 g, 6.0 mmol) and diethyl azodicarboxylate (0.95 mL, 6.0 mmol) were added. After stirring for an additional 2 h, the resulting mixture was evaporated to dryness in vacuo and the residue was purified via silica gel chromatography eluting with 15% MeOH in $CH_2Cl_2$ to yield a yellow oil (1.89 g) which contained approximately 60% of the title compound by HPLC analysis. HPLC retention time: 1.01 minutes. MS ESI (m/z): 363.6 $(M+H)^+$, calc. 362.

Preparation of 3-(1H-indol-5-yl)-5-(3-methoxy-4-(2-(piperazin-1-yl)ethoxy)phenyl)-1H-pyrrolo[2,3-b]pyridine (Compound AJ)

To a solution of 5-bromo-3-(1H-indol-5-yl)-1-tosyl-1H-pyrrolo[2,3-b]pyridine (Intermediate B) (92 mg, 0.20 mmol)

in $CH_3CN$ (2 mL) in a Personal Chemistry microwave reaction vial was added 1-(2-(2-methoxy-4-(4,4,5,5-tetramethyl-1,3,2-dioxaborolan-2-yl)phenoxy)ethyl)piperazine (Intermediate A) (72 mg, 0.20 mmol), bis(triphenylphosphine)-palladium(II) dichloride (20 mg, 0.028 mmol), and 1 M $Na_2CO_3$ (2 mL). The resulting mixture was de-gassed with Ar for 10 min, after which it was heated at 150° C. for 25 min in a Personal Chemistry Optimizer. The organic layer was separated, filtered, and concentrated in vacuo to give Intermediate C. The residue was dissolved in MeOH (3 mL) and acetone (2 mL), and 2 M NaOH (1.5 mL) was added. The resulting mixture was stirred at 50° C. for 2 h, after which it was partitioned between EtOAc and 1 M NaOH. The organic layer was separated, dried over $MgSO_4$, filtered, and stripped to give a residue that was subjected to preparatory HPLC to yield the title compound. HPLC retention time: 1.29 minutes; MS ESI (m/z) 468.6 $(M+1)^+$, calc. 467.

Example 35

Preparation of 2-(4-(3-(1H-indol-5-yl)-1H-pyrrolo[2,3-b]pyridin-5-yl)-2-methoxyphenoxy)-N,N-dimethylethanamine (Compound AK)

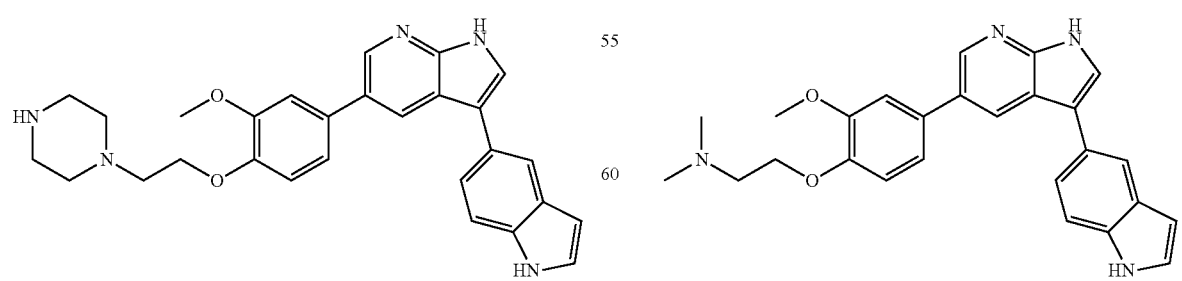

Compound AK was prepared by a method analogous to that described in Example 34 by substituting 2-(dimethylamino)ethanol for 2-(piperazin-1-yl)ethanol in the reaction with 2-methoxy-4-(4,4,5,5-tetramethyl-1,3,2-dioxaborolan-2-yl)phenol. HPLC retention time: 1.20 minutes. MS ESI (m/z): 427.2 (M+H)+, calc. 426.

Example 36

Scheme 5

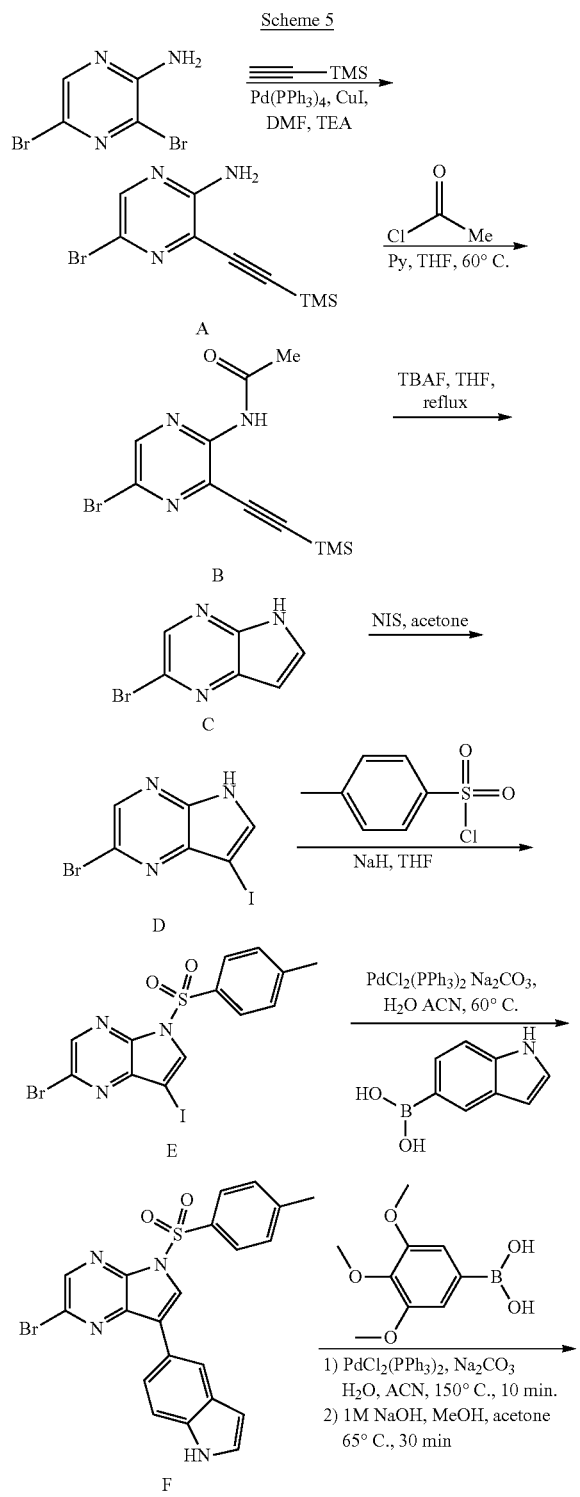

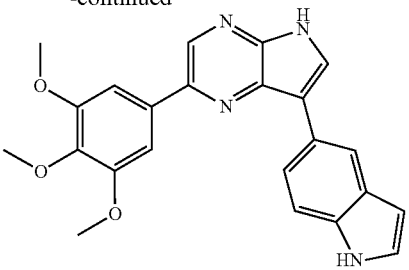

AL

Preparation of Intermediate A: 5-bromo-3-((trimethylsilyl)ethynyl)pyrazin-2-amine Making reference to Scheme 5, to a solution of 3,5-dibromopyrazin-2-amine (10 g, 40 mmol), copper(I) iodide (0.91 g, 4.7 mmol), diisopropylethylamine (53 mL, 0.55 mol), and tetrakis(triphenylphosphine)-palladium(0) (2.3 g, 1.9 mmol) in DMF (120 mL) that was de-gassed with Ar was added trimethylsilylacetylene (6.7 mL, 48 mmol). The resulting mixture was stirred under an Ar atmosphere for 1 h at 120° C., after which it was evaporated to dryness in vacuo. The residue was subjected to silica gel chromatography eluting with 35% EtOAc in hexanes to give a brown oil that was triturated with hexanes to give the title compound (5.0 g, 47%). $^1$H NMR (CDCl$_3$, 300 MHz): δ 8.04 (s, 1H), 5.10 (s, 2H), 0.28 (s, 9H). HPLC retention time: 2.75 minutes. MS ESI (m/z): 270.0, 272.0 (M+H)+, calc. 269.

Preparation of Intermediate B: N-(5-bromo-3-((trimethylsilyl)ethynyl)pyrazin-2-yl)acetamide To a solution of 5-bromo-3-((trimethylsilyl)ethynyl)pyrazin-2-amine (5.0 g, 19 mmol) and pyridine (3.8 mL, 46 mmol) in anhydrous THF (75 mL) was added acetyl chloride (1.6 mL, 23 mmol) in a drop-wise manner. After stirring for 48 hr at rt, additional acetyl chloride (0.4 mL, 6 mmol) was added and the mixture was stirred for an additional 48 hr at rt. The solvent was removed in vacuo, and the residue was diluted with 30% EtOAc in hexanes. The mixture was filtered, and the filtrate was purified via silica gel chromatography eluting with 30% EtOAc in hexanes to give a yellow-brown solid (1.8 g, 31%). $^1$H NMR (CDCl$_3$, 300 MHz): δ 8.34 (s, 1H), 8.08 (s, 1H), 2.46 (s, 3H), 0.32 (s, 9H). HPLC retention time: 2.29 minutes. MS ESI (m/z): 312.2, 314.2 (M+H)+, calc. 311.

Preparation of Intermediate C: 2-bromo-5H-pyrrolo[3,2-b]pyrazine

A solution of N-(5-bromo-3-((trimethylsilyl)ethynyl)pyrazin-2-yl)acetamide (2.6 g, 8.4 mmol) and tetrabutylammonium fluoride [1 M in THF] (18 mL, 18 mmol) in anhydrous THF (26 mL) was heated at 75° C. for 20 h, after which it was partitioned between EtOAc and H$_2$O. The organic layer was washed with brine, dried over Na$_2$SO$_4$, and evaporated in vacuo to yield a residue that was purified via silica gel chromatography eluting with 30% EtOAc in hexanes to give the title compound as a tan solid (0.69 g, 42%).
$^1$H NMR (CDCl$_3$, 300 MHz): δ 8.88 (bs, 1H), 8.34 (s, 1H), 7.62 (t, J=3.3 Hz, 1H), 6.71 (dd, J=3.6 Hz, 3.9 Hz, 1H). HPLC retention time: 1.73 minutes. MS ESI (m/z): 198.2, 200.2 (M+H)+, calc. 197.

Preparation of Intermediate D: 2-bromo-7-iodo-5H-pyrrolo[3,2-b]pyrazine

To a solution of 2-bromo-5H-pyrrolo[3,2-b]pyrazine (0.68 g, 3.4 mmol) in acetone (17 mL) was added N-iodo-succinimide (0.82 g, 3.6 mmol) and the resulting mixture was stirred for 4 h at rt. The mixture was evaporated in vacuo to yield a residue that was purified via silica gel chromatography eluting with 40% THF in hexanes to give the title compound as a yellow solid (0.99 g, 89%). $^1$H NMR (DMSO-d6, 300 MHz): δ 12.82 (s, 1H), 8.42 (s, 1H), 8.20 (s, 1H). HPLC retention time: 2.23 minutes. MS ESI (m/z): 324.0, 326.0 (M+H)$^+$, calc. 323.

Preparation of Intermediate E: 2-bromo-7-iodo-5-tosyl-5H-pyrrolo[3,2-b]pyrazine

To a stirred solution of 2-bromo-7-iodo-5H-pyrrolo[3,2-b]pyrazine (1.1 g, 3.5 mmol) in anhydrous THF (20 mL) cooled to 0° C. was added NaH [60% dispersion in mineral oil] (0.17 g, 4.3 mmol). The reaction mixture was stirred for 20 min at 0° C., after which p-toluenesulfonyl chloride (0.73 g, 3.8 mmol) in THF (8 mL) was added. The resulting mixture was stirred at rt for 3 hr, after which it was diluted with EtOAc and washed with H$_2$O and brine. The organic layer was separated, dried over Na$_2$SO$_4$, filtered, and evaporated in vacuo to yield a residue that was triturated with hexanes to yield the title compound (1.6 g, 94%) as a light yellow powder. $^1$H NMR (DMSO-d6, 300 MHz) δ 8.62 (d, J=7.5 Hz, 2H), 8.03 (s, 1H), 8.00 (s, 1H), 7.47 (d, J=8.1 Hz, 2H), 2.37 (s, 3H). HPLC retention time: 2.84 minutes. MS ESI (m/z): 478.0/480.0 (M+H)$^+$, calc. 477.

Preparation of Intermediate F: 2-bromo-7-(1H-indol-5-yl)-5-tosyl-5H-pyrrolo[3,2-b]pyrazine To a stirred suspension of 2-bromo-7-iodo-5-tosyl-5H-pyrrolo[3,2-b]pyrazine (0.25 g, 0.52 mmol) and 1H-indol-5-ylboronic acid (0.10 mg, 0.62 mmol) in CH$_3$CN (20 mL) was added 1 M Na$_2$CO$_3$ (20 mL) followed by bis(triphenyl-phosphine)-palladium(II) dichloride (60 mg, 0.086 mmol). The resulting mixture was stirred for 2 h at 60° C. The title compound was isolated as a yellow solid via filtration from the CH$_3$CN layer (0.23 g, 94%). HPLC retention time: 3.23 minutes. MS ESI (m/z): 467.2/469.2 (M+H)$^+$, calc. 466.

Preparation of 7-(1H-indol-5-yl)-2-(3,4,5-trimethoxyphenyl)-5H-pyrrolo[3,2-b]pyrazine (Compound AL)

To a solution of 2-bromo-7-(1H-indol-5-yl)-5-tosyl-5H-pyrrolo[3,2-b]pyrazine (65 mg, 0.14 mmol) in CH$_3$CN (1 mL) in a Personal Chemistry microwave reaction vial was added 3,4,5-trimethoxyphenylboronic acid (30 mg, 0.14 mmol), bis(triphenylphosphine)-palladium(II) dichloride (7.0 mg, 0.010 mmol), and 1 M Na$_2$CO$_3$ (1 mL). The resulting mixture was de-gassed with Ar for 10 min, after which it was heated at 150° C. for 10 min in a Personal Chemistry Optimizer. The organic layer was separated, filtered, and concentrated in vacuo. The residue was dissolved in MeOH (3 mL) and acetone (2 mL), and 2 M NaOH (1.5 mL) was added. The resulting mixture was stirred at 65° C. for 30 min, after which it was partitioned between EtOAc and 1 M NaOH. The organic layer was separated, dried over MgSO$_4$, filtered, and stripped to give a residue which was purified by preparatory HPLC to give the title compound as a yellow solid. HPLC retention time: 2.25 minutes; MS ESI (m/z) 401.2 (M+1)$^+$, calc. 400.

Example 37

Preparation of 2-(3,4-dimethoxyphenyl)-7-(1H-indol-5-yl)-5H-pyrrolo[3,2-b]pyrazine (Compound AM)

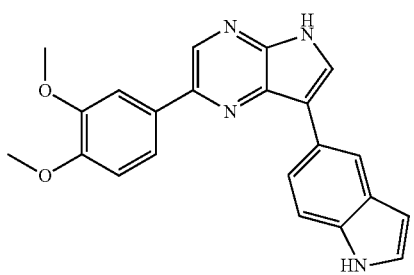 [SMILES: COc1ccc(-c2cnc3[nH]cc(-c4ccc5[nH]ccc5c4)c3n2)cc1OC]

Compound AM was prepared by a method analogous to that described in Example 36 by substituting 3,4-dimethoxy-boronic acid for 3,4,5-trimethoxyphenylboronic acid in the reaction with Intermediate F. HPLC retention time: 2.45 minutes. MS ESI (m/z): 371.2 (M+H)$^+$, calc. 370.

Example 38

Preparation of 4-(7-(1H-indol-5-yl)-5H-pyrrolo[3,2-b]pyrazin-2-yl)-2-methoxyaniline (Compound AN)

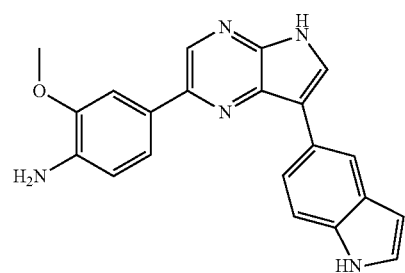 [SMILES: COc1cc(-c2cnc3[nH]cc(-c4ccc5[nH]ccc5c4)c3n2)ccc1N]

Compound AN was prepared by a method analogous to that described in Example 37 by substituting 4-amino-3-methoxyphenylboronic acid for 3,4,5-trimethoxyphenylboronic acid in the reaction with Intermediate F. HPLC retention time: 2.07 minutes. MS ESI (m/z): 356.4 (M+H)$^+$, calc. 355.

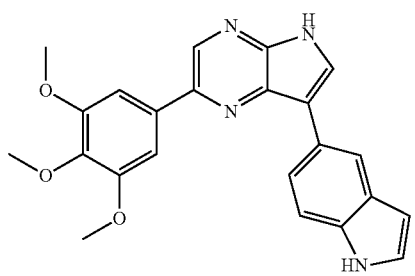

Example 39

Preparation of 4-(2-(4-(7-(1H-indol-5-yl)-5H-pyrrolo[3,2-b]pyrazin-2-yl)-2-methoxyphenoxy)ethyl)morpholine (Compound AO)

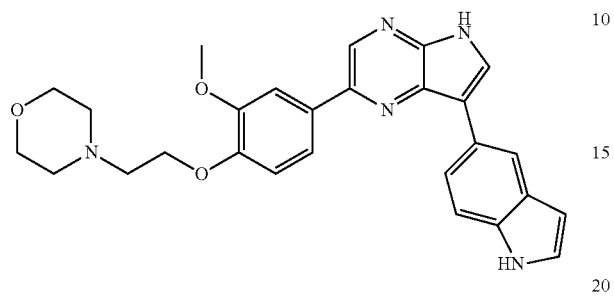

Compound AO was prepared by a method analogous to that described in Example 34 by substituting 4-(2-(2-methoxy-4-(4,4,5,5-tetramethyl-1,3,2-dioxaborolan-2-yl)phenoxy)ethyl)morpholine for 1-(2-(2-methoxy-4-(4,4,5,5-tetramethyl-1,3,2-dioxaborolan-2-yl)phenoxy)ethyl)piperazine and 2-bromo-7-(1H-indol-5-yl)-5-tosyl-5H-pyrrolo[3,2-b]pyrazine for Intermediate B. HPLC retention time: 1.59 minutes. MS ESI (m/z): 470.4 (M+H)$^+$, calc. 469.

Example 40

Scheme 6

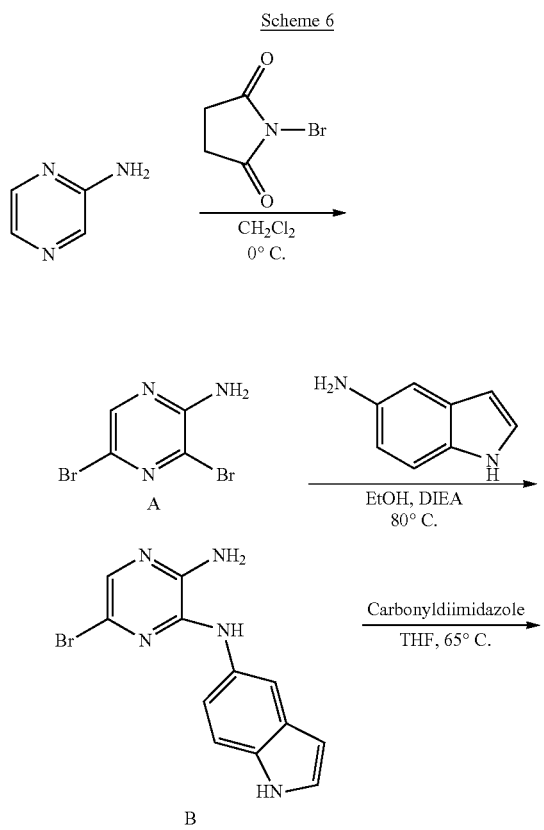

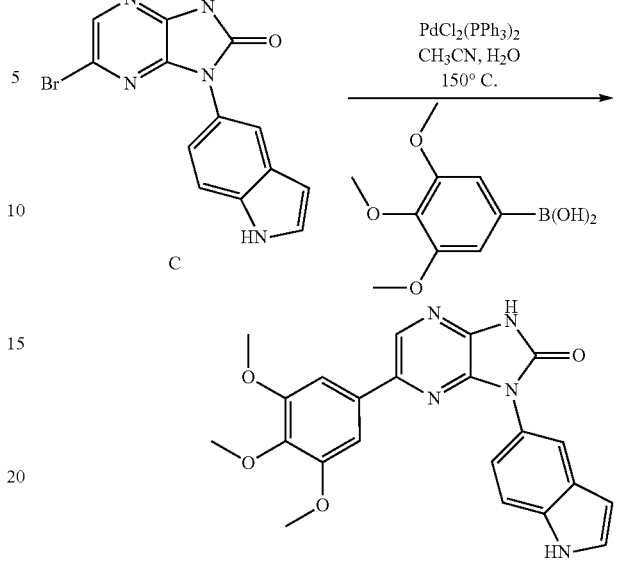

Preparation of Intermediate A: 3,5-dibromopyrazin-2-amine

Making reference to Scheme 6, to a stirred solution of aminopyrazine (8.21 g, 86.4 mmol) in anhydrous methylene chloride (215 mL) cooled to 0° C. was added N-bromosuccinimide (32.3 g, 181 mmol) in portions over a six hour period, during which time the temperature of the reaction was kept below 0° C. The resulting mixture was stored at 4° C. overnight, after which it was stirred vigorously and quenched with H$_2$O (100 mL). The organic layer was separated, after which it was washed with saturated aqueous NaHCO$_3$, washed with brine, dried over MgSO$_4$, filtered, and evaporated in vacuo to yield a residue that was triturated with 20% EtOAc in hexanes to yield the title compound (10.3 g, 47%) as a yellow/brown powder. $^1$H NMR (CDCl$_3$, 300 MHz) δ 8.02 (s, 1H), 5.05 (bs, 2H); HPLC retention time: 1.99 minutes; MS ESI (m/z): 252.0/254.0/256.2 (M+1)$^+$, calc. 251.

Preparation of Intermediate B: 6-bromo-N$^2$-(1H-indol-5-yl)pyrazine-2,3-diamine To a stirred suspension of 3,5-dibromopyrazin-2-amine (3.48 g, 13.7 mmol) and 1H-indol-5-amine (2.00 g, 15.0 mmol) in EtOH (3.5 mL) was added diisopropylethylamine [DIEA](2.60 mL, 15.0 mmol). The resulting mixture was stirred for 48 hr at 80° C., after which it was partitioned between EtOAc and H$_2$O. The organic layer was separated, after which it was washed with brine, dried over Na$_2$SO$_4$, filtered, and evaporated in vacuo to yield a residue that was purified via silica gel chromatography eluting with 1:1 EtOAc:hexanes to yield the title compound (1.75 g, 42%) as a red/brown solid. $^1$H NMR (DMSO-d6, 300 MHz): δ 10.98 (s, 1H), 8.22 (s, 1H), 7.83 (s, 1H), 7.31-7.28 (m, 3H), 7.19 (d, J=8.7 Hz, 1H), 6.43 (s, 2H), 6.36 (s, 1H); HPLC retention time: 2.07 minutes; MS ESI (m/z): 304.2/306.2 (M+1)$^+$, calc. 303.

Preparation of Intermediate C: 6-bromo-1-(1H-indol-5-yl)-1H-imidazo[4,5-b]pyrazin-2(3H)-one To a solution of 6-bromo-N$^2$-(1H-indol-5-yl)pyrazine-2,3-diamine (0.450 g, 1.48 mmol) in THF (5 mL) was added carbonyldiimidazole (1.20 g, 7.40 mmol). The resulting mixture was heated at 65° C. for 48 hr, after which it was concentrated in vacuo and partitioned between EtOAc and H₂O. The organic layer was separated, dried over MgSO₄, filtered, and concentrated in vacuo to yield a residue that was purified via silica gel chromatography eluting with EtOAc to yield the title compound (0.20 g, 41%). HPLC retention time: 2.07 minutes; MS ESI (m/z): 330.2/332.2 (M+1)⁺, calc. 329.

Preparation of 1-(1H-indol-5-yl)-6-(3,4,5-trimethoxyphenyl)-1H-imidazo[4,5-b]pyrazin-2(3H)-one (Compound AP)

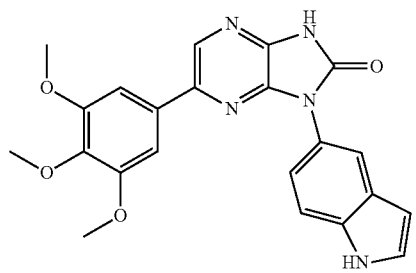

To a solution of 6-bromo-1-(1H-indol-5-yl)-1H-imidazo[4,5-b]pyrazin-2(3H)-one (27 mg, 0.08 mmol) in CH₃CN (1 mL) in a Personal Chemistry microwave reaction vial was added 3,4,5-trimethoxyphenylboronic acid (17 mg, 0.08 mmol), bis(triphenylphosphine)-palladium(II) dichloride (6.0 mg, 0.008 mmol), and 1 M Na₂CO₃ (1 mL). The resulting mixture was de-gassed with Ar for 10 min, after which it was heated at 150° C. for 10 min in a Personal Chemistry Optimizer. The organic layer was separated, filtered, and concentrated in vacuo. The residue was purified by preparatory HPLC to yield the title compound (6.5 mg, 19%). ¹H NMR (DMSO-d6, 300 MHz): δ 12.18 (s, 1H), 11.28 (s, 1H), 8.57 (s, 1H), 7.83 (d, J=1.8 Hz, 1H), 7.52 (d, J=8.4 Hz, 1H), 7.42 (m, 1H), 7.37 (dd, J=1.8, 8.4 Hz, 1H), 7.20 (s, 2H), 6.51 (m, 1H), 3.78 (s, 6H), 3.66 (s, 3H); HPLC retention time: 2.30 minutes; MS ESI (m/z): 418.4 (M+1)⁺, calc. 417.

Example 41

Preparation of 1-(1-methyl-1H-indol-5-yl)-6-(3,4,5-trimethoxyphenyl)-1H-imidazo[4,5-b]pyrazin-2(3H)-one (Compound AQ)

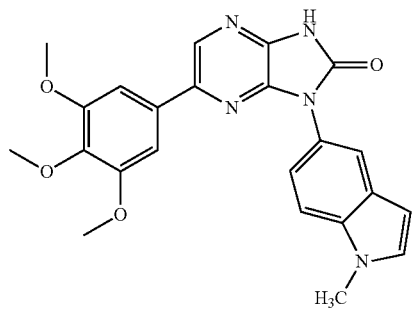 [SMILES: COc1cc(-c2cnc3[nH]c(=O)n(-c4ccc5c(ccn5C)c4)c3n2)cc(OC)c1OC]

Compound AQ was prepared by a method analogous to that described in Example 40 by substituting 1-methyl-1H-indol-5-amine for 1H-indol-5-amine in the reaction with Intermediate A. 4.0 mg recovered. ¹H NMR (DMSO-d6, 300 MHz): δ 12.22 (s, 1H), 8.57 (s, 1H), 7.85 (d, J=1.8 Hz, 1H), 7.57 (d, J=8.7 Hz, 1H), 7.45 (d, J=1.8 Hz), 7.41 (m, 2H), 7.20 (s, 2H), 6.50 (d, J=3.0 Hz, 1H), 3.84 (s, 3H), 3.78 (s, 6H), 3.66 (s, 3H); HPLC retention time: 2.50 minutes. MS ESI (m/z): 432.4 (M+H)⁺, calc. 431.

Example 42

Preparation of 6-(4-hydroxyphenyl)-1-(1-methyl-1H-indol-5-yl)-1H-imidazo[4,5-b]pyrazin-2(3H)-one (Compound AR)

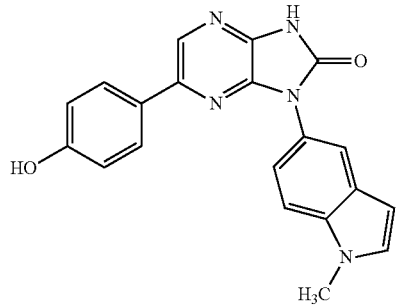 [SMILES: Cn1ccc2cc(-n3c(=O)[nH]c4ncc(-c5ccc(O)cc5)nc43)ccc21]

Compound AR was prepared by a method analogous to that described in Example 40 by substituting 1-methyl-1H-indol-5-amine for 1H-indol-5-amine in the reaction with Intermediate A to prepare 6-bromo-1-(1-methyl-1H-indol-5-yl)-1H-imidazo[4,5-b]pyrazin-2(3H)-one. In a procedure similar to that used to synthesize Compound D, 4-hydroxyphenylboronic acid was substituted for 3,4,5-trimethoxyphenylboronic acid and 6-bromo-1-(1-methyl-1H-indol-5-yl)-1H-imidazo[4,5-b]pyrazin-2(3H)-one was substituted for 6-bromo-1-(1H-indol-5-yl)-1H-imidazo[4,5-b]pyrazin-2(3H)-one to obtain the title compound. 2.2 mg recovered. HPLC retention time: 2.18 minutes. MS ESI (m/z): 358.2 (M+H)⁺, calc. 357.

Example 43

Preparation of 6-(3,5-dimethylphenyl)-1-(1-methyl-1H-indol-5-yl)-1H-imidazo[4,5-b]pyrazin-2(3H)-one (Compound AS)

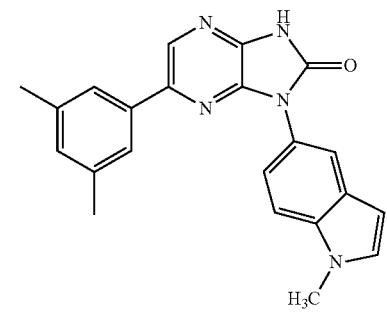 [SMILES: Cc1cc(C)cc(-c2cnc3[nH]c(=O)n(-c4ccc5c(ccn5C)c4)c3n2)c1]

Compound AS was prepared by a method analogous to that described in Example 42 by substituting 3,5-dimethylphenylboronic acid for 4-hydroxyphenylboronic acid in the reaction with 6-bromo-1-(1-methyl-1H-indol-5-yl)-1H-imidazo[4,5-b]pyrazin-2(3H)-one. 1.6 mg recovered. HPLC retention time: 3.04 minutes. MS ESI (m/z): 370.2 (M+H)+, calc. 369.

Example 44

Preparation of 1-(1H-indol-5-yl)-6-(pyridin-4-yl)-1H-imidazo[4,5-b]pyrazin-2(3H)-one (Compound AT)

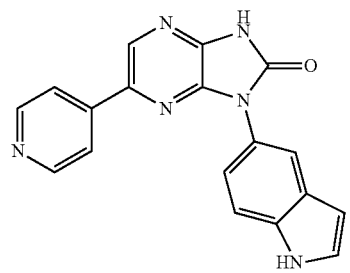

Compound AT was prepared by a method analogous to that described in Example 40 by substituting pyridin-4-ylboronic acid for 3,4,5-trimethoxyphenylboronic acid in the reaction with Compound C. 1.6 mg recovered. HPLC retention time: 1.10 minutes. MS ESI (m/z): 329.4 (M+H)+, calc. 328.

Example 45

Preparation of 6-(4-hydroxyphenyl)-1-(1H-indol-5-yl)-1H-imidazo[4,5-b]pyrazin-2(3H)-one (Compound AU)

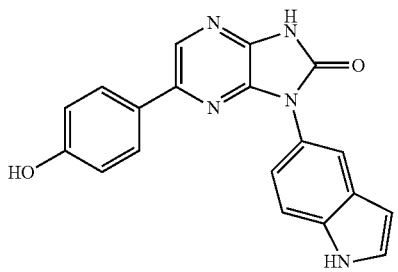 [SMILES: O=c1[nH]c2ncc(-c3ccc(O)cc3)nc2n1-c1ccc2[nH]ccc2c1]

Compound AU was prepared by a method analogous to that described in Example 40 by substituting by substituting 4-hydroxyphenylboronic acid for 3,4,5-trimethoxyphenylboronic acid in the reaction with Compound C. 13.7 mg recovered. $^1$H NMR (DMSO-d6, 300 MHz): δ 12.07 (s, 1H), 11.30 (s, 1H), 9.61 (s, 1H), 8.38 (s, 1H), 7.69 (m, 2H), 7.52 (d, J=8.4 Hz, 1H), 7.44 (m, 1H), 7.26 (dd, J=1.8, 8.7 Hz), 6.76 (dd, J=2.4, 12.9 Hz), 6.52 (m, 1H); HPLC retention time: 1.99 minutes. MS ESI (m/z): 344.2 (M+H)+, calc. 343.

Example 46

Preparation of 6-(3,5-dimethylphenyl)-1-(1H-indol-5-yl)-1H-imidazo[4,5-b]pyrazin-2(3H)-one (Compound AV)

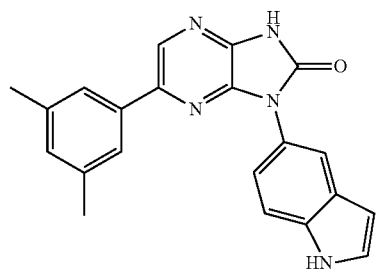 [SMILES: Cc1cc(C)cc(-c2cnc3[nH]c(=O)n(-c4ccc5[nH]ccc5c4)c3n2)c1]

Compound AV was prepared by a method analogous to that described in Example 40 by substituting 3,5-dimethylphenylboronic acid for 3,4,5-trimethoxyphenylboronic acid in the reaction with Compound C. 4.3 mg recovered. HPLC retention time: 2.80 minutes. MS ESI (m/z): 356.2 (M+H)+, calc. 355.

Examples 47-119, shown in Tables 1 and 2 below, were synthesized in parallel according to procedures given below in Schemes 7 and 8, using the reagents also shown in Tables 1 and 2.

Examples 47-67

Scheme 7

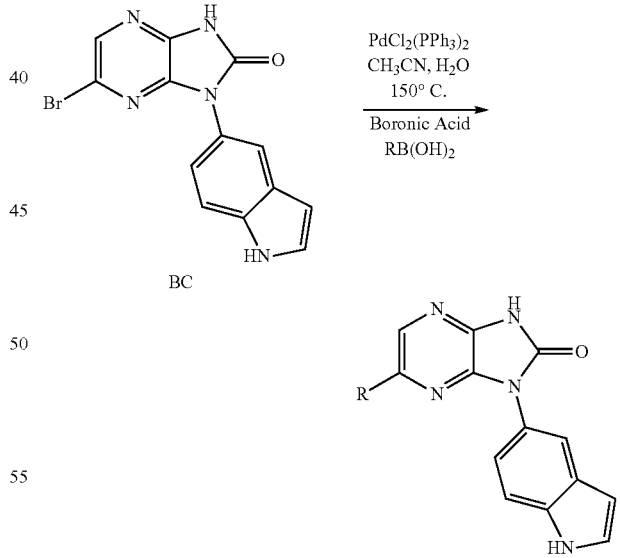

Preparation of 1H-imidazo[4,5-b]pyrazin-2(3H)-one compounds in Table 1

Making reference to Scheme 7, to a solution of 6-bromo-1-(1H-indol-5-yl)-1H-imidazo[4,5-b]pyrazin-2(3H)-one (27 mg, 0.08 mmol) (Intermediate C) in CH$_3$CN (1 mL) in a Personal Chemistry microwave reaction vial was added 3,4,5-trimethoxyphenylboronic acid (17 mg, 0.08 mmol), bis(triphenylphosphine)-palladium(II) dichloride (6.0 mg, 0.008 mmol), and 1 M $Na_2CO_3$ (1 mL). The resulting mixture was de-gassed with Ar for 10 min, after which it was heated at 150° C. for 10 min in a Personal Chemistry Optimizer. The organic layer was separated, filtered, and concentrated in vacuo. The residue was purified by preparatory HPLC to yield the title compounds (>3 mg) in Table 1, isolated as amorphous solids. Examples 47-67 were were also physically characterized by electrospray ionization mass spectrometry. Structures and molecular masses are given below in Table 1.

TABLE 1

| Ex. | Boronic Acid RB(OH)$_2$ | Structure | IUPAC Name | MW | Cmpd ID |
|---|---|---|---|---|---|
| 47 | 3,4-dimethoxyphenyl boronic acid | 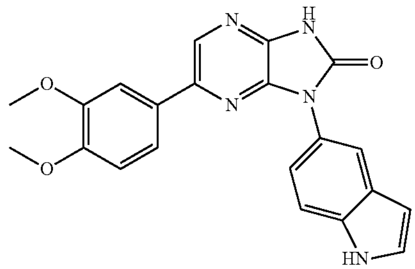 [SMILES: COc1ccc(-c2cnc3[nH]c(=O)n(-c4ccc5[nH]ccc5c4)c3n2)cc1OC] | 6-(3,4-dimethoxyphenyl)-1-(1H-indol-5-yl)-1H-imidazo[4,5-b]pyrazin-2(3H)-one | 387.13 | AW |
| 48 | 3,5-dichlorophenyl boronic acid | 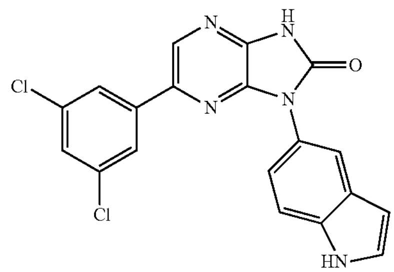 [SMILES: O=c1[nH]c2ncc(-c3cc(Cl)cc(Cl)c3)nc2n1-c1ccc2[nH]ccc2c1] | 6-(3,5-dichlorophenyl)-1-(1H-indol-5-yl)-1H-imidazo[4,5-b]pyrazin-2(3H)-one | 395.03 | AX |
| 49 | 3-fluoro-4-methoxyphenyl boronic acid | 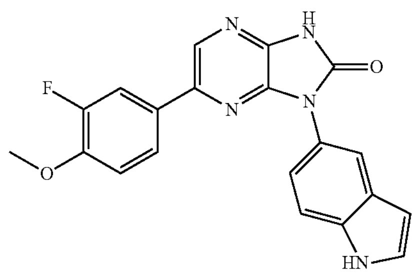 [SMILES: COc1ccc(-c2cnc3[nH]c(=O)n(-c4ccc5[nH]ccc5c4)c3n2)cc1F] | 6-(3-fluoro-4-methoxyphenyl)-1-(1H-indol-5-yl)-1H-imidazo[4,5-b]pyrazin-2(3H)-one | 375.11 | AY |
| 50 | 3-amino-4-methoxyphenyl boronic acid | 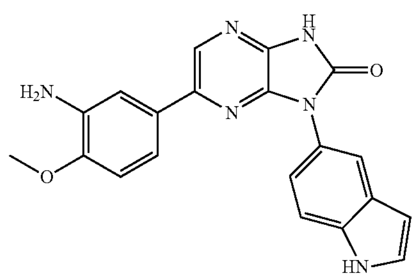 [SMILES: COc1ccc(-c2cnc3[nH]c(=O)n(-c4ccc5[nH]ccc5c4)c3n2)cc1N] | 6-(3-amino-4-methoxyphenyl)-1-(1H-indol-5-yl)-1H-imidazo[4,5-b]pyrazin-2(3H)-one | 372.13 | AZ |
| 51 | 4-methoxy-3,5-dimethylphenyl boronic acid | 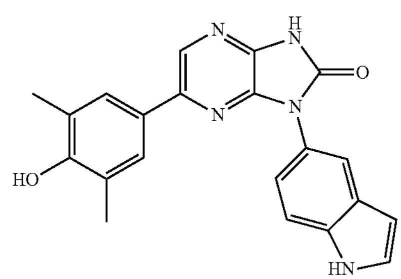 [SMILES: Cc1cc(-c2cnc3[nH]c(=O)n(-c4ccc5[nH]ccc5c4)c3n2)cc(C)c1O] | 1-(1H-indol-5-yl)-6-(4-methoxy-3,5-dimethylphenyl)-1H-imidazo[4,5-b]pyrazin-2(3H)-one | 371.40 | BA |

TABLE 1-continued

| Ex. | Boronic Acid RB(OH)$_2$ | Structure | IUPAC Name | MW | Cmpd ID |
|---|---|---|---|---|---|
| 52 | 4-morpholinophenyl boronic acid | 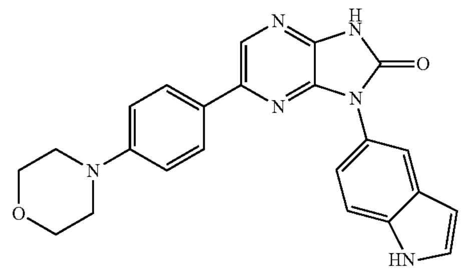 [SMILES: O=c1[nH]c2ncc(-c3ccc(N4CCOCC4)cc3)nc2n1-c1ccc2[nH]ccc2c1] | 1-(1H-indol-5-yl)-6-(4-morpholinophenyl)-1H-imidazo[4,5-b]pyrazin-2(3H)-one | 412.45 | BB |
| 53 | Indole-5-boronic acid | 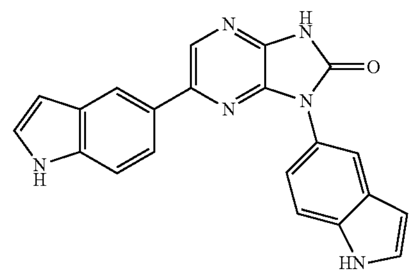 [SMILES: O=c1[nH]c2ncc(-c3ccc4[nH]ccc4c3)nc2n1-c1ccc2[nH]ccc2c1] | 1,6-di(1H-indol-5-yl)-1H-imidazo[4,5-b]pyrazin-2(3H)-one | 366.39 | BC |
| 54 | 3-hydroxyphenyl boronic acid | 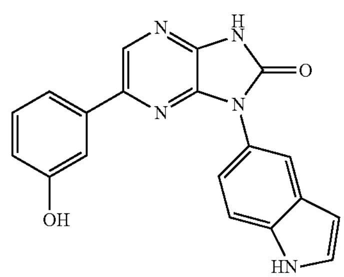 [SMILES: O=c1[nH]c2ncc(-c3cccc(O)c3)nc2n1-c1ccc2[nH]ccc2c1] | 6-(3-hydroxyphenyl)-1-(1H-indol-5-yl)-1H-imidazo[4,5-b]pyrazin-2(3H)-one | 343.35 | BD |
| 55 | 4-hydroxy-3-methoxyphenyl | 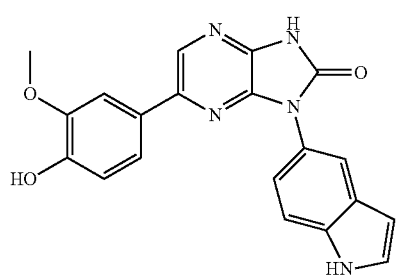 [SMILES: COc1cc(-c2cnc3[nH]c(=O)n(-c4ccc5[nH]ccc5c4)c3n2)ccc1O] | 6-(4-hydroxy-3-methoxyphenyl)-1-(1H-indol-5-yl)-1H-imidazo[4,5-b]pyrazin-2(3H)-one | 373.37 | BE |
| 56 | indole-6-boronic | 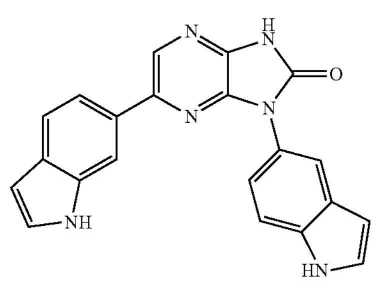 [SMILES: O=c1[nH]c2ncc(-c3ccc4cc[nH]c4c3)nc2n1-c1ccc2[nH]ccc2c1] | 1-(1H-indol-5-yl)-6-(1H-indol-6-yl)-1H-imidazo[4,5-b]pyrazin-2(3H)-one | 366.39 | BF |

TABLE 1-continued

| Ex. | Boronic Acid RB(OH)$_2$ | Structure | IUPAC Name | MW | Cmpd ID |
|---|---|---|---|---|---|
| 57 | 3-methoxy-4-(2-morpholinoethoxy) phenyl boronic acid | 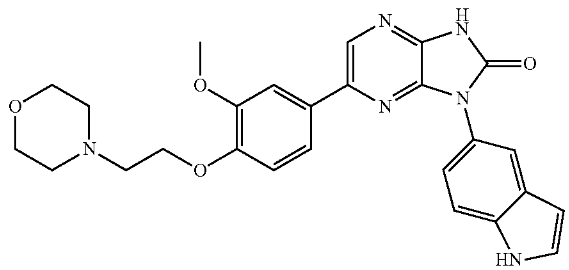 [SMILES: COc1cc(-c2cnc3[nH]c(=O)n(-c4ccc5[nH]ccc5c4)c3n2)ccc1OCCN1CCOCC1] | 1-(1H-indol-5-yl)-6-(3-methoxy-4-(2-morpholinoethoxy) phenyl)-1H-imidazo[4,5-b]pyrazin-2(3H)-one | 486.53 | BG |
| 58 | 2,5-difluoro-4-hydroxyphenyl boronic acid | 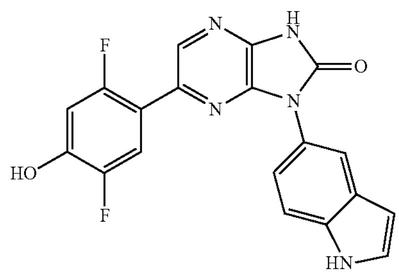 [SMILES: O=c1[nH]c2ncc(-c3cc(F)c(O)cc3F)nc2n1-c1ccc2[nH]ccc2c1] | 6-(2,5-difluoro-4-hydroxyphenyl)-1-(1H-indol-5-yl)-1H-imidazo[4,5-b]pyrazin-2(3H)-one | 379.33 | BH |
| 59 | 3,5-difluoro-4-hydroxyphenyl boronic acid | 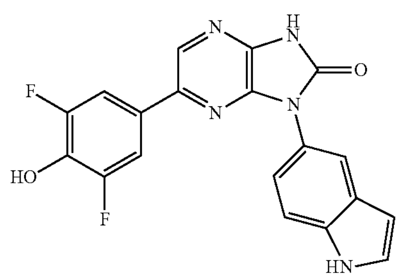 [SMILES: O=c1[nH]c2ncc(-c3cc(F)c(O)c(F)c3)nc2n1-c1ccc2[nH]ccc2c1] | 6-(3,5-difluoro-4-hydroxyphenyl)-1-(1H-indol-5-yl)-1H-imidazo[4,5-b]pyrazin-2(3H)-one | 379.33 | BI |
| 60 | 4-amino-3-methoxyphenyl boronic acid | 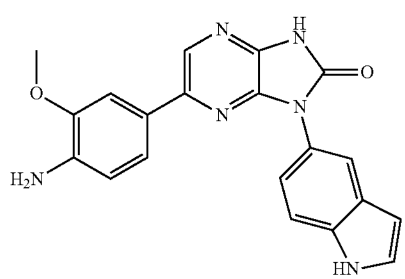 [SMILES: COc1cc(-c2cnc3[nH]c(=O)n(-c4ccc5[nH]ccc5c4)c3n2)ccc1N] | 6-(4-amino-3-methoxyphenyl)-1-(1H-indol-5-yl)-1H-imidazo[4,5-b]pyrazin-2(3H)-one | 372.39 | BJ |
| 61 | 3,5-difluorophenyl boronic acid | 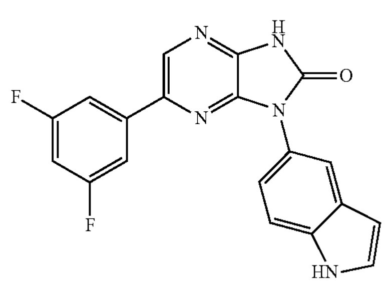 [SMILES: O=c1[nH]c2ncc(-c3cc(F)cc(F)c3)nc2n1-c1ccc2[nH]ccc2c1] | 6-(3,5-difluorophenyl)-1-(1H-indol-5-yl)-1H-imidazo[4,5-b]pyrazin-2(3H)-one | 363.33 | BK |

TABLE 1-continued

| Ex. | Boronic Acid RB(OH)₂ | Structure | IUPAC Name | MW | Cmpd ID |
|---|---|---|---|---|---|
| 62 | 4-hydroxy-3,5-dimethoxyphenyl boronic acid | 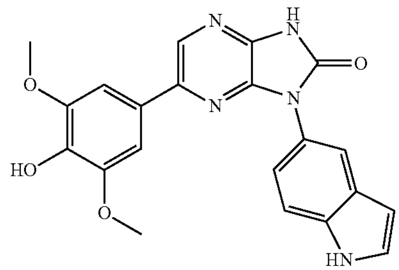 [SMILES: COc1cc(-c2cnc3[nH]c(=O)n(-c4ccc5[nH]ccc5c4)c3n2)cc(OC)c1O] | 6-(4-hydroxy-3,5-dimethoxyphenyl)-1-(1H-indol-5-yl)-1H-imidazo[4,5-b]pyrazin-2(3H)-one | 403.40 | BL |
| 63 | 2,3-dihydrobenzo[b][1,4]dioxin-6-boronic acid | 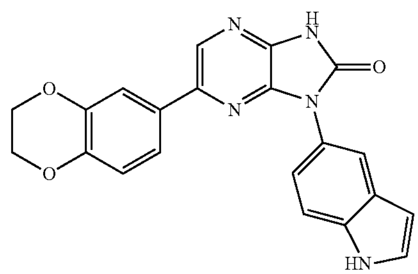 [SMILES: O=c1[nH]c2ncc(-c3ccc4c(c3)OCCO4)nc2n1-c1ccc2[nH]ccc2c1] | 6-(2,3-dihydrobenzo[b][1,4]dioxin-6-yl)-1-(1H-indol-5-yl)-1H-imidazo[4,5-b]pyrazin-2(3H)-one | 385.39 | BM |
| 64 | 4-hydroxy-3,5-dimethylphenyl boronic acid | 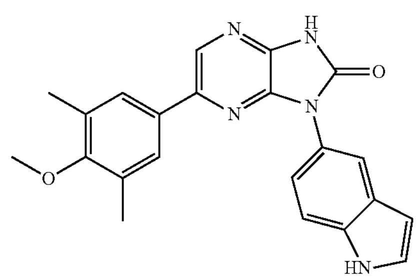 [SMILES: COc1c(C)cc(-c2cnc3[nH]c(=O)n(-c4ccc5[nH]ccc5c4)c3n2)cc1C] | 6-(4-hydroxy-3,5-dimethylphenyl)-1-(1H-indol-5-yl)-1H-imidazo[4,5-b]pyrazin-2(3H)-one | 385.43 | BN |
| 65 | 3,5-dimethoxyphenyl boronic acid | 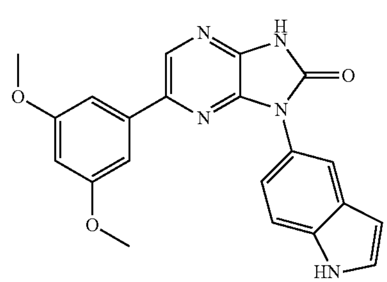 [SMILES: COc1cc(OC)cc(-c2cnc3[nH]c(=O)n(-c4ccc5[nH]ccc5c4)c3n2)c1] | 6-(3,5-dimethoxyphenyl)-1-(1H-indol-5-yl)-1H-imidazo[4,5-b]pyrazin-2(3H)-one | 387.40 | BO |

TABLE 1-continued

| Ex. | Boronic Acid RB(OH)$_2$ | Structure | IUPAC Name | MW | Cmpd ID |
|---|---|---|---|---|---|
| 66 | 2-(4-methylpiperazin-1-yl)pyridin-4-boronic acid | 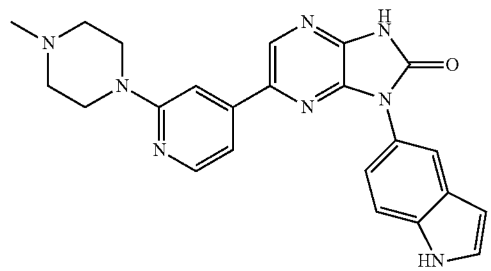 [SMILES: CN1CCN(c2cc(-c3cnc4[nH]c(=O)n(-c5ccc6[nH]ccc6c5)c4n3)ccn2)CC1] | 1-(1H-indol-5-yl)-6-(2-(4-methylpiperazin-1-yl)pyridin-4-yl)-1H-imidazo[4,5-b]pyrazin-2(3H)-one | 426.50 | BP |
| 67 | (3-methoxy-4-(2-(piperazin-1-yl)ethoxy)phenyl | 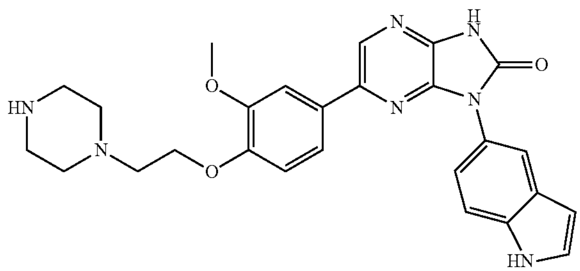 [SMILES: COc1cc(-c2cnc3[nH]c(=O)n(-c4ccc5[nH]ccc5c4)c3n2)ccc1OCCN1CCNCC1] | 1-(1H-indol-5-yl)-6-(3-methoxy-4-(2-(piperazin-1-yl)ethoxy)phenyl)-1H-imidazo[4,5-b]pyrazin-2(3H)-one | 485.55 | BQ |

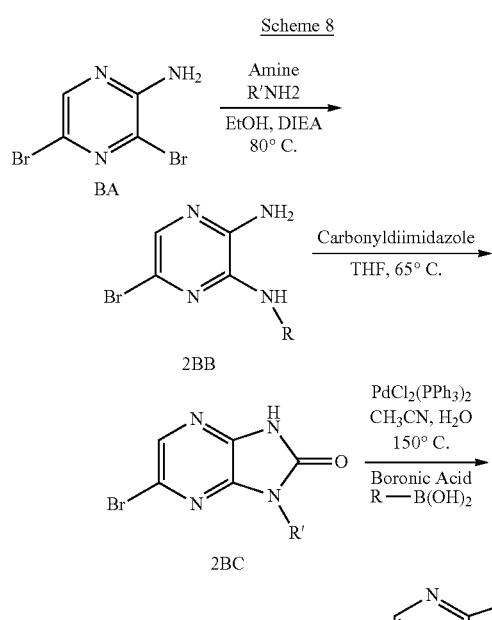

Preparation of Intermediates B

Making reference to Scheme 8, to a stirred suspension of 3,5-dibromopyrazin-2-amine (3.48 g, 13.7 mmol) and the corresponding alkyl, aryl, or heteroaryl amine (15.0 mmol) in EtOH (3.5 mL) was added diisopropylethylamine [DIEA] (2.60 mL, 15.0 mmol). The resulting mixture was stirred for 48 hr at 80° C., after which it was partitioned between EtOAc and H$_2$O. The organic layer was separated, after which it was washed with brine, dried over Na$_2$SO$_4$, filtered, and evaporated in vacuo to yield a residue that was purified by automated medium pressure silica gel chromatography eluting with 1:1 EtOAc:hexanes to yield the intermediates as amorphous solids.

Preparation of intermediates C

Intermediates B (0.450 g, 1.5 mmol) were dissolved in THF (5 mL) and treated with carbonyldiimidazole (1.20 g, 7.40 mmol). The resulting mixture was heated at 65° C. for 48 hr, after which it was concentrated in vacuo and partitioned between EtOAc and H$_2$O. The organic layer was separated, dried over MgSO$_4$, filtered, and concentrated in vacuo to yield a residue that was purified via automated silica gel chromatography eluting with hexane/EtOAc to yield the intermediates 2BC as amorphous solids.

Preparation of 1H-imidazo[4,5-b]pyrazin-2(3H)-one compounds in Table 2

Individual solutions of intermediates 2BC (0.08 mmol) in CH$_3$CN (1 mL) in a Personal Chemistry microwave reaction vial was added the corresponding lboronic acid (0.08 mmol), bis(triphenylphosphine)-palladium(II) dichloride (6.0 mg, 0.008 mmol), and 1 M Na$_2$CO$_3$ (1 mL). The resulting mixture was de-gassed with Ar for 10 min, after which it was heated at 150° C. for 10 min in a Personal Chemistry Optimizer. The organic layer was separated, filtered, and concentrated in vacuo. The residue was purified by preparatory HPLC to yield the title compounds in Table 2 (>3 mg) as amorphous solids. Examples 68-118 were were physically characterized by electrospray ionization mass spectrometry. Structures and molecular masses are given below in Table 2.

TABLE 2

| Ex | Boronic Acid RB(OH)$_2$ | Amine R'NH$_2$ | Structure | IUPAC Name | MW | Cmpd ID |
|---|---|---|---|---|---|---|
| 68 | 3,4,5-trimethoxyphenyl boronic acid | 4-methoxy-aniline | 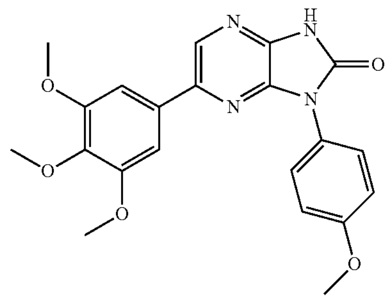 [SMILES: COc1ccc(-n2c(=O)[nH]c3ncc(-c4cc(OC)c(OC)c(OC)c4)nc32)cc1] | 1-(4-methoxyphenyl)-6-(3,4,5-trimethoxyphenyl)-1H-imidazo[4,5-b]pyrazin-2(3H)-one | 408.42 | BR |
| 69 | 3,4-dimethoxyphenyl boronic acid | 4-methoxy-aniline | 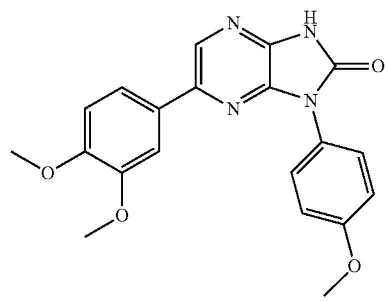 [SMILES: COc1ccc(-n2c(=O)[nH]c3ncc(-c4ccc(OC)c(OC)c4)nc32)cc1] | 6-(3,4-dimethoxyphenyl)-1-(4-methoxyphenyl)-1H-imidazo[4,5-b]pyrazin-2(3H)-one | 378.39 | BS |
| 70 | 4-hydroxyphenyl boronic acid | 4-methoxy-aniline | 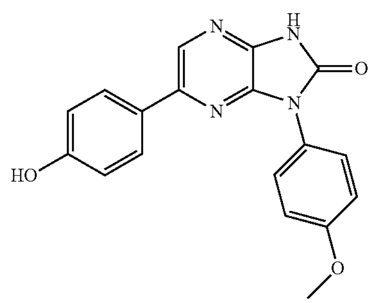 [SMILES: COc1ccc(-n2c(=O)[nH]c3ncc(-c4ccc(O)cc4)nc32)cc1] | 6-(4-hydroxyphenyl)-1-(4-methoxyphenyl)-1H-imidazo[4,5-b]pyrazin-2(3H)-one | 334.34 | BT |
| 71 | pyridin-4-boronic acid | 4-methoxy-aniline | 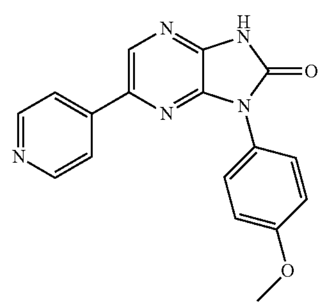 [SMILES: COc1ccc(-n2c(=O)[nH]c3ncc(-c4ccncc4)nc32)cc1] | 1-(4-methoxyphenyl)-6-(pyridin-4-yl)-1H-imidazo[4,5-b]pyrazin-2(3H)-one | 319.33 | BU |
| 72 | 3,4,5-trimethoxyphenyl boronic acid | 2-methyl-5-amino-indole | 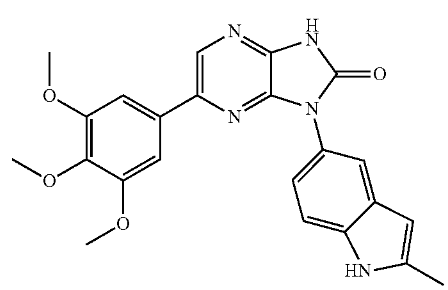 | 1-(2-methyl-1H-indol-5-yl)-6-(3,4,5-trimethoxyphenyl)-1H-imidazo[4,5-b]pyrazin-2(3H)-one | 431.45 | BV |

TABLE 2-continued

| Ex | Boronic Acid RB(OH)$_2$ | Amine R'NH$_2$ | Structure | IUPAC Name | MW | Cmpd ID |
|---|---|---|---|---|---|---|
| 73 | 3,5-dichlorophenyl boronic acid | 2-methyl-5-amino indole | 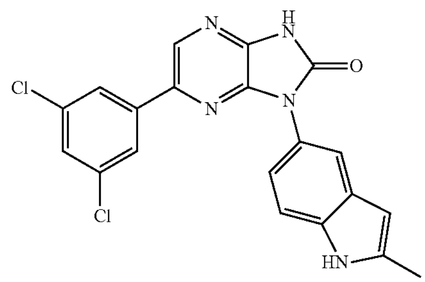 [SMILES: Cc1cc2cc(-n3c(=O)[nH]c4ncc(-c5cc(Cl)cc(Cl)c5)nc43)ccc2[nH]1] | 6-(3,5-dichlorophenyl)-1-(2-methyl-1H-indol-5-yl)-1H-imidazo[4,5-b]pyrazin-2(3H)-one | 410.27 | BW |
| 74 | 3,4,5-trimethoxyphenyl boronic acid | 1-amino-cyclopentane | 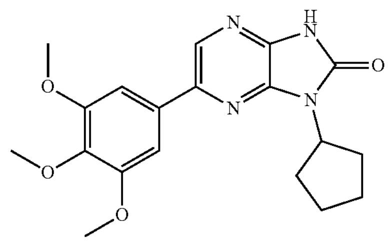 [SMILES: COc1cc(-c2cnc3[nH]c(=O)n(C4CCCC4)c3n2)cc(OC)c1OC] | 1-cyclopentyl-6-(3,4,5-trimethoxyphenyl)-1H-imidazo[4,5-b]pyrazin-2(3H)-one | 370.41 | BX |
| 75 | 3,4-dimethoxyphenyl boronic acid | 1-amino-cyclopentane | 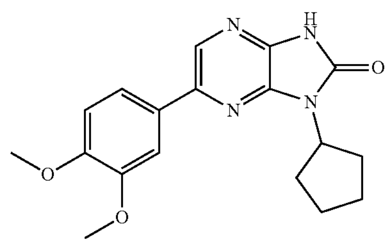 [SMILES: COc1ccc(-c2cnc3[nH]c(=O)n(C4CCCC4)c3n2)cc1OC] | 1-cyclopentyl-6-(3,4-dimethoxyphenyl)-1H-imidazo[4,5-b]pyrazin-2(3H)-one | 340.39 | BY |
| 76 | 4-hydroxyphenyl boronic acid | 1-amino-cyclopentane | 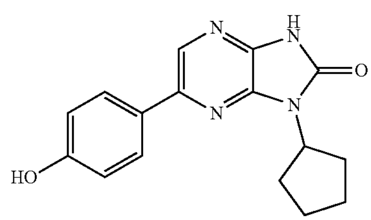 [SMILES: O=c1[nH]c2ncc(-c3ccc(O)cc3)nc2n1C1CCCC1] | 1-cyclopentyl-6-(4-hydroxyphenyl)-1H-imidazo[4,5-b]pyrazin-2(3H)-one | 296.33 | BZ |
| 77 | pyridin-4-boronic acid | 1-amino-cyclopentane | 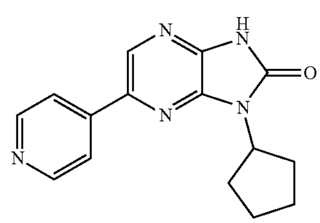 [SMILES: O=c1[nH]c2ncc(-c3ccncc3)nc2n1C1CCCC1] | 1-cyclopentyl-6-(pyridin-4-yl)-1H-imidazo[4,5-b]pyrazin-2(3H)-one | 281.32 | CA |
| 78 | 3,4,5-trimethoxyphenyl boronic acid | Cyclopropane-methyl amine | 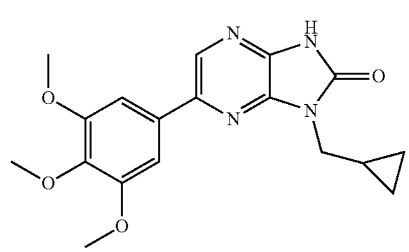 [SMILES: COc1cc(-c2cnc3[nH]c(=O)n(CC4CC4)c3n2)cc(OC)c1OC] | 1-(cyclopropylmethyl)-6-(3,4,5-trimethoxyphenyl)-1H-imidazo[4,5-b]pyrazin-2(3H)-one | 356.38 | CB |

TABLE 2-continued

| Ex | Boronic Acid RB(OH)$_2$ | Amine R'NH$_2$ | Structure | IUPAC Name | MW | Cmpd ID |
|---|---|---|---|---|---|---|
| 79 | 3,4-dimethoxyphenyl boronic acid | Cyclopropane-methyl amine | 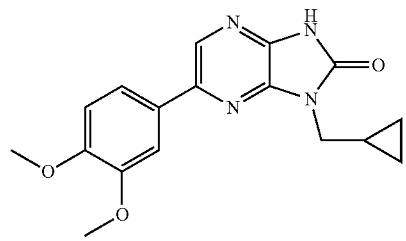 [SMILES: COc1ccc(-c2cnc3[nH]c(=O)n(CC4CC4)c3n2)cc1OC] | 1-(cyclopropylmethyl)-6-(3,4-dimethoxyphenyl)-1H-imidazo[4,5-b]pyrazin-2(3H)-one | 326.36 | CC |
| 80 | 3,5-dichlorophenyl boronic acid | Cyclopropane-methyl amine | 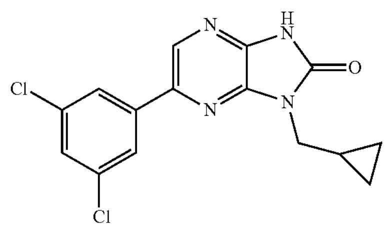 [SMILES: O=c1[nH]c2ncc(-c3cc(Cl)cc(Cl)c3)nc2n1CC1CC1] | 1-(cyclopropylmethyl)-6-(3,5-dichlorophenyl)-1H-imidazo[4,5-b]pyrazin-2(3H)-one | 335.20 | CD |
| 81 | 4-hydroxyphenyl boronic acid | Cyclopropane-methyl amine | 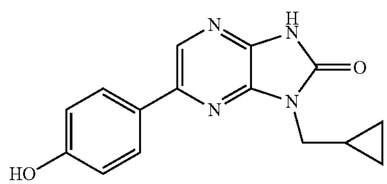 [SMILES: O=c1[nH]c2ncc(-c3ccc(O)cc3)nc2n1CC1CC1] | 1-(cyclopropylmethyl)-6-(4-hydroxyphenyl)-1H-imidazo[4,5-b]pyrazin-2(3H)-one | 282.30 | CE |
| 82 | 4-aminopyridine boronic acid | Cyclopropane-methyl amine | 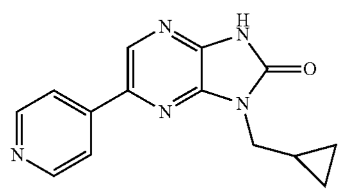 [SMILES: O=c1[nH]c2ncc(-c3ccncc3)nc2n1CC1CC1] | 1-(cyclopropylmethyl)-6-(pyridin-4-yl)-1H-imidazo[4,5-b]pyrazin-2(3H)-one | 267.29 | CF |
| 83 | 3,4,5-trimethoxyphenyl boronic acid | 1H-Indazol-5-amine | 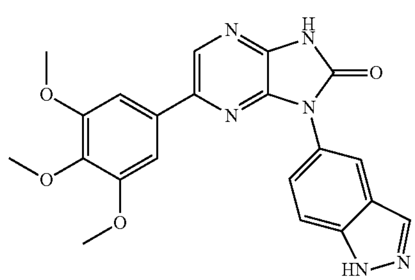 | 1-(1H-indazol-5-yl)-6-(3,4,5-trimethoxyphenyl)-1H-imidazo[4,5-b]pyrazin-2(3H)-one | 418.42 | CG |
| 84 | 4-hydroxypheny boronic acid | 2-methyl-5-amino-indole | 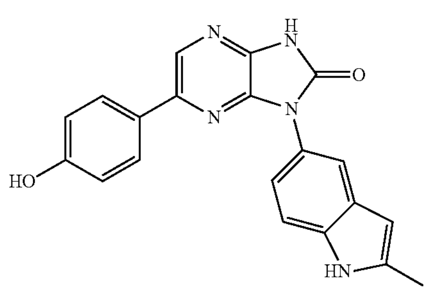 [SMILES: Cc1cc2cc(-n3c(=O)[nH]c4ncc(-c5ccc(O)cc5)nc43)ccc2[nH]1] | 6-(4-hydroxyphenyl)-1-(2-methyl-1H-indol-5-yl)-1H-imidazo[4,5-b]pyrazin-2(3H)-one | 357.37 | CH |

TABLE 2-continued

| Ex | Boronic Acid RB(OH)$_2$ | Amine R'NH$_2$ | Structure | IUPAC Name | MW | Cmpd ID |
|---|---|---|---|---|---|---|
| 85 | pyridin-4-boronic acid | 2-methyl-5-amino-indole | 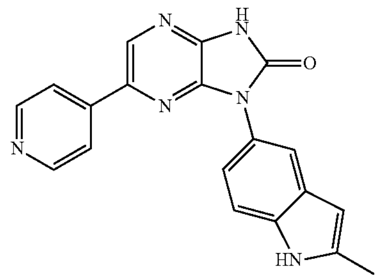 [SMILES: Cc1cc2cc(-n3c(=O)[nH]c4ncc(-c5ccncc5)nc43)ccc2[nH]1] | 1-(2-methyl-1H-indol-5-yl)-6-(pyridin-4-yl)-1H-imidazo[4,5-b]pyrazin-2(3H)-one | 342.36 | CI |
| 86 | 4-morpholinophenyl boronic acid | Cyclopropane-methyl amine | 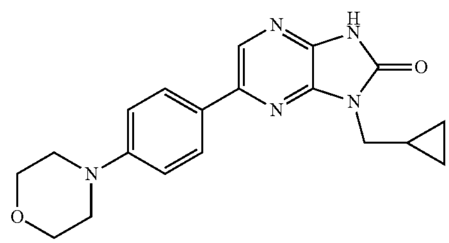 [SMILES: O=c1[nH]c2ncc(-c3ccc(N4CCOCC4)cc3)nc2n1CC1CC1] | 1-(cyclopropylmethyl)-6-(4-morpholinophenyl)-1H-imidazo[4,5-b]pyrazin-2(3H)-one | 351.41 | CJ |
| 87 | 3,4-dimethoxyphenyl boronic acid | 1H-Indazol-5-amine | 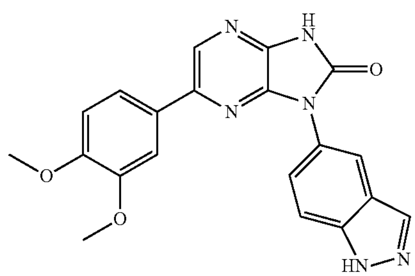 [SMILES: COc1ccc(-c2cnc3[nH]c(=O)n(-c4ccc5[nH]ncc5c4)c3n2)cc1OC] | 6-(3,4-dimethoxyphenyl)-1-(1H-indazol-5-yl)-1H-imidazo[4,5-b]pyrazin-2(3H)-one | 388.39 | CK |
| 88 | 4-aminopyridine boronic acid | 1H-Indazol-5-amine | 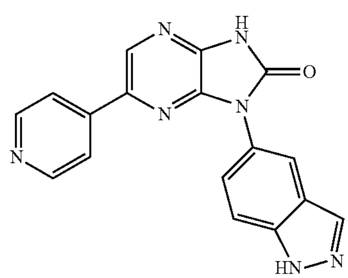 [SMILES: O=c1[nH]c2ncc(-c3ccncc3)nc2n1-c1ccc2[nH]ncc2c1] | 1-(1H-indazol-5-yl)-6-(pyridin-4-yl)-1H-imidazo[4,5-b]pyrazin-2(3H)-one | 329.32 | CL |
| 89 | 4-morpholinophenyl boronic acid | 1H-Indazol-5-amine | 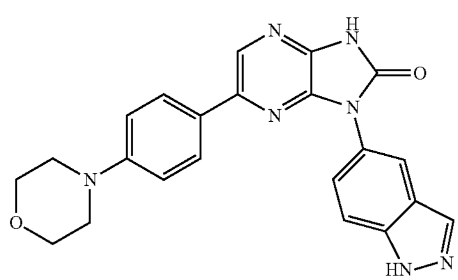 [SMILES: O=c1[nH]c2ncc(-c3ccc(N4CCOCC4)cc3)nc2n1-c1ccc2[nH]ncc2c1] | 1-(1H-indazol-5-yl)-6-(4-morpholinophenyl)-1H-imidazo[4,5-b]pyrazin-2(3H)-one | 413.44 | CM |

TABLE 2-continued

| Ex | Boronic Acid RB(OH)$_2$ | Amine R'NH$_2$ | Structure | IUPAC Name | MW | Cmpd ID |
|---|---|---|---|---|---|---|
| 90 | 3,4,5-trimethoxyphenyl boronic acid | 1H-Indazol-5-amine | 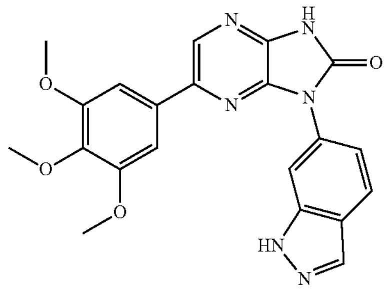 [SMILES: COc1cc(-c2cnc3[nH]c(=O)n(-c4ccc5cn[nH]c5c4)c3n2)cc(OC)c1OC] | 1-(1H-indazol-6-yl)-6-(3,4,5-trimethoxyphenyl)-1H-imidazo[4,5-b]pyrazin-2(3H)-one | 418.42 | CN |
| 91 | 3,4-dimethoxyphenyl boronic acid | 1H-Indazol-5-amine | 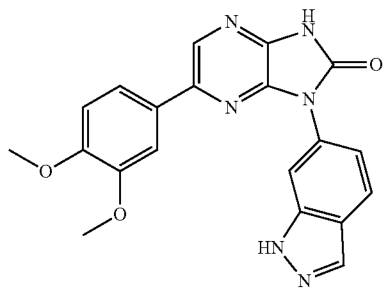 [SMILES: COc1ccc(-c2cnc3[nH]c(=O)n(-c4ccc5cn[nH]c5c4)c3n2)cc1OC] | 6-(3,4-dimethoxyphenyl)-1-(1H-indazol-6-yl)-1H-imidazo[4,5-b]pyrazin-2(3H)-one | 388.39 | CO |
| 92 | 4-hydroxyphenyl boronic acid | 1H-Indazol-5-amine | 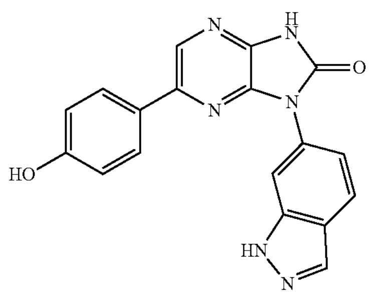 [SMILES: O=c1[nH]c2ncc(-c3ccc(O)cc3)nc2n1-c1ccc2cn[nH]c2c1] | 6-(4-hydroxyphenyl)-1-(1H-indazol-6-yl)-1H-imidazo[4,5-b]pyrazin-2(3H)-one | 344.34 | CP |
| 93 | 4-aminopyridine boronic acid | 1H-Indazol-5-amine | 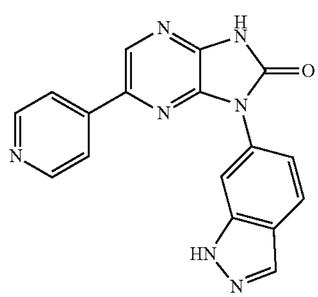 [SMILES: O=c1[nH]c2ncc(-c3ccncc3)nc2n1-c1ccc2cn[nH]c2c1] | 1-(1H-indazol-6-yl)-6-(pyridin-4-yl)-1H-imidazo[4,5-b]pyrazin-2(3H)-one | 329.32 | CQ |
| 94 | 2,4,6-trimethoxyphenyl | 1-amino-cyclopentane | 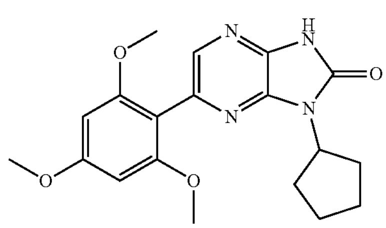 [SMILES: COc1cc(OC)c(-c2cnc3[nH]c(=O)n(C4CCCC4)c3n2)c(OC)c1] | 1-cyclopentyl-6-(2,4,6-trimethoxyphenyl)-1H-imidazo[4,5-b]pyrazin-2(3H)-one | 370.41 | CR |

TABLE 2-continued

| Ex | Boronic Acid RB(OH)$_2$ | Amine R'NH$_2$ | Structure | IUPAC Name | MW | Cmpd ID |
|---|---|---|---|---|---|---|
| 95 | 3,5-dimethylphenyl boronic acid | 1H-Indazol-5-amine | 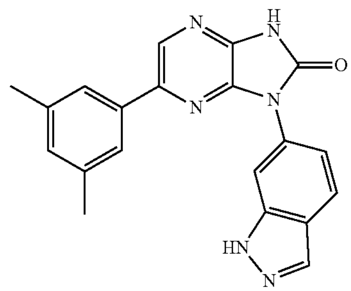 [SMILES: Cc1cc(C)cc(-c2cnc3[nH]c(=O)n(-c4ccc5cn[nH]c5c4)c3n2)c1] | 6-(3,5-dimethylphenyl)-1-(1H-indazol-6-yl)-1H-imidazo[4,5-b]pyrazin-2(3H)-one | 356.39 | CS |
| 96 | 3,4,5-trimethoxyphenyl boronic acid | benzo[d]thiazol-5-amine | 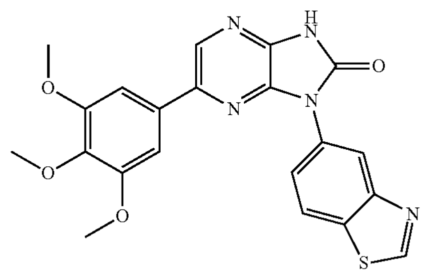 [SMILES: COc1cc(-c2cnc3[nH]c(=O)n(-c4ccc5scnc5c4)c3n2)cc(OC)c1OC] | 1-(benzo[d]thiazol-5-yl)-6-(3,4,5-trimethoxyphenyl)-1H-imidazo[4,5-b]pyrazin-2(3H)-one | 435.46 | CT |
| 97 | 4-hydroxyphenyl boronic acid | benzo[d]thiazol-5-amine | 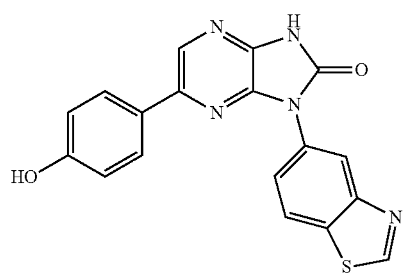 [SMILES: O=c1[nH]c2ncc(-c3ccc(O)cc3)nc2n1-c1ccc2scnc2c1] | 1-(benzo[d]thiazol-5-yl)-6-(4-hydroxyphenyl)-1H-imidazo[4,5-b]pyrazin-2(3H)-one | 361.38 | CU |
| 98 | 4-aminopyridine boronic acid | benzo[d]thiazol-5-amine | 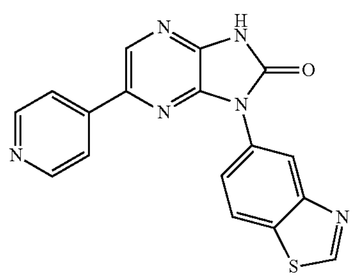 [SMILES: O=c1[nH]c2ncc(-c3ccncc3)nc2n1-c1ccc2scnc2c1] | 1-(benzo[d]thiazol-5-yl)-6-(pyridin-4-yl)-1H-imidazo[4,5-b]pyrazin-2(3H)-one | 346.37 | CV |
| 99 | 3,5-dimethylphenyl boronic acid | benzo[d]thiazol-5-amine | 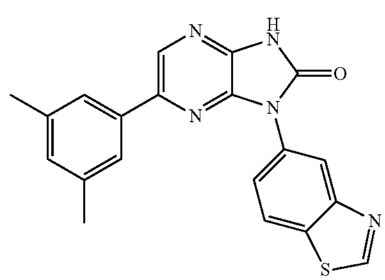 [SMILES: Cc1cc(C)cc(-c2cnc3[nH]c(=O)n(-c4ccc5scnc5c4)c3n2)c1] | 1-(benzo[d]thiazol-5-yl)-6-(3,5-dimethylphenyl)-1H-imidazo[4,5-b]pyrazin-2(3H)-one | 373.44 | CW |

TABLE 2-continued

| Ex | Boronic Acid RB(OH)$_2$ | Amine R'NH$_2$ | Structure | IUPAC Name | MW | Cmpd ID |
|---|---|---|---|---|---|---|
| 100 | 4-morpholinophenyl boronic acid | benzo[d]thiazol-5-amine | 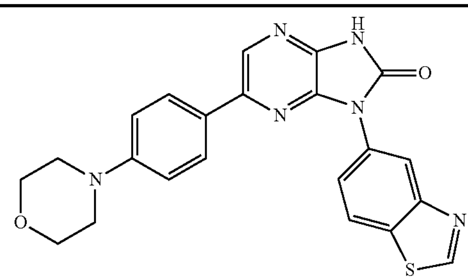 | 1-(benzo[d]thiazol-5-yl)-6-(4-morpholinophenyl)-1H-imidazo[4,5-b]pyrazin-2(3H)-one | 430.49 | CX |
| 101 | 3,4,5-trimethoxyphenyl boronic acid | 2,3-dihydro-1H-inden-1-amine | 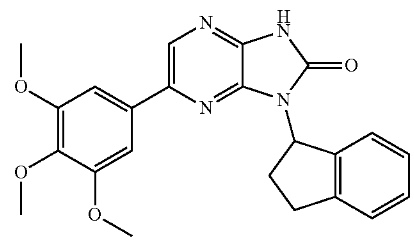 [SMILES: COc1cc(-c2cnc3[nH]c(=O)n(C4CCc5ccccc54)c3n2)cc(OC)c1OC] | 1-(2,3-dihydro-1H-inden-1-yl)-6-(3,4,5-trimethoxyphenyl)-1H-imidazo[4,5-b]pyrazin-2(3H)-one | 418.46 | CY |
| 102 | 3,4,5-trimethoxyphenyl boronic acid | 1H-benzo[d]imidazol-5-amine | 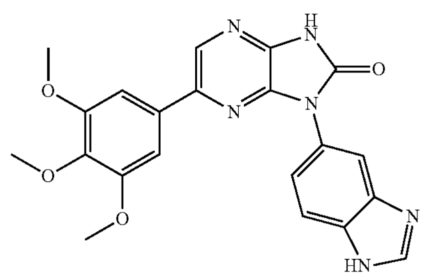 [SMILES: COc1cc(-c2cnc3[nH]c(=O)n(-c4ccc5[nH]cnc5c4)c3n2)cc(OC)c1OC] | 1-(1H-benzo[d]imidazol-5-yl)-6-(3,4,5-trimethoxyphenyl)-1H-imidazo[4,5-b]pyrazin-2(3H)-one | 418.42 | CZ |
| 103 | 3,4-dimethoxyphenyl boronic acid | 1H-benzo[d]imidazol-5-amine | 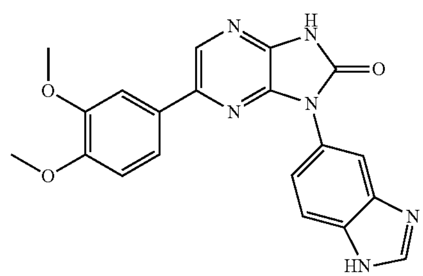 [SMILES: COc1ccc(-c2cnc3[nH]c(=O)n(-c4ccc5[nH]cnc5c4)c3n2)cc1OC] | 1-(1H-benzo[d]imidazol-5-yl)-6-(3,4-dimethoxyphenyl)-1H-imidazo[4,5-b]pyrazin-2(3H)-one | 388.39 | DA |
| 104 | 4-morpholinophenyl boronic acid | 1H-benzo[d]imidazol-5-amine | 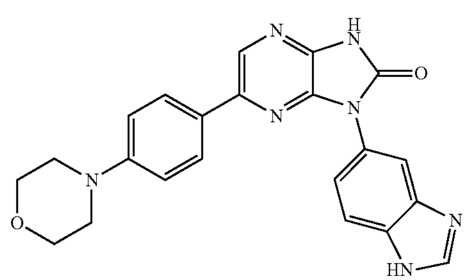 [SMILES: O=c1[nH]c2ncc(-c3ccc(N4CCOCC4)cc3)nc2n1-c1ccc2[nH]cnc2c1] | 1-(1H-benzo[d]imidazol-5-yl)-6-(4-morpholinophenyl)-1H-imidazo[4,5-b]pyrazin-2(3H)-one | 413.44 | DB |
| 105 | 3,4,5-trimethoxyphenyl boronic acid | aniline | 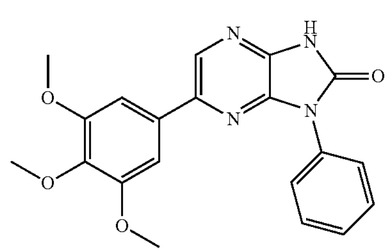 [SMILES: COc1cc(-c2cnc3[nH]c(=O)n(-c4ccccc4)c3n2)cc(OC)c1OC] | 1-phenyl-6-(3,4,5-trimethoxyphenyl)-1H-imidazo[4,5-b]pyrazin-2(3H)-one | 378.39 | DC |

TABLE 2-continued

| Ex | Boronic Acid RB(OH)$_2$ | Amine R'NH$_2$ | Structure | IUPAC Name | MW | Cmpd ID |
|---|---|---|---|---|---|---|
| 106 | 3,4-dimethoxyphenyl boronic acid | aniline | 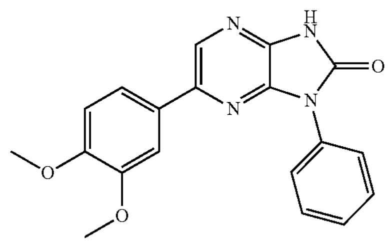 [SMILES: COc1ccc(-c2cnc3[nH]c(=O)n(-c4ccccc4)c3n2)cc1OC] | 6-(3,4-dimethoxyphenyl)-1-phenyl-1H-imidazo[4,5-b]pyrazin-2(3H)-one | 348.36 | DD |
| 107 | 3-methoxy-4-(2-morpholinoethoxy)phenyl boronic acid | Cyclopropanemethylamine | 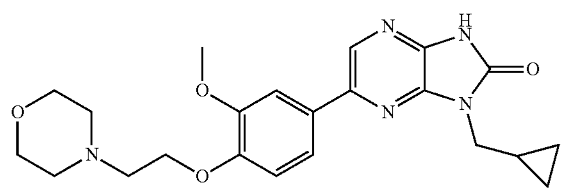 [SMILES: COc1cc(-c2cnc3[nH]c(=O)n(CC4CC4)c3n2)ccc1OCCN1CCOCC1] | 1-(cyclopropylmethyl)-6-(3-methoxy-4-(2-morpholinoethoxy)phenyl)-1H-imidazo[4,5-b]pyrazin-2(3H)-one | 425.49 | DE |
| 108 | 3-methoxy-4-(2-morpholinoethoxy)phenyl | 1-aminocyclopentane | 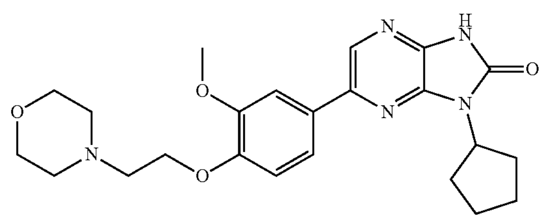 [SMILES: COc1cc(-c2cnc3[nH]c(=O)n(C4CCCC4)c3n2)ccc1OCCN1CCOCC1] | 1-cyclopentyl-6-(3-methoxy-4-(2-morpholinoethoxy)phenyl)-1H-imidazo[4,5-b]pyrazin-2(3H)-one | 439.52 | DF |
| 109 | 3,4,5-trimethoxyphenyl boronic acid | 6-morpholinopyridin-3-amine | 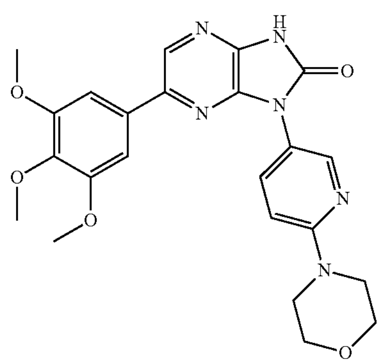 [SMILES: COc1cc(-c2cnc3[nH]c(=O)n(-c4ccc(N5CCOCC5)nc4)c3n2)cc(OC)c1OC] | 1-(6-morpholinopyridin-3-yl)-6-(3,4,5-trimethoxyphenyl)-1H-imidazo[4,5-b]pyrazin-2(3H)-one | 464.48 | DG |
| 110 | 3,4,5-trimethoxyphenyl boronic acid | 2,3-dihydro-1H-inden-2-amine | 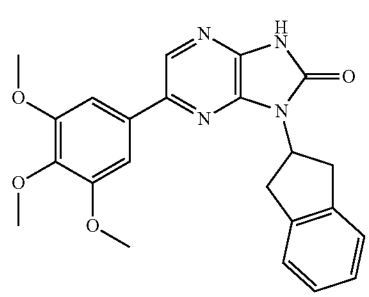 [SMILES: COc1cc(-c2cnc3[nH]c(=O)n(C4Cc5ccccc5C4)c3n2)cc(OC)c1OC] | 1-(2,3-dihydro-1H-inden-2-yl)-6-(3,4,5-trimethoxyphenyl)-1H-imidazo[4,5-b]pyrazin-2(3H)-one | 418.46 | DH |

TABLE 2-continued

| Ex | Boronic Acid RB(OH)$_2$ | Amine R'NH$_2$ | Structure | IUPAC Name | MW | Cmpd ID |
|---|---|---|---|---|---|---|
| 111 | 3,4-dimethoxyphenyl boronic acid | 1H-pyrrolo[2,3-b]pyridin-5-amine | 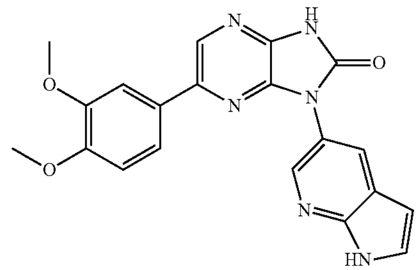 [SMILES: COc1ccc(-c2cnc3[nH]c(=O)n(-c4cnc5[nH]ccc5c4)c3n2)cc1OC] | 6-(3,4-dimethoxyphenyl)-1-(1H-pyrrolo[2,3-b]pyridin-5-yl)-1H-imidazo[4,5-b]pyrazin-2(3H)-one | 388.39 | DI |
| 112 | 3,4,5-trimethoxyphenyl boronic acid | 1H-pyrrolo[2,3-b]pyridin-5-amine | 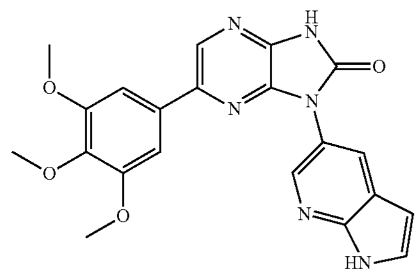 | 1-(1H-pyrrolo[2,3-b]pyridin-5-yl)-6-(3,4,5-trimethoxyphenyl)-1H-imidazo[4,5-b]pyrazin-2(3H)-one | 418.42 | DJ |
| 113 | 3,4,5-trimethoxyphenyl boronic acid | 1H-indol-6-amine | 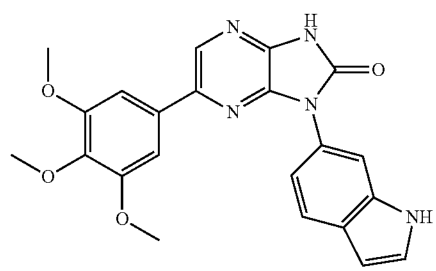 [SMILES: COc1cc(-c2cnc3[nH]c(=O)n(-c4ccc5cc[nH]c5c4)c3n2)cc(OC)c1OC] | 1-(1H-indol-6-yl)-6-(3,4,5-trimethoxyphenyl)-1H-imidazo[4,5-b]pyrazin-2(3H)-one | 418.42 | DK |
| 114 | 3,4,5-trimethoxyphenyl boronic acid | 4-aminophenol | 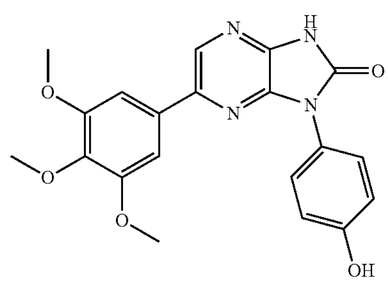 [SMILES: COc1cc(-c2cnc3[nH]c(=O)n(-c4ccc(O)cc4)c3n2)cc(OC)c1OC] | 1-(4-hydroxyphenyl)-6-(3,4,5-trimethoxyphenyl)-1H-imidazo[4,5-b]pyrazin-2(3H)-one | 394.50 | DL |
| 115 | 3,4-dimethoxyphenyl boronic acid | 4-aminophenol | 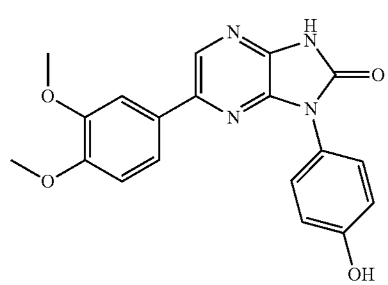 [SMILES: COc1ccc(-c2cnc3[nH]c(=O)n(-c4ccc(O)cc4)c3n2)cc1OC] | 6-(3,4-dimethoxyphenyl)-1-(4-hydroxyphenyl)-1H-imidazo[4,5-b]pyrazin-2(3H)-one | 364.50 | DM |

TABLE 2-continued

| Ex | Boronic Acid RB(OH)$_2$ | Amine R'NH$_2$ | Structure | IUPAC Name | MW | Cmpd ID |
|---|---|---|---|---|---|---|
| 116 | 4-morpholinophenyl boronic acid | 4-aminophenol | 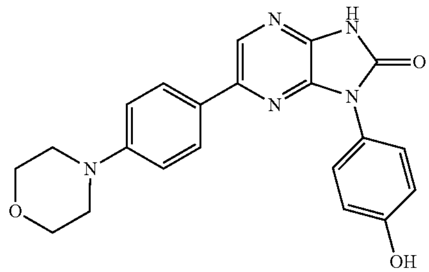 [SMILES: O=c1[nH]c2ncc(-c3ccc(N4CCOCC4)cc3)nc2n1-c1ccc(O)cc1] | 1-(4-hydroxyphenyl)-6-(4-morpholinophenyl)-1H-imidazo[4,5-b]pyrazin-2(3H)-one | 389.50 | DN |
| 117 | 6-aminopyridin-3-boronic acid | 1-amino-cyclopentane | 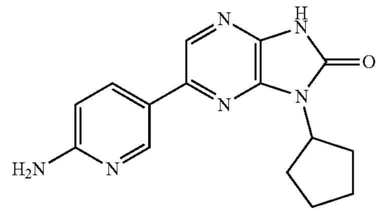 [SMILES: Nc1ccc(-c2cnc3[nH]c(=O)n(C4CCCC4)c3n2)cn1] | 6-(6-aminopyridin-3-yl)-1-cyclopentyl-1H-imidazo[4,5-b]pyrazin-2(3H)-one | 296.33 | DO |
| 118 | 4-amino-3-methoxyphenyl boronic acid | 1-amino-cyclopentane | 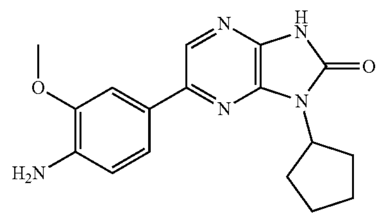 [SMILES: COc1cc(-c2cnc3[nH]c(=O)n(C4CCCC4)c3n2)ccc1N] | 6-(4-amino-3-methoxyphenyl)-1-cyclopentyl-1H-imidazo[4,5-b]pyrazin-2(3H)-one | 325.37 | DP |

Example 119

Preparation of 5-chloro-1-(cyclopropylmethyl)-6-(3,4,5-trimethoxyphenyl)-1H-imidazo[4,5-b]pyrazin-2(3H)-one (Compound DQ)

Compound DQ was prepared by a method analogous to that described in Examples 68-118 by substituting 6 chloro-3,5-dibromopyrazin-2-amine for 3,5-dibromopyrazin-2-amine in the reaction with aminomethylcyclopropane. MS ESI (m/z): 390.83 calc

Example 120

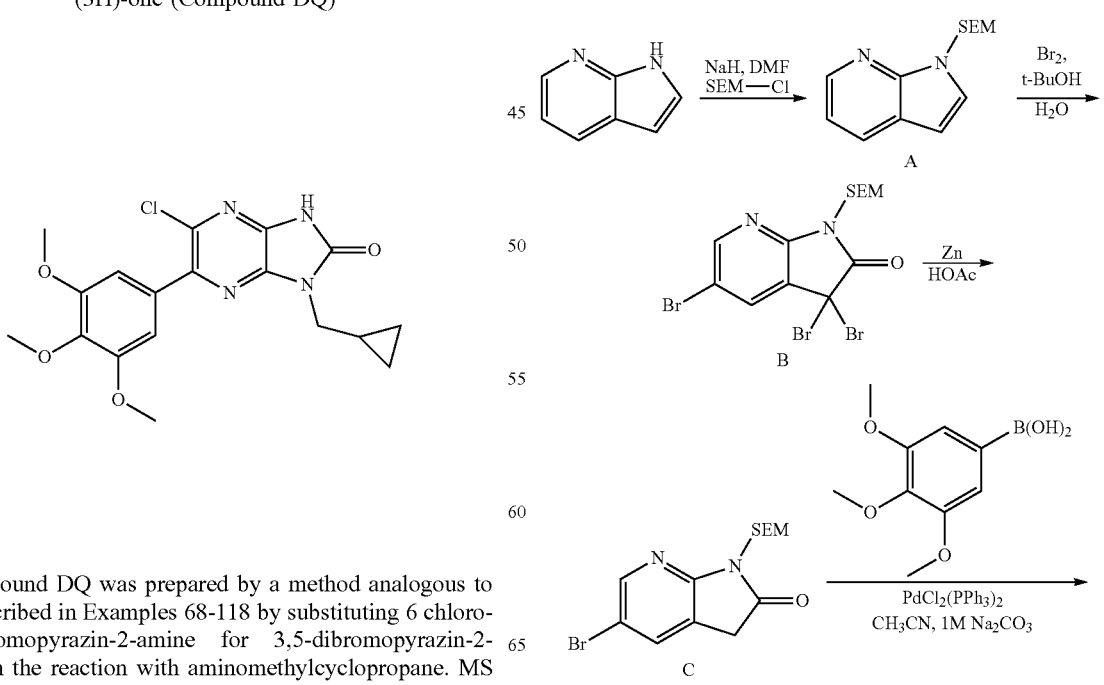

Scheme 9

-continued

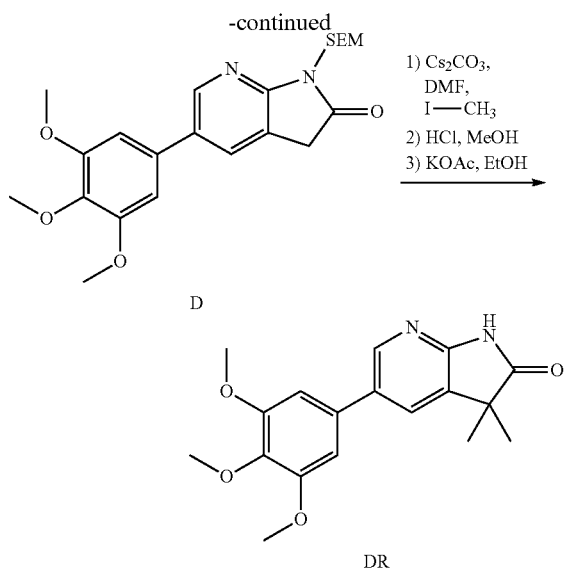

Preparation of Intermediate A: 1-((2-(trimethylsilyl)ethoxy)methyl)-1H-pyrrolo[2,3-b]pyridine In reference to Scheme 9, to a stirred solution of 7-azaindole (1.18 g, 10.0 mmol) in anhydrous dimethylformamide (10 mL) cooled to 0° C. was added NaH [60% dispersion in mineral oil] (0.480 g, 12.0 mmol) in portions over 15 min. The resulting mixture was allowed to stir for 1 hr at 0° C., after which (2-(chloromethoxy)ethyl)trimethylsilane [SEM-Cl] (2.12 mL, 12.0 mmol) was added over 15 min. The resulting mixture was stirred for 1 hr, after which it was quenched with $H_2O$ (50 mL), and partioned between EtOAc and $H_2O$. The organic layer was separated, washed with brine, dried over $MgSO_4$, filtered, and evaporated in vacuo to yield a yellow oil (2.50 g, 100%). HPLC retention time: 2.66 minutes; MS ESI (m/z): 249.4 (M+1)$^+$, calc. 248.

Preparation of Intermediate B: 3,3,5-tribromo-1-((2-(trimethylsilyl)ethoxy)methyl)-1H-pyrrolo[2,3-b]pyridin-2(3H)-one To a solution of 1-((2-(trimethylsilyl)ethoxy)methyl)-1H-pyrrolo[2,3-b]pyridine (2.50 g, 10.0 mmol) in 1:1 tert-butanol/$H_2O$ (140 mL) at room temperature was added bromine (6.40 mL, 126 mmol). After stirring for 3.5 hr at room temperature, an additional portion of bromine was added (6.40 mL, 126 mmol) and the resulting mixture was stirred for 18 hr. The resulting mixture was concentrated in vacuo to yield the title compound, which was used without any further purification. HPLC retention time: 2.97 minutes; MS ESI (m/z): 441.0/443.0/445.2 (Fragment+1)$^+$, calc. 498.

Preparation of Intermediate C: 5-bromo-1-((2-(trimethylsilyl)ethoxy)methyl)-1H-pyrrolo[2,3-b]pyridin-2(3H)-one To a solution of 3,3,5-tribromo-1-((2-(trimethylsilyl)ethoxy)methyl)-1H-pyrrolo[2,3-b]pyridin-2(3H)-one (4.98 g, 10.0 mmol) in AcOH (50 mL) was added zinc dust (1.28 g, 20.0 mmol). The resulting mixture was stirred at room temperature for 2 hr, after which it was filtered thru Celite and concentrated in vacuo. The resulting residue was purified via silica gel chromatography eluting with 1:1 Hexanes:EtOAc to yield the title compound as a yellow oil (0.85 g, 25% over three steps). HPLC retention time: 2.60 minutes; MS ESI (m/z): 287.2 (Fragment+1)$^+$, calc. 342.

Preparation of Intermediate D: 5-(3,4,5-trimethoxyphenyl)-1-((2-(trimethylsilyl)ethoxy)-methyl)-1H-pyrrolo[2,3-b]pyridin-2(3H)-one (Compound EM)

To a solution of 5-bromo-1-((2-(trimethylsilyl)ethoxy)methyl)-1H-pyrrolo[2,3-b]pyridin-2(3H)-one (0.85 g, 2.5 mmol) in $CH_3CN$ (5 mL) was added 3,4,5-trimethoxyphenylboronic acid (525 mg, 2.5 mmol), bis(triphenylphosphine)-palladium(II) dichloride (250 mg, 0.35 mmol), and 1 M $Na_2CO_3$ (5 mL). The resulting mixture was de-gassed with Ar for 10 min, after which it was heated at 80° C. for 2 hr. The reaction mixture was partitioned between EtOAc and $H_2O$, and the organic layer was separated, filtered, and concentrated in vacuo. The residue was purified by silica gel chromatography eluting with 3:1 EtOAc:Hexanes to yield the title compound (640 mg, 60%). HPLC retention time: 2.51 minutes; MS ESI (m/z): 431.4 (M+1)$^+$, calc. 430.

Preparation of 3,3-dimethyl-5-(3,4,5-trimethoxyphenyl)-1H-pyrrolo[2,3-b]pyridin-2(3H)-one (Compound DR)

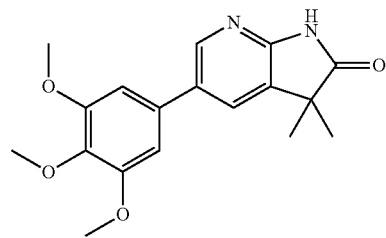 [SMILES: COc1cc(-c2cnc3c(c2)C(C)(C)C(=O)N3)cc(OC)c1OC]

To a solution of 5-(3,4,5-trimethoxyphenyl)-1-((2-(trimethylsilyl)ethoxy)-methyl)-1H-pyrrolo[2,3-b]pyridin-2(3H)-one (43 mg, 0.10 mmol) in DMF (2 mL) was added cesium carbonate (0.17 g, 0.50 mmol) and methyl iodide (19 μL, 0.30 mmol). The resulting solution was stirred for 48 hr at room temperature, after which it was partitioned between EtOAc and $H_2O$. The organic layer was separated, dried over $MgSO_4$, filtered, and concentrated in vacuo. The residue was dissolved in 6 N HCl (10 mL) and MeOH (5 mL), and the resulting mixture was stirred at room temperature overnight, after which it was partitioned between EtOAc and $H_2O$. The organic layer was concentrated in vacuo, and the residue was dissolved in EtOH (2 mL). Potassium acetate (100 mg) was then added, and the reaction was stirred for 2 hr. The resulting solution was purified via preparatory HPLC to give the title compound (24 mg, 73%). $^1$H NMR (CDCl$_3$, 300 MHz): δ 9.72 (s, 1H), 8.35 (d, J=2.1 Hz, 1H), 7.60 (d, J=1.8 Hz, 1H), 6.71 (s, 2H), 3.95 (s, 6H), 3.90 (s, 3H), 1.49 (s, 6H). HPLC retention time: 1.80 minutes; MS ESI (m/z): 329.4 (M+1)$^+$, calc. 328.

Example 121

Scheme 10

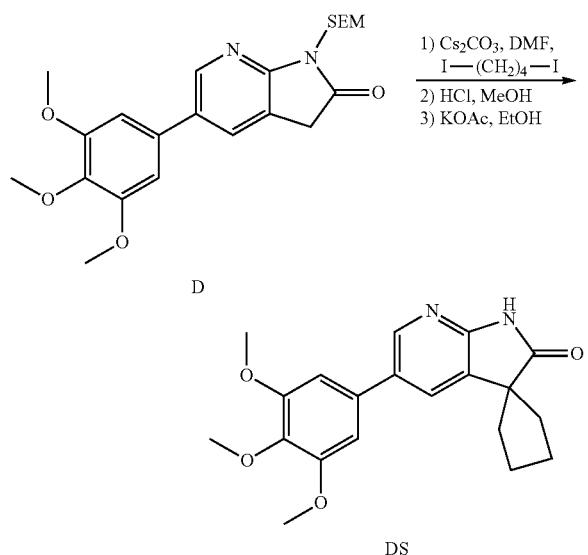

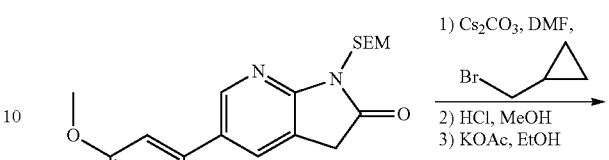

Preparation of 5'-(3,4,5-trimethoxyphenyl)spiro[cyclopentane-1,3'-pyrrolo[2,3-b]pyridin]-2'(1'H)-one (Compound DS)

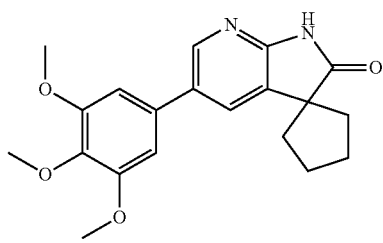 [SMILES: COc1cc(-c2cnc3c(c2)C2(CCCC2)C(=O)N3)cc(OC)c1OC]

Making reference to Scheme 10, to a solution of 5-(3,4,5-trimethoxyphenyl)-1-((2-(trimethylsilyl)ethoxy)-methyl)-1H-pyrrolo[2,3-b]pyridin-2(3H)-one (Intermediate D, 43 mg, 0.10 mmol) in DMF (2 mL) was added cesium carbonate (0.17 g, 0.50 mmol) and 1,4-diiodobutane (13 µL, 0.10 mmol). The resulting solution was stirred for 4 hr at room temperature, after which it was partitioned between EtOAc and H$_2$O. The organic layer was separated, dried over MgSO$_4$, filtered, and concentrated in vacuo. The residue was dissolved in 6 N HCl (10 mL) and MeOH (5 mL), and the resulting mixture was stirred at room temperature overnight, after which it was partitioned between EtOAc and H$_2$O. The organic layer was concentrated in vacuo, and the residue was dissolved in EtOH (2 mL). Potassium acetate (100 mg) was then added, and the reaction was stirred for 2 hr. The resulting solution was purified via preparatory HPLC to give the title compound (18 mg, 51%). $^1$H NMR (CDCl$_3$, 300 MHz): δ 9.53 (s, 1H), 8.32 (d, J=2.1 Hz, 1H), 7.56 (s, 1H), 6.69 (s, 2H), 3.95 (s, 6H), 3.90 (s, 3H), 2.28 (m, 2H), 2.24 (m, 2H), 1.97 (m, 4H). HPLC retention time: 2.00 minutes; MS ESI (m/z): 355.4 (M+1)$^+$, calc. 354.

Examples 122 and 123

Scheme 11

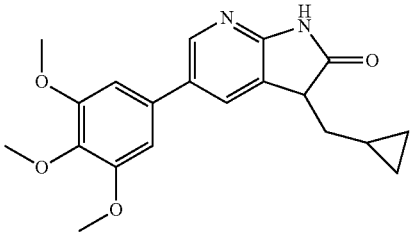

Preparation of 3,3-bis(cyclopropylmethyl)-5-(3,4,5-trimethoxyphenyl)-1H-pyrrolo[2,3-b]pyridin-2(3H)-one (Example 122, Compound DT) and 3-(cyclopropylmethyl)-5-(3,4,5-trimethoxyphenyl)-1H-pyrrolo[2,3-b]pyridin-2(3H)-one (Example 123, Compound DU)

Making reference to Scheme 11, to a solution of 5-(3,4,5-trimethoxyphenyl)-1-((2-(trimethylsilyl)ethoxy)-methyl)-1H-pyrrolo[2,3-b]pyridin-2(3H)-one (43 mg, 0.10 mmol) in DMF (2 mL) was added cesium carbonate (0.17 g, 0.50 mmol), (bromomethyl)cyclopropane (10 µL, 0.10 mmol), and potassium iodide (83 mg, 0.50 mmol). The resulting solution was stirred for 4 hr at room temperature, after which it was partitioned between EtOAc and H$_2$O. The organic layer was separated, dried over MgSO$_4$, filtered, and concentrated in vacuo. The residue was dissolved in 6 N HCl (10 mL) and MeOH (5 mL), and the resulting mixture was stirred at room temperature overnight, after which it was partitioned between EtOAc and H$_2$O. The organic layer was concentrated in vacuo, and the residue was dissolved in EtOH (2 mL). Potassium acetate (100 mg) was then added, and the reaction was stirred for 2 hr. The resulting solution was purified via preparatory HPLC to give the Compound EP (11.4 mg) and Compound EQ (4.1 mg). Compound DT: $^1$H NMR (CDCl$_3$, 300 MHz): δ 8.37 (d, J=2.1 Hz, 1H), 7.71 (s, 1H), 6.72 (s, 2H), 3.96 (s, 6H), 3.91 (s, 3H), 2.04 (m, 2H), 1.69 (m, 2H), 1.26 (m, 2H), 0.88 (m, 2H), 0.40 (m, 2H), 0.29 (m, 2H), −0.07 (m, 2H). HPLC retention time: 2.49 minutes; MS ESI (m/z): 409.4 (M+1)+, calc. 408. Compound DU: $^1$H NMR (CDCl$_3$, 300 MHz): δ 8.31 (s, 1H), 7.92 (s, 1H), 6.69 (s, 2H), 3.95 (s, 6H), 3.91 (s, 3H), 3.50 (m, 1H), 2.18 (m, 1H), 1.78 (m, 1H), 1.26 (m, 1H), 0.83 (m, 2H), 0.25 (m, 2H). HPLC retention time: 2.32 minutes; MS ESI (m/z): 355.0 (M+1)+, calc. 354.

Example 124

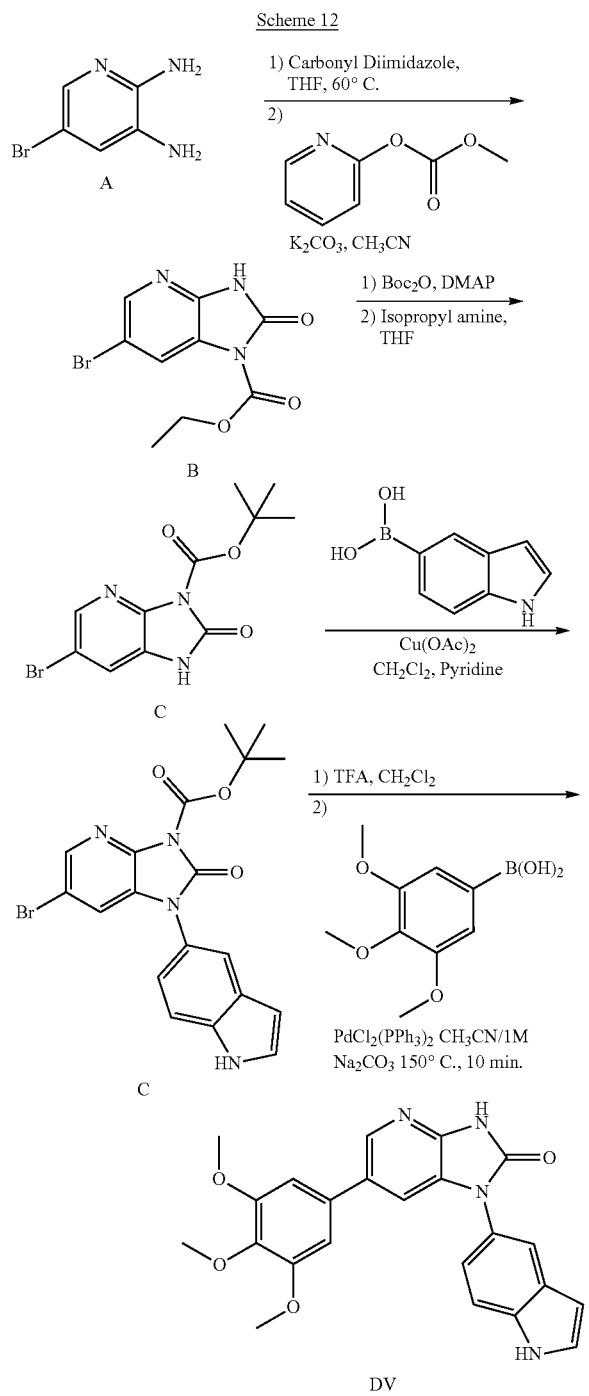

Scheme 12

Preparation of 1-(1H-indol-5-yl)-6-(3,4,5-trimethoxyphenyl)-1H-imidazo[4,5-b]pyridin-2(3H)-one (Compound DV)

In reference to Scheme 12, commercially available 5-bromopyridine-2,3-diamine 3 was converted to 6-bromo-1H-imidazo[4,5-b]pyridin-2(3H)-one via treatment with carbonyl diimidazole in THF at 60° C., which was then protected as the monoethoxy carbonyl Intermediate B in a fashion similar to that described in J. Org. Chem., 1995, 1565-1582. Intermediate B was subjected to an NOE analysis, and interactions between the 7-position hydrogen and the carbamate ethyl group were apparent, supporting the structure that is shown above. Following protection of the 3-position amine with a tert-butyl carboxylate group and deprotection of the ethyl carboxylate group using isopropyl amine, Intermediate D was coupled to indole-5-boronic acid using copper acetate in a mixture of DCM/pyridine, after which it was deprotected using TFA/CH$_2$Cl$_2$. To the resulting 6-bromo-1-(1H-indol-5-yl)-1H-imidazo[4,5-b]pyridin-2(3H)-one in CH$_3$CN (1 mL) in a microwave reaction vial was added 3,4,5-trimethoxyphenylboronic acid (30 mg, 0.14 mmol), bis(triphenylphosphine)-palladium(II) dichloride (7.0 mg, 0.010 mmol), and 1 M Na$_2$CO$_3$ (1 mL). The resulting mixture was de-gassed with Ar for 10 min, after which it was heated at 150° C. for 10 min in a Personal Chemistry Optimizer. The resulting mixture was partitioned between EtOAc and 1 M NaOH. The organic layer was separated, dried over MgSO$_4$, filtered, and stripped to give a residue that was purified via preparatory HPLC to give 1.8 mg of the title compound. HPLC retention time: 2.36 minutes; MS ESI (m/z): 417.4 (M+1)+, calc. 416.

Example 125

Preparation of 1-(cyclopropylmethyl)-6-(3,4,5-trimethoxyphenyl)-1H-imidazo[4,5-b]pyridin-2(3H)-one (Compound DW)

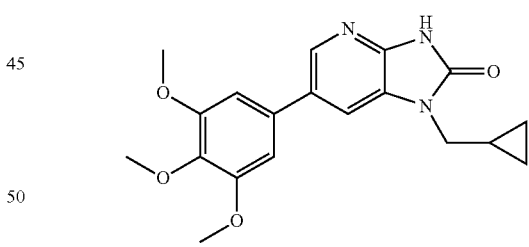

Intermediate C from Example 124 was alkylated with (bromomethyl)cyclopropane using K$_2$CO$_3$ in acetone, after which it was deprotected using TFA/CH$_2$Cl$_2$. To the resulting 6-bromo-1-(cyclopropylmethyl)-1H-imidazo[4,5-b]pyridin-2(3H)-one in CH$_3$CN (1 mL) in a microwave reaction vial was added 3,4,5-trimethoxyphenylboronic acid (30 mg, 0.14 mmol), bis(triphenylphosphine)-palladium(II) dichloride (7.0 mg, 0.010 mmol), and 1 M Na$_2$CO$_3$ (1 mL). The resulting mixture was de-gassed with Ar for 10 min, after which it was heated at 150° C. for 10 min in a Personal Chemistry Optimizer. The resulting mixture was partitioned between EtOAc and 1 M NaOH. The organic layer was separated, dried over MgSO$_4$, filtered, and stripped to give a residue that was purified via preparatory HPLC to give 3.7 mg of the title compound. HPLC retention time: 1.90 minutes; MS ESI (m/z): 356.2 (M+1)+, calc. 355.

Example 126

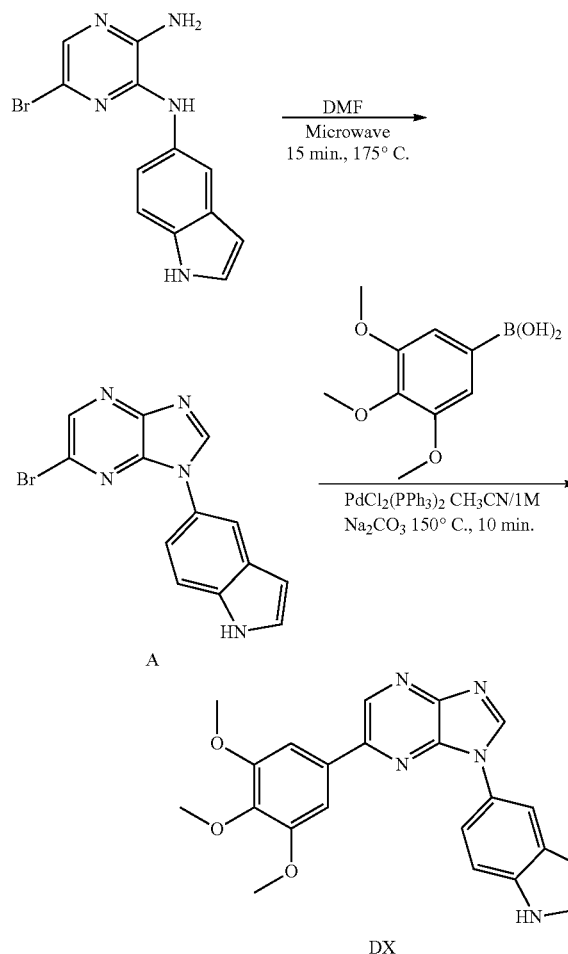

Preparation of 1-(1H-indol-5-yl)-6-(3,4,5-trimethoxyphenyl)-1H-imidazo[4,5-b]pyrazine (Compound DX)

Following a method described in Pteridines, 2002, Vol. 13, 65-72, (Scheme 13) 6-bromo-N2-(1H-indol-5-yl)pyrazine-2,3-diamine was heated in anhydrous DMF at 175° C. for 15 min. in a Personal Chemistry Optimizer. To the resulting 6-bromo-1-(1H-indol-5-yl)-1H-imidazo[4,5-b]pyrazine 1 in CH$_3$CN (1 mL) in a microwave reaction vial was added 3,4,5-trimethoxyphenylboronic acid (30 mg, 0.14 mmol), bis(triphenylphosphine)-palladium(II) dichloride (7.0 mg, 0.010 mmol), and 1 M Na$_2$CO$_3$ (1 mL). The resulting mixture was de-gassed with Ar for 10 min, after which it was heated at 150° C. for 10 min in a Personal Chemistry Optimizer. The resulting mixture was partitioned between EtOAc and 1 M NaOH. The organic layer was separated, dried over MgSO$_4$, filtered, and stripped to give a residue that was purified via preparatory HPLC to give 4.7 mg of the title compound. HPLC retention time: 2.43 minutes; MS ESI (m/z): 402.8 (M+1)+, calc. 401.

Example 127

Preparation of 1-(cyclopropylmethyl)-6-(3,4,5-trimethoxyphenyl)-1H-imidazo[4,5-b]pyrazine-2(3H)-thione (Compound DY)

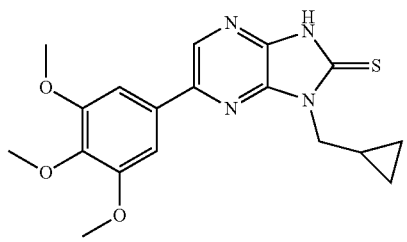 [SMILES: COc1cc(-c2cnc3[nH]c(=S)n(CC4CC4)c3n2)cc(OC)c1OC]

Compound DY was prepared by reacting Example 78 with Lawesson's reagent in refluxing toluene. The resulting mixture was partitioned between EtOAc and 1 M NaHCO$_3$. The organic layer was separated, dried over MgSO$_4$, filtered, and stripped to give a residue that was purified via preparatory HPLC to give 2.0 mg of the title compound. HPLC retention time: 2.29 minutes; MS ESI (m/z): 373.2 (M+1)+, calc. 372.

Example 128

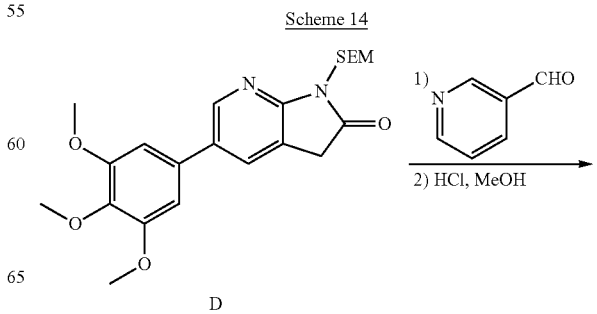

-continued

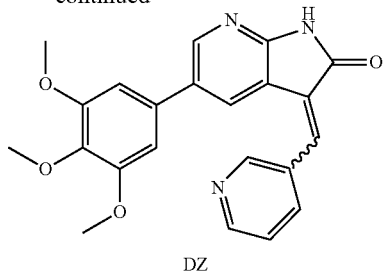

DZ

Preparation of 3-pyridin-3-ylmethylene-5-(3,4,5-trimethoxy-phenyl)-1,3-dihydro-pyrrolo[2,3-b]pyridin-2-one (Compound DZ)

In reference to Scheme 14, to a solution of 5-(3,4,5-trimethoxy-phenyl)-1-(2-trimethylsilanyl-ethoxymethyl)-1,3-dihydro-pyrrolo[2,3-b]pyridin-2-one (157 mg, 0.365 mmol) (See Intermediate D, Example 120) in toluene (2 mL) was added triethylamine (56 µl, 0.365 mmol), molecular sieves 4 Å (100 mg), and 3-pyridinecarboxaldehyde (38 al, 0.401 mmol). The resulting mixture was stirred overnight at room temperature, after which it was filtered and partitioned between DCM and H$_2$O. The organic layer was separated, dried over MgSO$_4$, filtered, and concentrated in vacuo. The residue was purified by silica gel chromatography eluting with 40-70% EtOAc:Hexanes to yield the SEM-protected precursor as a mixture of cis and trans isomers (101 mg, 53%). 41 mg (0.079 mmol) of this material was dissolved in MeOH (1.5 ml), 6 N HCl (3 ml) was added, and the mixture was stirred for 3 hours at 45° C. The reaction was quenched with 1 N NaOH (15 ml), neutralized by the addition of saturated NaHCO$_3$ and extracted with DCM. Silica gel chromatography eluting with 0-5% MeOH:DCM yielded the title compound (22 mg, 72%) as a cis/trans-mixture. $^1$H NMR (CDCl$_3$, 300 MHz): δ 9.15 (d, J=4.8 Hz, 1H), 9.11 (bs, 1H), 9.02 (d, J=1.2 Hz, 1H), 8.98 (d, J=1.1, 1H), 8.69 (dd, J=0.9, 2.9 Hz, 1H), 8.66 (dd, J=0.9, 2.8 Hz, 1H), 8.39 (d, J=1.2 Hz, 1H), 8.37 (d, J=1.2 Hz, 1H), 7.95 (m, 1H), 7.93 (s, 1H), 7.87 (d, J=1.1 Hz, 1H), 7.44 (m, 1H), 6.75 (s, 2H), 6.59 (s, 2H), 3.97 (s, 6H), 3.91 (s, 3H), 3.90 (s, 6H), 3.86 (s, 3H).

Example 129

Preparation of (E)- and (Z)-3-pyridin-4-ylmethylene-5-(3,4,5-trimethoxy-phenyl)-1,3-dihydro-pyrrolo[2,3-b]pyridin-2-one (Compound EA)

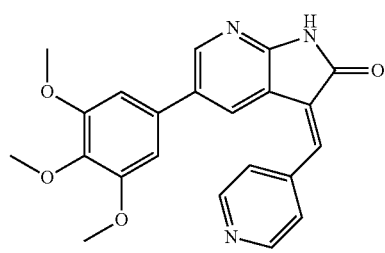

(E)- and (Z)-3-pyridin-4-ylmethylene-5-(3,4,5-trimethoxy-phenyl)-1,3-dihydro-pyrrolo[2,3-b]pyridin-2-one (Compounds EA) were prepared by a method analogous to that described in Example 128 by substituting 3-pyridinecarboxaldehyde for 4-pyridinecarboxaldehyde in the reaction with Intermediate D. The isomers were separated using silica gel chromatography eluting with 0-5% MeOH:DCM. Assignment of stereochemistry is tentatively based on the $^1$H NMR spectra. $^1$H NMR (CDCl$_3$, 300 MHz): E-isomer: δ 8.91 (s, 1H), 8.76 (d, (J=3.6 Hz, 1H), 8.39 (d, J=1.2 Hz, 1H), 8.02 (d, J=3.7 Hz, 1H), 7.91 (d, J=1.2 Hz, 1H), 7.52 (s, 1H), 6.74 (s, 2H), 3.96 (s, 6H), 3.91 (s, 3H). Z-isomer: δ 9.01 (s, 1H), 8.78 (d, (J=3.5 Hz, 1H), 8.38 (d, J=1.2 Hz, 1H), 7.87 (s, 1H), 7.81 (d, J=1.2 Hz, 1H), 7.52 (d, J=6.1 Hz, 1H), 6.56 (s, 2H), 3.89 (s, 6H), 3.88 (s, 3H).

Example 130

Preparation of 3-benzylidene-5-(3,4,5-trimethoxy-phenyl)-1,3-dihydro-pyrrolo[2,3-b]pyridin-2-one (Compound EB)

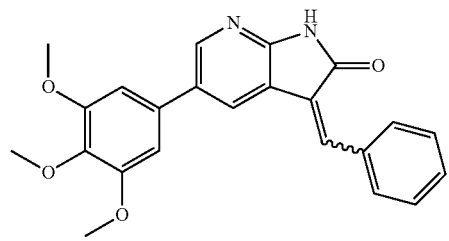 [SMILES: COc1cc(-c2cnc3c(c2)C(=Cc2ccccc2)C(=O)N3)cc(OC)c1OC]

3-Benzylidene-5-(3,4,5-trimethoxy-phenyl)-1,3-dihydro-pyrrolo[2,3-b]pyridin-2-one was prepared by a method analogous to that described in Example 128 by substituting 3-pyridinecarboxaldehyde for benzaldehyde in the reaction with Intermediate D. 15 mg (33%) of the title compound were obtained.

Example 131

Preparation of 4-[2-oxo-5-(3,4,5-trimethoxy-phenyl)-1,2-dihydro-pyrrolo[2,3-b]pyridin-3-ylidenemethyl]-benzamide (Compound EC)

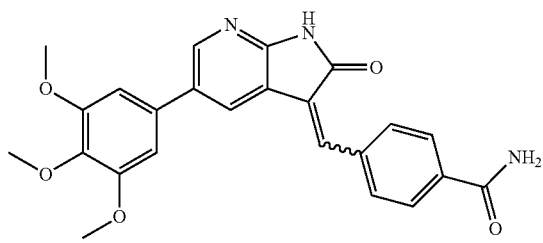 [SMILES: COc1cc(-c2cnc3c(c2)C(=Cc2ccc(C(N)=O)cc2)C(=O)N3)cc(OC)c1OC]

4-[2-Oxo-5-(3,4,5-trimethoxy-phenyl)-1,2-dihydro-pyrrolo[2,3-b]pyridin-3-ylidenemethyl]-benzamideone was prepared by a method analogous to that described in Example 128 by substituting 3-pyridinecarboxaldehyde for 4-formylbenzamide in the reaction with Intermediate D. 25 mg (50%) of the title compound were obtained.

Example 132

Preparation of 3-[2-oxo-5-(3,4,5-trimethoxy-phenyl)-1,2-dihydro-pyrrolo[2,3-b]pyridin-3-ylidenemethyl]-benzamide (Compound ED)

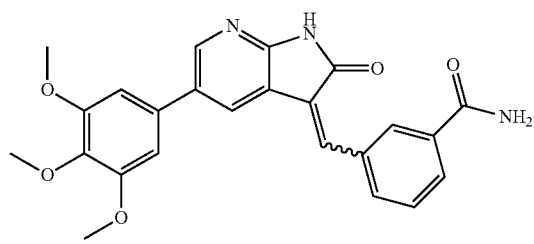 [SMILES: COc1cc(-c2cnc3c(c2)C(=Cc2cccc(C(N)=O)c2)C(=O)N3)cc(OC)c1OC]

3-[2-Oxo-5-(3,4,5-trimethoxy-phenyl)-1,2-dihydro-pyrrolo[2,3-b]pyridin-3-ylidenemethyl]-benzamideone was prepared by a method analogous to that described in Example 128 by substituting 3-pyridinecarboxaldehyde for 3-formylbenzamide in the reaction with Intermediate D. 26 mg (52%) of the title compound were obtained.

Example 133

Scheme 15

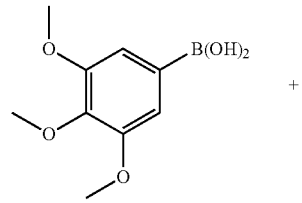

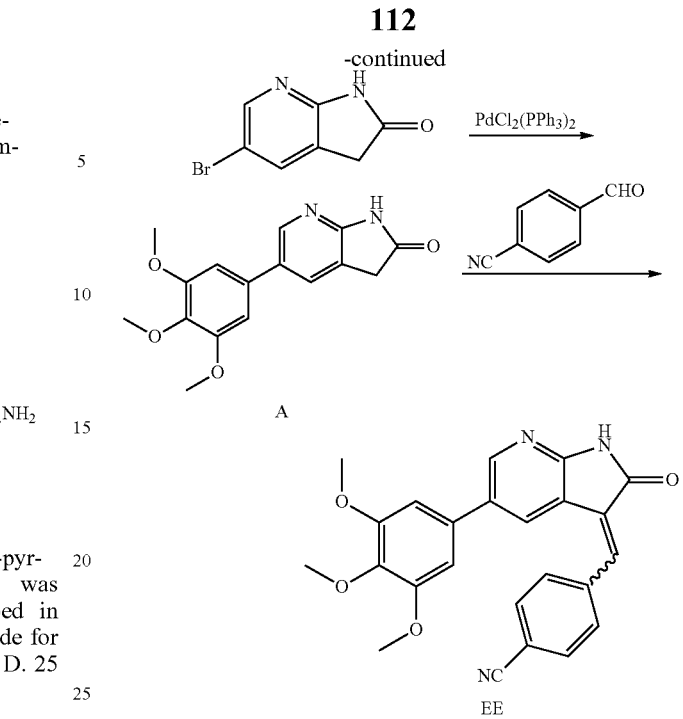

Preparation of Intermediate A: 5-(3,4,5-trimethoxy-phenyl)-1,3-dihydro-pyrrolo[2,3-b]pyridin-2-one In reference to Scheme 15, a mixture of 5-bromo-1,3-dihydro-pyrrolo[2,3-b]pyridin-2-one (200 mg, 0.939 mmol), 3,4,5-trimethoxyphenylboronic acid (239 mg, 1.127 mmol) and dichlorobis(triphenylphosphine)palladium (II) (33 mg, 0.047 mmol) in CH$_3$CN (5 ml) and 1 M Na$_2$CO$_3$ (5 ml) was heated in a microwave reactor for 10 min at 150° C. The reaction mixture was filtered, evaporated, partitioned between water and DCM and purified by silica gel chromatography with 0-10% MeOH:DCM to obtain 85 mg (30%) of Intermediate A. $^1$H NMR (CDCl$_3$/DMSO-d$_6$, 300 MHz): δ 10.19 (bs, 1H), 8.18 (d, J=1.1 Hz, 1H), 7.54 (s, 1H), 6.57 (s, 2H), 3.80 (s, 6H), 3.75 (s, 3H), 3.47 (s, 2H).

Preparation of 4-[2-oxo-5-(3,4,5-trimethoxy-phenyl)-1,2-dihydro-pyrrolo[2,3-b]pyridin-3-ylidenemethyl]-benzonitrile (Compound EE)

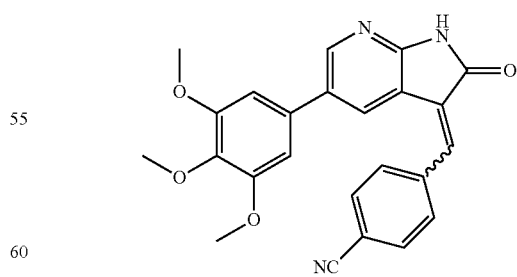

A mixture of 5-(3,4,5-trimethoxy-phenyl)-1,3-dihydro-pyrrolo[2,3-b]pyridin-2-one (Intermediate A, 42 mg, 0.14 mmol), 4-cyanobenzaldehyde (22 mg, 0.168 mmol), triethylamine (22 μl, 0.168 mmol) and molecular sieves 4 Å (100 mg) in toluene (2 ml) was reacted at 80° C. for 1 d. The

Example 134

Preparation of 3-[2-oxo-5-(3,4,5-trimethoxy-phenyl)-1,2-dihydro-pyrrolo[2,3-b]pyridin-3-ylidenemethyl]-benzonitrile (Compound EF)

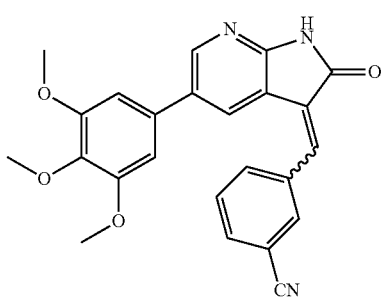 [SMILES: COc1cc(-c2cnc3c(c2)C(=Cc2cccc(C#N)c2)C(=O)N3)cc(OC)c1OC]

3-[2-oxo-5-(3,4,5-trimethoxy-phenyl)-1,2-dihydro-pyrrolo[2,3-b]pyridin-3-ylidenemethyl]-benzonitrile was prepared by a method analogous to that described in Example 133 by substituting 4-cyanobenzaldehyde for 3-cyanobenzaldehyde in the reaction with Intermediate A. 36 mg (62%) of the title compound were obtained as a mixture of cis- and trans-isomers.

Example 135

Scheme 16

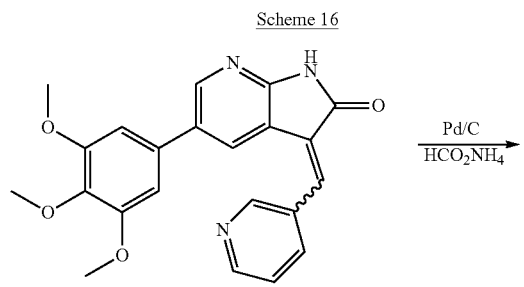

DZ

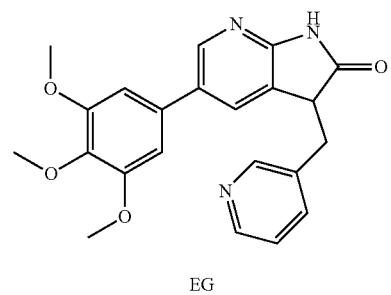

EG mixture was partitioned between DCM and water, the aqueous phase extracted with DCM, combined organic phases dried, evaporated and purified by silica gel chromatography (0-5% MeOH:DCM) to obtain 31 mg (54%) of the title compound as a mixture of (E)- and (Z)-isomers.

Preparation of 3-pyridin-3-ylmethyl-5-(3,4,5-trimethoxy-phenyl)-1,3-dihydro-pyrrolo[2,3-b]pyridin-2-one (Compound EG)

In reference to Scheme 16, to a solution of 3-pyridin-4-ylmethylene-5-(3,4,5-trimethoxy-phenyl)-1,3-dihydro-pyrrolo[2,3-b]pyridin-2-one (Compound DX; Example 128) (50 mg, 0.128 mmol) in MeOH (4 ml) was added ammonium formate (245 mg, 3.85 mmol) and Pd/C (10%, 30 mg). The mixture was stirred at room temperature for 3 hrs after which it was filtered, evaporated, and partitioned between water and DCM. The title compound (33 mg, 66%) was obtained after silica gel chromatography eluting with 0-10% MeOH:DCM. $^1$H NMR (CDCl$_3$, 300 MHz): δ 10.05 (s, 1H), 8.60 (d, J=2.6 Hz, 1H), 8.45 (d, J=1.1 Hz, 1H), 8.38 (d, J=1.2 Hz, 1H), 7.62 (d, J=4.7 Hz, 1H), 7.35 (dd, J=2.9, 4.7 Hz, 1H), 6.53 (d, J=1.2 Hz, 1H), 6.38 (s, 1H), 3.95 (m, 1H), 3.90 (m, 1H), 3.85 (s, 6H), 3.84 (s, 3H), 3.84 (m, 1H).

Example 136

Preparation of 3-pyridin-4-ylmethyl-5-(3,4,5-trimethoxy-phenyl)-1,3-dihydro-pyrrolo[2,3-b]pyridin-2-one (Compound EH)

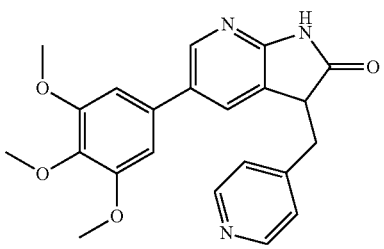 [SMILES: COc1cc(-c2cnc3c(c2)C(Cc2ccncc2)C(=O)N3)cc(OC)c1OC]

3-Pyridin-4-ylmethyl-5-(3,4,5-trimethoxy-phenyl)-1,3-dihydro-pyrrolo[2,3-b]pyridin-2-one was prepared by a method analogous to that described in Example 135 using Compound EA (Example 129). The title compound (14 mg, 61%) was obtained after silica gel chromatography eluting with 0-8% MeOH:DCM. $^1$H NMR (CDCl$_3$, 300 MHz): δ 9.52 (bs, 1H), 8.54 (d, J=3.5 Hz, 1H), 8.32 (d, J=1.1 Hz, 1H), 7.18 (d, J=3.6 Hz, 1H), 7.12 (m, 1H), 6.54 (s, 1H), 3.91 (s, 6H), 3.89 (m, 1H), 3.88 (s, 3H), 3.54 (dd, J=3.1, 8.3 Hz, 1H), 3.03 (dd, J=5.6, 8.3 Hz, 1H).

Example 137

Scheme 17

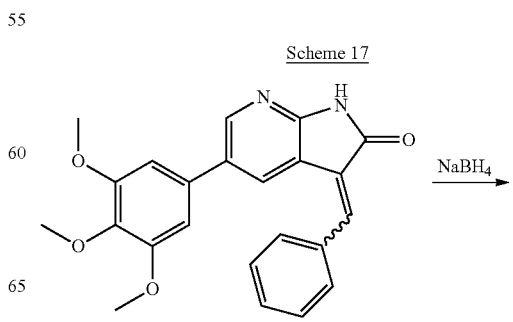

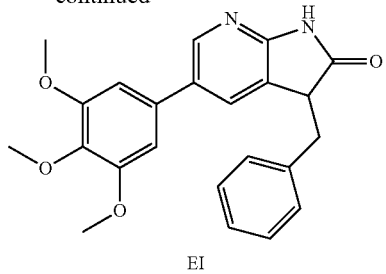

EI

Preparation of 3-benzyl-5-(3,4,5-trimethoxy-phenyl)-1,3-dihydro-pyrrolo[2,3-b]pyridin-2-one (Compound EI)

In reference to Scheme 17, to a solution of 3-benzylidene-5-(3,4,5-trimethoxy-phenyl)-1,3-dihydro-pyrrolo[2,3-b]pyridin-2-one (Compound EB; Example 130) (41 mg, 0.106 mmol) in a mixture of MeOH (2 ml), THF (1 ml) and water (0.3 ml) was added sodium borohydride (40 mg, 1.06 mmol). The reaction was stirred at room temperature for 10 min after which it was quenched by the addition of 1 N HCl and partitioned between water and DCM. The residue was purified by preparatory HPLC to yield the title compound (5.2 mg, 13%).

Example 138

Preparation of 4-[2-oxo-5-(3,4,5-trimethoxy-phenyl)-2,3-dihydro-1H-pyrrolo[2,3-b]pyridin-3-ylmethyl]-benzamide (Compound EJ)

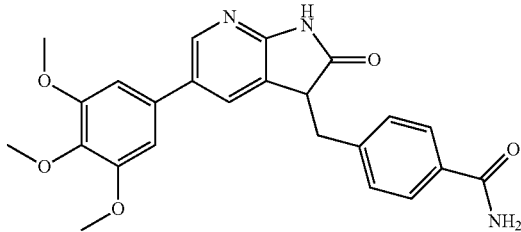 [SMILES: COc1cc(-c2cnc3c(c2)C(Cc2ccc(C(N)=O)cc2)C(=O)N3)cc(OC)c1OC]

4-[2-Oxo-5-(3,4,5-trimethoxy-phenyl)-2,3-dihydro-1H-pyrrolo[2,3-b]pyridin-3-ylmethyl]-benzamide was prepared from 4-[2-oxo-5-(3,4,5-trimethoxy-phenyl)-1,2-dihydro-pyrrolo[2,3-b]pyridin-3-ylidenemethyl]-benzamideone (Compound EC; Example 130) by a method analogous to that described in Example 137. The title compound (12 mg, 54%) was obtained after silica gel chromatography eluting with 0-10% MeOH:DCM. $^1$H NMR (DMSO-d6, 300 MHz): δ 11.06 (s, 1H), 8.34 (d, J=1.5 Hz, 1H), 7.88 (s, 1H), 7.75 (d, J=5.0 Hz, 2H), 7.41 (d, J=0.5 Hz, 1H), 7.30 (s, 1H), 7.28 (d, J=5.0 Hz, 2H), 6.74 (s, 2H), 4.03 (m, 1H), 3.82 (s, 6H), 3.67 (s, 3H), 3.44 (dd, J=3.4, 8.2 Hz, 1H), 3.11 (dd, J=4.6, 8.2 Hz, 1H).

Example 139

Scheme 18

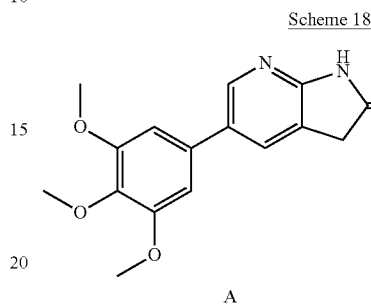

Preparation of 3,3-dibenzyl-5-(3,4,5-trimethoxy-phenyl)-1,3-dihydro-pyrrolo[2,3-b]pyridin-2-one (Compound EI)

In reference to Scheme B, 5-(3,4,5-Trimethoxy-phenyl)-1,3-dihydro-pyrrolo[2,3-b]pyridin-2-one (95 mg, 0.316 mmol) and TMEDA (96 µl, 0.623 mmol) were dissolved in anhydrous THF (4 ml) and cooled to −78° C. n-BuLi (1.6 M in hexanes, 415 µl, 0.664 mmol) was added dropwise. After completed addition stirring was continued for 1 hr at −78° C. Benzyl bromide (41.3 µl, 0.348 mmol) was added dropwise as a 10% solution in anh. THF. After completed addition the reaction was allowed to warm up to room temperature while stirring overnight. The reaction was quenched by the addition of MeOH, evaporated and partitioned between water and DCM. Silica gel chromatography eluting with 0-50% EtOAc:Hexanes yielded the title compound (47 mg, 38%). $^1$H NMR (CDCl$_3$, 300 MHz): δ 8.83 (s, 1H), 8.18 (d, J=1.2 Hz, 1H), 7.19 (d, J=1.2 Hz, 1H), 7.14 (m, 6H), 6.99 (m, 4H), 6.61 (s, 2H), 3.96 (s, 6H), 3.90 (s, 3H), 3.30 (d, J=8.0 Hz, 2H), 3.26 (d, J=8.0 Hz, 2H).

Example 140

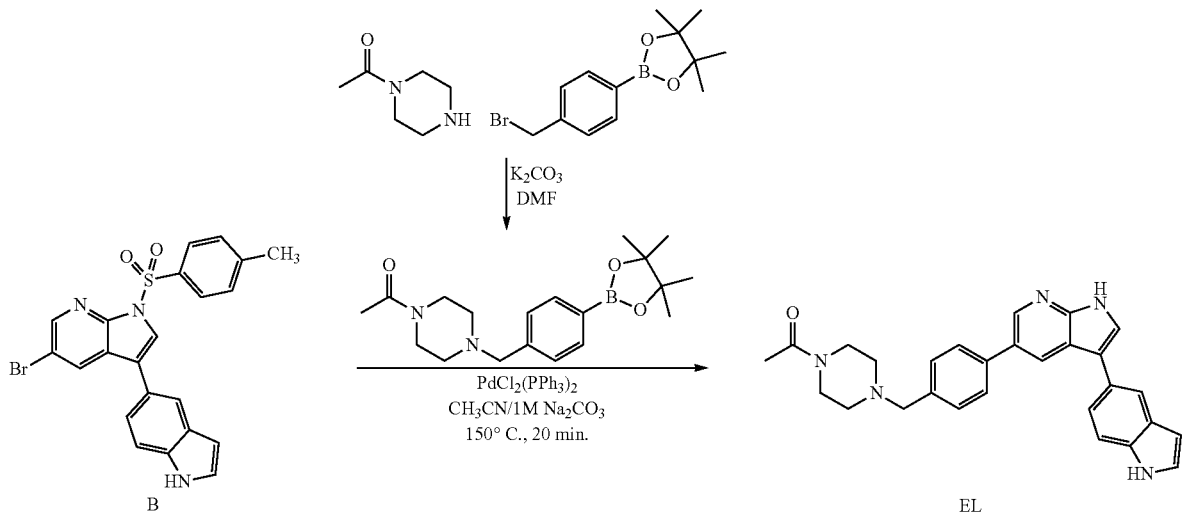

Preparation of 1-(4-{4-[3-(1H-indol-5-yl)-1H-pyrrolo[2,3-b]pyridin-5-yl]-benzyl}-piperazin-1-yl)-ethanone (Compound EL)

In reference to Scheme 19, 2-(4-Bromomethyl-phenyl)-4,4,5,5-tetramethyl-[1,3,2]dioxaborolane (100 mg, 0.337 mmol), N-acetylpiperazine (47 mg, 0.37 mmol) and K₂CO₃ (93 mg, 0.675 mmol) were combined in DMF (2.5 ml) and stirred overnight at room temperature. The reaction was quenched by the addition of water, extracted with DCM and dried. The residue was taken up in CH₃CN (2 ml), Intermediate B (120 mg, 0.275 mmol) and dichlorobis(triphenylphosphine)palladium (II) (10 mg, 0.013 mmol) were added and the reaction was heated to 150° C. in a microwave reactor for 20 min. The mixture was partitioned between water and DCM, the organic phase dried, evaporated and purified by silica gel chromatography using 0-5% MeOH:DCM. 53 mg (46%) of the title compound were obtained. MS ESI (m/z): 450.4 (M+1)⁺, calc. 449.

Example 141

Preparation of 4-{4-[3-(1H-indol-5-yl)-1H-pyrrolo[2,3-b]pyridin-5-yl]-benzyl}-1-methyl-piperazin-2-one (Compound EM)

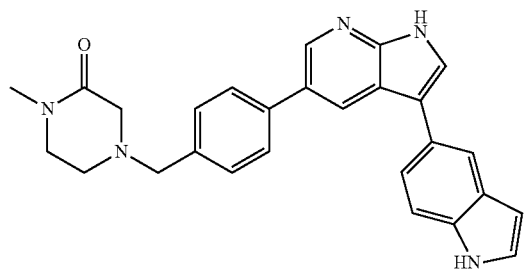 [SMILES: CN1CCN(Cc2ccc(-c3cnc4[nH]cc(-c5ccc6[nH]ccc6c5)c4c3)cc2)CC1=O]

4-{4-[3-(1H-Indol-5-yl)-1H-pyrrolo[2,3-b]pyridin-5-yl]-benzyl}-1-methyl-piperazin-2-one was prepared by a method analogous to that described in Example 140 by substituting N-acetylpiperazine for 1-methyl-piperazin-2-one. The title compound (14 mg, 28%) was obtained after silica gel chromatography eluting with 0-10% MeOH:DCM. MS ESI (m/z): 435.9 (M+1)⁺, calc. 435.

Example 142

Preparation of 4-{4-[3-(1H-indol-5-yl)-1H-pyrrolo[2,3-b]pyridin-5-yl]-benzyl}-piperazin-2-one (Compound EN)

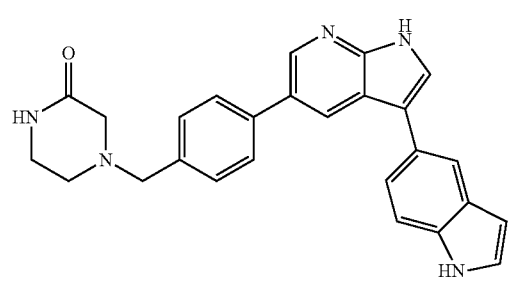 [SMILES: O=C1CN(Cc2ccc(-c3cnc4[nH]cc(-c5ccc6[nH]ccc6c5)c4c3)cc2)CCN1]

4-{4-[3-(1H-Indol-5-yl)-1H-pyrrolo[2,3-b]pyridin-5-yl]-benzyl}-piperazin-2-one was prepared by a method analogous to that described in Example 140 by substituting N-acetylpiperazine for piperazin-2-one. The title compound (22 mg, 45%) was obtained after silica gel chromatography eluting with 0-10% MeOH:DCM. MS ESI (m/z): 422.2 (M+1)⁺, calc. 421.

Example 143

Preparation of 4-{3-[3-(1H-indol-5-yl)-1H-pyrrolo[2,3-b]pyridin-5-yl]-benzyl}-1-methyl-piperazin-2-one (Compound EO)

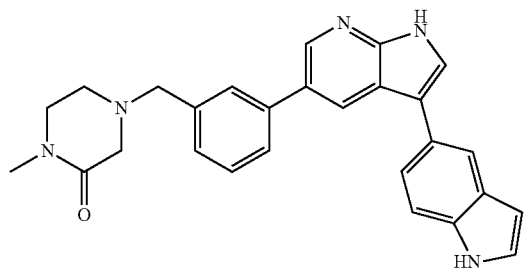 [SMILES: CN1CCN(Cc2cccc(-c3cnc4[nH]cc(-c5ccc6[nH]ccc6c5)c4c3)c2)CC1=O]

4-{3-[3-(1H-Indol-5-yl)-1H-pyrrolo[2,3-b]pyridin-5-yl]-benzyl}-1-methyl-piperazin-2-one was prepared by a method analogous to that described in Example 140 by substituting N-acetylpiperazine for 1-methyl-piperazin-2-one and 2-(4-bromomethyl-phenyl)-4,4,5,5-tetramethyl-[1,3,2]dioxaborolane for 3-(bromomethyl)phenylboronic acid. The title compound (22 mg, 45%) was obtained after silica gel chromatography eluting with 0-10% MeOH:DCM. MS ESI (m/z): 436.4 (M+1)$^+$, calc. 435.

Example 144

Preparation of 4-{4-[3-(1H-indol-5-yl)-1H-pyrrolo[2,3-b]pyridin-5-yl]-benzyl}-piperazine-1-carboxylic acid tert-butyl ester (Compound EP)

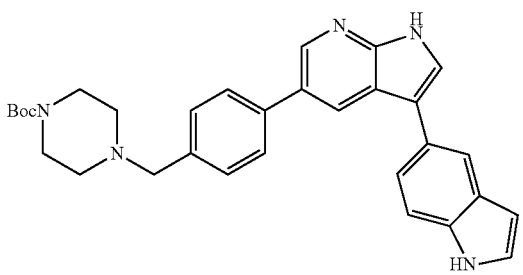 [SMILES: CC(C)(C)OC(=O)N1CCN(Cc2ccc(-c3cnc4[nH]cc(-c5ccc6[nH]ccc6c5)c4c3)cc2)CC1]

4-{4-[3-(1H-Indol-5-yl)-1H-pyrrolo[2,3-b]pyridin-5-yl]-benzyl}-piperazine-1-carboxylic acid tert-butyl ester was prepared by a method analogous to that described in Example 140 by substituting N-acetylpiperazine for N-Boc-piperazine. The title compound (20 mg, 33%) was obtained after silica gel chromatography eluting with 0-3% MeOH:DCM. MS ESI (m/z): 508.2 (M+1)$^+$, calc. 507.

Example 145

Scheme 20

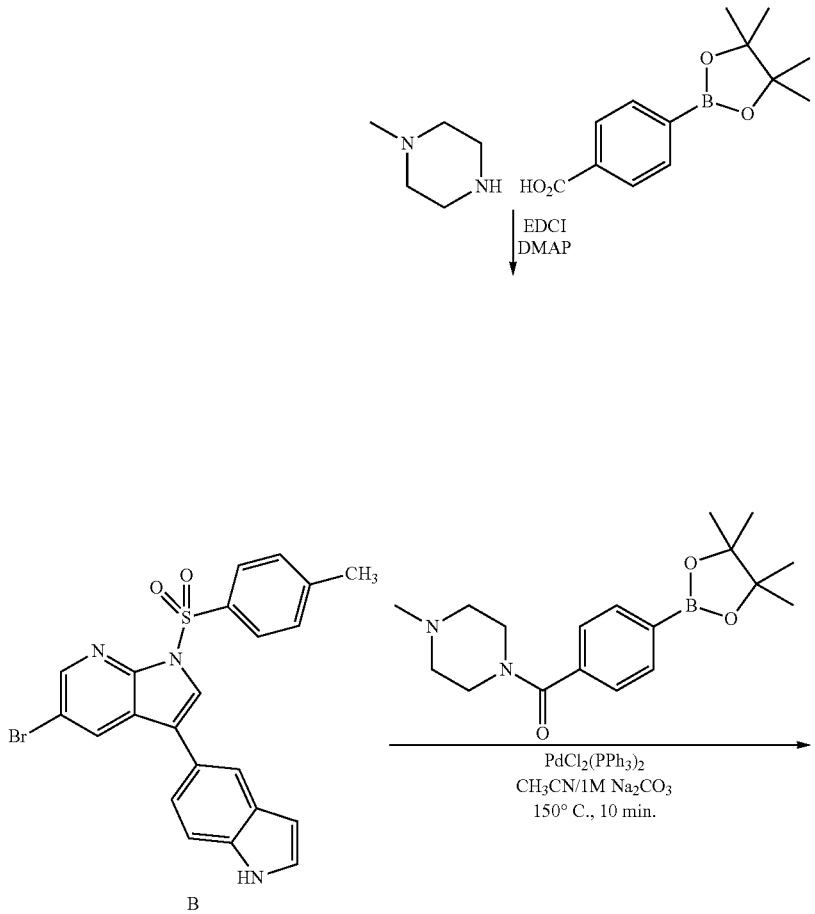

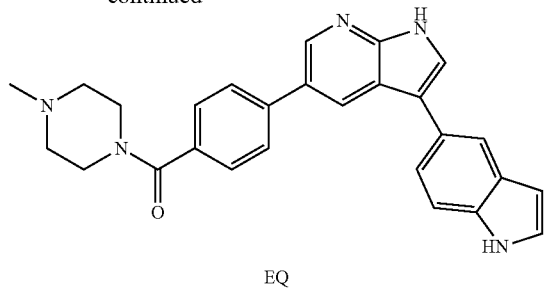

EQ

Preparation of {4-[3-(1H-indol-5-yl)-1H-pyrrolo[2,3-b]pyridin-5-yl]-phenyl}-(4-methyl-piperazin-1-yl)-methanone (Compound EQ)

In reference to Scheme 20, 4-(4,4,5,5-Tetramethyl-[1,3,2]dioxaborolan-2-yl)-benzoic acid (100 mg, 0.403 mmol), EDCI (97 mg, 0.504 mmol) and DMAP (catalytic amount) were combined in CH$_3$CN, stirred for 10 min and treated with N-methylpiperazine (54 µl, 0.484 mmol). The mixture was stirred overnight at room temperature. An aliquot of 650 µl was taken, combined with Intermediate B (50 mg, 0.107 mmol) and dichlorobis(triphenylphosphine)palladium (II) (10 mg, 0.013 mmol) and heated to 150° C. in a microwave reactor for 20 min. The mixture was partitioned between water and DCM, the organic phase dried, evaporated and purified by silica gel chromatography using 0-6% MeOH:DCM. 13 mg (28%) of the title compound were obtained. $^1$H NMR (DMSO-d6, 300 MHz): δ 11.88 (d, J=1.5 Hz, 1H), 11.08 (s, 1H), 8.57 (d, J=2.1 Hz, 1H), 8.45 (d, J=1.8 Hz, 1H), 7.90 (s, 1H), 7.82 (d, J=8.4 Hz, 1H), 7.77 (d, J=2.4 Hz, 1H), 7.47 (m, 4H), 7.34 (t, J=2.6 Hz, 1H), 6.47 (t, J=2.4 Hz, 1H), 3.58 (bs, 4H), 2.3 (bs, 4H), 2.18 (s, 3H).

Example 146

Preparation of 1-(4-{4-[3-(1H-indol-5-yl)-1H-pyrrolo[2,3-b]pyridin-5-yl]-benzoyl}-piperazin-1-yl)-ethanone (Compound ER)

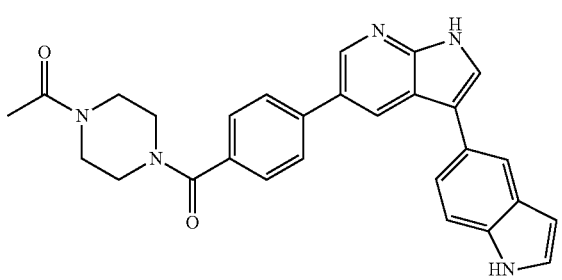 [SMILES: CC(=O)N1CCN(C(=O)c2ccc(-c3cnc4[nH]cc(-c5ccc6[nH]ccc6c5)c4c3)cc2)CC1]

1-(4-{4-[3-(1H-Indol-5-yl)-1H-pyrrolo[2,3-b]pyridin-5-yl]-benzoyl}-piperazin-1-yl)-ethanone was synthesized by a method analogous to that described in Example 144 by substituting N-methylpiperazine for N-acetylpiperazine. The title compound (13 mg, 26%) was obtained after silica gel chromatography eluting with 0-5% MeOH:DCM. MS ESI (m/z): 464.2 (M+1)$^+$, calc. 463.

Example 147

Preparation of {3-[3-(1H-indol-5-yl)-1H-pyrrolo[2,3-b]pyridin-5-yl]-phenyl}-(4-methyl-piperazin-1-yl)-methanone (Compound ES)

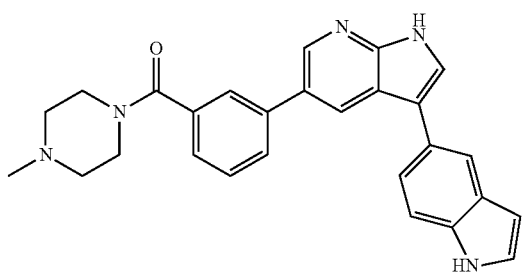 [SMILES: CN1CCN(C(=O)c2cccc(-c3cnc4[nH]cc(-c5ccc6[nH]ccc6c5)c4c3)c2)CC1]

{3-[3-(1H-Indol-5-yl)-1H-pyrrolo[2,3-b]pyridin-5-yl]-phenyl}-(4-methyl-piperazin-1-yl)-methanone was synthesized by a method analogous to that described in Example 144 by substituting 4-(4,4,5,5-tetramethyl-[1,3,2]dioxaborolan-2-yl)-benzoic acid for 3-carboxyphenylboronic acid. The title compound (23 mg, 49%) was obtained after silica gel chromatography eluting with 5-10% MeOH:DCM. MS ESI (m/z): 436.4 (M+1)$^+$, calc. 435.

Example 148

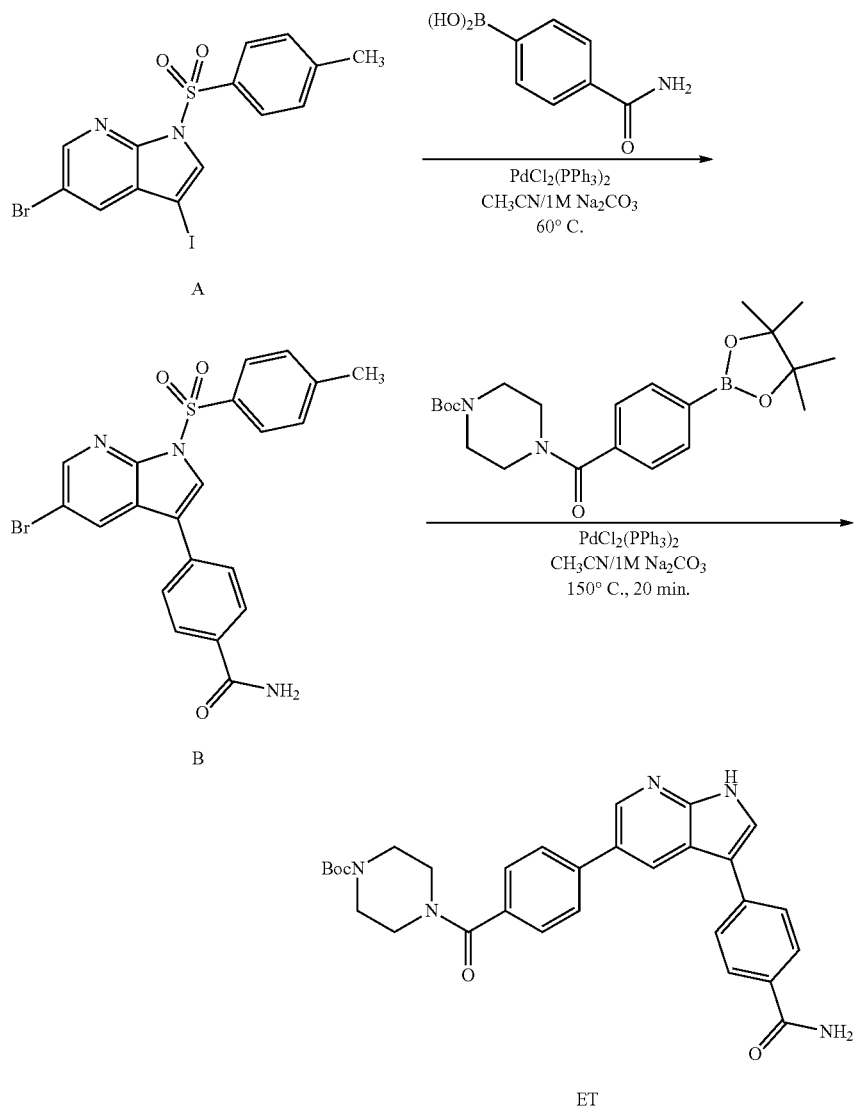

Preparation of Intermediate B: 4-[5-bromo-1-(toluene-4-sulfonyl)-1H-pyrrolo[2,3-b]pyridin-3-yl]-benzamide In reference to Scheme 21, 5-Bromo-3-iodo-1-(toluene-4-sulfonyl)-1H-pyrrolo[2,3-b]pyridine (Intermediate A, 483 mg, 1.01 mmol), 4-aminocarbonylphenylboronic acid (196 mg, 1.22 mmol) and dichlorobis(triphenylphosphine)palladium (II) (71 mg, 0.1 mmol) were combined in CH$_3$CN (10 ml) and 1 M Na$_2$CO$_3$ (10 ml) and stirred at 60° C. for 3 hrs. Water was added and the mixture was extracted with DCM and purified by silica gel chromatography using 0-30% EtOAc/Hexanes. The title compound FR was obtained in 79% yield (373 mg). $^1$H NMR (CDCl$_3$, 300 MHz): δ 8.51 (d, J=1.2 Hz, 1H), 8.20 (d, J=1.2 Hz, 1H), 8.11 (d, J=5.1 Hz, 2H), 7.96 (s, 1H), 7.93 (d, J=5.0 Hz, 2H), 7.64 (d, J=5.1 Hz, 2H), 7.31 (d, J=4.8 Hz, 2H), 6.1 (bs, 1H), 5.7 (bs, 1H), 2.39 (s, 3H).

Preparation of 4-{4-[3-(4-carbamoyl-phenyl)-1H-pyrrolo[2,3-b]pyridin-5-yl]-benzoyl}-piperazine-1-carboxylic acid tert-butyl ester (Compound ET)

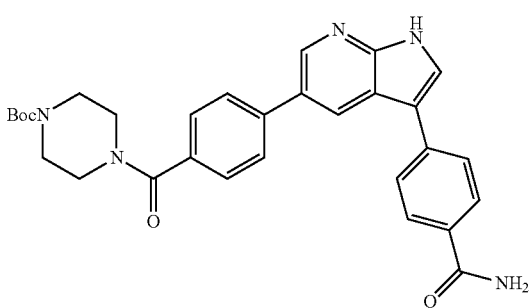 [SMILES: CC(C)(C)OC(=O)N1CCN(C(=O)c2ccc(-c3cnc4[nH]cc(-c5ccc(C(N)=O)cc5)c4c3)cc2)CC1]

4-[5-Bromo-1-(toluene-4-sulfonyl)-1H-pyrrolo[2,3-b]pyridin-3-yl]-benzamide (Intermediate B) 200 mg, 0.425 mmol), 4-[4-(4,4,5,5-tetramethyl-[1,3,2]dioxaborolan-2-yl)-benzoyl]-piperazine-1-carboxylic acid tert-butyl ester (212 mmg, 0.51 mmol) and dichlorobis(triphenylphosphine)palladium (II) (15 mg, 0.021 mmol) were combined in CH$_3$CN (5 ml) and 1 M Na$_2$CO$_3$ (5 ml) and reacted in a microwave reactor at 150° C. for 10 min. The mixture was filtered, water was added, extracted with EtOAc and purified by silica gel chromatography using 0-8% MeOH:DCM. The title compound was obtained in 46% yield (102 mg). $^1$H NMR (DMSO-d6, 300 MHz): δ 12.2 (bs, 1H), 8.63 (d, J=1.1 Hz, 1H), 8.54 (d, J=1.1 Hz, 1H), 8.08 (s, 1H), 7.98 (bs, 1H), 7.96 (d, J=5.1 Hz, 2H), 7.89 (m, 4H), 7.54 (d, J=4.9 Hz, 2H), 7.32 (bs, 1H), 3.6 (bs, 2H), 3.4 (bs), 1.41 (s, 9H).

Example 149

Example 150

Scheme 23

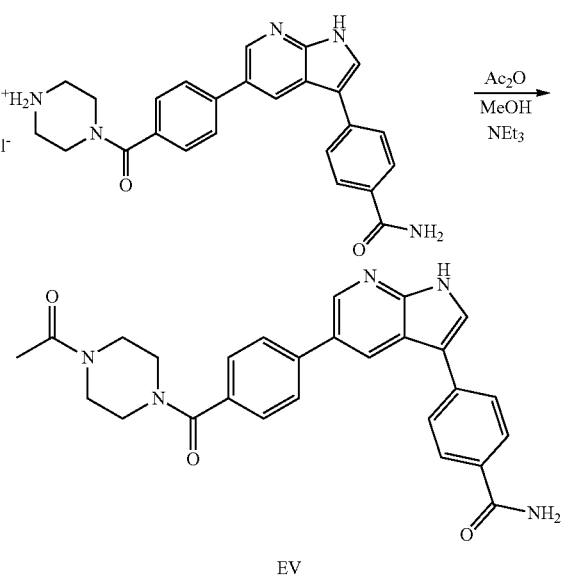

Preparation of 4-{5-[4-(4-acetyl-piperazine-1-carbonyl)-phenyl]-1H-pyrrolo[2,3-b]pyridin-3-yl}-benzamide (Compound EV)

In reference to Scheme 23, to a solution of 4-{5-[4-(piperazine-1-carbonyl)-phenyl]-1H-pyrrolo[2,3-b]pyridin-3-yl}-benzamide, hydrochloride salt (19 mg, 0.041 mmol) in MeOH (2 ml) was added triethylamine (400 µl, 2.88 mmol) and acetic anhydride (100 µl, 1.06 mmol). The mixture was stirred for 1 hr at room temperature. EtOAc was added and washed with saturated aqu. NaHCO$_3$, water, brine and dried and evacuated.

Purification on silica gel employing 0-10% MeOH:DCM provided 4.7 mg (25%) of the title compound. MS ESI (m/z): 468.3 (M+1)$^+$, calc. 467.

Example 151

Preparation of 4-{3-[3-(4-carbamoyl-phenyl)-1H-pyrrolo[2,3-b]pyridin-5-yl]-benzoyl}-piperazine-1-carboxylic acid tert-butyl ester (Compound EW)

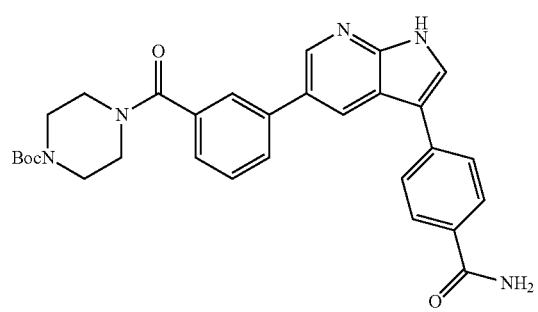 [SMILES: CC(C)(C)OC(=O)N1CCN(C(=O)c2cccc(-c3cnc4[nH]cc(-c5ccc(C(N)=O)cc5)c4c3)c2)CC1]

Scheme 22

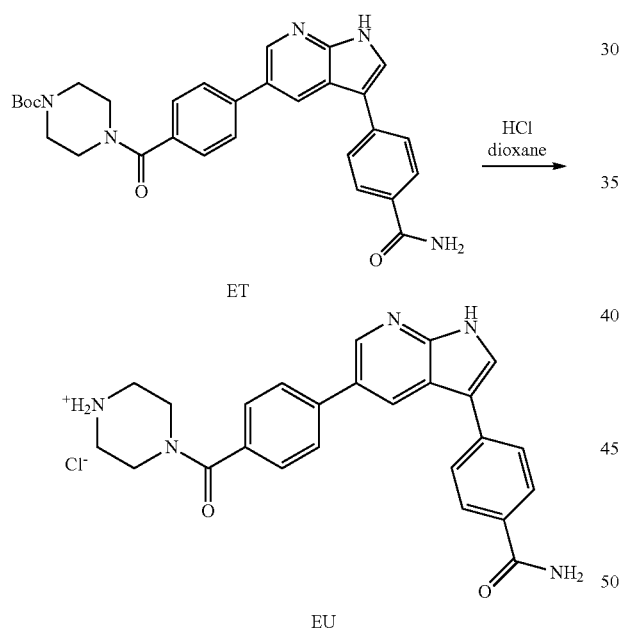

Preparation of 4-{5-[4-(piperazine-1-carbonyl)-phenyl]-1H-pyrrolo[2,3-b]pyridin-3-yl}-benzamide, hydrochloride salt (Compound EU)

In reference to Scheme 22, a solution of 4-{4-[3-(4-carbamoyl-phenyl)-1H-pyrrolo[2,3-b]pyridin-5-yl]-benzoyl}-piperazine-1-carboxylic acid tert-butyl ester (100 mg, 0.19 mmol) in MeOH (3 ml) was treated with 4 N HCl in dioxane (2.5 ml) and stirred at room temperature for 1 hr. The mixture was evaporated, taken up in MeOH and evaporated again. This was repeated twice to give 102 mg (116%) of the title compound. MS ESI (m/z): MS ESI (m/z): 426.4 (M+1)$^+$, calc. 425.

4-{3-[3-(4-Carbamoyl-phenyl)-1H-pyrrolo[2,3-b]pyridin-5-yl]-benzoyl}-piperazine-1-carboxylic acid tert-butyl ester was prepared by a method analogous to that described in Example 148 by substituting 4-[4-(4,4,5,5-tetramethyl-[1,3,2]dioxaborolan-2-yl)-benzoyl]-piperazine-1-carboxylic acid tert-butyl ester for 4-[3-(4,4,5,5-tetramethyl-[1,3,2]dioxaborolan-2-yl)-benzoyl]-piperazine-1-carboxylic acid tert-butyl ester. The title compound (109 mg, 49%) was obtained after silica gel chromatography eluting with 0-8% MeOH:DCM. $^1$H NMR (DMSO-d6, 300 MHz): δ 12.18 (bs, 1H), 8.61 (d, J=1.2 Hz, 1H), 8.52 (d, J=1.2 Hz, 1H), 8.07 (s, 1H), 7.96 (m, 3H), 7.89 (m, 3H), 7.80 (s, 1H), 7.57 (t, J=4.6 Hz, 1H), 7.41 (d, J=4.6 Hz, 1H), 7.32 (s, 1H), 3.63 (bs, 2H), 3.4 (bs, 2H), 1.40 (s, 9H).

Example 152

Preparation of 4-{5-[3-(piperazine-1-carbonyl)-phenyl]-1H-pyrrolo[2,3-b]pyridin-3-yl}-benzamide, hydrochloride salt (Compound EX)

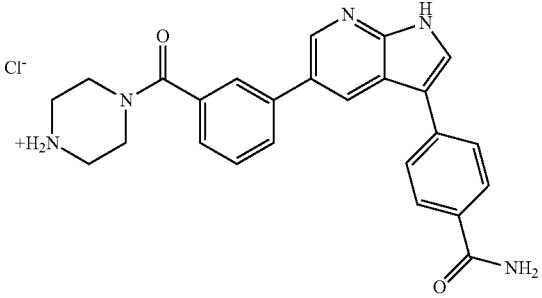 [SMILES: [Cl-] ; NC(=O)c1ccc(-c2c[nH]c3ncc(-c4cccc(C(=O)N5CC[NH2+]CC5)c4)cc23)cc1]

The hydrochloride salt of 4-{5-[3-(piperazine-1-carbonyl)-phenyl]-1H-pyrrolo[2,3-b]pyridin-3-yl}-benzamide was prepared by a method analogous to that described in Example 149 by substituting 4-{4-[3-(4-carbamoyl-phenyl)-1H-pyrrolo[2,3-b]pyridin-5-yl]-benzoyl}-piperazine-1-carboxylic acid tert-butyl ester for 4-{3-[3-(4-carbamoyl-phenyl)-1H-pyrrolo[2,3-b]pyridin-5-yl]-benzoyl}-piperazine-1-carboxylic acid tert-butyl ester. 105 mg (128%) of the title compound were obtained. $^1$H NMR (DMSO-d6, 300 MHz): δ 12.32 (s, 1H), 9.52 (s, 2H), 8.66 (d, J=1.8 Hz, 1H), 8.59 (d, J=1.8 Hz, 1H), 8.11 (d, J=2.7 Hz, 1H), 7.95 (m, 5H), 7.60 (t, J=7.8 Hz, 1H), 7.52 (d, J=7.2 Hz, 1H), 7.36 (bs, 1H), 3.6-4.0 (bs, 8H).

Example 153

Preparation of 4-{5-[3-(4-acetyl-piperazine-1-carbonyl)-phenyl]-1H-pyrrolo[2,3-b]pyridin-3-yl}-benzamide (Compound EY)

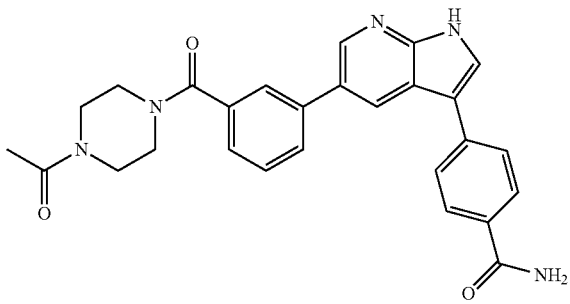 [SMILES: CC(=O)N1CCN(C(=O)c2cccc(-c3cnc4[nH]cc(-c5ccc(C(N)=O)cc5)c4c3)c2)CC1]

4-{5-[3-(4-Acetyl-piperazine-1-carbonyl)-phenyl]-1H-pyrrolo[2,3-b]pyridin-3-yl}-benzamide was prepared by a method analogous to that described in Example 150 by substituting 4-{5-[4-(piperazine-1-carbonyl)-phenyl]-1H-pyrrolo[2,3-b]pyridin-3-yl}-benzamide, hydrochloride salt for 4-{5-[3-(piperazine-1-carbonyl)-phenyl]-1H-pyrrolo[2,3-b]pyridin-3-yl}-benzamide, hydrochloride salt. 3.1 mg (14%) of the title compound were obtained. $^1$H NMR (CD$_3$OD, 300 MHz): δ 8.56 (d, J=1.2 Hz, 1H), 8.55 (d, J=1.2 Hz, 1H), 7.99 (d, J=4.2 Hz, 2H), 7.86 (m, 4H), 7.81 (d, J=1.8 Hz, 1H), 7.62 (t, J=4.6 Hz, 1H), 7.47 (dd, J=0.7, 3.8 Hz, 1H), 3.5-3.9 (m, 8H), 2.14 (bd, 3H).

Example 154

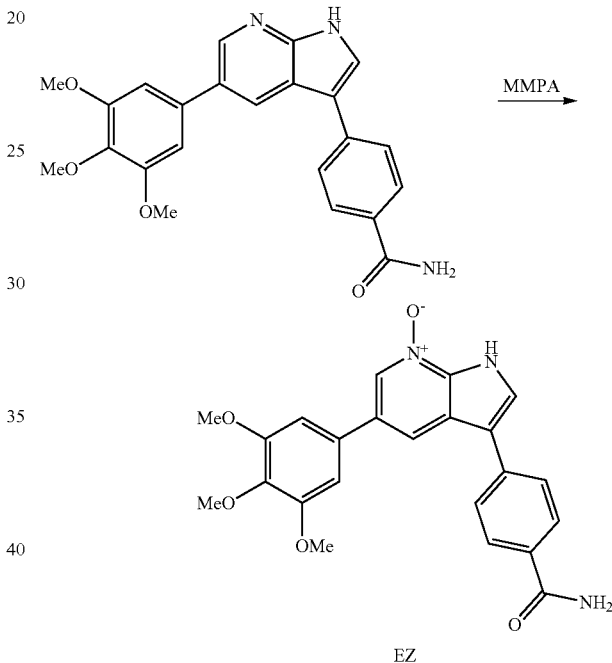

Preparation of 4-[7-oxy-5-(3,4,5-trimethoxy-phenyl)-1H-pyrrolo[2,3-b]pyridin-3-yl]-benzamide (Compound EZ)

In reference to Scheme 24, 4-[5-(3,4,5-Trimethoxy-phenyl)-1H-pyrrolo[2,3-b]pyridin-3-yl]-benzamide (50 mg, 0.124 mmol), magnesium monoperoxyphthalic acid (80%, 300 mg, 0.46 mmol) and acetic acid (10 drops were combined in EtOH (3 ml) and stirred at 50° C. for 1 hr. After adding EtOAc the mixture was washed with saturated NaHCO$_3$, dried and purified by silica gel chromatography using 0-8% MeOH:DCM to provide 18 mg (33%) of the title compound. $^1$H NMR (DMSO-d6, 300 MHz): δ 12.9 (bs, 1H), 8.62 (s, 1H), 8.14 (s, 1H), 8.0 (bs, 2H), 7.97 (d, J=5.0 Hz, 2H), 7.89 (d, J=5.0 Hz, 2H), 7.34 (bs, 1H), 7.04 (s, 2H), 3.89 (s, 6H), 3.70 (s, 3H).

Example 155

Preparation of 4-{5-[4-(4-methyl-piperazin-1-ylmethyl)-phenyl]-1H-pyrrolo[2,3-b]pyridin-3-yl}-benzamide (Compound FA)

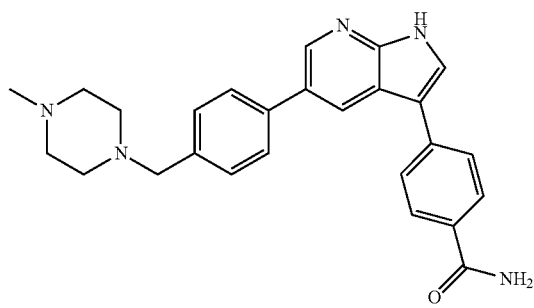 [SMILES: CN1CCN(Cc2ccc(-c3cnc4[nH]cc(-c5ccc(C(N)=O)cc5)c4c3)cc2)CC1]

4-{5-[4-(4-Methyl-piperazin-1-ylmethyl)-phenyl]-1H-pyrrolo[2,3-b]pyridin-3-yl}-benzamide was prepared by a method analogous to that described in Example 148 by substituting 4-[4-(4,4,5,5-tetramethyl-[1,3,2]dioxaborolan-2-yl)-benzoyl]-piperazine-1-carboxylic acid tert-butyl ester for 1-methyl-4-[4-(4,4,5,5-tetramethyl-[1,3,2]dioxaborolan-2-yl)-benzyl]-piperazine. The title compound (24 mg, 44%) was obtained by precipitation from DCM. $^1$H NMR (DMSO-d6, 300 MHz): δ 12.1 (s, 1H), 8.57 (d, J=1.2 Hz, 1H), 8.48 (d, J=1.2 Hz, 1H), 8.05 (d, J=1.3 Hz, 1H), 7.98 (bs, 1H), 7.96 (d, J=5.0 Hz, 2H), 7.88 (d, J=5.1 Hz, 2H), 7.73 (d, J=4.5 Hz, 2H), 7.40 (d, J=4.5 Hz, 2H), 7.31 (bs, 1H), 3.50 (s, 2H), 2.2-2.45 (bs, 8H), 2.15 (s, 3H).

Example 156

Preparation of 4-{5-[3-(4-methyl-piperazin-1-ylmethyl)-phenyl]-1H-pyrrolo[2,3-b]pyridin-3-yl}-benzamide (Compound FB)

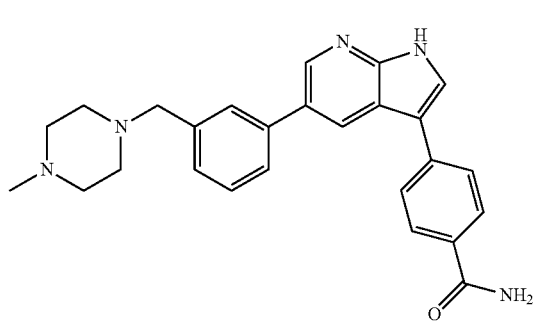 [SMILES: CN1CCN(Cc2cccc(-c3cnc4[nH]cc(-c5ccc(C(N)=O)cc5)c4c3)c2)CC1]

4-{5-[3-(4-Methyl-piperazin-1-ylmethyl)-phenyl]-1H-pyrrolo[2,3-b]pyridin-3-yl}-benzamide was prepared by a method analogous to that described in Example 148 by substituting 4-[4-(4,4,5,5-tetramethyl-[1,3,2]dioxaborolan-2-yl)-benzoyl]-piperazine-1-carboxylic acid tert-butyl ester for 1-methyl-4-[3-(4,4,5,5-tetramethyl-[1,3,2]dioxaborolan-2-yl)-benzyl]-piperazine. The title compound (8 mg, 15%) was obtained by precipitation from DCM. $^1$H NMR (DMSO-d6, 300 MHz): δ 12.1 (s, 1H), 8.56 (d, J=1.2 Hz, 1H), 8.46 (d, J=1.2 Hz, 1H), 8.05 (d, J=1.3 Hz, 1H), 7.96 (m, 3H), 7.88 (d, J=5.1 Hz, 2H), 7.66 (m, 2H), 7.45 (m, 1H), 7.31 (m, 2H), 3.55 (s, 2H), 2.2-2.45 (bs, 8H), 2.14 (s, 3H).

Example 157

Preparation of 4-{5-[4-(4-acetyl-piperazin-1-ylmethyl)-phenyl]-1H-pyrrolo[2,3-b]pyridin-3-yl}-benzamide (Compound FC)

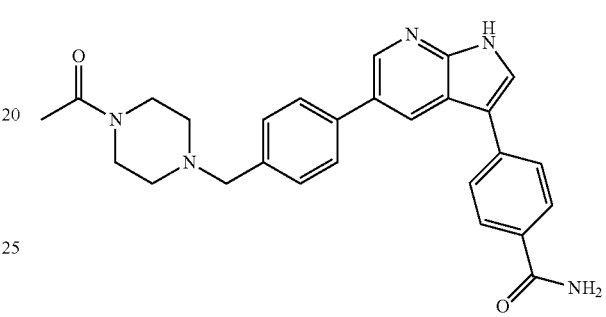

4-{5-[4-(4-Acetyl-piperazin-1-ylmethyl)-phenyl]-1H-pyrrolo[2,3-b]pyridin-3-yl}-benzamide was prepared by a method analogous to that described in Example 140 by substituting Intermediate B with compound FR. Purification by silica gel chromatography using 4-5% MeOH:DCM yielded the title compound (13 mg, 30%). MS ESI (m/z): 454.1 (M+1)$^+$, calc. 453.

Example 158

Preparation of 4-{5-[4-(4-methyl-3-oxo-piperazin-1-ylmethyl)-phenyl]-1H-pyrrolo[2,3-b]pyridin-3-yl}-benzamide (Compound FD)

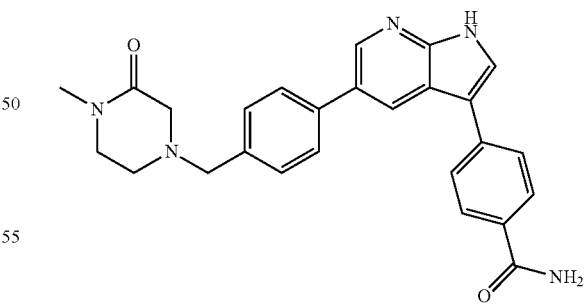

4-{5-[4-(4-Methyl-3-oxo-piperazin-1-ylmethyl)-phenyl]-1H-pyrrolo[2,3-b]pyridin-3-yl}-benzamide was prepared by a method analogous to that described in Example 140 by substituting Intermediate B with Compound FR and N-acetylpiperazine for 1-methyl-piperazin-2-one. Purification by silica gel chromatography using 4-5% MeOH:DCM yielded the title compound (4 mg, 10%). MS ESI (m/z): 440.3 (M+1)$^+$, calc. 439.

Example 159

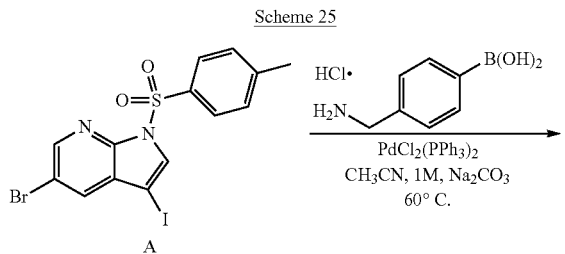

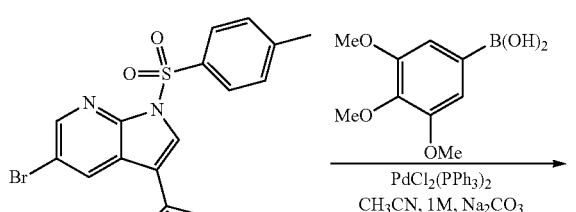

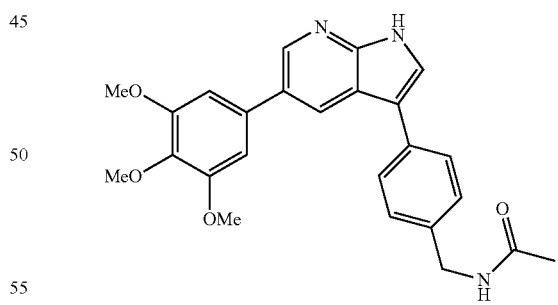

Preparation of Intermediate B: 4-[5-bromo-1-(toluene-4-sulfonyl)-1H-pyrrolo[2,3-b]pyridin-3-yl]-benzylamine In reference to Scheme 25, 5-Bromo-3-iodo-1-(toluene-4-sulfonyl)-1H-pyrrolo[2,3-b]pyridine (200 mg, 0.419 mmol), 4-aminomethylphenylboronic acid hydrochloride (95 mg, 0.503 mmol) and dichlorobis(triphenylphosphine)palladium (II) (29 mg, 0.042 mmol) were combined in $CH_3CN$ (5 ml) and 1 M $Na_2CO_3$ (5 ml) and stirred at 60° C. for 3 hrs. EtOAc was added, the organic phase was washed with water, dried and evaporated. to yield 136 mg (71%) of the title compound. MS ESI (m/z): 455.9/458.1 $(M+1)^+$, calc. 455/457.

Preparation of Intermediate C: N-{4-[5-bromo-1-(toluene-4-sulfonyl)-1H-pyrrolo[2,3-b]pyridin-3-yl]-benzyl}-acetamide 4-[5-Bromo-1-(toluene-4-sulfonyl)-1H-pyrrolo[2,3-b]pyridin-3-yl]-benzylamine (Intermediate B, 45 mg, 0.1 mmol) was combined with triethylamine (45 µl, 0.3 mmol) and acetic anhydride (11 µl, 0.11 mmol) in anh. DCM (2 ml). The mixture was stirred for 2 hrs, EtOAc, was added and washed with 0.5 N HCl, saturated $NaHCO_3$, water and brine. Evaporation yielded the title compound (48 mg, 96%). MS ESI (m/z): 498.1/500.1 $(M+1)^+$, calc. 497/499.

Preparation of N-{4-[5-(3,4,5-Trimethoxy-phenyl)-1H-pyrrolo[2,3-b]pyridin-3-yl]-benzyl}-acetamide (Compound FE)

N-{4-[5-Bromo-1-(toluene-4-sulfonyl)-1H-pyrrolo[2,3-b]pyridin-3-yl]-benzyl}-acetamide (Intermediate C, 24 mg, 0.048 mmol), 3,4,5-trimethoxyphenyl boronic acid (13 mg, 0.058 mmol) and dichlorobis(triphenylphosphine)palladium (II) (2 mg, 0.002 mmol) were combined in $CH_3CN$ (1 ml) and 1 M $Na_2CO_3$ (2 ml) and heated in a microwave reactor at 150° C. for 20 min. EtOAc was added, washed with water, dried and purified by silica gel chromatography eluting with 0-4% MeOH:DCM to give 11 mg (53%) of the title compound. MS ESI (m/z): 432.2 $(M+1)^+$, calc. 431.

Example 160

Preparation of 2-phenyl-N-{4-[5-(3,4,5-trimethoxy-phenyl)-1H-pyrrolo[2,3-b]pyridin-3-yl]-benzyl}-acetamide (Compound FF)

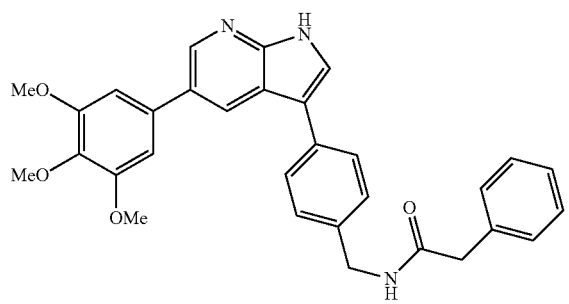 [SMILES: COc1cc(-c2cnc3[nH]cc(-c4ccc(CNC(=O)Cc5ccccc5)cc4)c3c2)cc(OC)c1OC]

2-Phenyl-N-{4-[5-(3,4,5-trimethoxy-phenyl)-1H-pyrrolo[2,3-b]pyridin-3-yl]-benzyl}-acetamide was prepared by a method analogous to that described in Example 159 by substituting acetic anhydride for phenacetyl chloride. Purification by silica gel chromatography using 0-4% MeOH:DCM yielded the title compound (9 mg, 38%). MS ESI (m/z): 508.3 (M+1)$^+$, calc. 507.

Example 161

Preparation of 3-phenyl-N-{4-[5-(3,4,5-trimethoxy-phenyl)-1H-pyrrolo[2,3-b]pyridin-3-yl]-benzyl}-propionamide (Compound FGI)

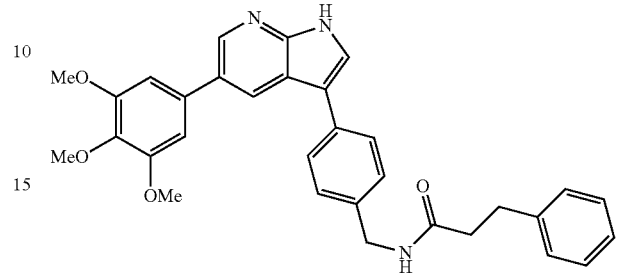

3-Phenyl-N-{4-[5-(3,4,5-trimethoxy-phenyl)-1H-pyrrolo[2,3-b]pyridin-3-yl]-benzyl}-propionamide was prepared by a method analogous to that described in Example 159 by substituting acetic anhydride for phenylpropionyl chloride. Purification by silica gel chromatography using 0-4% MeOH:DCM yielded the title compound (13 mg, 54%). MS ESI (m/z): 522.4 (M+1)$^+$, calc. 521.

Example 162

Scheme 26

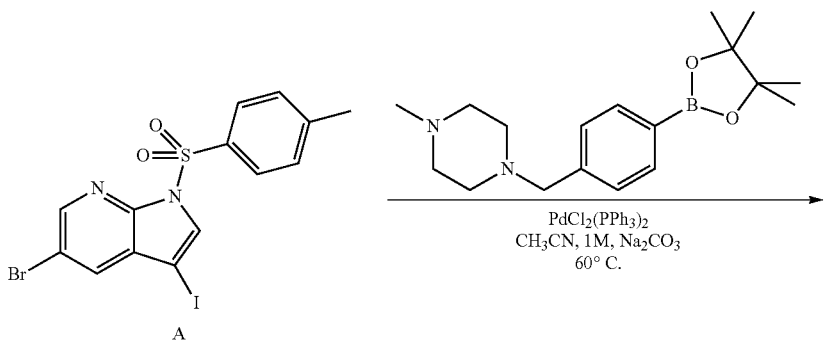

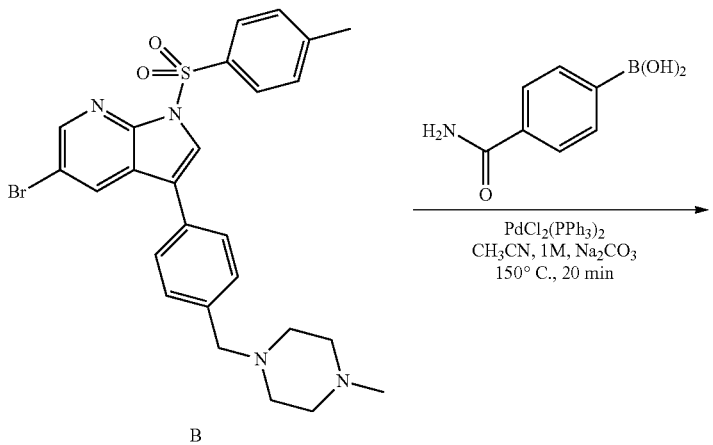

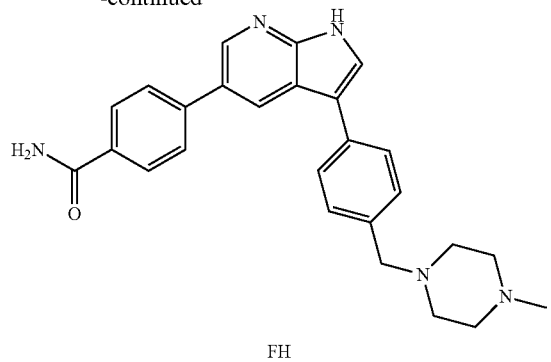

FH

Preparation of Intermediate B: 5-bromo-3-[4-(4-methyl-piperazin-1-ylmethyl)-phenyl]-1-(toluene-4-sulfonyl)-1H-pyrrolo[2,3-b]pyridine In reference to Scheme 26, 5-Bromo-3-iodo-1-(toluene-4-sulfonyl)-1H-pyrrolo[2,3-b]pyridine (200 mg, 0.419 mmol), 1-methyl-4-[4-(4,4,5,5-tetramethyl-[1,3,2]dioxaborolan-2-yl)-benzyl]-piperazine (160 mg, 0.503 mmol) and dichlorobis(triphenylphosphine)palladium (II) (30 mg, 0.042 mmol) were combined in $CH_3CN$ (5 ml) and 1 M $Na_2CO_3$ (5 ml) and stirred at 60° C. for 2 hrs. EtOAc was added and the organic phase was washed with water, dried and evaporated. Purification by silica gel chromatography using 0-20% MeOH:DCM yielded 235 mg (104%) of the title compound.

MS ESI (m/z): 539.0/541.2 $(M+1)^+$, calc. 538/540.

Preparation of 4-{3-[4-(4-methyl-piperazin-1-ylmethyl)-phenyl]-1H-pyrrolo[2,3-b]pyridin-5-yl}-benzamide (Compound FH)

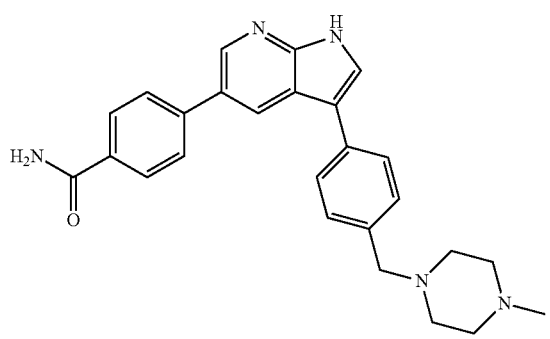 [SMILES: CN1CCN(Cc2ccc(-c3c[nH]c4ncc(-c5ccc(C(N)=O)cc5)cc34)cc2)CC1]

5-Bromo-3-[4-(4-methyl-piperazin-1-ylmethyl)-phenyl]-1-(toluene-4-sulfonyl)-1H-pyrrolo[2,3-b]pyridine (Intermediate B, 70 mg, 0.13 mmol), aminocarbonylphenylboronic acid (26 mg, 0.156 mmol) and dichlorobis(triphenylphosphine)palladium (II) (5 mg, 0.0065 mmol) were combined in $CH_3CN$ (2 ml) and 1 M $Na_2CO_3$ (2 ml) and reacted in a microwave reactor for 20 min at 150° C. Water was added and the aqueous phase was extracted with DCM, dried and evaporated. Purification by reversed phase chromatography using 0-100% MeOH:water yielded 6 mg (11%) of the title compound. MS ESI (m/z): 426.7 $(M+1)^+$, calc. 425.

Example 163

Preparation of 5-(1H-indol-5-yl)-3-[4-(4-methyl-piperazin-1-ylmethyl)-phenyl]-1H-pyrrolo[2,3-b]pyridine (Compound FI)

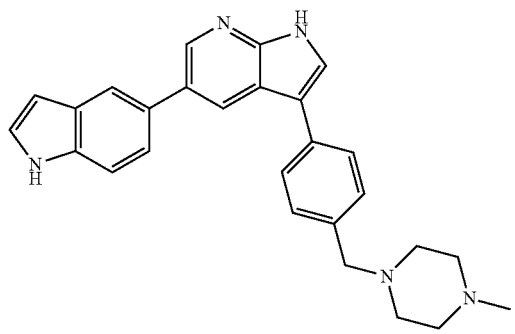 [SMILES: CN1CCN(Cc2ccc(-c3c[nH]c4ncc(-c5ccc6[nH]ccc6c5)cc34)cc2)CC1]

5-(1H-Indol-5-yl)-3-[4-(4-methyl-piperazin-1-ylmethyl)-phenyl]-1H-pyrrolo[2,3-b]pyridine was prepared by a method analogous to that described in Example 162 by substituting aminocarbonylphenylboronic acid for indole-5-boronic acid. Purification by silica gel chromatography using 0-10% MeOH:DCM yielded the title compound (28 mg, 60%). MS ESI (m/z): 422.4 $(M+1)^+$, calc. 421.

Example 164

Scheme 27

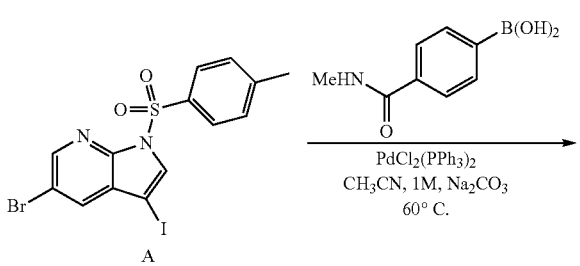

137

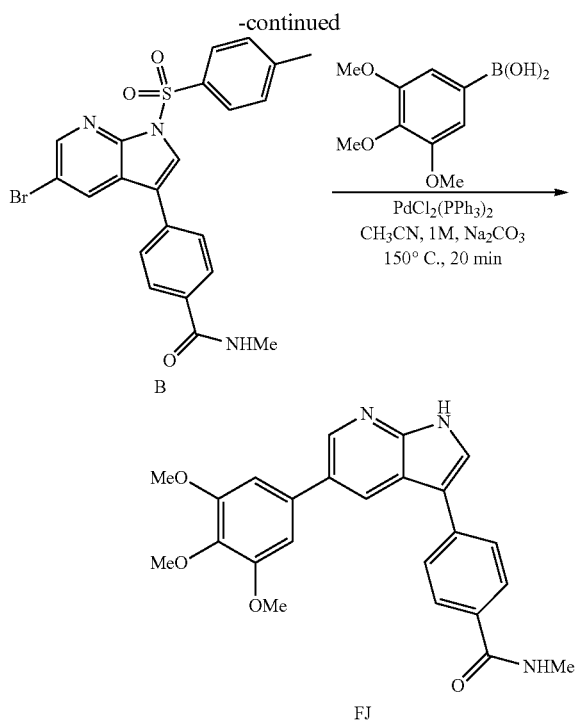

Preparation of Intermediate B: 4-[5-bromo-1-(toluene-4-sulfonyl)-1H-pyrrolo[2,3-b]pyridin-3-yl]-N-methyl-benzamide In reference to Scheme 27, 5-Bromo-3-iodo-1-(toluene-4-sulfonyl)-1H-pyrrolo[2,3-b]pyridine (350 mg, 0.73 mmol), 4-(N-methylaminocarbonyl)phenylboronic acid (160 mg, 0.88 mmol) and dichlorobis(triphenylphosphine) palladium (II) (52 mg, 0.073 mmol) were combined in CH$_3$CN (10 ml) and 1 M Na$_2$CO$_3$ (10 ml) and stirred at 60° C. for 5 hrs. Water was added and the mixture was extracted with DCM, combined organic phases were dried and evaporated to yield 428 mg (121%) of the title compound. $^1$H NMR (CDCl$_3$, 300 MHz): δ 8.50 (d, J=1.3 Hz, 1H), 8.20 (d, J=1.2 Hz, 1H), 8.09 (d, J=5.1 Hz, 2H), 7.94 (s, 1H), 7.87 (d, J=5.1, 2H), 7.61 (d, J=5.0 Hz, 2H), 7.31 (d, J=5.0 Hz, 2H), 6.21 (bd, J=2.5 Hz, 1H), 3.06, (d, J=2.9 Hz, 3H), 2.39 (s, 3H).

138

Preparation of N-methyl-4-[5-(3,4,5-trimethoxyphenyl)-1H-pyrrolo[2,3-b]pyridin-3-yl]-benzamide (Compound FJ)

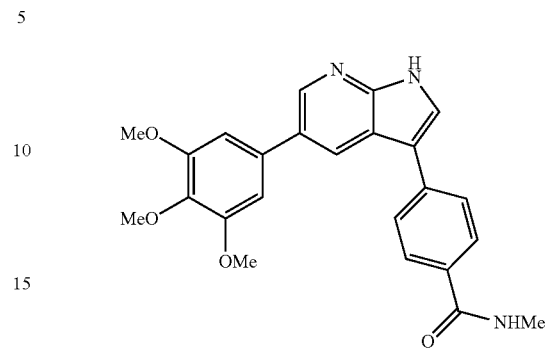

4-[5-Bromo-1-(toluene-4-sulfonyl)-1H-pyrrolo[2,3-b]pyridin-3-yl]-N-methyl-benzamide (Intermediate B, 100 mg, 0.206 mmol), 3,4,5-trimethoxyphenylboronic acid (53 mg, 0.248 mmol) and dichlorobis(triphenylphosphine)palladium (II) (9 mg, 0.012 mmol) were combined in CH$_3$CN (2 ml) and 1 M Na$_2$CO$_3$ (2 ml) and reacted in a microwave reactor for 20 min at 150° C. Water was added, the aqueous phase was extracted with DCM and the organic phase was dried and evaporated. Purification by silica gel chromatography using 0-8% MeOH:DCM yielded 40 mg (47%) of the title compound. $^1$H NMR (CDCl$_3$, 300 MHz): δ 12.09 (s, 1H), 8.59 (d, J=1.2 Hz, 1H), 8.48 (d, J=1.2 Hz, 1H), 8.43 (q, J=2.7 Hz, 1H), 8.04 (s, 1H), 7.94 (d, J=4.0, 2H), 7.91 (d, J=4.0 Hz, 2H), 7.00 (s, 2H), 3.89 (s, 6H), 3.70 (s, 3H), 2.80, (d, J=4.5 Hz, 3H).

Example 165

Preparation of N-methyl-4-{5-[4-(4-methyl-piperazin-1-ylmethyl)-phenyl]-1H-pyrrolo[2,3-b]pyridin-3-yl}-benzamide (Compound FK)

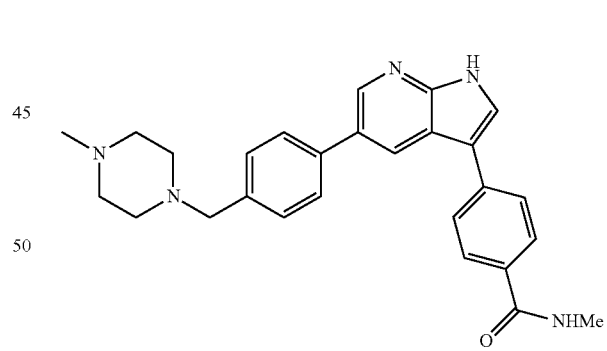

N-Methyl-4-{5-[4-(4-methyl-piperazin-1-ylmethyl)-phenyl]-1H-pyrrolo[2,3-b]pyridin-3-yl}-benzamide was prepared by a method analogous to that described in Example 164 by substituting 3,4,5-trimethoxyphenylboronic acid for 1-methyl-4-[4-(4,4,5,5-tetramethyl-[1,3,2]dioxaborolan-2-yl)-benzyl]-piperazine. Purification by precipitation from hot DCM yielded the title compound (46 mg, 51%). $^1$H NMR (CDCl$_3$, 300 MHz): δ 12.09 (s, 1H), 8.57 (d, J=1.2 Hz, 1H), 8.48 (d, J=1.2 Hz, 1H), 8.43 (q, J=2.7 Hz, 1H), J=1.5 Hz, 1H), 7.92 (d, J=5.2 Hz, 2H), 7.89 (d, J=5.2 Hz, 2H), 7.73 (d, J=4.9 Hz, 2H), 7.40 (d, J=4.9 Hz, 2H), 3.50 (s, 2H), 2.81, (d, J=2.7 Hz, 3H), 2.2-2.45 (bs. 8H), 2.15 (s, 3H).

Example 166

Preparation of 3-(4-fluoro-phenyl)-5-(3,4,5-trimethoxy-phenyl)-1H-pyrrolo[2,3-b]pyridine (Compound FL)

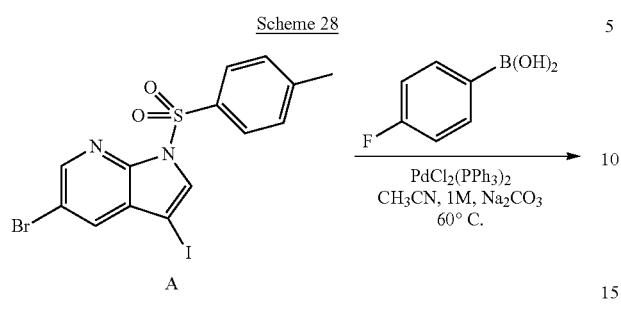

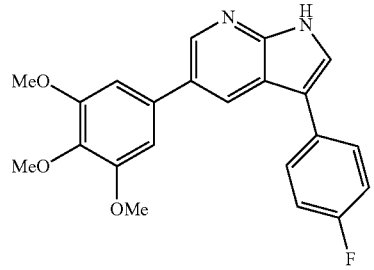 [SMILES: COc1cc(-c2cnc3[nH]cc(-c4ccc(F)cc4)c3c2)cc(OC)c1OC]

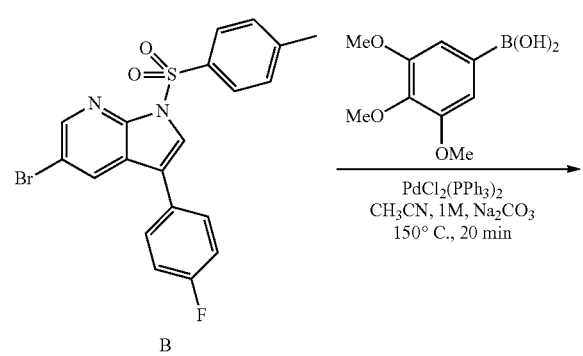

5-Bromo-3-(4-fluoro-phenyl)-1-(toluene-4-sulfonyl)-1H-pyrrolo[2,3-b]pyridine (37 mg, 0.083 mmol), 3,4,5-trimethoxyphenylboronic acid (21 mg, 0.1 mmol) and dichlorobis(triphenylphosphine)palladium (II) (3 mg, 0.004 mmol) were combined in $CH_3CN$ (1.5 ml) and 1 M $Na_2CO_3$ (2 ml) and reacted in a microwave reactor for 20 min at 150° C. EtOAc was added and the mixture was washed with water, dried, evaporated and purified by silica gel chromatography using 0-2% MeOH:DCM to yield 9 mg (29%) of the title compound. MS ESI (m/z): 379.2 $(M+1)^+$, calc. 378.

Example 167

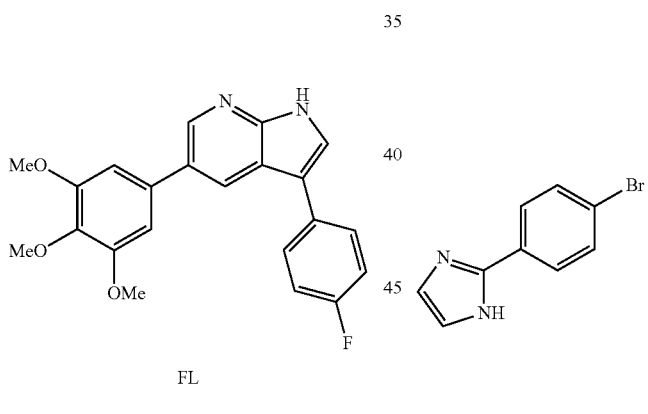

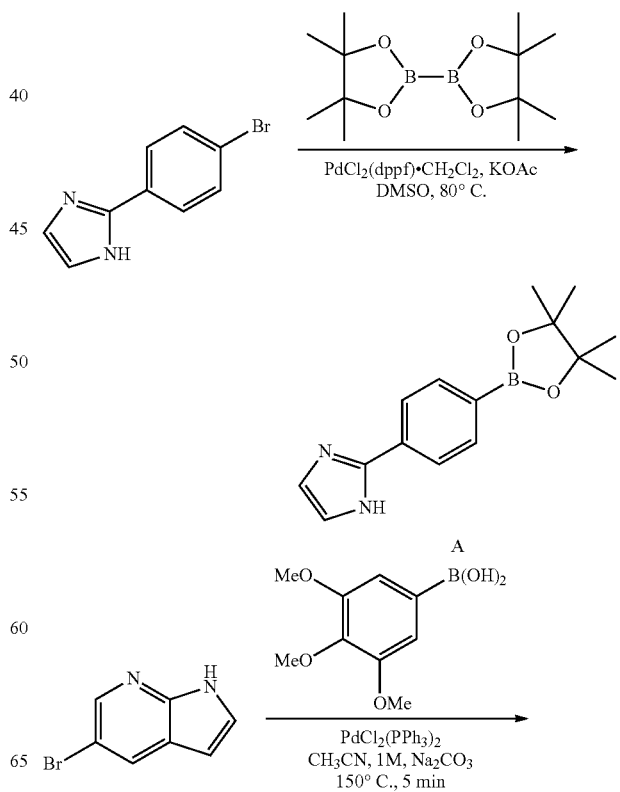

Preparation of Intermediate B: 5-bromo-3-(4-fluoro-phenyl)-1-(toluene-4-sulfonyl)-1H-pyrrolo[2,3-b]pyridine In reference to Scheme 28, 5-Bromo-3-iodo-1-(toluene-4-sulfonyl)-1H-pyrrolo[2,3-b]pyridine (70 mg, 0.147 mmol), 4-fluorophenylboronic acid (25 mg, 0.176 mmol) and dichlorobis(triphenylphosphine)palladium (II) (10 mg, 0.015 mmol) were combined in $CH_3CN$ (2 ml) and 1 M $Na_2CO_3$ (2 ml) and stirred at 60° C. for 3 hrs. EtOAc was added and the mixture was washed with water, dried and evaporated to yield 73 mg (112%) of the title compound. MS ESI (m/z): 445.1/447.2 $(M+1)^+$, calc. 444/446.

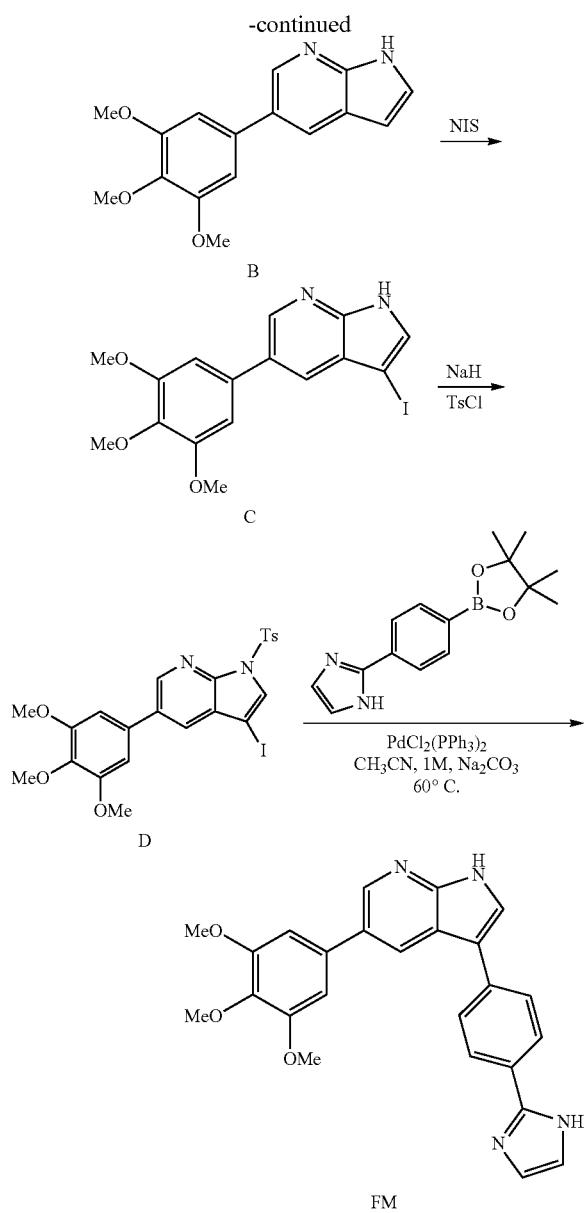

and dichlorobis(triphenylphosphine)palladium (II) (275 mg, 0.39 mmol) were combined in CH$_3$CN (10 ml) and 1 M Na$_2$CO$_3$ (10 ml) and reacted in a microwave reactor for 5 min at 150° C. EtOAc was added and the mixture was washed with water, brine, dried, evaporated and purified by silica gel chromatography using 0-2% MeOH:DCM to yield 1.86 g (84%) of the title compound. $^1$H NMR (CDCl$_3$, 300 MHz): δ 9.9 (bs, 1H), 8.54 (d, J=2.1 Hz, 1H), 8.11 (d. J=2.1 Hz, 1H), 7.41 (t, J=2.1 Hz, 1H), 6.82 (s, 2H), 6.58 (t, J=1.5 Hz, 1H), 3.96 (s, 6H), 3.92 (s, 3H).

Preparation of Intermediate C: 3-iodo-5-(3,4,5-trimethoxy-phenyl)-1H-pyrrolo[2,3-b]pyridine To a solution of 5-(3,4,5-trimethoxy-phenyl)-1H-pyrrolo[2,3-b]pyridine (510 mg, 1.79 mmol) in acetone (100 ml) was added N-iodosuccinimide (444 mg, 1.97 mmol) under stirring. After 1 hr the mixture was evaporated and purified by silica gel chromatography using 0-2% MeOH:DCM to give the title compound (870 mg, 118%). MS ESI (m/z): 411.1 (M+1)$^+$, calc. 410.

Preparation of Intermediate D: 3-iodo-1-(toluene-4-sulfonyl)-5-(3,4,5-trimethoxy-phenyl)-1H-pyrrolo[2,3-b]pyridine A solution of 3-iodo-5-(3,4,5-trimethoxy-phenyl)-1H-pyrrolo[2,3-b]pyridine (870 mg, 2.12 mmol) in anh. THF (10 ml) was cooled to 0° C. and NaH (60% dispersion, 130 mg, 3.18 mmol) was added. After 20 min tosyl chloride (450 mg, 2.33 mmol) was added and the mixture was allowed to warm to room temperature. After 3 hrs the mixture was cooled to 0° C. and quenched by the addition of 0.5 N HCl. The product was extracted with DCM and purified by silica gel chromatography using DCM as an eluent affording 648 mg (54%). $^1$H NMR (CDCl$_3$, 300 MHz): δ 8.61 (d, J=2.4 Hz, 1H), 8.12 (d. J=8.4 Hz, 1H), 7.91 (s, 1H), 7.74 (d, J=2.1 Hz, 1H), 7.31 (d, J=8.4 Hz, 2H), 6.73 (s, 2H), 3.94 (s, 6H), 3.90 (s, 3H), 2.39 (s, 3H).

Preparation of 3-[4-(1H-imidazol-2-yl)-phenyl]-5-(3,4,5-trimethoxy-phenyl)-1H-pyrrolo[2,3-b]pyridine (Compound FM)

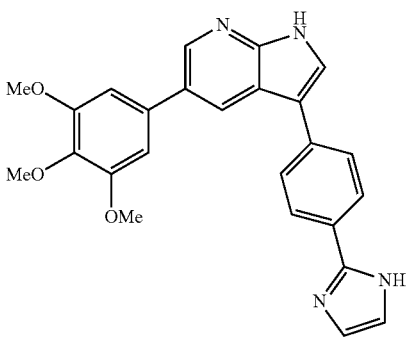 [SMILES: COc1cc(-c2cnc3[nH]cc(-c4ccc(-c5ncc[nH]5)cc4)c3c2)cc(OC)c1OC]

Preparation of Intermediate A: 2-[4-(4,4,5,5-tetramethyl-[1,3,2]dioxaborolan-2-yl)-phenyl]-1H-imidazole In reference to Scheme 29, 2-(4-Bromo-phenyl)-1H-imidazole (300 mg, 1.3 mmol), bis(pinacolato)diboron (376 mg, 1.48 mmol), KOAc (400 mg, 4.03 mmol) and PdCl$_2$(dppf).CH$_2$Cl$_2$ (50 mg, 0.067 mmol) were combined in DMSO (8 ml) and stirred t 80° C. overnight. EtOAc was added, washed with water, dried, evaporated and purified by silica gel chromatography eluting with 0-5% MeOH:DCM to give 116 mg (36%) of the title compound. $^1$H NMR (CDCl$_3$, 300 MHz): δ 7.86 (s, 4H), 7.18 (s, 2H), 1.36 (s, 12H).

Preparation of Intermediate B: 5-(3,4,5-trimethoxy-phenyl)-1H-pyrrolo[2,3-b]pyridine 5-Bromo-1H-pyrrolo[2,3-b]pyridine (1.54 g, 7.83 mmol), 3,4,5-trimethoxyphenylboronic acid (1.83 g, 8.61 mmol)

3-Iodo-1-(toluene-4-sulfonyl)-5-(3,4,5-trimethoxy-phenyl)-1H-pyrrolo[2,3-b]pyridine (Intermediate D, 30 mg, 0.053 mmol), 2-[4-(4,4,5,5-tetramethyl-[1,3,2]dioxaborolan-2-yl)-phenyl]-1H-imidazole (Intermediate A, 18 mg, 0.064 mmol) and dichlorobis(triphenylphosphine)palladium (II) (2 mg, 0.003 mmol) were combined in CH$_3$CN (1 ml) and 1 M Na$_2$CO$_3$ (1 ml) and stirred at 60° C. for 2 d.

Additional Intermediate GQ (18 mg, 0.064 mmol) was added and stirring was continued for another day. EtOAc was added and the mixture was washed with water, dried, evaporated and purified by silica gel chromatography using 0-5% MeOH:DCM to yield 5 mg (22%) of the title compound.

MS ESI (m/z): 427.2 (M+1)$^+$, calc. 426.

Mass spectra for the following examples were obtained on a PE-SCIEX 150 spectrometer using API ionization mode.

Example 168

3-(1H-indol-5-yl)-5-(4-(piperazin-1-ylmethyl)phenyl)-1H-pyrrolo[2,3-b]pyridine (Compound FN)

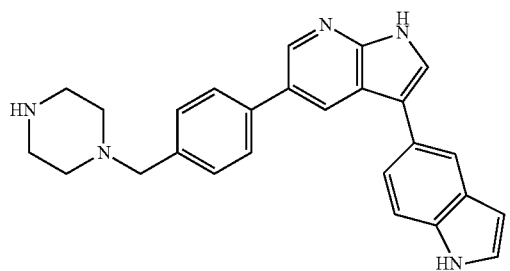 [SMILES: c1cc2cc(-c3c[nH]c4ncc(-c5ccc(CN6CCNCC6)cc5)cc34)ccc2[nH]1]

tert-butyl 4-(4-(3-(1H-indol-5-yl)-1H-pyrrolo[2,3-b]pyridin-5-yl)benzyl)piperazine-1-carboxylate (63 mg) (Compound FM; Example 144) was suspended in dichloromethane (2 mL) and treated with TFA (2 mL). The resulting mixture was stirred for 90 minutes at room temperature, after which the solvent was removed in vacuo. The residue was dissolved in EtOAc and washed with 10% sodium hydroxide solution, water, and brine. The organic layer was dried over MgSO$_4$, and the solvent was removed in vacuo. MPLC silica gel chromatography (0-20% MeOH in dichloromethane) provided an analytical sample (10 mg, 408 M+H) of the title compound.

Examples 169-183

Method Y: Synthesis Via Aryl Bromides

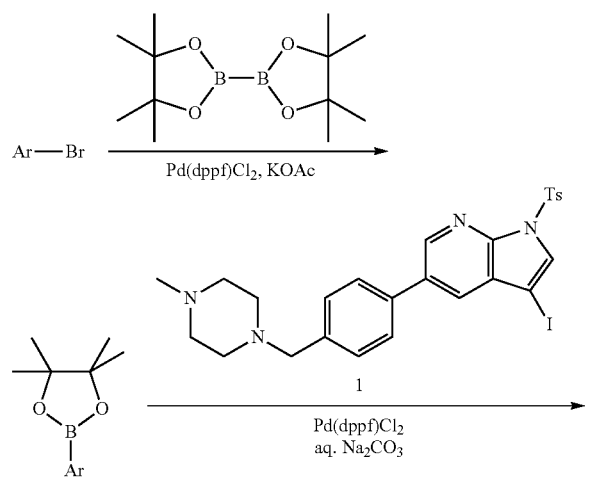

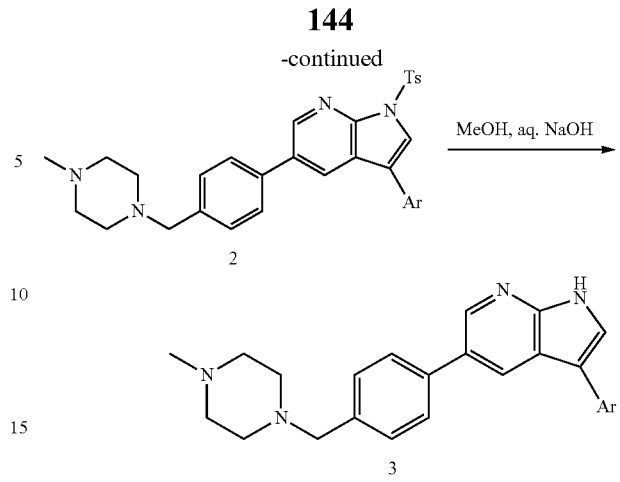

Synthesis of 5-(4-((4-methylpiperazin-1-yl)methyl)phenyl)-1H-pyrrolo[2,3-b]pyridine In a 100 mL rb flask, 5-bromo-7-azaindole (2 mmol), 4-(4-methyl-1-piperazinylmethyl)benzeneboronic acid pinacolester (2.2 mmol), Pd(PPh$_3$)$_4$ (0.01 mmol) and NaHCO$_3$ (6 mmol) were suspended in dioxane (16 mL) and water (4 mL) and heated at 110° C. overnight. Upon complete consumption of starting bromide, the reaction mixture was extracted with ethyl acetate 3 times and the combined organic layers were washed with brine, dried over Na$_2$SO$_4$, and evaporated to afford crude product. The crude residue was purified with methylene chloride and methanol on silica gel column using ISCO to afford 5-(4-((4-methylpiperazin-1-yl)methyl)phenyl)-1H-pyrrolo[2,3-b]pyridine.

Synthesis of 3-Iodo-5-(4-((4-methylpiperazin-1-yl)methyl)phenyl)-1H-pyrrolo[2,3-b]pyridine In a 100 mL rb flask, 5-(3-Iodo-5-(4-((4-methylpiperazin-1-yl)methyl)phenyl)-1H-pyrrolo[2,3-b]pyridine 4-((4-methylpiperazin-1-yl)methyl)phenyl)-1H-pyrrolo[2,3-b]pyridine (2 mmol), was dissolved in acetone (20 mL) and N-iodosuccinamide (2.2 mmol) was added in 3 portions with 5 min. intervals, resulting mixture was stirred at room temperature for 1 hour. Upon complete consumption of starting material, product was precipitated out as solid was filtered and washed with acetone and dried to afford pure 3-iodo-5-(4-((4-methylpiperazin-1-yl)methyl)phenyl)-1H-pyrrolo[2,3-b]pyridine.

Synthesis of Method Y Intermediate 1: 3-Iodo-5-(4-((4-methylpiperazin-1-yl)methyl)phenyl)-1-tosyl-1H-pyrrolo[2,3-b]pyridine In a 100 mL rb flask, 3-iodo-5-(4-((4-methylpiperazin-1-yl)methyl)phenyl)-1H-pyrrolo[2,3-b]pyridine (2 mmol), was suspended in THF (20 mL) and NaH (3 mmol) was added in 3 portions with 5 min. intervals at 0° C., resulting mixture was stirred at 0° C. to room temperature for 1 hour. Upon complete consumption of starting material, solvents evaporated to afford crude solid was precipitated out using hexane (20 mL) and cold 1N NaOH (10 mL) to afford pure 3-iodo-5-(4-((4-methylpiperazin-1-yl)methyl)phenyl)-1-tosyl-1H-pyrrolo[2,3-b]pyridine.

General Procedure for Boronic Ester Synthesis

In a microwave tube, bromo compound (1 mmol), bis(pinacolato)diboron (1.1 mmol), PdCl$_2$dppf (0.01 mmol)

and KOAc (3 mmol) were suspended in acetonitrile (2 mL), sealed the tube and heated at 80° C. overnight. Upon complete consumption of starting bromide, extracted with ethyl acetate 3 times and combined organic layer was washed with brine and dried over Na$_2$SO$_4$ and evaporated to afford crude product. The crude residue was triturated with hexane and dried in vacuo to yield the corresponding boronic ester.

General Procedure for Suzuki Coupling Reaction

In a microwave reaction tube, intermediate 1 (2 mmol), corresponding boronic ester (2.2 mmol), PdCl$_2$dppf (0.01 mmol) 1M Na$_2$CO$_3$ (1 mL) and acetonitrile (1 mL) were heated 90° C. overnight. Upon complete consumption of starting materials, extracted with ethyl acetate 3 times and combined organic layer was washed with brine and dried over Na$_2$SO$_4$ and evaporated to afford crude product. The crude residue was purified on silicagel column on ISCO using methylene chloride and methanol.

General Procedure for De-Tosylation Reaction

In a 50 mL rb flask, intermediate 2 (2 mmol) was treated with 1N NaOH (2 mL) in methanol (2 mL) were heated 60° C. for 2 hours. Upon complete consumption of starting material, extracted with ethyl acetate 3 times and combined organic layer was washed with brine and dried over Na$_2$SO$_4$ and evaporated to afford crude product. The crude residue was purified on silicagel column on ISCO using methylene chloride and methanol.

Using the corresponding aryl bromides the following compounds were prepared using Method Y.

| Example | Structure | M + H | Cmpd ID |
|---|---|---|---|
| 169 | 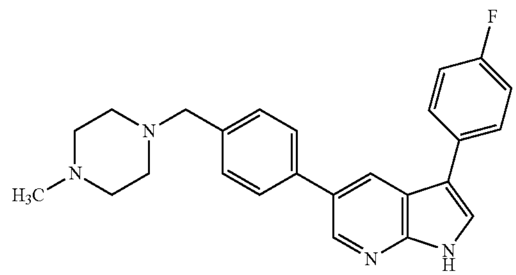 [SMILES: CN1CCN(Cc2ccc(-c3cnc4[nH]cc(-c5ccc(F)cc5)c4c3)cc2)CC1] | 401 | FO |
| 170 | 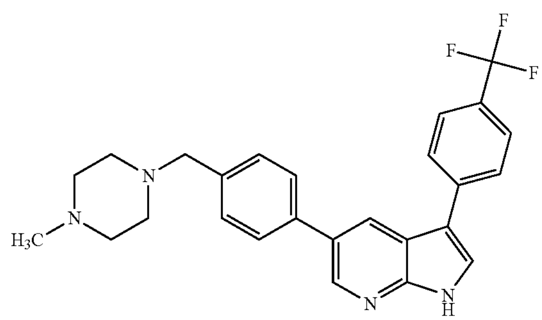 [SMILES: CN1CCN(Cc2ccc(-c3cnc4[nH]cc(-c5ccc(C(F)(F)F)cc5)c4c3)cc2)CC1] | 451 | FP |
| 171 | 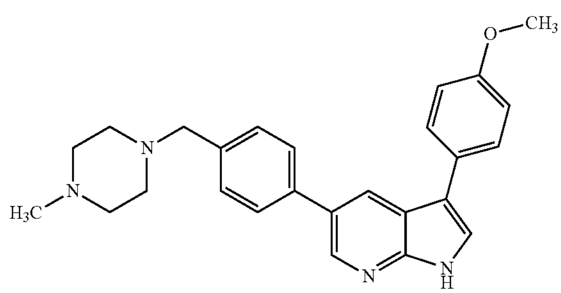 | 413 | FQ |
| 172 | 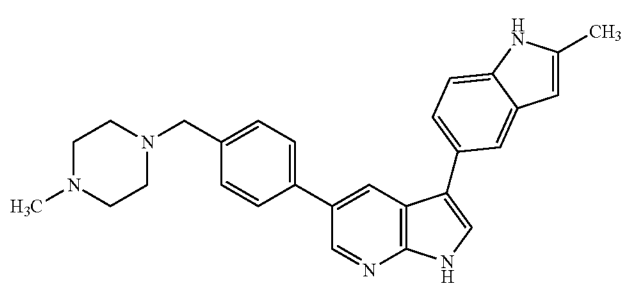 | 436 | FR |

| Example | Structure | M + H | Cmpd ID |
|---|---|---|---|
| 173 | 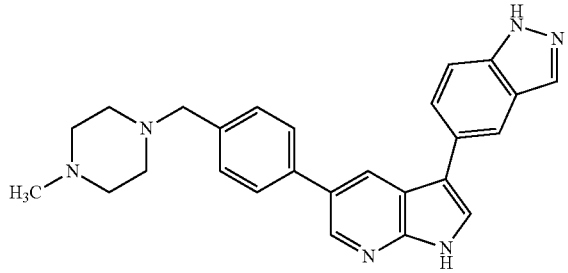 [SMILES: CN1CCN(Cc2ccc(-c3cnc4[nH]cc(-c5ccc6[nH]ncc6c5)c4c3)cc2)CC1] | 423 | FS |
| 174 | 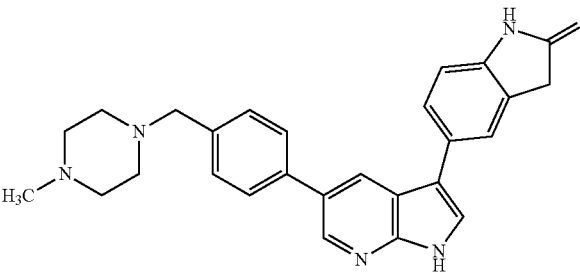 | 438 | FT |
| 175 | 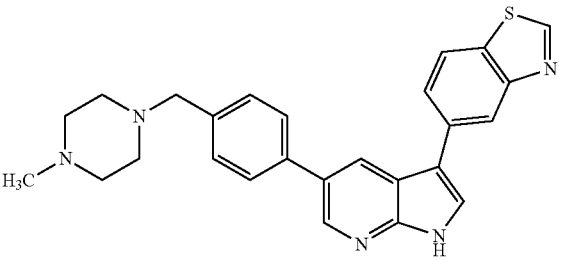 [SMILES: CN1CCN(Cc2ccc(-c3cnc4[nH]cc(-c5ccc6scnc6c5)c4c3)cc2)CC1] | 440 | FU |
| 176 | 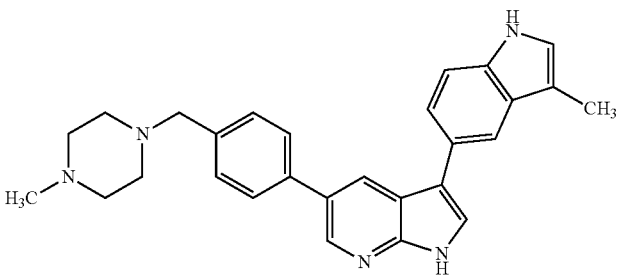 | 436 | FV |
| 177 | 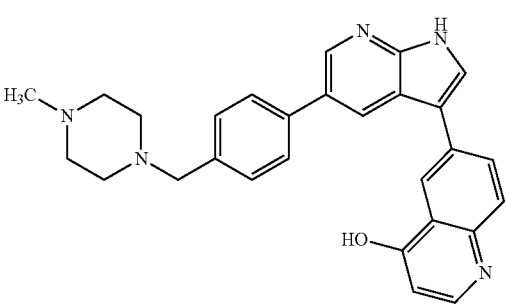 [SMILES: CN1CCN(Cc2ccc(-c3cnc4[nH]cc(-c5ccc6nccc(O)c6c5)c4c3)cc2)CC1] | 450 | FW |

| Example | Structure | M + H | Cmpd ID |
|---------|-----------|-------|---------|
| 178 | 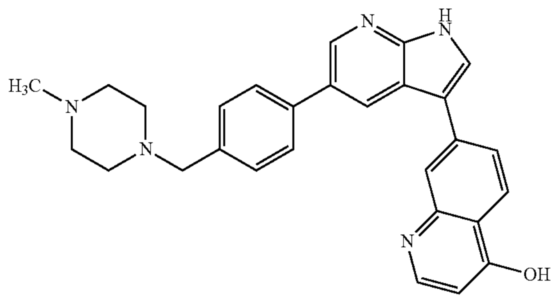 [SMILES: CN1CCN(Cc2ccc(-c3cnc4[nH]cc(-c5ccc6c(O)ccnc6c5)c4c3)cc2)CC1] | 450 | FX |
| 179 | 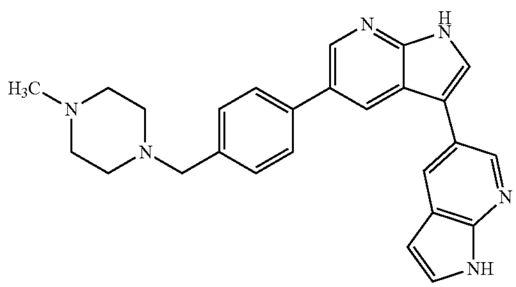 [SMILES: CN1CCN(Cc2ccc(-c3cnc4[nH]cc(-c5cnc6[nH]ccc6c5)c4c3)cc2)CC1] | 423 | FY |
| 180 | 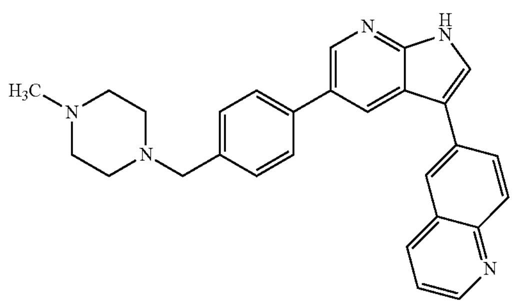 [SMILES: CN1CCN(Cc2ccc(-c3cnc4[nH]cc(-c5ccc6ncccc6c5)c4c3)cc2)CC1] | 434 | FZ |
| 181 | 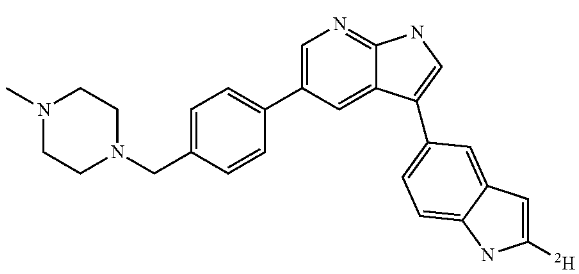 [SMILES: [2H]c1cc2cc(-c3c[nH]c4ncc(-c5ccc(CN6CCN(C)CC6)cc5)cc34)ccc2[nH]1] | 423 | GA |
| 182 | 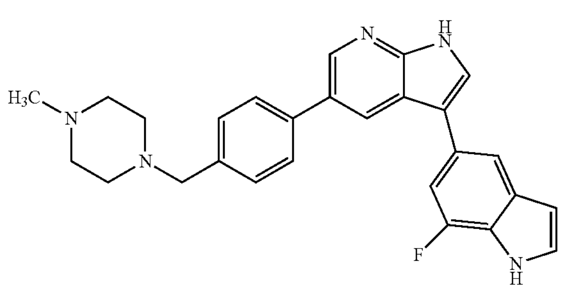 [SMILES: CN1CCN(Cc2ccc(-c3cnc4[nH]cc(-c5cc(F)c6[nH]ccc6c5)c4c3)cc2)CC1] | 440 | GB |

-continued
| Example | Structure | M + H | Cmpd ID |
|---|---|---|---|
| 183 | 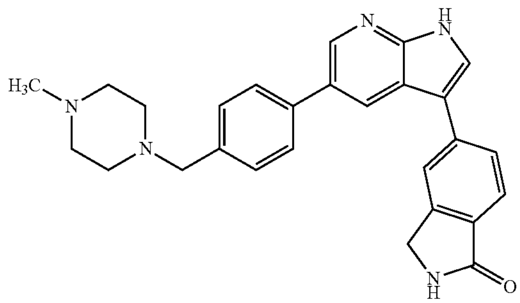 [SMILES: CN1CCN(Cc2ccc(-c3cnc4[nH]cc(-c5ccc6c(c5)CNC6=O)c4c3)cc2)CC1] | 437.55 | GC |
Method X: Reductive Amination
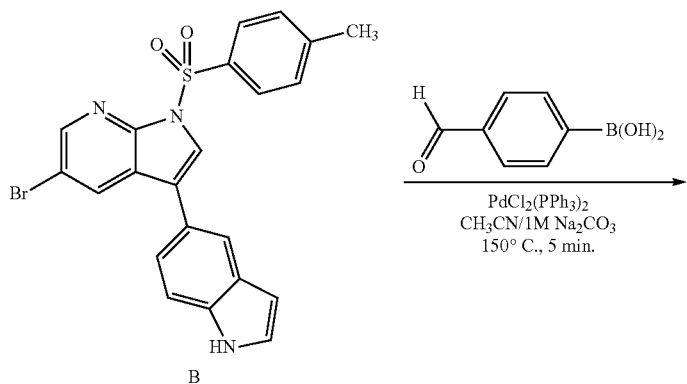
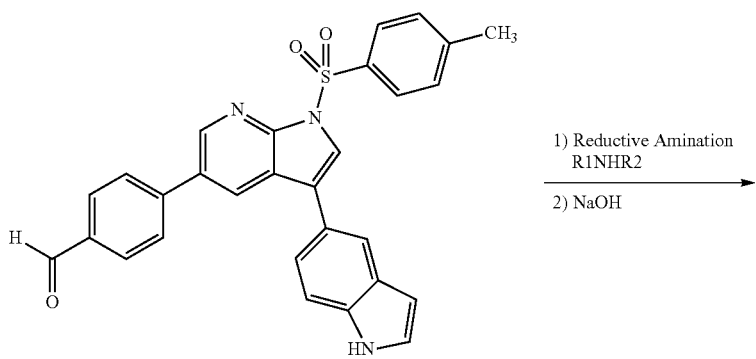
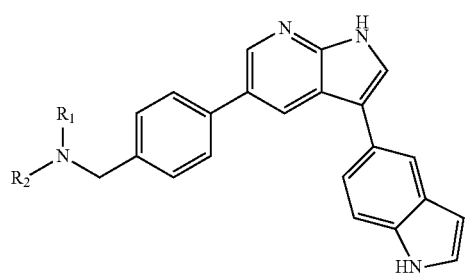

Synthesis of Method X Intermediate 1: 4-(3-(1H-indol-5-yl)-1-tosyl-1H-pyrrolo[2,3-b]pyridin-5-yl)benzaldehyde Intermediate B (4.04 g) and 4-formylphenylboronic acid (1.56 g) were suspended in 150 mL of acetonitrile and treated with 150 mL of 1 M sodium carbonate solution. To this was added dichloro-bis-(triphenylphosphine)-palladium (II) (608 mg) and the mixture was heated at reflux for 2.5 hours. The reaction mixture was filtered and the residue washed with EtOAc, the filtrates were combined and washed with water, and brine, dried over MgSO4, and concentrated. MPLC silica gel chromatography eluting with 0-30% EtOAc in hexane, produced 3.77 g of the title compound (M+H 492).

Example 184

Preparation of 4-(4-(3-(1H-indol-5-yl)-1H-pyrrolo[2,3-b]pyridin-5-yl)benzyl)morpholine (Compound GD)

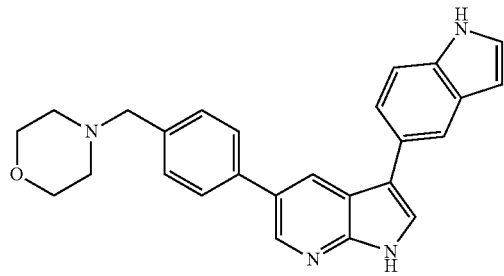 [SMILES: c1cc2cc(-c3c[nH]c4ncc(-c5ccc(CN6CCOCC6)cc5)cc34)ccc2[nH]1]

Intermediate 1 from Method X (60 mg) was suspended in anhydrous methanol (3 mL), dichloromethane (0.5 mL) and THF (1.5 mL) and treated with morpholine (45 uL) and stirred for 10 minutes, to this was added sodium triacetoxy borohydride 39 mg, the reaction stirred over night and was diluted with water and extracted with dichloromethane. The organic layers were washed with brine and dried over MgSO4 and purified by MPLC silica gel chromatography (50-100% EtOAc in hexane) to yield an analytical sample (28 mg, M+H 563). The tosyl group was removed using the general procedure for hydrolysis above, and the resulting material was purified by crystallization from EtOH/water to give 10 mg (M+H, 609) of an analytical sample of the title compound.

Example 185

Preparation of 5-(4-((4,4-difluoropiperidin-1-yl)methyl)phenyl)-3-(1H-indol-5-yl)-1H-pyrrolo[2,3-b]pyridine (Compound GE)

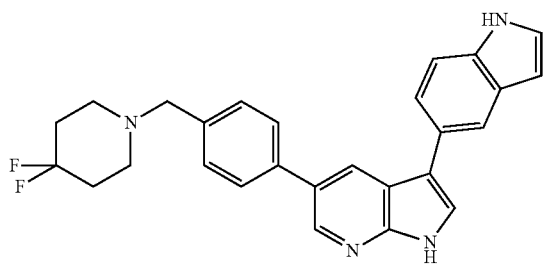 [SMILES: FC1(F)CCN(Cc2ccc(-c3cnc4[nH]cc(-c5ccc6[nH]ccc6c5)c4c3)cc2)CC1]

Intermediate 1 from Method X (50 mg) was dissolved in anhydrous dichloromethane (3 mL) and treated with 33 mg of 4,4-difluro-piperidine, to this was added activated 4 A molecular sieves, and the mixture stirred 1.5 hrs, to this was added 33 mg of sodium triacetoxy borohydride, and the reaction stirred overnight. The reaction was diluted with dichloromethane and washed with water, brine and dried over MgSO4. MPLC purification on silica gel (30-70% EtOAc in hexane) provided 45 mg of crude product. Hydrolysis according to the general method above provided the de-tosylated compound which was purified by MPLC silica gel chromatography (2% MeOH in DCM) to provide the title compound (M+H 443)

Example 186

Preparation of (4-((4-benzylpiperazin-1-yl)methyl)phenyl)-3-(1H-indol-5-yl)-1H-pyrrolo[2,3-b]pyridine (Compound GF)

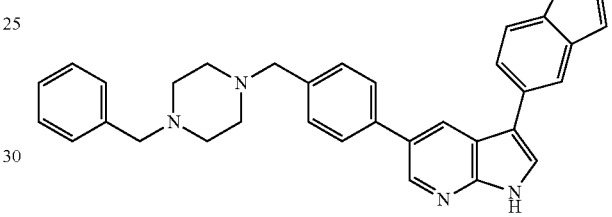

Intermediate 1 from Method X (100 mg) was dissolved in anhydrous dichloromethane (3 mL) and treated with 54 mg of 4-benzylpiperazine, to this was added activated 4 angstrom molecular sieves, and the mixture stirred 2 hrs. To this mixture, was added 65 mg of sodium triacetoxy borohydride, and the reaction stirred overnight. The reaction was diluted with dichloromethane and washed with water, brine and dried over MgSO4. MPLC purification on silica gel (0-2% MeOH in dichoromethane) provided 69 mg of crude product. Hydrolysis according to the general method above provided the de-tosylated compound which was purified by MPLC silica gel chromatography (2% MeOH in DCM) to provide 45 mg of the title compound (M+H 498)

Example 187

Preparation of tert-butyl 4-(4-(3-(1H-indol-5-yl)-1-tosyl-1H-pyrrolo[2,3-b]pyridin-5-yl)benzyl)-2-methylpiperazine-1-carboxylate (Compound GG)

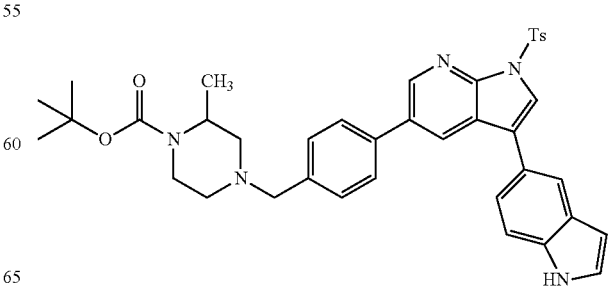

Intermediate 1 from Method X (50 mg) was dissolved in anhydrous dichloromethane (3 mL) and treated with 41 mg of tert-butyl 2-methylpiperazine-1-carboxylate. To the resulting solution was added activated 4 Å molecular sieves, and the mixture was stirred 2 hrs at room temperature. 33 mg of sodium triacetoxy borohydride was added, and the reaction was stirred overnight, after which it was diluted with dichloromethane, washed with water and brine, and dried over MgSO₄ to yield the title compound.

Preparation of 3-(1H-indol-5-yl)-5-(4-((3-methyl-piperazin-1-yl)methyl)phenyl)-1-tosyl-1H-pyrrolo[2,3-b]pyridine (Compound GH)

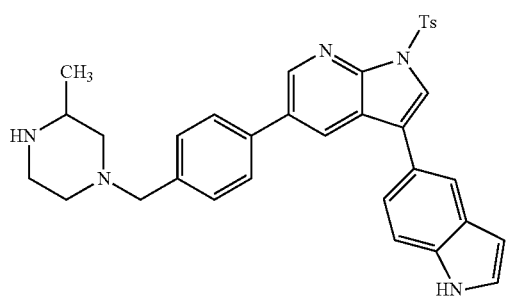 [SMILES: Cc1ccc(S(=O)(=O)n2cc(-c3ccc4[nH]ccc4c3)c3cc(-c4ccc(CN5CCNC(C)C5)cc4)cnc32)cc1]

Compound GH was dissolved in dichloromethane, and treated with 2 mL of TFA, stirred 30 minutes, the solvent was removed in vacuo and the residue was taken up in dichloromethane and washed with sodium hydroxide solution, water and brine to yield 80 mg of crude material.

Example 188

Preparation of 1-(4-(4-(3-(1H-indol-5-yl)-1H-pyrrolo[2,3-b]pyridin-5-yl)benzyl)-2-methylpiperazin-1-yl)ethanone (Compound GI)

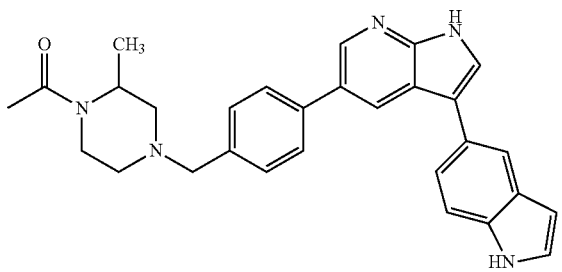 [SMILES: CC(=O)N1CCN(Cc2ccc(-c3cnc4[nH]cc(-c5ccc6[nH]ccc6c5)c4c3)cc2)CC1C]

3-(1H-indol-5-yl)-5-(4-((3-methylpiperazin-1-yl)methyl)phenyl)-1-tosyl-1H-pyrrolo[2,3-b]pyridine (Compound GF) (50 mg) was suspended in 1 mL dichloromethane and 1 mL of methanol and treated with triethylamine (100 mL) and acetic anhydride (20 µL) and stirred for one hour. The mixture was concentrated in vacuo, taken up in EtOAc and washed with water and brine and dried over MgSO4. The residue was suspended in methanol and treated with 5 N NaOH and heated at 50° C. for one hour. The mixture was diluted with dichloromethane and washed with water and brine, dried over MgSO₄ and purified by MPLC silica gel chromatography (0-20% MeOH in DCM) to yield an analytical sample (464 M+H).

Example 189

5-(4-((3,4-dimethylpiperazin-1-yl)methyl)phenyl)-3-(1H-indol-5-yl)-1H-pyrrolo[2,3-b]pyridine (Compound GJ)

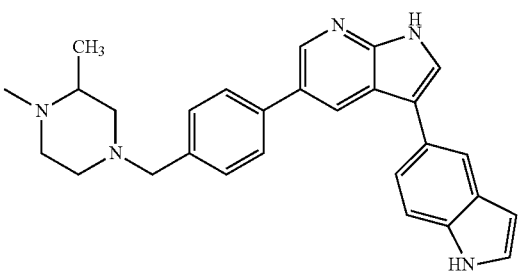 [SMILES: CC1CN(Cc2ccc(-c3cnc4[nH]cc(-c5ccc6[nH]ccc6c5)c4c3)cc2)CCN1C]

3-(1H-indol-5-yl)-5-(4-((3-methylpiperazin-1-yl)methyl)phenyl)-1-tosyl-1H-pyrrolo[2,3-b]pyridine (Compound HN) (40 mg) was suspended in 3 mL of methanol and THF (1 mL) and treated with paraformaldehyde (50 mg) and stirred for one hour. To this was added 50 mg of sodium triacetoxyborohydride. The reaction stirred 1 hr at room temperature. The mixture was concentrated in vacuo, taken up in EtOAc and washed with water and brine and dried over MgSO₄. The residue was suspended in methanol and treated with 5 N NaOH and heated at 50 C for one hour. The mixture was diluted with dichloromethane and washed with water and brine, dried over MgSO₄ and purified by MPLC silica gel chromatography (0-20% MeOH in DCM) to yield an analytical sample 10 mg (436 M+H).

Analogs Via Suzuki Method as in Example 140

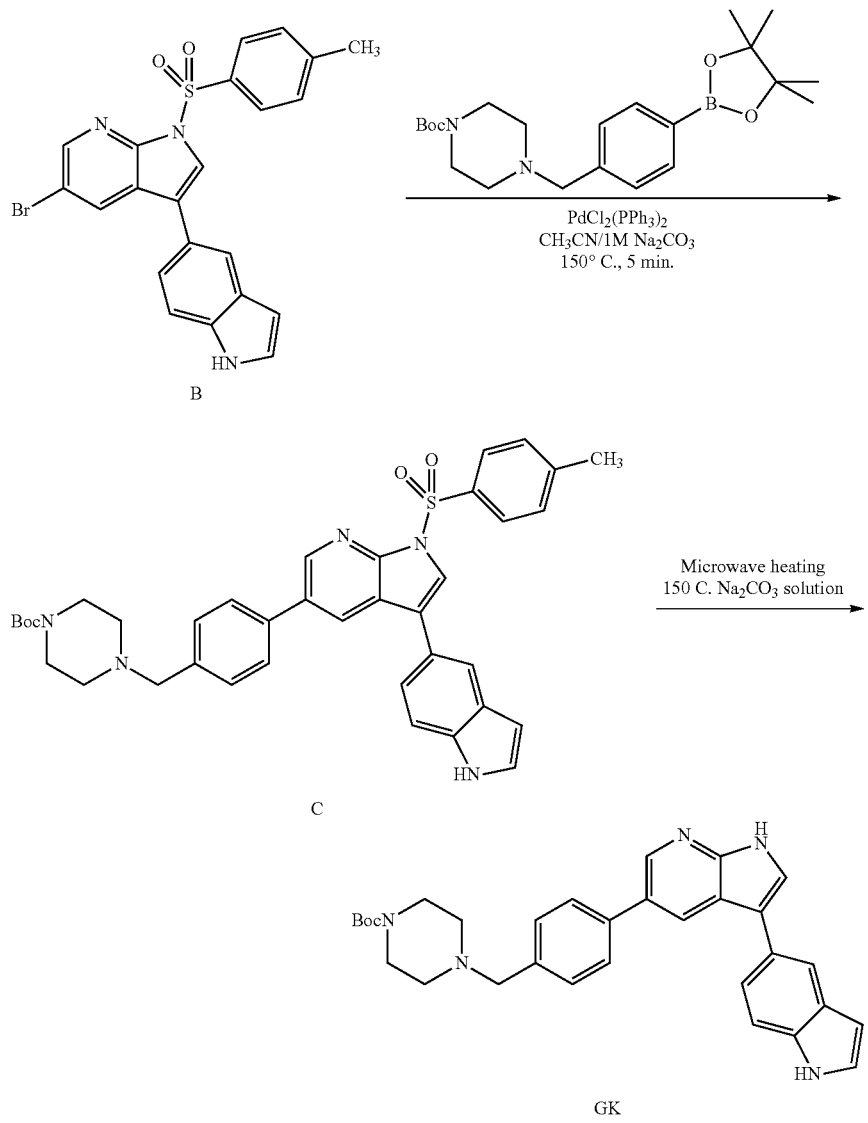

Preparation of tert-butyl 4-(4-(3-(1H-indol-5-yl)-1H-pyrrolo[2,3-b]pyridin-5-yl)benzyl)piperazine-1-carboxylate (Compound GK)

Intermediate B of Scheme 30 (131 mg) and tert-butyl 4-(4-(4,4,5,5-tetramethyl-1,3,2-dioxaborolan-2-yl)benzyl)piperazine-1-carboxylate (136 mg) were suspended in 2 mL of acetonitrile and treated with 2 mL of 1 M sodium carbonate solution and dichloro-bis-(triphenylphosphine)-palladium(II) (10 mg). The resulting mixture was heated in a microwave reactor cell for 20 minutes at 150° C., resulting in de-tosylated material which was purified by MPLC chromatography (0-3% methanol) to provide an analytical sample of the title compound (50 mg, 508 M+H).

Example 190

Preparation of 5-(4-((1H-imidazol-1-yl)methyl)phenyl)-3-(1H-indol-5-yl)-1H-pyrrolo[2,3-b]pyridine (Compound GL)

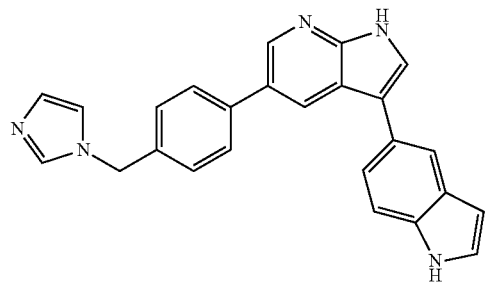 [SMILES: c1cn(Cc2ccc(-c3cnc4[nH]cc(-c5ccc6[nH]ccc6c5)c4c3)cc2)cn1]

Intermediate B of Scheme 30 (50 mg) and 1-(4-(4,4,5,5-tetramethyl-1,3,2-dioxaborolan-2-yl)benzyl)-1H-imidazole (37 mg) were suspended in 2 mL acetonitrile and 2 mL 1 M sodium carbonate solution, treated with dichloro-bis-(triphenylphosphine)-palladium(II) (8 mg) and microwaved 15 minutes at 150° C. to produce the detosylated product. Water was added to the cooled reaction mixture, which was then extracted with EtOAc. The combined organic layers were washed with brine and dried over MgSO$_4$. After removal of solvent, the residue was purified by MPLC silica gel chromatrography (0-20% MeOH in dichloromethane) and recrystallized from EtOH/water, to yield 22 mg of an analytical sample (390 M+H).

Piperazines Methods A-C

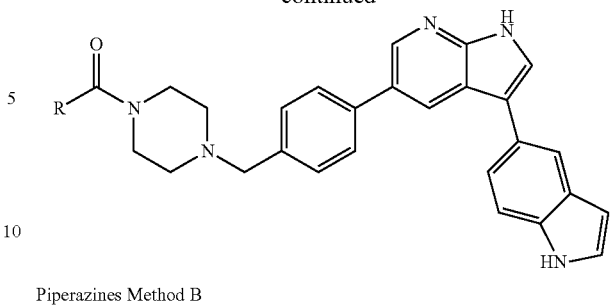

Piperazines Method B

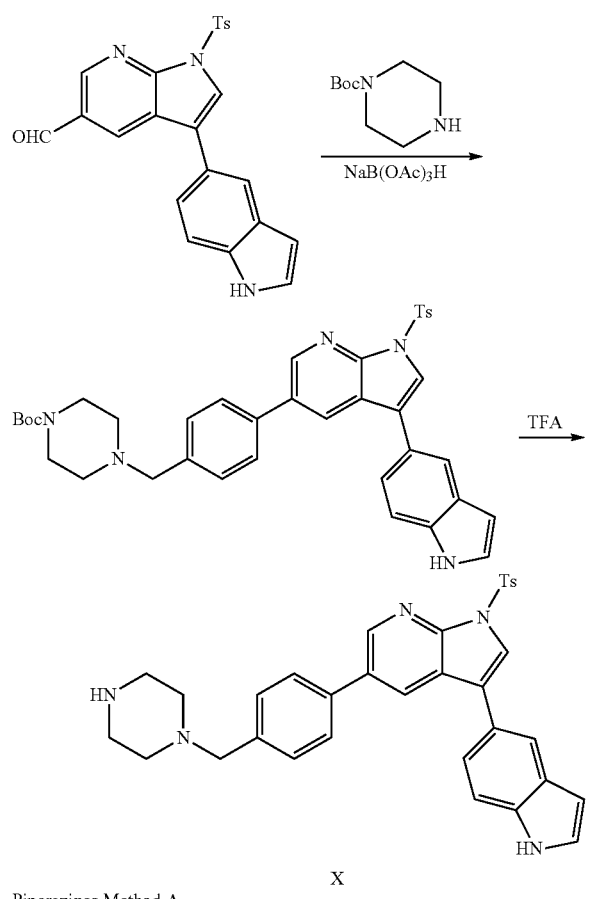

Piperazines Method A

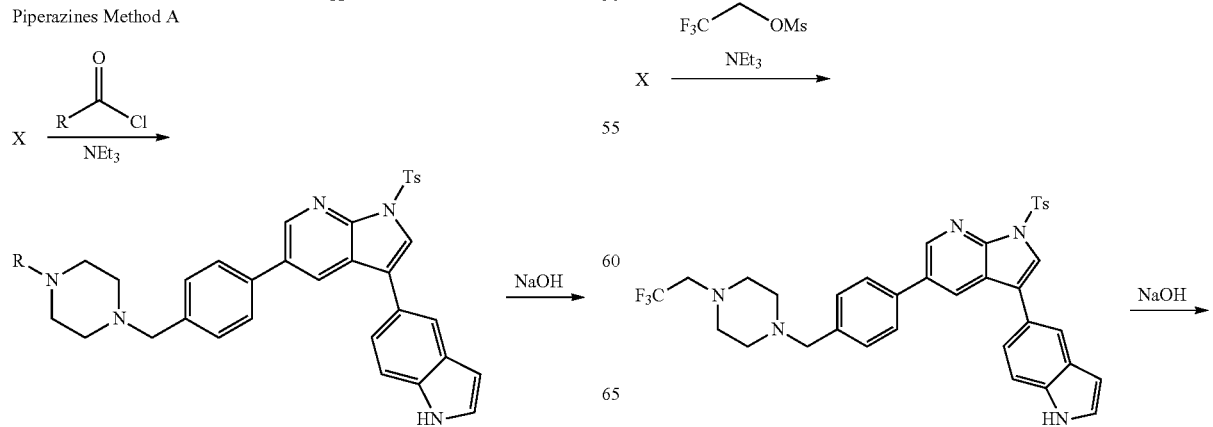

Piperazines Method C

161

-continued

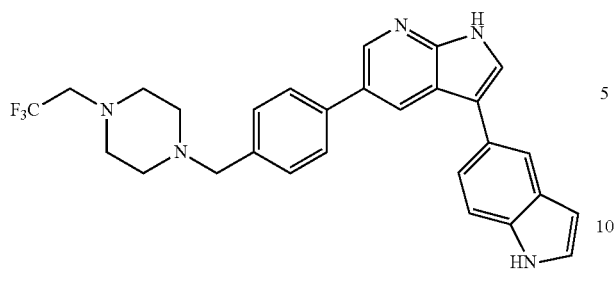

Preparation of tert-butyl 4-(4-(3-(1H-indol-5-yl)-1-tosyl-1H-pyrrolo[2,3-b]pyridin-5-yl)benzyl)piperazine-1-carboxylate (Compound GM)

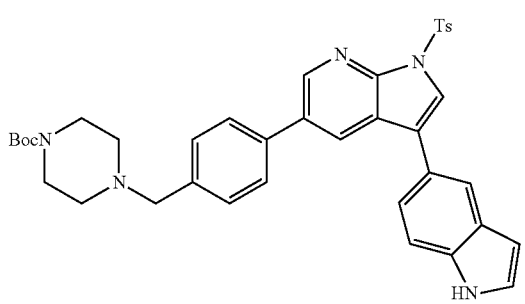 [SMILES: Cc1ccc(S(=O)(=O)n2cc(-c3ccc4[nH]ccc4c3)c3cc(-c4ccc(CN5CCN(C(=O)OC(C)(C)C)CC5)cc4)cnc32)cc1]

4-(3-(1H-indol-5-yl)-1-tosyl-1H-pyrrolo[2,3-b]pyridin-5-yl)benzaldehyde (2.1 g) was suspended in anhydrous dichloromethane (15 mL), treated with tert-butyl piperazine-1-carboxylate (1.6 g), and stirred for one hour. To the resulting mixture was added sodium triacetoxy borohydride 1.36 g in three portions. The reaction was stirred for 3 hours, diluted with water and extracted with dichloromethane. The organic layers were washed with brine, dried over MgSO$_4$, and purified by MPLC silica gel chromatography (30-60% EtOAc in hexane) to yield 2.62 g of the title compound (M+H 662).

162

Preparation of 3-(1H-indol-5-yl)-5-(4-(piperazin-1-ylmethyl)phenyl)-1-tosyl-1H-pyrrolo[2,3-b]pyridine (Compound FN)

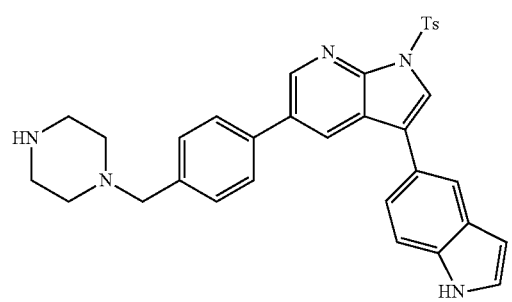 [SMILES: Cc1ccc(S(=O)(=O)n2cc(-c3ccc4[nH]ccc4c3)c3cc(-c4ccc(CN5CCNCC5)cc4)cnc32)cc1]

tert-butyl 4-(4-(3-(1H-indol-5-yl)-1-tosyl-1H-pyrrolo[2,3-b]pyridin-5-yl)benzyl)piperazine-1-carboxylate (500 mg) was suspended in 6 mL of dichloromethane and treated with TFA (5 mL) and reacted for 30 minutes. The solvent was removed in vacuo and the residue washed with 1 N sodium hydroxide solution, water and brine and dried over MgSO$_4$ to yield 418 mg of crude product that was used without further purification (562 M+H).

Examples 191-200

General Method A: Electrophiles Parallel Synthesis 3-(1H-indol-5-yl)-5-(4-(piperazin-1-ylmethyl)phenyl)-1-tosyl-1H-pyrrolo[2,3-b]pyridine (40 mg) was dissolved in a mixture of acetonitrile (0.5 mL), methanol (0.5 mL), THF (1 mL) and treated with 100 microliters of triethylamine. To this mixture was added a solution of 200 µL of a 10% solution of the designated electrophile in acetonitrile. After one hour the reaction was treated with an additional 200 µL of the electrophile solution and the reactions were allowed to stir for approximately 15 hours. The products were detosylated directly by the addition of 0.5 mL sodium hydroxide solution, followed by stirring over night and heated to 50 C for one hour. The reactions were diluted with water, extracted with dichloromethane and purified by MPLC, on silica gel, eluting with methanol in dichloromethane.

The following compounds were synthesized by this route:

| Example | Structure | M + H | Electrophile | Cmpd ID |
|---|---|---|---|---|
| 191 | 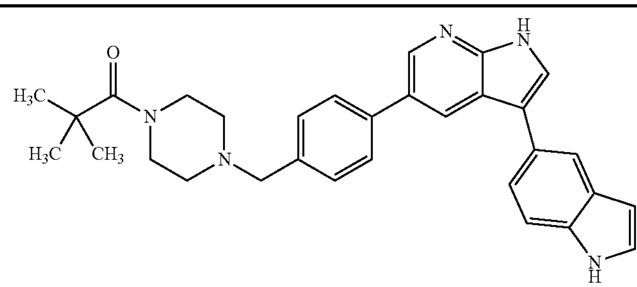 | 492 | 2,2-dimethylpropanic acid | GN |

| Example | Structure | M + H | Electrophile | Cmpd ID |
|---|---|---|---|---|
| 192 | 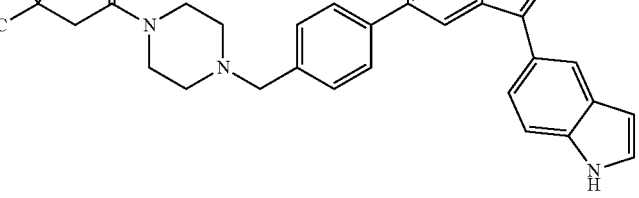 | 506 | 3,3,-dimethyl-butanoic acid | GO |
| 193 | 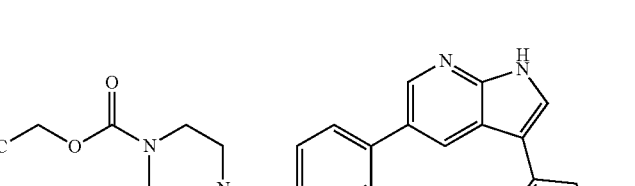 | 480 | ethyl chloroformate | GP |
| 194 | 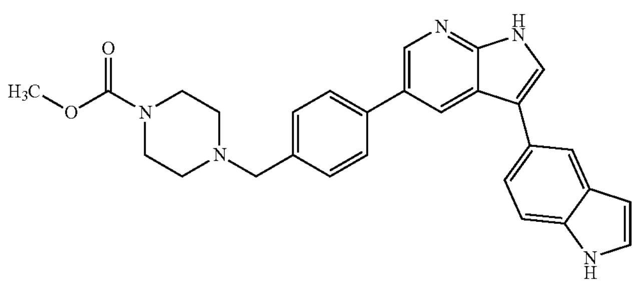 | 466 | methyl chloroformate | GQ |
| 195 | 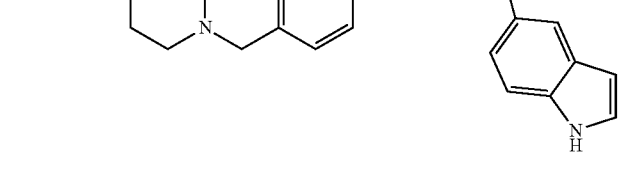 | 494 | isobutyl chloroformate | GR |
| 196 | 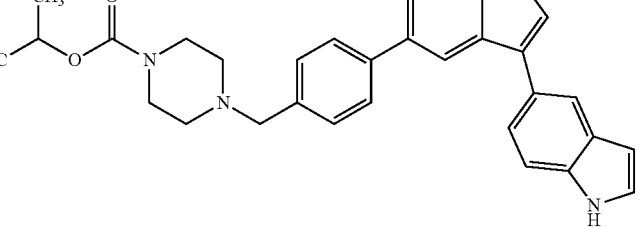 | 478 | 2-methyl propionyl chloride | GS |

-continued
| Example | Structure | M + H | Electrophile | Cmpd ID |
|---|---|---|---|---|
| 197 | 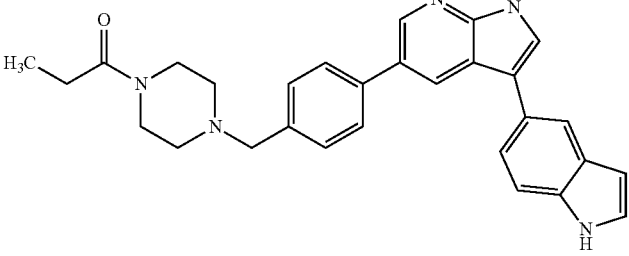 | 464 | Propionyl chloride | GT |
| 198 | 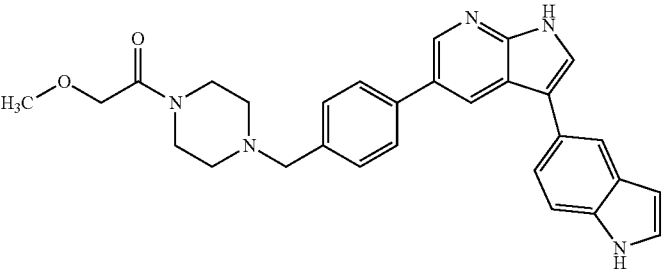 [SMILES: CCOC(=O)N1CCN(Cc2ccc(-c3cnc4[nH]cc(-c5ccc6[nH]ccc6c5)c4c3)cc2)CC1] | 480 | 2-methoxy acetyl chloride | GU |
| 199 | 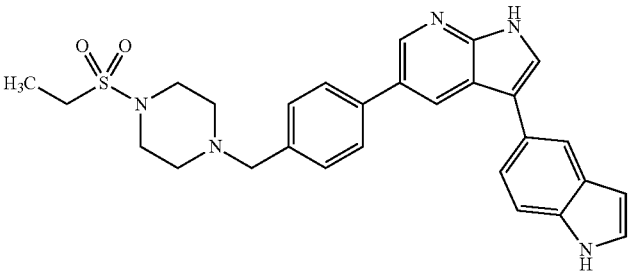 [SMILES: CCS(=O)(=O)N1CCN(Cc2ccc(-c3cnc4[nH]cc(-c5ccc6[nH]ccc6c5)c4c3)cc2)CC1] | 500 | Ethane sulfonyl chloride | GV |
| 200 | 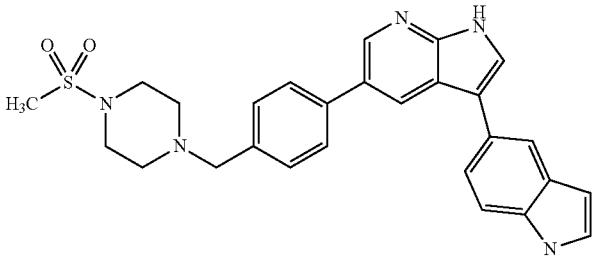 | 486 | Methane sulfonyl chloride | GW |

Examples 201-206

General Method B: Carbodiimide Couplings
Parallel Synthesis 3-(1H-indol-5-yl)-5-(4-(piperazin-1-ylmethyl)phenyl)-1-tosyl-1H-pyrrolo[2,3-b]pyridine (50 mg) was dissolved in a mixture of acetonitrile (1 mL), methanol (1 mL), THF (1 mL) and the corresponding carboxylic acids (20 mg) then treated with N-(3-dimethylaminopropyl)-N-ethylcarbodiimide hydrochloride (22 mg). The reactions were allowed to stir for approximately 15 hours, diluted with dichloromethane and washed with 1 N sodium hydroxide, water and brine and evaporated. The products were suspended in MeOH and (2 mL) detosylated directly by the addition of 0.5 mL sodium hydroxide solution, followed by stirring over night and heated to 50 C for one hour. The reactions were diluted with water, extracted with dichloromethane and purified by MPLC, on silica gel, eluting with methanol in dichloromethane.

The following compounds were synthesized by this route:

| Example | Structure | M + H | Acids | Cmpd ID |
|---|---|---|---|---|
| 201 | 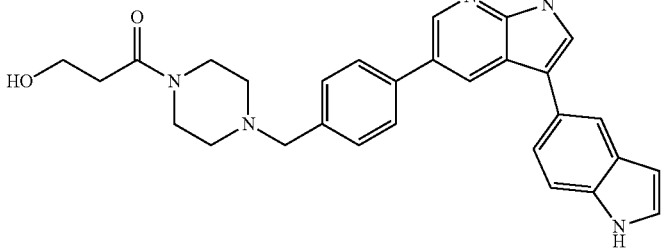 | 480 | 3-hydroxypropanoic acid | GX |
| 202 | 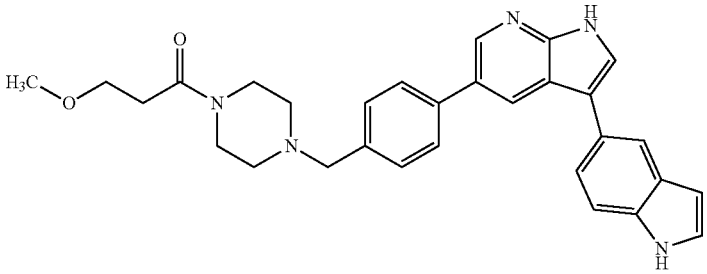 [SMILES: COCCC(=O)N1CCN(Cc2ccc(-c3cnc4[nH]cc(-c5ccc6[nH]ccc6c5)c4c3)cc2)CC1] | 494 | 3-methoxypropanic acid | GY |
| 203 | 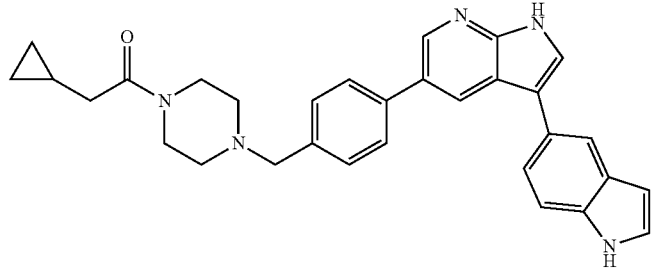 [SMILES: O=C(CC1CC1)N1CCN(Cc2ccc(-c3cnc4[nH]cc(-c5ccc6[nH]ccc6c5)c4c3)cc2)CC1] | 490 | 2-cyclopropylacetic acid | GZ |
| 204 | 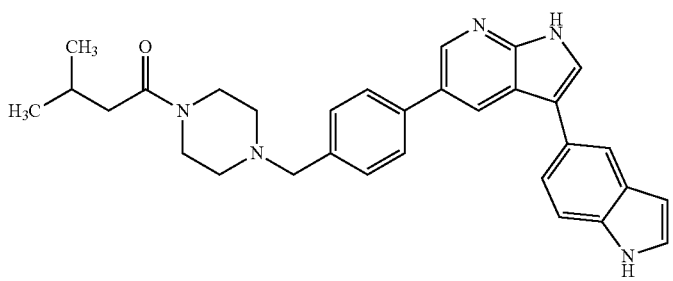 [SMILES: CC(C)CC(=O)N1CCN(Cc2ccc(-c3cnc4[nH]cc(-c5ccc6[nH]ccc6c5)c4c3)cc2)CC1] | 492 | 3-methylbutanoic acid | HA |

| Example | Structure | M + H | Acids | Cmpd ID |
|---|---|---|---|---|
| 205 | 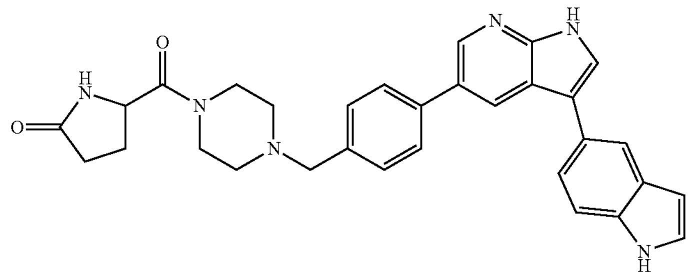 [SMILES: O=C1CCC(C(=O)N2CCN(Cc3ccc(-c4cnc5[nH]cc(-c6ccc7[nH]ccc7c6)c5c4)cc3)CC2)N1] | 519 | 5-oxopyrrolidine-2-carboxylic acid | HB |
| 206 | 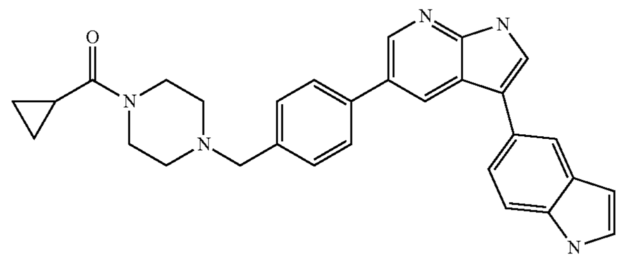 [SMILES: O=C(C1CC1)N1CCN(Cc2ccc(-c3cnc4[nH]cc(-c5ccc6[nH]ccc6c5)c4c3)cc2)CC1] | 476 | Cyclopropane carboxylic acid | HC |

Example 207

3-(1H-indol-5-yl)-5-(4-((4-(2,2,2-trifluoroethyl)piperazin-1-yl)methyl)phenyl)-1H-pyrrolo[2,3-b]pyridine (Compound HD)

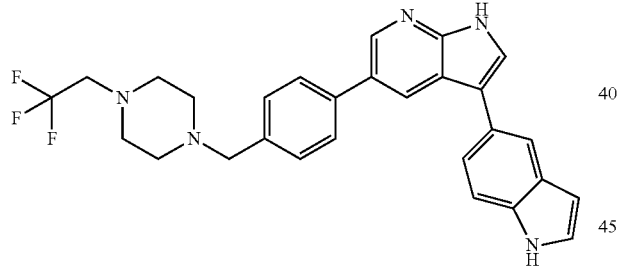

3-(1H-indol-5-yl)-5-(4-(piperazin-1-ylmethyl)phenyl)-1-tosyl-1H-pyrrolo[2,3-b]pyridine (50 mg) (Compound FN) was dissolved in THF (1 mL) and treated with triethylamine (13 uL), and 2,2,2-trifluoroethyl methanesulfonate (13 μL); the reaction was allowed to stir for approximately 15 hours, diluted water and extracted with EtOAC and washed with 1 N sodium hydroxide, water and brine and evaporated. The product was suspended in MeOH and (2 mL) detosylated directly by the addition of 0.5 mL sodium hydroxide solution, heated to 50 C for one hour. The reaction was diluted with water, extracted with dichloromethane and purified by MPLC, on silica gel, eluting with methanol in dichloromethane to yield 6 mg of an analytical sample (490 M+H).

Example 208

Method A: Synthesis of 2-Methylazaindole Derivatives

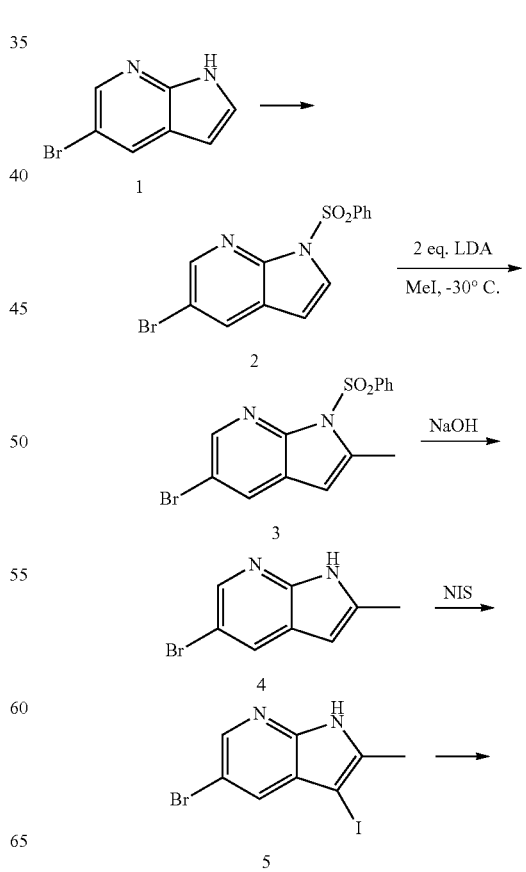

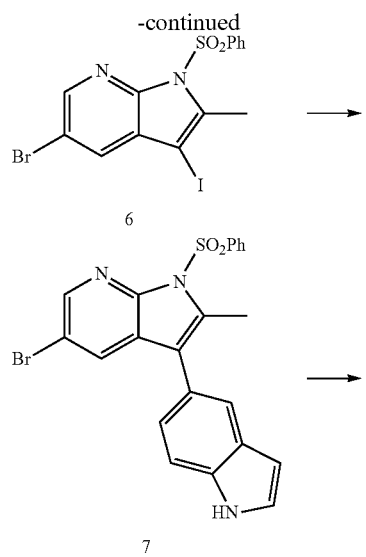

Preparation of Method A Intermediate 2: 1-Benzenesulfonyl-5-bromo-1H-pyrrolo[2,3-b]pyridine 5-Bromoazaindole (1, 2.00 g, 10.1 mmol), tetrabutylammonium bromide (0.03 eq, 0.25 mmol, 82 mg) and powdered NaOH (3 eq, 30.45 mmol, 1.22 g) are combined in DCM (100 ml) and cooled to 0° C. Phenylsulfonyl chloride (1.25 eq, 12.69 mmol, 1.62 mL) is added dropwise. After the addition is completed the mixture is stirred for 2 h at 0° C. The mixture is filtered, absorbed on Celite and purified by silica gel chromatography with a 40 to 60% gradient of EtOAc in hexane. 2.58 g (7.65 mmol, 75% yield) of 2 is obtained. $^1$H NMR (CDCl$_3$, 300 MHz): δ 8.45 (d, J=1.8 Hz, 1H), 8.17 (m, 2H), 7.98 (d, J=2.1 Hz, 1H), 7.74 (d, J=3.9 Hz, 1H), 7.60 (m, 1H), 7.50 (m, 2H), 6.55 (d, J=3.9 Hz, 1H). MS (m/z): 338 (M+H).

Preparation of Method A Intermediate 3: 1-Benzenesulfonyl-5-bromo-2-methyl-1H-pyrrolo[2,3-b]pyridine To a solution of diisopropylamine (2.8 eq, 1.66 mmol, 240 μL) in THF (2 ml) at −10° C. is added n-butyllithium (1.6 M in hexane, 2.6 eq, 1.54 mmol, 965 l) dropwise. The mixture is allowed to stir for 30 min and then cooled to −35° C. A solution of compound 2 (1 eq., 200 mg, 0.593 mmol) in THF is added dropwise and the mixture is stirred for 30 min at −35° C. Iodomethane (3 eq, 1.78 mmol, 111 μL) is added in a dropwise fashion and the mixture is stirred for 2 h while warming up to room temperature. The reaction is quenched by addition of a saturated NH$_4$Cl solution, extracted with EtOAc and purified by silica gel chromatography (stepwise gradient of 0 to 15% EtOAc in hexane). 126 mg (0.359 mmol, 60%) of compound 3 are obtained. $^1$H NMR (CDCl$_3$, 300 MHz): δ 8.37 (d, J=2.4 Hz, 1H), 8.12 (m, 2H), 7.81 (d, J=2.4 Hz, 1H), 7.58 (m, 1H), 7.50 (m, 2H), 6.24 (d, J=1.2 Hz, 1H), 2.73 (d, J=1.2 Hz, 3H). MS (m/z): 352 (M+H).

Preparation of Method A Intermediate 4: 5-Bromo-2-methyl-1H-pyrrolo[2,3-b]pyridine Starting material 3 (88 mg, 0.251 mmol) is dissolved in MeOH (4 ml), 2 N NaOH (1 ml) is added and the mixture is refluxed for 2 h. EtOAc is added and the organic phase is washed with 1 N NaOH and water. After purification by silica gel chromatography (slow gradient from 0 to 2% MeOH in DCM), 40 mg (0.19 mmol, 76%) of 4 is obtained. $^1$H NMR (CDCl$_3$, 300 MHz): δ 10.26 (bs, 1H), 8.22 (d, J=2.1 Hz, 1H), 8.92 (d, J=2.1 Hz, 1H), 6.13 (s, 1H), 2.52 (s, 3H). MS (m/z): 210 (M+H).

Preparation of Method A Intermediate 5: 5-Bromo-3-iodo-2-methyl-1H-pyrrolo[2,3-b]pyridine A mixture of 4 (85 mg, 0.378 mmol) and N-iodosuccinimide (1.1 eq, 0.42 mmol, 95 mg) in acetone (1.5 ml) is stirred for 1 h at room temperature. The precipitate is filtered off, washed with cold acetone and dried to yield 90 mg (0.267 mmol, 71%) of the desired product.

Preparation of Method A Intermediate 6: 1-Benzenesulfonyl-5-bromo-3-iodo-2-methyl-1H-pyrrolo[2,3-b]pyridine Compound 5 (90 mg, 0.267 mmol), tetrabutylammonium bromide (0.025 eq, 0.0067 mmol, 3 mg) and powdered NaOH (3 eq, 0.8 mmol, 32 mg) are combined in DCM (3 ml) and cooled to 0° C. Phenylsulfonyl chloride (1.25 eq, 0.334 mmol, 43 l) is added dropwise. After the addition is completed the mixture is stirred for 15 min at 0° C. and then allowed to warm up to room temperature over 2 h. The mixture is filtered, absorbed on Celite and purified by silica gel chromatography eluting with DCM. 112 mg (0.235 mmol, 88% yield) of 6 is obtained.

Preparation of Method A Intermediate 7: 1-Benzenesulfonyl-5-bromo-3-(1H-indol-5-yl)-2-methyl-1H-pyrrolo[2,3-b]pyridine A mixture of 6 (112 mg, 0.235 mmol), 5-indoleboronic acid (1.1 eq, 0.26 mmol, 42 mg) and dichlorobis(triphenylphosphine)palladium(II) (0.05 eq, 0.0118 mmol, 8.5 mg) in MeCN (3 ml) and 1 M Na$_2$CO$_3$ (3 ml) is stirred at 45° C. for 1 h. Water is added, and the mixture is extracted with EtOAc and purified by silica gel chromatography (0 to 40% stepwise gradient of EtOAc in hexane). 76 mg (0.163 mmol, 69%) of the desired product 7 are obtained.

Preparation of Method A Intermediate 8: 1-Benzenesulfonyl-3-(1H-indol-5-yl)-2-methyl-5-[4-(4-methyl-piperazin-1-ylmethyl)-phenyl]-1H-pyrrolo[2,3-b]pyridine A mixture of 7 (76 mg, 0.163 mmol), 1-methyl-4-[4-(4,4,5,5-tetramethyl-[1,3,2]dioxaborolan-2-yl)-benzyl]-piperazine (1.2 eq, 0.196 mmol, 62 mg) and dichlorobis(triphenylphosphine)palladium(II) (0.05 eq, 0.008 mmol, 6 mg) in MeCN (2.5 ml) and 1 M Na$_2$CO$_3$ (2 ml) is reacted at 150° C. for 5 min by microwave reactor (Biotage initiator). Water is added, and the mixture is extracted with EtOAc and purified by silica gel chromatography (0 to 20% gradient of MeOH in DCM). A mixture of the desired product 8 with some deprotected material HC is obtained.

Preparation of Method A (Compound HE): 3-(1H-Indol-5-yl)-2-methyl-5-[4-(4-methyl-piperazin-1-ylmethyl)-phenyl]-1H-pyrrolo[2,3-b]pyridine The mixture obtained in the last step is dissolved in MeOH (4 ml), 2 N NaOH (1 ml) is added and refluxed for 2 h. EtOAc is added and the organic phase is washed with 1 N NaOH and water. After purification by silica gel chromatography (gradient from 0 to 20% MeOH in DCM) 5 mg of Compound HC are obtained. $^1$H NMR (CDCl$_3$, 300 MHz): δ 9.89 (s, 1H), 8.48 (s, 1H), 8.35 (s, 1H), 8.15 (s, 1H), 7.76 (s, 1H), 7.53 (m, 3H), 7.37 (m, 3H), 7.27 m, 1H), 6.62 (s, 1H), 3.56 (s, 2H), 2.63 (s, 3H), 2.53 (bs, 8H) 2.32 (s, 3H). MS (m/z): 436 (M+H).

Method C: Synthesis of 2-Methylazaindole Derivatives

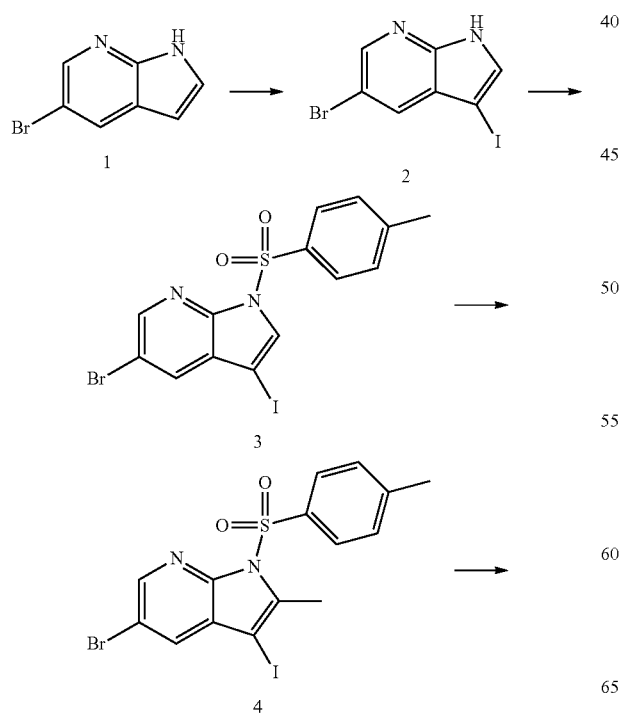

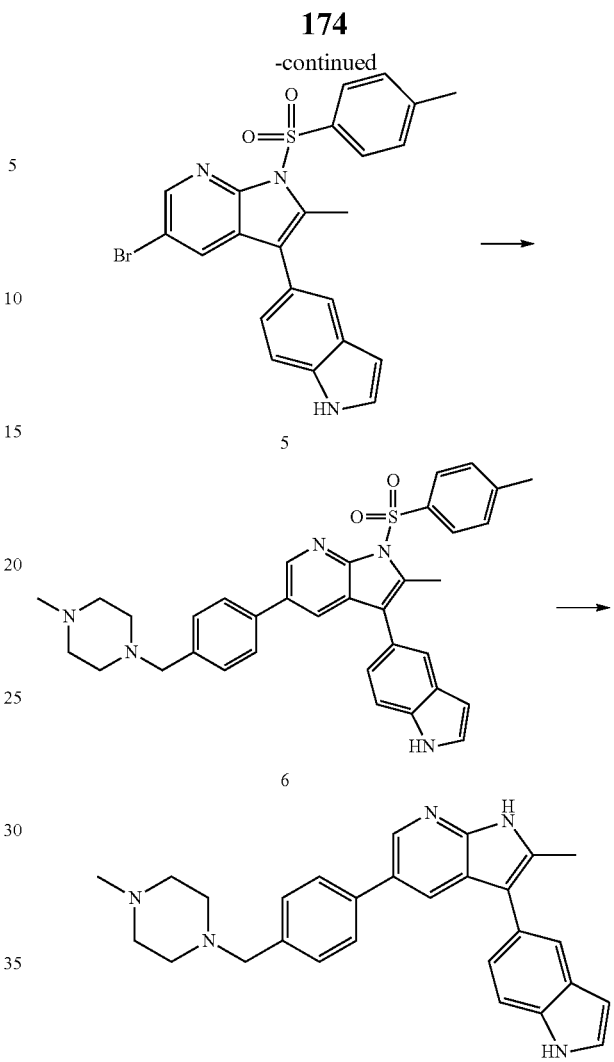

Preparation of Method C Intermediate 2: 5-bromo-3-iodo-1H-pyrrolo[2,3-b]pyridine To a stirred solution of 5-bromo-1H-pyrrolo[2,3-b]pyridine (10 g, 50.76 mmol) in 500 mL of acetone N-idodosuccinamide was added and the reaction mixture was stirred for 20 min at room temperature. The product was crashed out as white solid was filtered and washed with 100 mL acetone. Resulting solid was dried under vacuum to afford 5-bromo-3-iodo-1H-pyrrolo[2,3-b]pyridine (16.34 g, 100%) as a light yellow powder. $^1$H NMR (DMSO-d6, 300 MHz) δ 8.51 (d, J=2.1 Hz, 1H), 8.22 (s, 1H), 8.02 (d, J=1.2 Hz, 1H), 8.00 (d, J=5.1 Hz, 2H), 7.44 (dd, J=8.7 Hz, 0.6 Hz, 2H), 2.35 (s, 3H); MS ESI (m/z): 322/324 (M+1)$^+$, calc. 322.

Preparation of Method C Intermediate 3: 5-bromo-3-iodo-1-tosyl-1H-pyrrolo[2,3-b]pyridine To a stirred solution of 5-bromo-3-iodo-1H-pyrrolo[2,3-b]pyridine (16.82 g, 52.23 mmol) in 522 mL of anhydrous THF cooled to 0° C. with an ice bath was added NaH [60% dispersion in mineral oil] (3.76 g, 156.7 mmol). The reaction mixture was stirred for 20 min at 0° C., after which p-toluenesulfonyl chloride (14.88 g, 78.3 mmol) was added. The resulting mixture was stirred at 0° C. for 1.5 hr, after which cold 0.5 M HCl (20 mL) was added. The mixture was partitioned between EtOAc and 0.5 M HCl, after which the organic layer was separated, dried over MgSO₄, filtered, and evaporated in vacuo to yield a residue that was triturated with 20% CH₂Cl₂ in hexanes to yield the title compound (0.84 g, 81%) as a light yellow powder. ¹H NMR (DMSO-d6, 300 MHz) δ 8.51 (d, J=2.1 Hz, 1H), 8.22 (s, 1H), 8.02 (d, J=1.2 Hz, 1H), 8.00 (d, J=5.1 Hz, 2H), 7.44 (dd, J=8.7 Hz, 0.6 Hz, 2H), 2.35 (s, 3H); MS ESI (m/z): 477.0/479.0 (M+1)⁺, calc. 476.

Preparation of Method D Intermediate 4: 5-Bromo-3-iodo-2-methyl-1-(toluene-4-sulfonyl)-1H-pyrrolo[2,3-b]pyridine To a solution of diisopropylamine (2.8 eq, 1.66 mmol, 240 µL) in THF (2 ml) at −10° C. is added n-butyllithium (1.6 M in hexane, 2.6 eq, 1.54 mmol, 965 µL) dropwise. The mixture is allowed to stir for 30 min and then cooled to −40° C. A solution of compound 2 (1 eq., 200 mg, 0.593 mmol) in THF is added dropwise and the mixture is stirred for 30 min at −35° C. Iodomethane (3 eq, 1.78 mmol, 111 µL) is added in a dropwise fashion and the mixture is stirred for 2 h while warming up to room temperature. The reaction is quenched by addition of a saturated NH₄Cl solution, extracted with EtOAc and purified by silica gel chromatography (stepwise gradient of 0 to 15% EtOAc in hexane). 126 mg (0.359 mmol, 60%) of compound 4 are obtained. ¹H NMR (CDCl₃, 300 MHz): δ 8.37 (d, J=2.4 Hz, 1H), 8.12 (m, 2H), 7.81 (d, J=2.4 Hz, 1H), 7.58 (m, 1H), 7.50 (m, 2H), 6.24 (d, J=1.2 Hz, 1H), 2.73 (d, J=1.2 Hz, 3H). MS (m/z): 352 (M+H).

Preparation of Method C Intermediate 5: 4-[5-Bromo-1-(toluene-4-sulfonyl)-1H-pyrrolo[2,3-b]pyridin-3-yl]-phenol To a stirred suspension of 5-bromo-3-iodo-1-tosyl-1H-pyrrolo[2,3-b]pyridine (0.30 g, 0.62 mmol) and 1H-indol-5-ylboronic acid (0.12 mg, 0.75 mmol) in CH₃CN (3 mL) was added 1 M Na₂CO₃ (3 mL) followed by bis(triphenylphosphine)palladium(II) dichloride (0.004 g, 0.062 mmol). The resulting mixture was stirred overnight at 60° C. After the mixture was evaporated to dryness in vacuo, it was dissolved in DMF (3 mL), absorbed onto Celite, and dried. The residue was purified via silica gel chromatography using CH₂Cl₂ as the eluent to obtain the title compound (0.26 g, 76%). ¹H NMR (CDCl₃, 300 MHz): δ 8.48 (d, J=2.1 Hz, 1H), 8.27 (bs, 1H), 8.26 (d, J=2.4 Hz, 1H), 8.08 (d, J=8.1 Hz, 1H), 7.85 (s, 1H), 7.81 (m, 1H), 7.50 (d, J=8.7 Hz, 1H), 7.37 (dd, J=1.8, 8.4 Hz), 7.30 (m, 3H), 6.63 (m, 1H), 2.39 (s, 3H); MS ESI (m/z): 466.2/468.2 (M+1)⁺, calc. 465.

Preparation of Method C (Compound HE): 3-(1H-Indol-5-yl)-2-methyl-5-[4-(4-methyl-piperazin-1-ylmethyl)-phenyl]-1H-pyrrolo[2,3-b]pyridine To a solution of 5-bromo-3-(1H-indol-5-yl)-1-tosyl-1H-pyrrolo[2,3-b]pyridine (0.220 g, 0.5 mmol) in CH₃CN (2.5 mL) in a Personal Chemistry microwave reaction vial was added 1-Methyl-4-[4-(4,4,5,5-tetramethyl-[1,3,2]dioxaborolan-2-yl)-benzyl]-piperazine (0.20 g, 0.65 mmol), bis(triphenylphosphine)-palladium(II) dichloride (0.003 g, 0.005 mmol), and 1 M Na₂CO₃ (1 mL). The resulting mixture was de-gassed with Ar for 10 min, after which it was heated at 150° C. for 30 min in a Personal Chemistry Optimizer. The organic layer was separated, filtered, and concentrated in vacuo. The residue was dissolved in MeOH (3 mL) and acetone (2 mL), and 2 M NaOH (1.5 mL) was added. The resulting mixture was stirred at 65° C. for 30 min, after which it was partitioned between EtOAc and 1 M NaOH. The organic layer was separated, dried over MgSO₄, filtered, and stripped to give a residue purified via preparatory HPLC to give the title compound as a white solid. ¹H NMR (DMSO-d6, 300 MHz): δ 11.78 (s, 1H), 11.03 (s, 1H), 8.51 (d, J=2.1 Hz, 1H), 8.36 (d, J=1.8 Hz, 1H), 7.86 (s, 1H), 7.72 (d, J=2.4 Hz, 1H), 7.45 (s, 2H), 7.32 (m, 1H), 6.92 (s, 2H), 6.45 (m, 1H), 3.85 (s, 6H), 3.70 (s, 3H); HPLC retention time: 2.04 minutes; MS ESI (m/z): 399 (M+1)⁺, calc. 398.51.

Example 209

Method B: Synthesis of 2-Methyl Azaindoles 4-(2-methyl-5-(4-((4-methylpiperazin-1-yl)methyl)phenyl)-1H-pyrrolo[2,3-b]pyridin-3-yl)benzamide

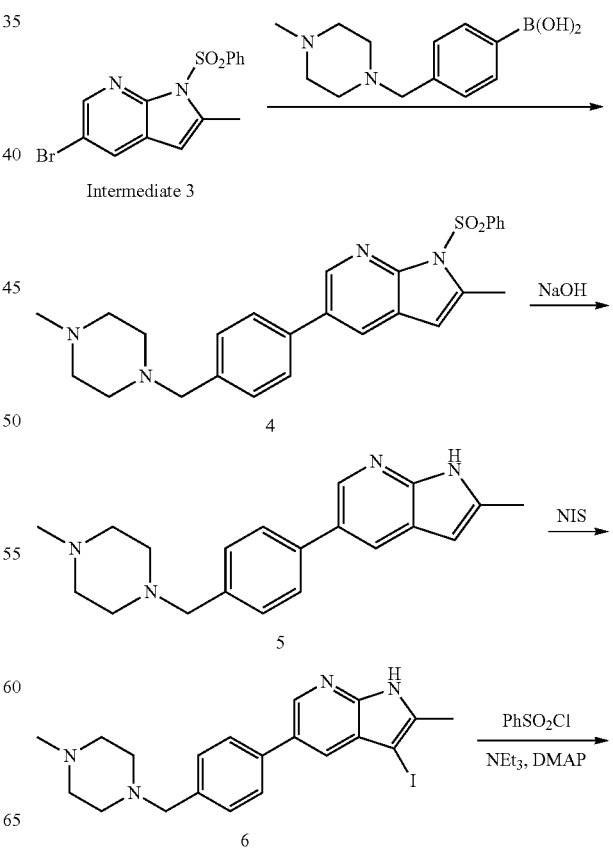

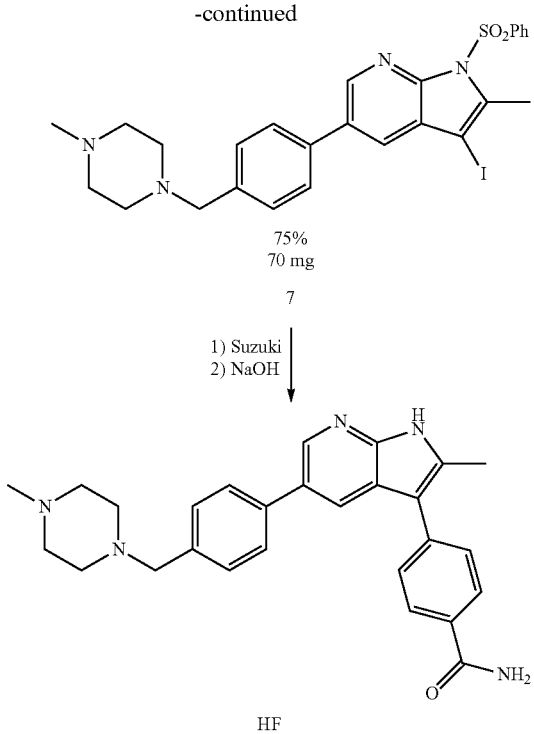

Preparation of Method B Intermediate 4: 2-methyl-5-(4-((4-methylpiperazin-1-yl)methyl)phenyl)-1-(phenylsulfonyl)-1H-pyrrolo[2,3-b]pyridine 1-Benzenesulfonyl-5-bromo-2-methyl-1H-pyrrolo[2,3-b]pyridine (378 mg, 1.076 mmole) and 4-((4-methylpiperazin-1-yl)methyl)phenylboronic acid (303 mg, 1.29 mmole) are dissolved in acetonitrile (10 mL) and treated with 10 mL 1 M sodium carbonate solution. To this is added 40 mg of PdCl$_2$(PPh$_3$)$_2$ catalyst, and the mixture is irradiated for 5 minutes at 150 degrees in a Biotage microwave reactor. After cooling, the reaction mixture is diluted with water and extracted with ethyl acetate, dried, and concentrated. MPLC silica gel chromotagraphy 5-20% MeOH in dichloromethane gradient elution, provided 367 mg of the title compound as a solid.

Preparation of Method B Intermediate 5: 2-methyl-5-(4-((4-methylpiperazin-1-yl)methyl)phenyl)-1H-pyrrolo[2,3-b]pyridine Intermediate 4 (367 mg) in 4 mL MeOH, was treated with 1.2 mL of 2 N NaOH and stirred 15 hours at room temperature, then refluxed 2 hours, and cooled. The volatiles were removed on a rotovap, and partitioned between EtOAc and 1 N NaOH solution. The EtOAc layers were washed with water and saturated sodium chloride solution and dried over MgSO4. The solvent was removed in vacuo to produce 204 mg of crude material (M+H 321).

Preparation of Method B Intermediate 6: 3-iodo-2-methyl-5-(4-((4-methylpiperazin-1-yl)methyl)phenyl)-1H-pyrrolo[2,3-b]pyridine Intermediate 5 (204 mg, 0.637 mmole) was dissolved in 10 mL acetone and treated with 160 mg of iodosuccinimide. The reaction stirred 1 hour at room temperature and the product was collected by filtration and purified by MPLC silica gel chromatography by a 0-10% gradient of MeOH in dichloromethane to yield 215 mg of the title compound.

Preparation of Method B Intermediate 7: 3-iodo-2-methyl-5-(4-((4-methylpiperazin-1-yl)methyl)phenyl)-1-(phenylsulfonyl)-1H-pyrrolo[2,3-b]pyridine Intermediate 6 (70 mg) in dichloromethane (10 mL) was treated with triethylamine (70 microliters) DMAP (5 mg) and benzenesulfonyl chloride (30 microliters) and stirred 24 hours, an additional 30 microliters of benzenesulfonyl chloride was added and stirred for an additional 24 hours. The reaction mixture was diluted with dichloromethane and washed with 1 N NaOH, water, and sodium chloride solution and dried over MgSO4. Removal of solvent in vacuo produced 70 mg of the crude title compound.

Preparation of Method B, Compound HF: 4-(2-methyl-5-(4-((4-methylpiperazin-1-yl)methyl)phenyl)-1H-pyrrolo[2,3-b]pyridin-3-yl)benzamide Intermediate 7 (70 mg) and the 4-benzamide boronic acid (24 mg) was dissolved in 5 mL of acetonitrile and mixed with 5 mL of 1 M sodium carbonate solution and treated with Pd(Cl$_2$)(PPh$_3$)$_2$ catalyst (9 mg), the reaction stirred 2 hours at 60° C. After cooling the mixture was diluted with EtOAc and washed with water and sodium chloride solution and dried over MgSO$_4$. The crude material was suspended in MeOH (3.5 mL), treated with 1 mL of 2 N NaOH solution and refluxed 2 hr. The mixture was extracted with EtOAc and extracts were washed with 1 N NaOH, water and sodium chloride solution, and dried over MgSO4. Reverse phase chromatography (C18) eluting with a 0-100% methanol gradient in water provided an analytical sample, 15 mg of the title compound as a solid. (440, M+H).

Examples 210-223

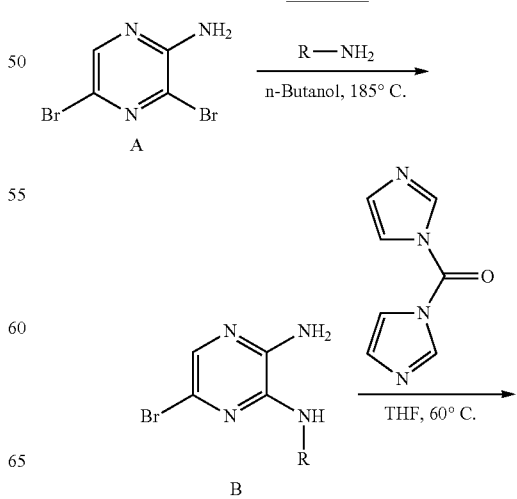

Scheme 31

-continued

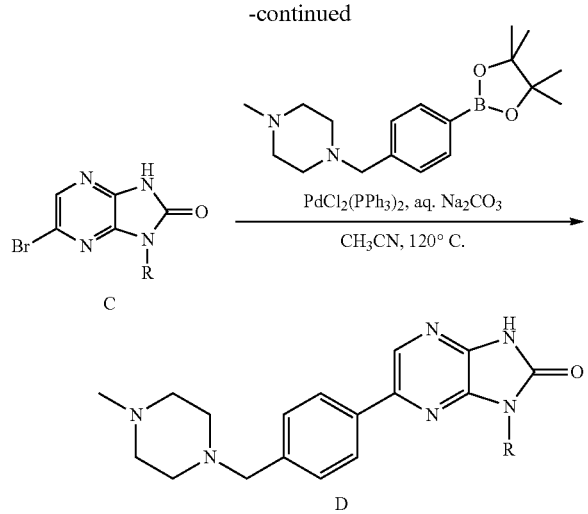

Preparation of Intermediate B: 4-(3-Amino-6-bromo-pyrazin-2-ylamino)-aryl/hetero-aryl/alkyl In reference to Scheme 31, to a stirred suspension of 3,5-dibromopyrazin-2-amine (2.0 g, 7.93 mmol) and the in n-butanol (8 mL) was added corresponding alkyl, aryl, or heteroaryl amine (1.37 g, 10.31 mmol). The resulting mixture was stirred for 2 hrs at 185° C., after which it was partitioned between EtOAc and $H_2O$. The organic layer was separated, after which it was washed with brine, dried over $Na_2SO_4$, filtered, and evaporated in vacuo to yield a residue that was purified by automated medium pressure silica gel chromatography eluting with 1:1 EtOAc:hexanes to yield the XB intermediates as amorphous solids.

Preparation of Intermediate C: 6-Bromo-1-(4-aryl/hetero-aryl/alkyl)-1,3-dihydro-imidazo[4,5-b]pyrazin-2-one Intermediates B (2.5 g, 8.19 mmol) were dissolved in THF (40 mL) and treated with carbonyldiimidazole (7.96 g, 49.18 mmol). The resulting mixture was heated at 65° C. for 24-48 hr, after which it was concentrated in vacuo and partitioned between EtOAc and $H_2O$. The organic layer was separated, dried over $MgSO_4$, filtered, and concentrated in vacuo to yield a residue that was purified via automated silica gel chromatography eluting with hexane/EtOAc to yield the Intermediates C as amorphous solids.

Preparation of 1-aryl/hetero-aryl/alkyl-6-[4-(4-methyl-piperazin-1-ylmethyl)-phenyl]-1,3-dihydro-imidazo[4,5-b]pyrazin-2-one compounds Individual solutions of Intermediates C (0.18 mmol) in $CH_3CN$ (2 mL) in a Personal Chemistry microwave reaction vial was added the 1-Methyl-4-[4-(4,4,5,5-tetramethyl-[1,3,2]dioxaborolan-2-yl)-benzyl]-piperazine (0.21 mmol), bis(triphenylphosphine)-palladium(II) dichloride (2.1 mg, 0.003 mmol), and 1 M $Na_2CO_3$ (1 mL). The resulting mixture was de-gassed with Ar for 10 min, after which it was heated at 150° C. for 30 min in a Personal Chemistry Optimizer. The organic layer was separated, filtered, and concentrated in vacuo. The residue was purified by preparatory HPLC to yield the title compounds in Table 3 (>5 mg) as amorphous solids. Examples 210-223 were were physically characterized by electrospray ionization mass spectrometry. Structures and molecular masses are also given below in Table 3.

TABLE 3

| Ex. | Boronic Acid | Amine | Structure | Purified Compound Isolated | MW | Cmpd ID |
|---|---|---|---|---|---|---|
| 210 | 1-Methyl-4-[4-(4,4,5,5-tetramethyl-[1,3,2]dioxaborolan-2-yl)-benzyl]-fpiperazine | 2-Methyl-1H-indol-5-ylamine | 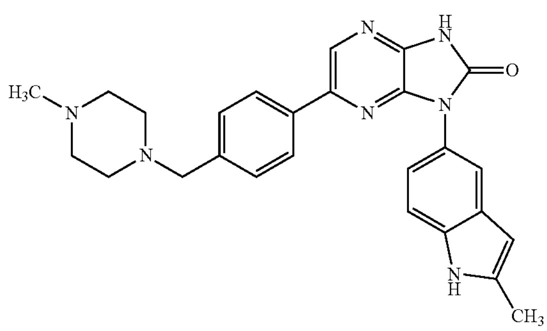 | 1-(2-Methyl-1H-indol-5-yl)-6-[4-(4-methyl-piperazin-1-ylmethyl)-phenyl]-1,3-dihydro-imidazo[4,5-b]pyrazin-2-one | 453.55 | HG |
| 211 | 1-Methyl-4-[4-(4,4,5,5-tetramethyl-[1,3,2]dioxaborolan-2-yl)-benzyl]-piperazine | 1H-Indazol-5-ylamine | 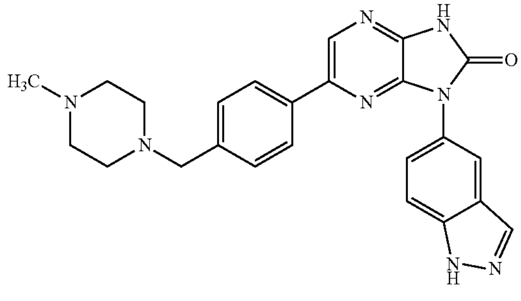 [SMILES: CN1CCN(Cc2ccc(-c3cnc4[nH]c(=O)n(-c5ccc6[nH]ncc6c5)c4n3)cc2)CC1] | 1-(1H-Indazol-5-yl)-6-[4-(4-methyl-piperazin-1-ylmethyl)-phenyl]-1,3-dihydro-imidazo[4,5-b]pyrazin-2-one | 440.51 | HH |

TABLE 3-continued

| Ex. | Boronic Acid | Amine | Structure | Purified Compound Isolated | MW | Cmpd ID |
|---|---|---|---|---|---|---|
| 212 | 1-Methyl-4-[4-(4,4,5,5-tetramethyl-[1,3,2]di-oxaborolan-2-yl)-benzyl]-piperazine | 1H-Indol-5-ylamine | 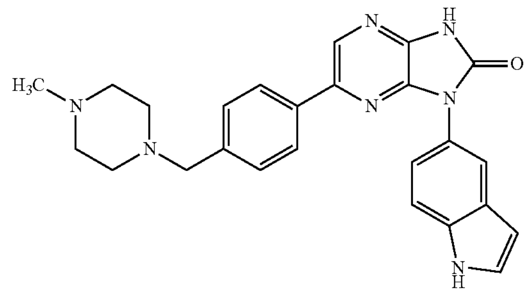 [SMILES: CN1CCN(Cc2ccc(-c3cnc4[nH]c(=O)n(-c5ccc6[nH]ccc6c5)c4n3)cc2)CC1] | 1-(1H-Indol-5-yl)-6-[4-(4-methyl-piperazin-1-ylmethyl)-phenyl]-1,3-dihydro-imidazo[4,5-b]pyrazin-2-one | 439.52 | HI |
| 213 | 1-Methyl-4-[4-(4,4,5,5-tetramethyl-[1,3,2]di-oxaborolan-2-yl)-benzyl]-piperazine | 4-Amino-phenol | 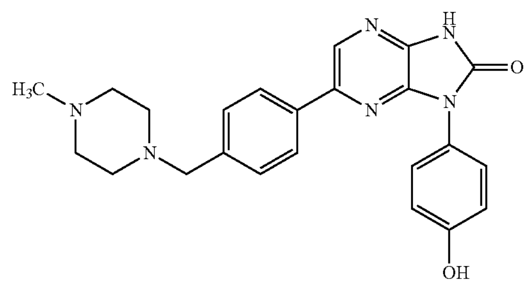 [SMILES: CN1CCN(Cc2ccc(-c3cnc4[nH]c(=O)n(-c5ccc(O)cc5)c4n3)cc2)CC1] | 1-(4-Hydroxy-phenyl)-6-[4-(4-methyl-piperazin-1-ylmethyl)-phenyl]-1,3-dihydro-imidazo[4,5-b]pyrazin-2-one | 416.49 | HJ |
| 214 | 1-Methyl-4-[4-(4,4,5,5-tetramethyl-[1,3,2]di-oxaborolan-2-yl)-benzyl]-piperazine | Benzo-thiazol-5-ylamine | 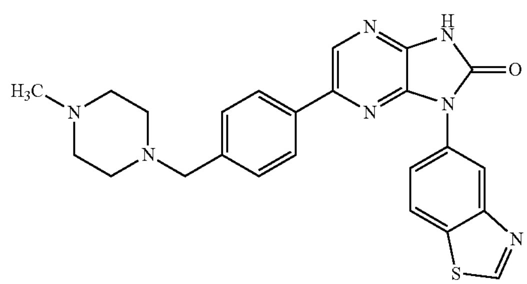 [SMILES: CN1CCN(Cc2ccc(-c3cnc4[nH]c(=O)n(-c5ccc6scnc6c5)c4n3)cc2)CC1] | 1-Benzothiazol-5-yl-6-[4-(4-methyl-piperazin-1-ylmethyl)-phenyl]-1,3-dihydro-imidazo[4,5-b]pyrazin-2-one | 457.56 | HK |
| 215 | 1-Methyl-4-[4-(4,4,5,5-tetramethyl-[1,3,2]di-oxaborolan-2-yl)-benzyl]-piperazine | Phenyl-amine | 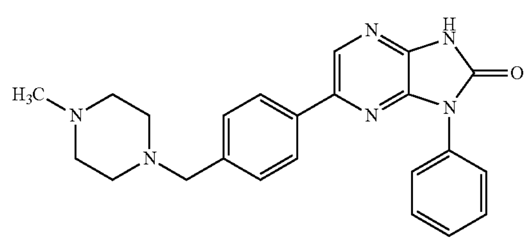 [SMILES: CN1CCN(Cc2ccc(-c3cnc4[nH]c(=O)n(-c5ccccc5)c4n3)cc2)CC1] | 6-[4-(4-Methyl-piperazin-1-ylmethyl)-phenyl]-1-phenyl-1,3-dihydro-imidazo[4,5-b]pyrazin-2-one | 400.49 | HL |
| 216 | 1-Methyl-4-[4-(4,4,5,5-tetramethyl-[1,3,2]di-oxaborolan-2-yl)-benzyl]-piperazine | 4-Methoxy-phenyl-amine | 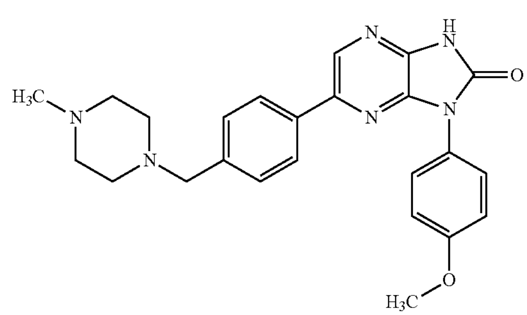 [SMILES: COc1ccc(-n2c(=O)[nH]c3ncc(-c4ccc(CN5CCN(C)CC5)cc4)nc32)cc1] | 1-(4-Methoxy-phenyl)-6-[4-(4-methyl-piperazin-1-ylmethyl)-phenyl]-1,3-dihydro-imidazo[4,5-b]pyrazin-2-one | 430.51 | HM |

TABLE 3-continued

| Ex. | Boronic Acid | Amine | Structure | Purified Compound Isolated | MW | Cmpd ID |
|---|---|---|---|---|---|---|
| 217 | 1-Methyl-4-[3-(4,4,5,5-tetramethyl-[1,3,2]dioxaborolan-2-yl)-benzyl]-piperazine | 1H-Indol-5-ylamine | 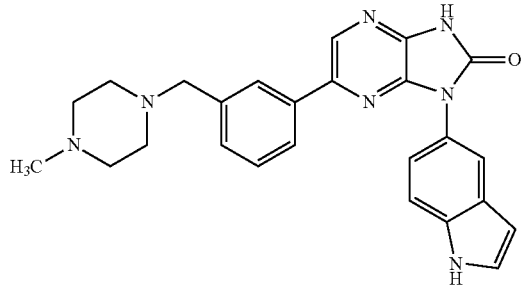 [SMILES: CN1CCN(Cc2cccc(-c3cnc4[nH]c(=O)n(-c5ccc6[nH]ccc6c5)c4n3)c2)CC1] | 1-(1H-Indol-5-yl)-6-[3-(4-methyl-piperazin-1-ylmethyl)-phenyl]-1,3-dihydro-imidazo[4,5-b]pyrazin-2-one | 439.52 | HN |
| 218 | 3-Fluoro-4-(methyl-sulfonyl)-phenyl-boronic acid | 1H-Indol-5-ylamine | 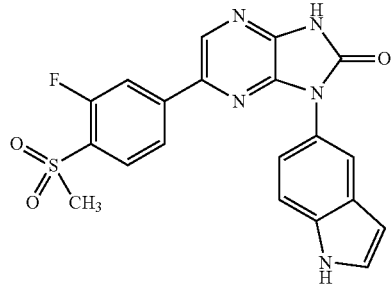 [SMILES: CS(=O)(=O)c1ccc(-c2cnc3[nH]c(=O)n(-c4ccc5[nH]ccc5c4)c3n2)cc1F] | 6-(3-Fluoro-4-methanesulfonyl-phenyl)-1-(1H-indol-5-yl)-1,3-dihydro-imidazo[4,5-b]pyrazin-2-one | 423.43 | HO |
| 219 | 3-Fluoro-4-methoxy-phenyl-boronic acid | 1H-Indol-5-ylamine | 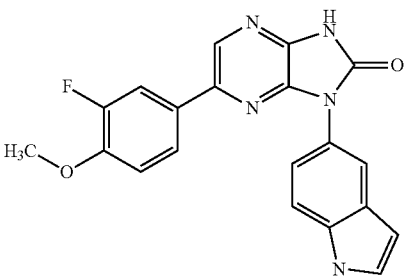 | 6-(3-Fluoro-4-methoxy-phenyl)-1-(1H-indol-5-yl)-1,3-dihydro-imidazo[4,5-b]pyrazin-2-one | 375.37 | HP |
| 220 | 1-Methyl-4-[4-(4,4,5,5-tetramethyl-[1,3,2]dioxaborolan-2-yl)-benzyl]-piperazine | Indan-2-ylamine | 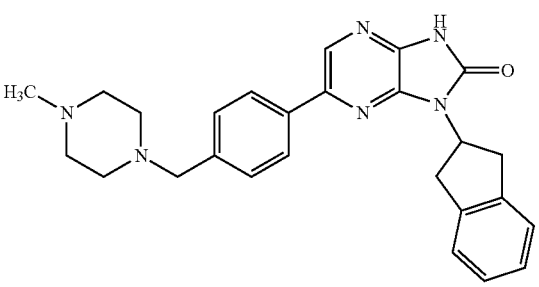 [SMILES: CN1CCN(Cc2ccc(-c3cnc4[nH]c(=O)n(C5Cc6ccccc6C5)c4n3)cc2)CC1] | 1-Indan-2-yl-6-[4-(4-methyl-piperazin-1-ylmethyl)-phenyl]-1,3-dihydro-imidazo[4,5-b]pyrazin-2-one | 440.55 | HQ |
| 221 | 1-Methyl-4-[3-(4,4,5,5-tetramethyl-[1,3,2]dioxaborolan-2-yl)-benzyl]-piperazine | Indan-2-ylamine | 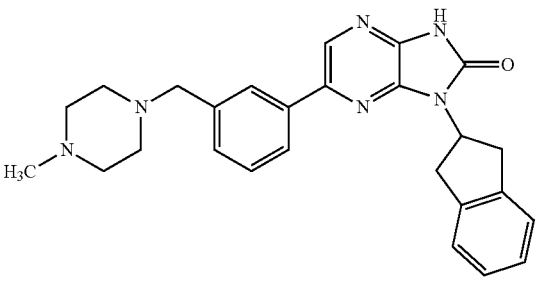 [SMILES: CN1CCN(Cc2cccc(-c3cnc4[nH]c(=O)n(C5Cc6ccccc6C5)c4n3)c2)CC1] | 1-Indan-2-yl-6-[3-(4-methyl-piperazin-1-ylmethyl)-phenyl]-1,3-dihydro-imidazo[4,5-b]pyrazin-2-one | 440.55 | HR |

TABLE 3-continued

| Ex. | Boronic Acid | Amine | Structure | Purified Compound Isolated | MW | Cmpd ID |
|---|---|---|---|---|---|---|
| 222 | 1-Methyl-4-[4-(4,4,5,5-tetramethyl-[1,3,2]dioxaborolan-2-yl)-benzyl]-piperazine | C-Cyclopropyl-methyl-amine | 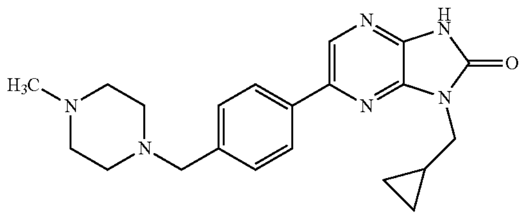 [SMILES: CN1CCN(Cc2ccc(-c3cnc4[nH]c(=O)n(CC5CC5)c4n3)cc2)CC1] | 1-Cyclopropylmethyl-6-[4-(4-methyl-piperazin-1-ylmethyl)-phenyl]-1,3-dihydro-imidazo[4,5-b]pyrazin-2-one | 378.48 | HS |
| 223 | 1-Methyl-4-[3-(4,4,5,5-tetramethyl-[1,3,2]dioxaborolan-2-yl)-benzyl]-piperazine | C-Cyclopropyl-methyl-amine | 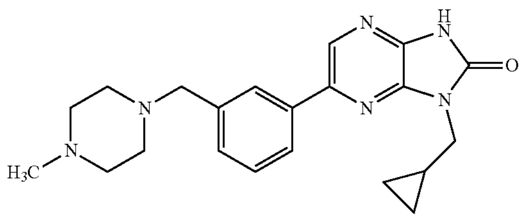 [SMILES: CN1CCN(Cc2cccc(-c3cnc4[nH]c(=O)n(CC5CC5)c4n3)c2)CC1] | 1-Cyclopropylmethyl-6-[3-(4-methyl-piperazin-1-ylmethyl)-phenyl]-1,3-dihydro-imidazo[4,5-b]pyrazin-2-one | 378.48 | HT |

Example 224

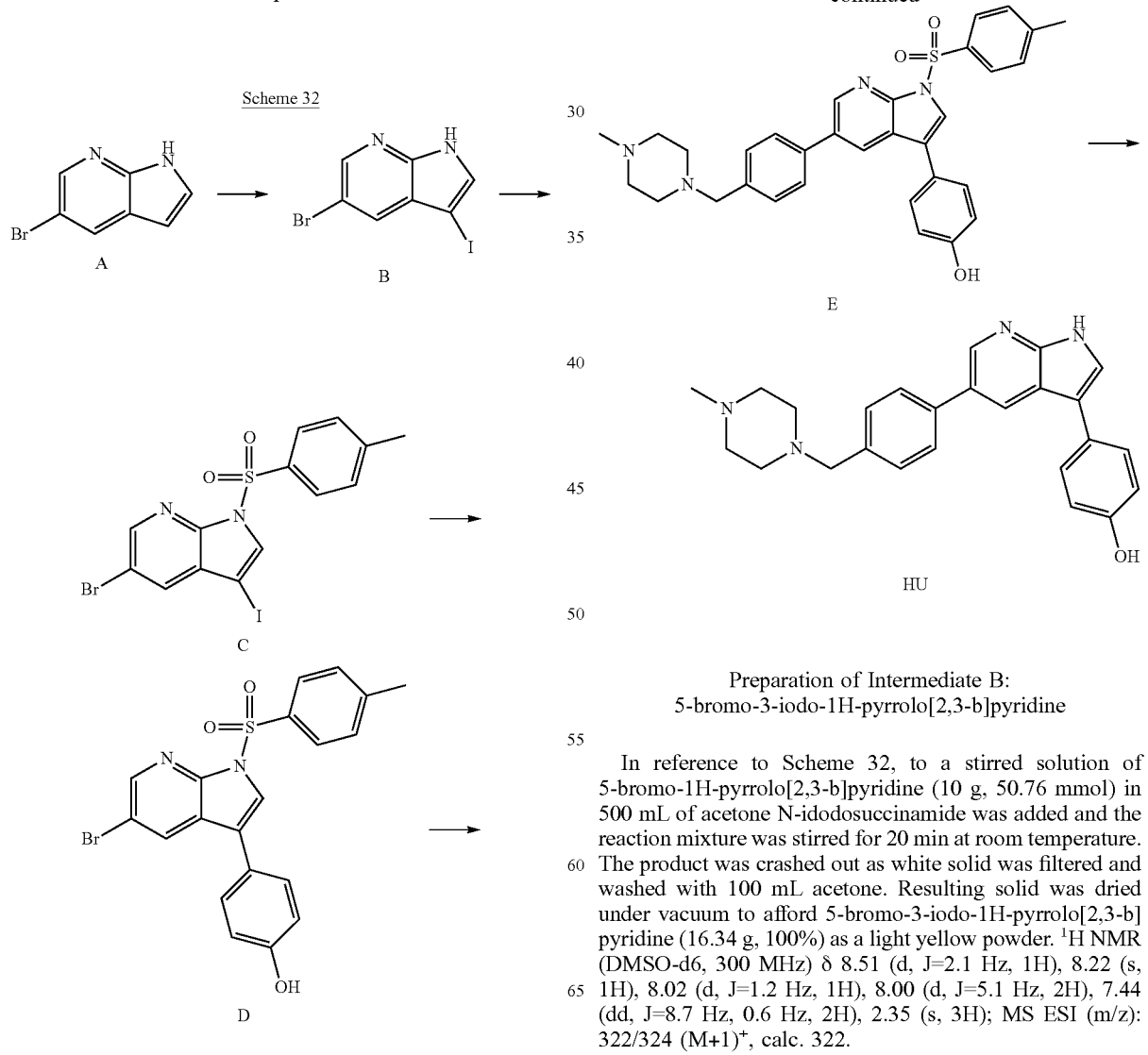

Preparation of Intermediate B:
5-bromo-3-iodo-1H-pyrrolo[2,3-b]pyridine

In reference to Scheme 32, to a stirred solution of 5-bromo-1H-pyrrolo[2,3-b]pyridine (10 g, 50.76 mmol) in 500 mL of acetone N-idodosuccinamide was added and the reaction mixture was stirred for 20 min at room temperature. The product was crashed out as white solid was filtered and washed with 100 mL acetone. Resulting solid was dried under vacuum to afford 5-bromo-3-iodo-1H-pyrrolo[2,3-b]pyridine (16.34 g, 100%) as a light yellow powder. $^1$H NMR (DMSO-d6, 300 MHz) δ 8.51 (d, J=2.1 Hz, 1H), 8.22 (s, 1H), 8.02 (d, J=1.2 Hz, 1H), 8.00 (d, J=5.1 Hz, 2H), 7.44 (dd, J=8.7 Hz, 0.6 Hz, 2H), 2.35 (s, 3H); MS ESI (m/z): 322/324 (M+1)$^+$, calc. 322.

Preparation of Intermediate C: 5-bromo-3-iodo-1-tosyl-1H-pyrrolo[2,3-b]pyridine To a stirred solution of 5-bromo-3-iodo-1H-pyrrolo[2,3-b]pyridine (16.82 g, 52.23 mmol) in 522 mL of anhydrous THF cooled to 0° C. with an ice bath was added NaH [60% dispersion in mineral oil] (3.76 g, 156.7 mmol). The reaction mixture was stirred for 20 min at 0° C., after which p-toluenesulfonyl chloride (14.88 g, 78.3 mmol) was added. The resulting mixture was stirred at 0° C. for 1.5 hr, after which cold 0.5 M HCl (20 mL) was added. The mixture was partitioned between EtOAc and 0.5 M HCl, after which the organic layer was separated, dried over MgSO₄, filtered, and evaporated in vacuo to yield a residue that was triturated with 20% CH₂Cl₂ in hexanes to yield the title compound (0.84 g, 81%) as a light yellow powder. ¹H NMR (DMSO-d6, 300 MHz) δ 8.51 (d, J=2.1 Hz, 1H), 8.22 (s, 1H), 8.02 (d, J=1.2 Hz, 1H), 8.00 (d, J=5.1 Hz, 2H), 7.44 (dd, J=8.7 Hz, 0.6 Hz, 2H), 2.35 (s, 3H); MS ESI (m/z): 477.0/479.0 (M+1)⁺, calc. 476.

Preparation of Intermediate D: 4-[5-Bromo-1-(toluene-4-sulfonyl)-1H-pyrrolo[2,3-b]pyridin-3-yl]-phenol To a stirred suspension of 5-bromo-3-iodo-1-tosyl-1H-pyrrolo[2,3-b]pyridine (0.30 g, 0.62 mmol) and 4-hydroxyphenylboronic acid (0.12 mg, 0.75 mmol) in CH₃CN (3 mL) was added 1 M Na₂CO₃ (3 mL) followed by bis(triphenylphosphine)palladium(II) dichloride (0.004 g, 0.062 mmol). The resulting mixture was stirred overnight at 60° C. After the mixture was evaporated to dryness in vacuo, it was dissolved in DMF (3 mL), absorbed onto Celite, and dried. The residue was purified via silica gel chromatography using CH₂Cl₂ as the eluent to obtain the title compound (0.26 g, 76%). ¹H NMR (CDCl₃, 300 MHz): δ 8.48 (d, J=2.1 Hz, 1H), 8.27 (bs, 1H), 8.26 (d, J=2.4 Hz, 1H), 8.08 (d, J=8.1 Hz, 1H), 7.85 (s, 1H), 7.81 (m, 1H), 7.50 (d, J=8.7 Hz, 1H), 7.37 (dd, J=1.8, 8.4 Hz), 7.30 (m, 3H), 6.63 (m, 1H), 2.39 (s, 3H); MS ESI (m/z): 443/445 (M+1)⁺, calc. 443.31.

Preparation of 4-{5-[4-(4-Methyl-piperazin-1-ylmethyl)-phenyl]-1H-pyrrolo[2,3-b]pyridin-3-yl}-phenol (Compound HU)

To a solution of 5-bromo-3-(1H-indol-5-yl)-1-tosyl-1H-pyrrolo[2,3-b]pyridine (0.220 g, 0.5 mmol) in CH₃CN (2.5 mL) in a Personal Chemistry microwave reaction vial was added 1-Methyl-4-[4-(4,4,5,5-tetramethyl-[1,3,2]dioxaborolan-2-yl)-benzyl]-piperazine (0.20 g, 0.65 mmol), bis(triphenylphosphine)-palladium(II) dichloride (0.003 g, 0.005 mmol), and 1 M Na₂CO₃ (1 mL). The resulting mixture was de-gassed with Ar for 10 min, after which it was heated at 150° C. for 30 min in a Personal Chemistry Optimizer. The organic layer was separated, filtered, and concentrated in vacuo. The residue was dissolved in MeOH (3 mL) and acetone (2 mL), and 2 M NaOH (1.5 mL) was added. The resulting mixture was stirred at 65° C. for 30 min, after which it was partitioned between EtOAc and 1 M NaOH. The organic layer was separated, dried over MgSO₄, filtered, and stripped to give a residue purified via preparatory HPLC to give the title compound as a white solid. ¹H NMR (DMSO-d6, 300 MHz): δ 11.78 (s, 1H), 11.03 (s, 1H), 8.51 (d, J=2.1 Hz, 1H), 8.36 (d, J=1.8 Hz, 1H), 7.86 (s, 1H), 7.72 (d, J=2.4 Hz, 1H), 7.45 (s, 2H), 7.32 (m, 1H), 6.92 (s, 2H), 6.45 (m, 1H), 3.85 (s, 6H), 3.70 (s, 3H); HPLC retention time: 2.04 minutes; MS ESI (m/z): 399 (M+1)⁺, calc. 398.51.

Examples 225-245

Using similar procedure described for Example 224, the following compounds were prepared by changing boronic acids in the B to C coupling as described in Table 4 unless otherwise indicated. Examples 225-245 were were physically characterized by electrospray ionization mass spectrometry. Structures and molecular masses are given below in Table 4.

TABLE 4

| Ex. | Boronic Acid | IUPAC Name | Structure | MW | Cmpd ID |
|---|---|---|---|---|---|
| 225 | 6-Aminopyridine-3-boronic acid pinacol ester | 5-(5-(4-((4-methylpiperazin-1-yl)methyl)phenyl)-1H-pyrrolo[2,3-b]pyridin-3-yl)pyridin-2-amine | 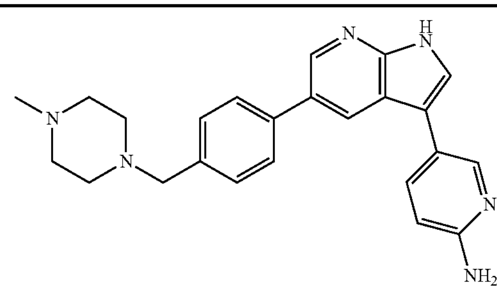 | 398.50 | HV |
| 226 | 6-Aminopyridine-3-boronic acid pinacol ester for B to C coupling, 1-methyl-4-(3-(4,4,5,5-tetramethyl-1,3,2-dioxaborolan-2-yl)benzyl)piperazine for C to D coupling | 5-{5-[3-(4-Methyl-piperazin-1-ylmethyl)-phenyl]-1H-pyrrolo[2,3-b]pyridin-3-yl}-pyridin-2-ylamine | 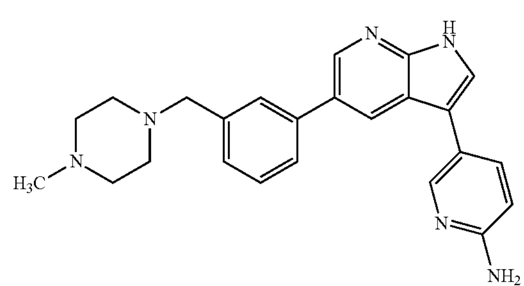 [SMILES: CN1CCN(Cc2cccc(-c3cnc4[nH]cc(-c5ccc(N)nc5)c4c3)c2)CC1] | 398.50 | HW |

TABLE 4-continued

| Ex. | Boronic Acid | IUPAC Name | Structure | MW | Cmpd ID |
|---|---|---|---|---|---|
| 227 | 7-Azaindole-5-boronic acid pinacol ester | 5-[3-(4-Methyl-piperazin-1-ylmethyl)-phenyl]-1H,1'H-[3,5']bi[pyrrolo[2,3-b]pyridinyl] | 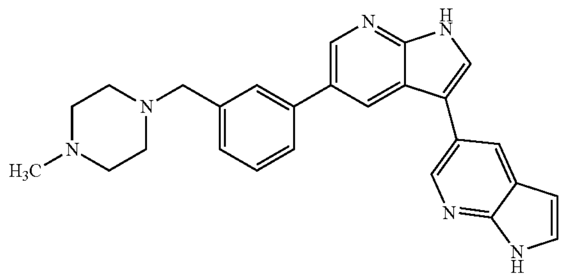 [SMILES: CN1CCN(Cc2cccc(-c3cnc4[nH]cc(-c5cnc6[nH]ccc6c5)c4c3)c2)CC1] | 422.52 | HX |
| 228 | 4-Aminophenyl-boronic acid | 4-{5-[4-(4-Methyl-piperazin-1-ylmethyl)-phenyl]-1H-pyrrolo[2,3-b]pyridin-3-yl}-phenylamine | 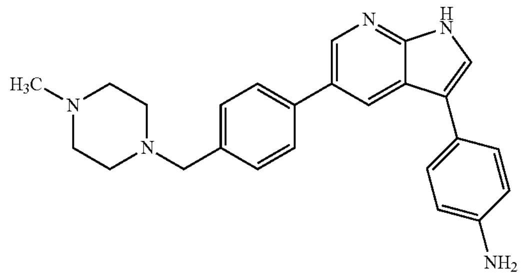 [SMILES: CN1CCN(Cc2ccc(-c3cnc4[nH]cc(-c5ccc(N)cc5)c4c3)cc2)CC1] | 397.52 | HY |
| 229 | 4-Hydroxyphenyl-boronic acid | 4-{5-[4-(4-Methyl-piperazin-1-ylmethyl)-phenyl]-1H-pyrrolo[2,3-b]pyridin-3-yl}-phenol | 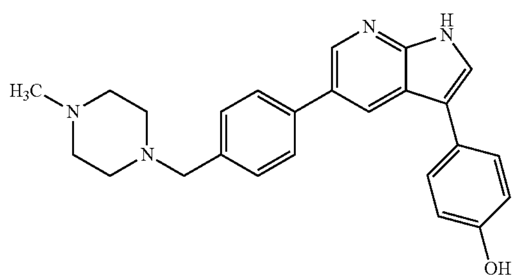 [SMILES: CN1CCN(Cc2ccc(-c3cnc4[nH]cc(-c5ccc(O)cc5)c4c3)cc2)CC1] | 398.51 | HZ |
| 230 | 3-Hydroxyphenyl-boronic acid | 3-{5-[4-(4-Methyl-piperazin-1-ylmethyl)-phenyl]-1H-pyrrolo[2,3-b]pyridin-3-yl}-phenol | 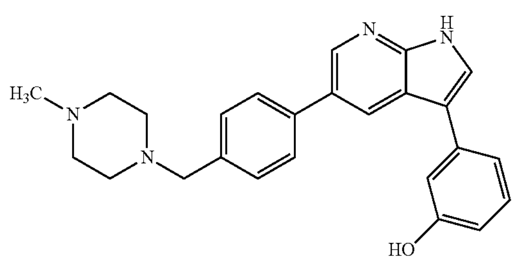 [SMILES: CN1CCN(Cc2ccc(-c3cnc4[nH]cc(-c5cccc(O)c5)c4c3)cc2)CC1] | 398.51 | IA |
| 231 | 6-Hydroxypyridine-3-boronic acid | 5-{5-[4-(4-Methyl-piperazin-1-ylmethyl)-phenyl]-1H-pyrrolo[2,3-b]pyridin-3-yl}-pyridin-2-ol | 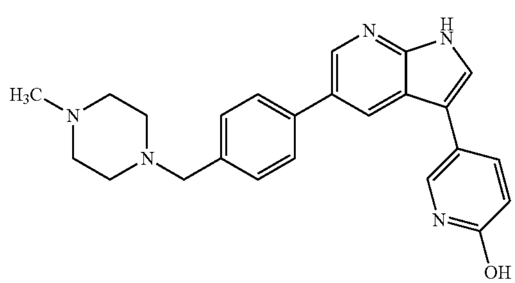 [SMILES: CN1CCN(Cc2ccc(-c3cnc4[nH]cc(-c5ccc(O)nc5)c4c3)cc2)CC1] | 399.5 | IB |

TABLE 4-continued

| Ex. | Boronic Acid | IUPAC Name | Structure | MW | Cmpd ID |
|---|---|---|---|---|---|
| 232 | 2-Hydroxypyrimidine-5-boronic acid | 5-{5-[4-(4-Methyl-piperazin-1-ylmethyl)-phenyl]-1H-pyrrolo[2,3-b]pyridin-3-yl}-pyrimidin-2-ol | 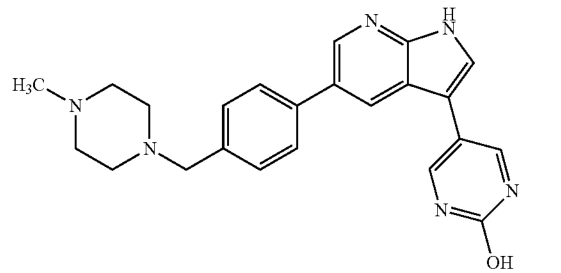 [SMILES: CN1CCN(Cc2ccc(-c3cnc4[nH]cc(-c5cnc(O)nc5)c4c3)cc2)CC1] | 400.49 | IC |
| 233 | 3-Fluoro-4-hydroxyphenyl-boronic acid | 2-Fluoro-4-{5-[4-(4-methyl-piperazin-1-ylmethyl)-phenyl]-1H-pyrrolo[2,3-b]pyridin-3-yl}-phenol | 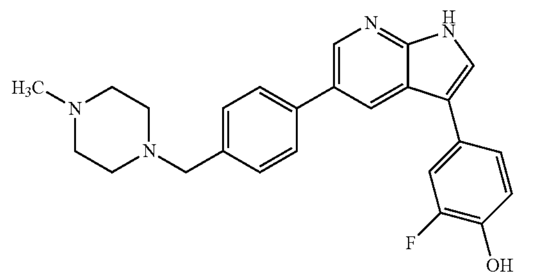 [SMILES: CN1CCN(Cc2ccc(-c3cnc4[nH]cc(-c5ccc(O)c(F)c5)c4c3)cc2)CC1] | 416.5 | ID |
| 234 | 4-Hydroxy-3-methoxyphenyl-boronic acid | 2-Methoxy-4-{5-[4-(4-methyl-piperazin-1-ylmethyl)-phenyl]-1H-pyrrolo[2,3-b]pyridin-3-yl}-phenol | 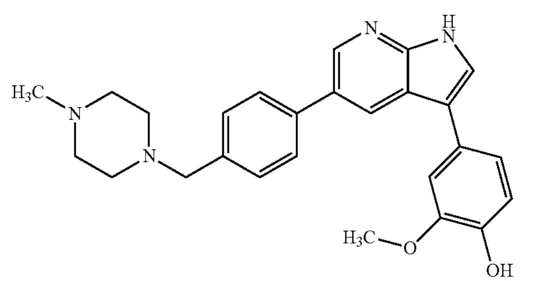 [SMILES: COc1cc(-c2c[nH]c3ncc(-c4ccc(CN5CCN(C)CC5)cc4)cc23)ccc1O] | 428.54 | IE |
| 235 | 3,4-Methylenedioxy phenylboronic acid | 3-Benzo[1,3]dioxol-5-yl-5-[4-(4-methyl-piperazin-1-ylmethyl)-phenyl]-1H-pyrrolo[2,3-b]pyridine | 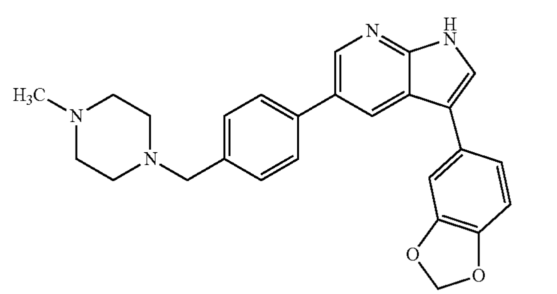 [SMILES: CN1CCN(Cc2ccc(-c3cnc4[nH]cc(-c5ccc6c(c5)OCO6)c4c3)cc2)CC1] | 426.52 | IF |
| 236 | 3,6-Dihydro-2H-pyridine-1-N-Boc-4-boronic acid, pinacol ester | 4-{5-[4-(4-Methyl-piperazin-1-ylmethyl)-phenyl]-1H-pyrrolo[2,3-b]pyridin-3-yl}-3,6-dihydro-2H-pyridine-1-carboxylic acid tert-butyl ester | 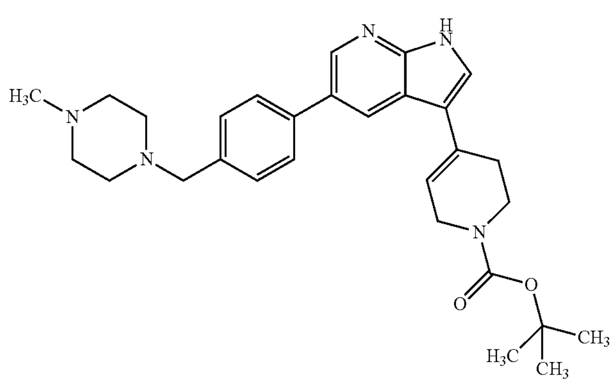 [SMILES: CN1CCN(Cc2ccc(-c3cnc4[nH]cc(C5=CCN(C(=O)OC(C)(C)C)CC5)c4c3)cc2)CC1] | 487.65 | IG |

TABLE 4-continued

| Ex. | Boronic Acid | IUPAC Name | Structure | MW | Cmpd ID |
|---|---|---|---|---|---|
| 237 | 1,2,3,6-Tetrahydropyridine-4-yl-boronic acid pinacol ester hydrochloride | 5-[4-(4-Methyl-piperazin-1-ylmethyl)-phenyl]-3-(1,2,3,6-tetrahydro-pyridin-4-yl)-1H-pyrrolo[2,3-b]pyridine | 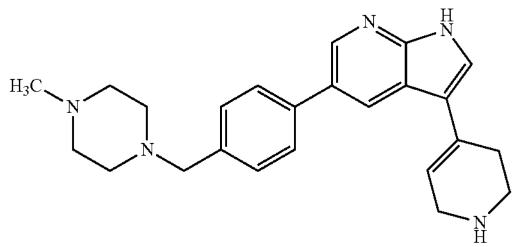 [SMILES: CN1CCN(Cc2ccc(-c3cnc4[nH]cc(C5=CCNCC5)c4c3)cc2)CC1] | 387.53 | IH |
| 238 | 4-Fluoro-3-hydroxyphenyl-boronic acid | 2-Fluoro-5-{5-[4-(4-methyl-piperazin-1-ylmethyl)-phenyl]-1H-pyrrolo[2,3-b]pyridin-3-yl}-phenol | 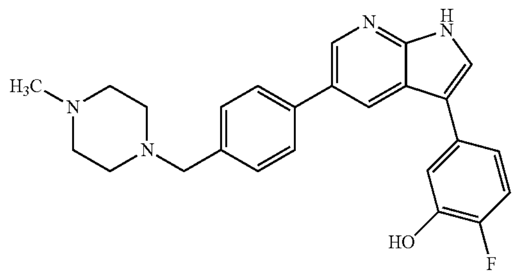 [SMILES: CN1CCN(Cc2ccc(-c3cnc4[nH]cc(-c5ccc(F)c(O)c5)c4c3)cc2)CC1] | 416.5 | II |
| 239 | 3-Hydroxy-4-methoxyphenyl-boronic acid | 2-Methoxy-5-{5-[4-(4-methyl-piperazin-1-ylmethyl)-phenyl]-1H-pyrrolo[2,3-b]pyridin-3-yl}-phenol | 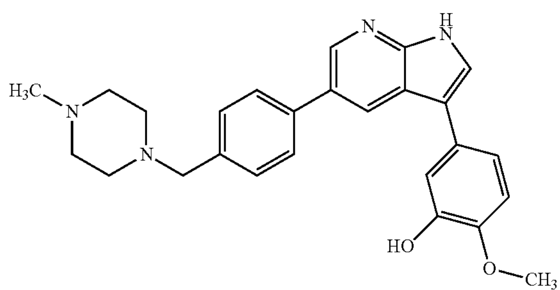 | 428.54 | IJ |
| 240 | 4-Hydroxy-2-methylphenyl-boronic acid | 3-Methyl-4-{5-[4-(4-methyl-piperazin-1-ylmethyl)-phenyl]-1H-pyrrolo[2,3-b]pyridin-3-yl}-phenol | 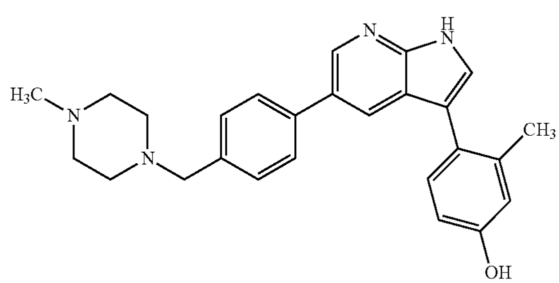 | 412.54 | IK |
| 241 | 5-Hydroxy-2-methoxyphenyl-boronic acid | 4-Methoxy-3-{5-[4-(4-methyl-piperazin-1-ylmethyl)-phenyl]-1H-pyrrolo[2,3-b]pyridin-3-yl}-phenol | 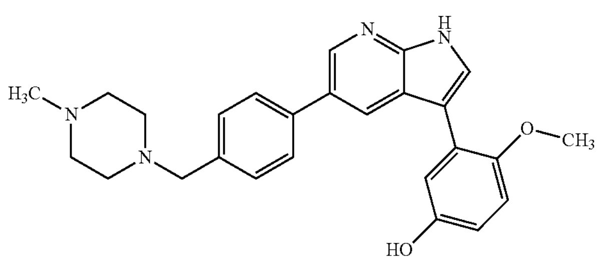 | 428.54 | IL |

TABLE 4-continued

| Ex. | Boronic Acid | IUPAC Name | Structure | MW | Cmpd ID |
|---|---|---|---|---|---|
| 242 | 3-Aminocarbonyl-phenylboronic acid | 3-{5-[4-(4-Methyl-piperazin-1-ylmethyl)-phenyl]-1H-pyrrolo[2,3-b]pyridin-3-yl}-benzamide | 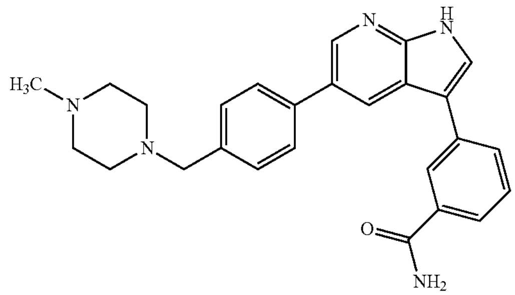 [SMILES: CN1CCN(Cc2ccc(-c3cnc4[nH]cc(-c5cccc(C(N)=O)c5)c4c3)cc2)CC1] | 425.54 | IM |
| 243 | 3-(N-Methylamino-carbonyl)phenyl-boronic acid | N-Methyl-3-{5-[4-(4-methyl-piperazin-1-ylmethyl)-phenyl]-1H-pyrrolo[2,3-b]pyridin-3-yl}-benzamide | 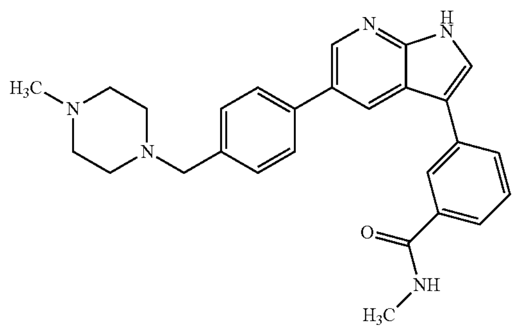 [SMILES: CNC(=O)c1cccc(-c2c[nH]c3ncc(-c4ccc(CN5CCN(C)CC5)cc4)cc23)c1] | 439.57 | IN |
| 244 | 3-Hydroxy-4-methylphenyl-boronic acid | 2-Methyl-5-{5-[4-(4-methyl-piperazin-1-ylmethyl)-phenyl]-1H-pyrrolo[2,3-b]pyridin-3-yl}-phenol | 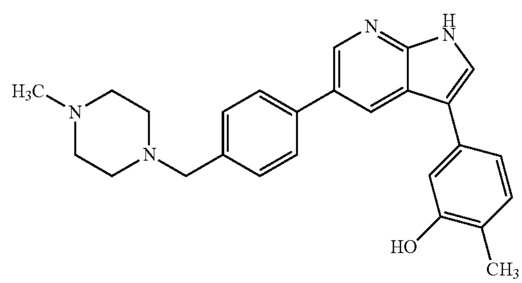 [SMILES: Cc1ccc(-c2c[nH]c3ncc(-c4ccc(CN5CCN(C)CC5)cc4)cc23)cc1O] | 412.54 | IO |
| 245 | 1H-indol-5-ylboronic acid for B to C coupling; 1-methyl-4-(4-(4,4,5,5-tetramethyl-1,3,2-dioxaborolan-2-yl)phenoxy)piperidine for C to D coupling | 3-(1H-indol-5-yl)-5-(4-(1-methylpiperidin-4-yloxy)phenyl)-1H-pyrrolo[2,3-b]pyridine | 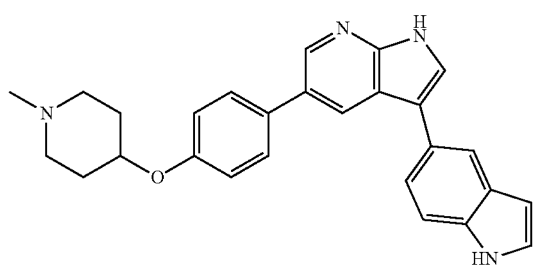 [SMILES: CN1CCC(Oc2ccc(-c3cnc4[nH]cc(-c5ccc6[nH]ccc6c5)c4c3)cc2)CC1] | 422.52 | IP |

Example 246

Scheme 32

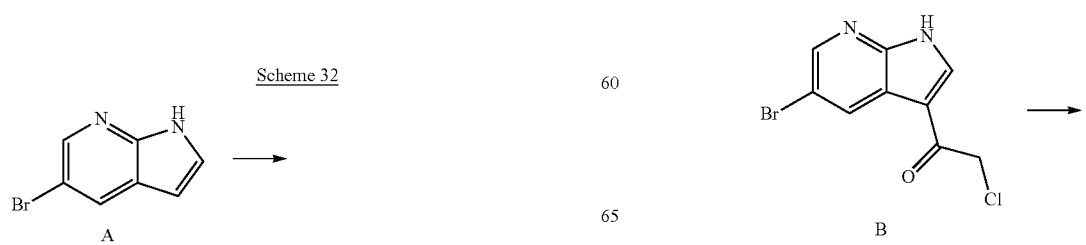

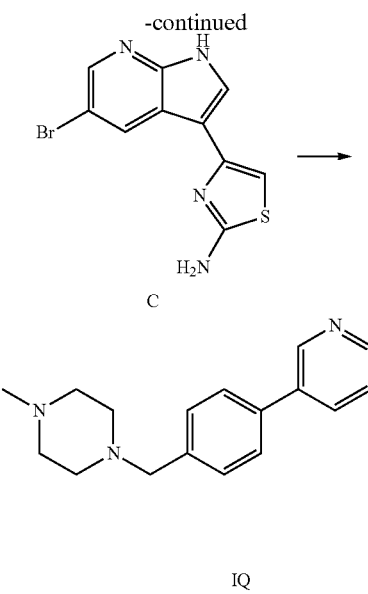

C

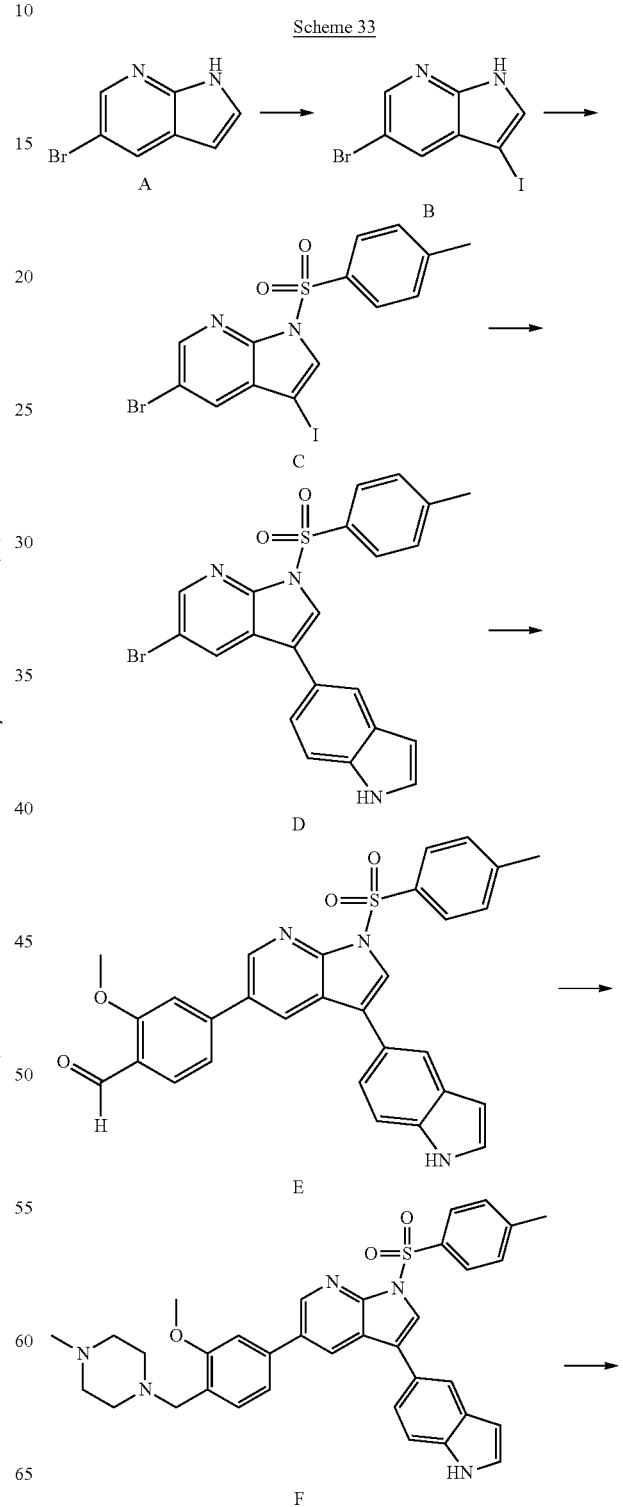

vacuo and purified on silica gel column using dichloromethane and methanol to afford 4-{5-[4-(4-Methyl-piperazin-1-ylmethyl)-phenyl]-1H-pyrrolo[2,3-b]pyridin-3-yl}-thiazol-2-ylamine.

Examples 247

Scheme 33

Preparation of Intermediate B: 1-(5-Bromo-1H-pyrrolo[2,3-b]pyridin-3-yl)-2-chloro-ethanone In reference to Scheme 32, to a suspension of $AlCl_3$ (3.38 g, 25.38 mmol) in dichloromethane (100 mL) was added 5-Bromo-1H-pyrrolo[2,3-b]pyridine (1 g, 5.07 mmol). After stirring for 30 min, chloroacetyl chloride (2.84 g, 25.38 mmol) was added and the reaction mixture was stirred for 2 hours at room temperature. On completion, solvents were evaporated and quenched with aq. $NaHCO_3$ solution at 0° C. Resulting mixture was extracted with EtOAc. The organic layer was dried over Na2SO4 and filtered through a plug of silica gel. Solvent was evaporated to dryness to give 1-(5-Bromo-1H-pyrrolo[2,3-b]pyridin-3-yl)-2-chloro-ethanone (1.3 g, 93% yield).

Preparation of Intermediate C: 4-(5-Bromo-2-methyl-1H-pyrrolo[2,3-b]pyridin-3-yl)-thiazol-2-ylamine A solution 1-(5-Bromo-1H-pyrrolo[2,3-b]pyridin-3-yl)-2-chloro-ethanone (0.32 g, 1.17 mmol) and thio urea (0.097 g, 1.28 mmol) in ethanol (4 mL) was stirred at 80° C. for 1.5 hours. The resulting precipitate was filtered, washed with MeOH, and dried under vacuum to give 4-(5-Bromo-1H-pyrrolo[2,3-b]pyridin-3-yl)-thiazol-2-ylamine (0.34 g, 99% yield).

Preparation of 4-{5-[4-(4-Methyl-piperazin-1-ylmethyl)-phenyl]-1H-pyrrolo[2,3-b]pyridin-3-yl}-thiazol-2-ylamine (Compound IQ)

In a personal chemistry microwave reaction vial 4-(5-Bromo-1H-pyrrolo[2,3-b]pyridin-3-yl)-thiazol-2-ylamine (0.2 g, 0.67 mmol) and 1-Methyl-4-[4-(4,4,5,5-tetramethyl-[1,3,2]dioxaborolan-2-yl)-benzyl]-piperazine (0.23 g, 0.74 mmol), bis(triphenylphosphine)-palladium(II) dichloride (0.004 g, 0.006 mmol) in acetonitrile (2 mL), and 1 M $Na_2CO_3$ (2 mL) were added. The resulting mixture was de-gassed with $N_2$ for 10 min, after which it was heated at 175° C. for 30 min in a Personal Chemistry Optimizer. The mixture was diluted with DMF (3 mL), and concentrated in

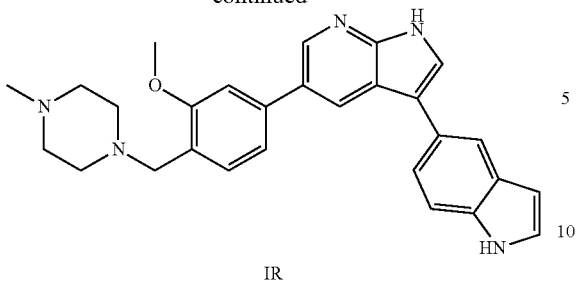

IR

Preparation of Intermediate B: 5-bromo-3-iodo-1H-pyrrolo[2,3-b]pyridine

In reference to Scheme 33, to a stirred solution of 5-bromo-1H-pyrrolo[2,3-b]pyridine (10 g, 50.76 mmol) in 500 mL of acetone N-idodosuccinamide was added and the reaction mixture was stirred for 20 min at room temperature. The product was crashed out as white solid was filtered and washed with 100 mL acetone. Resulting solid was dried under vacuum to afford 5-bromo-3-iodo-1H-pyrrolo[2,3-b]pyridine (16.34 g, 100%) as a light yellow powder. $^1$H NMR (DMSO-d6, 300 MHz) δ 8.51 (d, J=2.1 Hz, 1H), 8.22 (s, 1H), 8.02 (d, J=1.2 Hz, 1H), 8.00 (d, J=5.1 Hz, 2H), 7.44 (dd, J=8.7 Hz, 0.6 Hz, 2H), 2.35 (s, 3H); MS ESI (m/z): 322/324 (M+1)$^+$, calc. 322.

Preparation of Intermediate C: 5-bromo-3-iodo-1-tosyl-1H-pyrrolo[2,3-b]pyridine To a stirred solution of 5-bromo-3-iodo-1H-pyrrolo[2,3-b]pyridine (16.82 g, 52.23 mmol) in 522 mL of anhydrous THF cooled to 0° C. with an ice bath was added NaH [60% dispersion in mineral oil] (3.76 g, 156.7 mmol). The reaction mixture was stirred for 20 min at 0° C., after which p-toluenesulfonyl chloride (14.88 g, 78.3 mmol) was added. The resulting mixture was stirred at 0° C. for 1.5 hr, after which cold 0.5 M HCl (20 mL) was added. The mixture was partitioned between EtOAc and 0.5 M HCl, after which the organic layer was separated, dried over MgSO$_4$, filtered, and evaporated in vacuo to yield a residue that was triturated with 20% CH$_2$Cl$_2$ in hexanes to yield the title compound (0.84 g, 81%) as a light yellow powder. $^1$H NMR (DMSO-d6, 300 MHz) δ 8.51 (d, J=2.1 Hz, 1H), 8.22 (s, 1H), 8.02 (d, J=1.2 Hz, 1H), 8.00 (d, J=5.1 Hz, 2H), 7.44 (dd, J=8.7 Hz, 0.6 Hz, 2H), 2.35 (s, 3H); MS ESI (m/z): 477.0/479.0 (M+1)$^+$, calc. 476.

Preparation of Intermediate D: 4-[5-Bromo-1-(toluene-4-sulfonyl)-1H-pyrrolo[2,3-b]pyridin-3-yl]-phenol To a stirred suspension of 5-bromo-3-iodo-1-tosyl-1H-pyrrolo[2,3-b]pyridine (2.66 g, 5.57 mmol) and 1H-indol-5-ylboronic acid (0.89 g, 5.57 mmol) in CH$_3$CN (36 mL) was added 1 M Na$_2$CO$_3$ (18 mL) followed by bis(triphenylphosphine)palladium(II) dichloride (0.20 g, 0.275 mmol). The resulting mixture was stirred overnight at 60° C. After the mixture was evaporated to dryness in vacuo, it was dissolved in DMF (3 mL), absorbed onto Celite, and dried. The residue was purified via silica gel chromatography using CH$_2$Cl$_2$ as the eluent to obtain the title compound (1.65 g, 63%). $^1$H NMR (CDCl$_3$, 300 MHz): δ 8.48 (d, J=2.1 Hz, 1H), 8.27 (bs, 1H), 8.26 (d, J=2.4 Hz, 1H), 8.08 (d, J=8.1 Hz), 7.85 (s, 1H), 7.81 (m, 1H), 7.50 (d, J=8.7 Hz, 1H), 7.37 (dd, J=1.8, 8.4 Hz), 7.30 (m, 3H), 6.63 (m, 1H), 2.39 (s, 3H); MS ESI (m/z): 466.2/468.2 (M+1)$^+$, calc. 465.

Preparation of Intermediate E: 4-[3-(1H-Indol-5-yl)-1-(toluene-4-sulfonyl)-1H-pyrrolo[2,3-b]pyridin-5-yl]-2-methoxy-benzaldehyde To a solution of 5-bromo-3-(1H-indol-5-yl)-1-tosyl-1H-pyrrolo[2,3-b]pyridine (0.100 g, 0.21 mmol) in CH$_3$CN (1 mL) in a Personal Chemistry microwave reaction vial was added 1-2-methoxy-4-(4,4,5,5-tetramethyl-[1,3,2]dioxaborolan-2-yl)-benzaldehyde (0.042 g, 0.25 mmol), bis(triphenylphosphine)-palladium(II) dichloride (0.02 g, 0.002 mmol), and 1 M Na$_2$CO$_3$ (1 mL). The resulting mixture was de-gassed with Ar for 10 min, after which it was heated at 150° C. for 30 min in a Personal Chemistry Optimizer. The organic layer was separated, filtered, and concentrated in vacuo. The residue purified on silica gel column to give 4-[3-(1H-Indol-5-yl)-1-(toluene-4-sulfonyl)-1H-pyrrolo[2,3-b]pyridin-5-yl]-2-methoxy-benzaldehyde (0.66 g, 59% yield). MS ESI (m/z): 521/523 (M+1)$^+$, calc. 521.51.

Preparation of 3-(1H-Indol-5-yl)-5-[3-methoxy-4-(4-methyl-piperazin-1-ylmethyl)-phenyl]-1H-pyrrolo[2,3-b]pyridine (Compound IR)

To a solution of 4-[3-(1H-Indol-5-yl)-1-(toluene-4-sulfonyl)-1H-pyrrolo[2,3-b]pyridin-5-yl]-2-methoxy-benzaldehyde (0.066 g, 0.128 mmol) in CH$_2$Cl$_2$ (3 mL) was added 1-methylpiperazine (22 mL, 0.19 mmol) and sodium triacetoxyborohydride (81 mg, 0.38 mmol). The reaction mixture was stirred for 1 hr at room temperature, after which it was partitioned between CH$_2$Cl$_2$ and 1 M NaOH. The organic layer was separated, dried over MgSO$_4$, and concentrated in vacuo. The residue was dissolved in 3:2 MeOH:acetone (5 mL), and 2 M NaOH (1.5 mL) was added. The resulting mixture was stirred at 65° C. for 30 min, after which it was partitioned between EtOAc and 1 M NaOH. The organic layer was separated, dried over MgSO$_4$, filtered, and stripped to provide a residue that was subjected to preparatory HPLC to yield 3-(1H-Indol-5-yl)-5-[3-methoxy-4-(4-methyl-piperazin-1-ylmethyl)-phenyl]-1H-pyrrolo[2,3-b]pyridine (0.037 g, 63% yield). $^1$H NMR (CDCl$_3$, 400 MHz): δ 11.81 (s, 1H), 11.06 (s, 1H), 8.55 (d, J=2.1 Hz, 1H), 8.40 (d, J=2.4 Hz, 1H), 7.88 (d, J=1.6 Hz, 1H), 7.74 (d, J=1.6 Hz, 1H), 7.46 (s, 2H), 7.37 (dd, J=6.4 Hz, 1H), 7.35 (d, J=6.4 Hz, 1H), 7.26 (dd, J=1.8, 6.4 Hz, 2H)), 6.46 (s, 1H), 3.86 (d, J=1.2 Hz, 2H), 3.32 (s, 3H), 2.49-42 (m, 8H), 2.13 (s, 3H); MS ESI (m/z) 452 (M+1)$^+$, calc. 451.56.

Example 248

Scheme 34

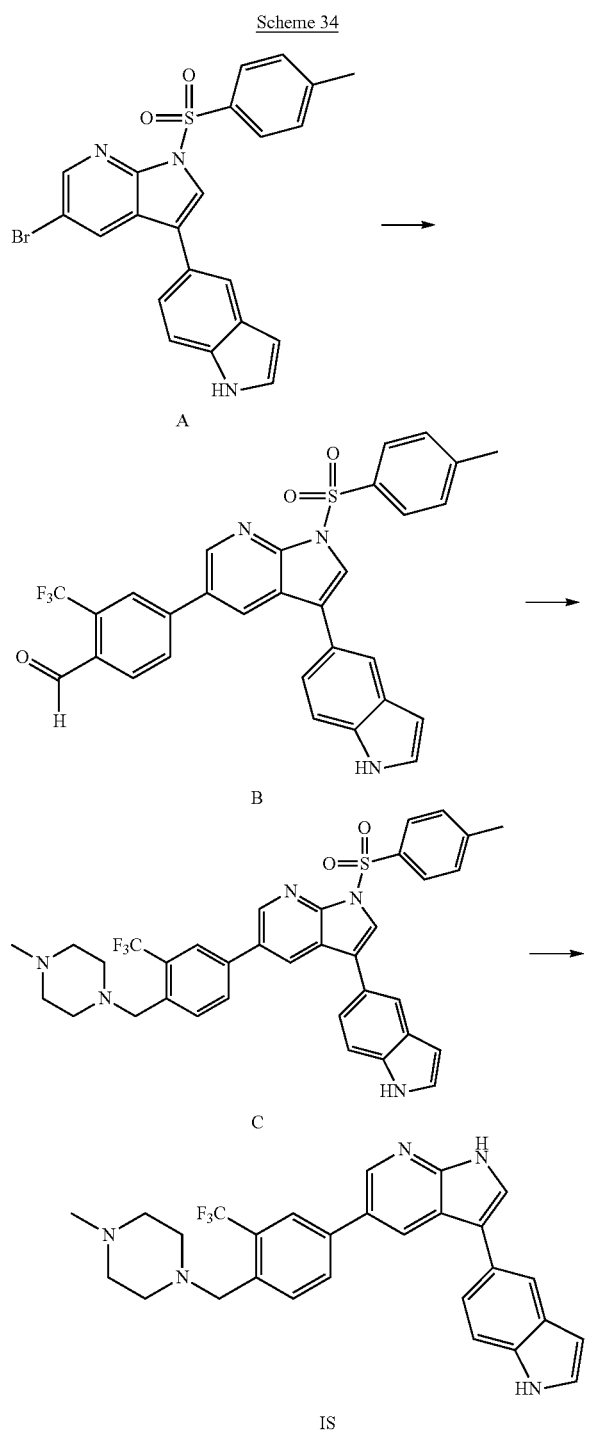

Preparation of Intermediate B: 4-[3-(1H-Indol-5-yl)-1-(toluene-4-sulfonyl)-1H-pyrrolo[2,3-b]pyridin-5-yl]-2-trifluoromethyl-benzaldehyde In reference to Scheme 34, to a solution of 5-bromo-3-(1H-indol-5-yl)-1-tosyl-1H-pyrrolo[2,3-b]pyridine (0.100 g, 0.21 mmol) in CH₃CN (1 mL) in a Personal Chemistry microwave reaction vial was added 1-2-trifluromethyl-4-(4,4,5,5-tetramethyl-[1,3,2]dioxaborolan-2-yl)-benzaldehyde (0.056 g, 0.25 mmol), bis(triphenylphosphine)-palladium (II) dichloride (0.020 g, 0.028 mmol), and 1 M Na₂CO₃ (1 mL). The resulting mixture was de-gassed with Ar for 10 min, after which it was heated at 150° C. for 30 min in a Personal Chemistry Optimizer. The organic layer was separated, filtered, and concentrated in vacuo. The residue purified via preparatory HPLC to give 4-[3-(1H-Indol-5-yl)-1-(toluene-4-sulfonyl)-1H-pyrrolo[2,3-b]pyridin-5-yl]-2-trifluoromethyl-benzaldehyde as a white solid. MS ESI (m/z): 551/553 (M+1)⁺, calc. 551.63.

Preparation of 3-(1H-Indol-5-yl)-5-[3-methoxy-4-(4-methyl-piperazin-1-ylmethyl)-phenyl]-1H-pyrrolo[2,3-b]pyridine (Compound IS)

To a solution of 4-[3-(1H-indol-5-yl)-1-(toluene-4-sulfonyl)-1H-pyrrolo[2,3-b]pyridin-5-yl]-2-trifluoromethyl-benzaldehyde (0.12 g, 0.214 mmol) in CH₂Cl₂ (3 mL) was added 1-methylpiperazine (32 mL, 0.32 mmol) and sodium triacetoxyborohydride (136 mg, 0.64 mmol). The reaction mixture was stirred for 1 hr at room temperature, after which it was partitioned between CH₂Cl₂ and 1 M NaOH. The organic layer was separated, dried over MgSO₄, and concentrated in vacuo. The residue was dissolved in 3:2 MeOH:acetone (5 mL), and 2 M NaOH (1.5 mL) was added. The resulting mixture was stirred at 65° C. for 30 min, after which it was partitioned between EtOAc and 1 M NaOH. The organic layer was separated, dried over MgSO₄, filtered, and stripped to provide a residue that was subjected to silica gel column to yield 3-(1H-indol-5-yl)-5-[4-(4-methyl-piperazin-1-ylmethyl)-3-trifluoromethyl-phenyl]-1H-pyrrolo[2,3-b]pyridine (0.024 g, 24% yield). ¹H NMR (CDCl₃, 400 MHz): δ 11.89 (s, 1H), 11.07 (s, 1H), 8.57 (d, J=2.1 Hz, 1H), 8.45 (d, J=2.4 Hz, 1H), 8.03 (d, J=8.0 Hz, 1H), 7.92 (d, J=1.6 Hz, 1H), 7.89 (s, 1H), 7.84 (d, J=8.0 Hz, 1H), 7.77 (s, 1H), 7.46 (dd, J=1.8, 6.4 Hz, 2H)), 7.34 (d, J=2.4 Hz, 1H), 6.46 (s, 1H), 3.63 (s, 2H), 3.32 (s, 3H), 2.49-42 (m, 8H), 2.14 (s, 3H); MS ESI (m/z) 490 (M+1)⁺, calc. 489.53.

Example 249

Method B: Synthesis of 2-Methylazaindole Derivatives

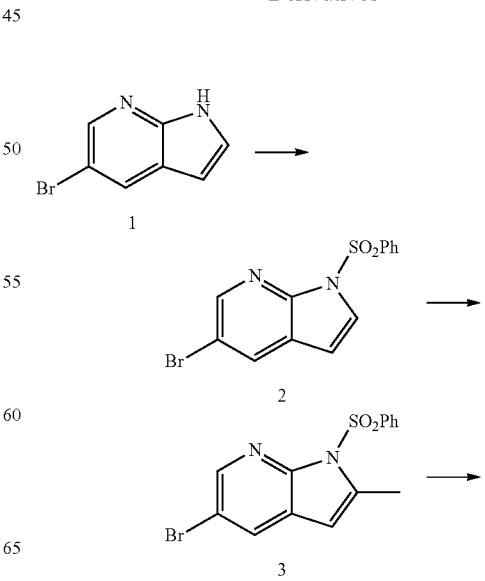

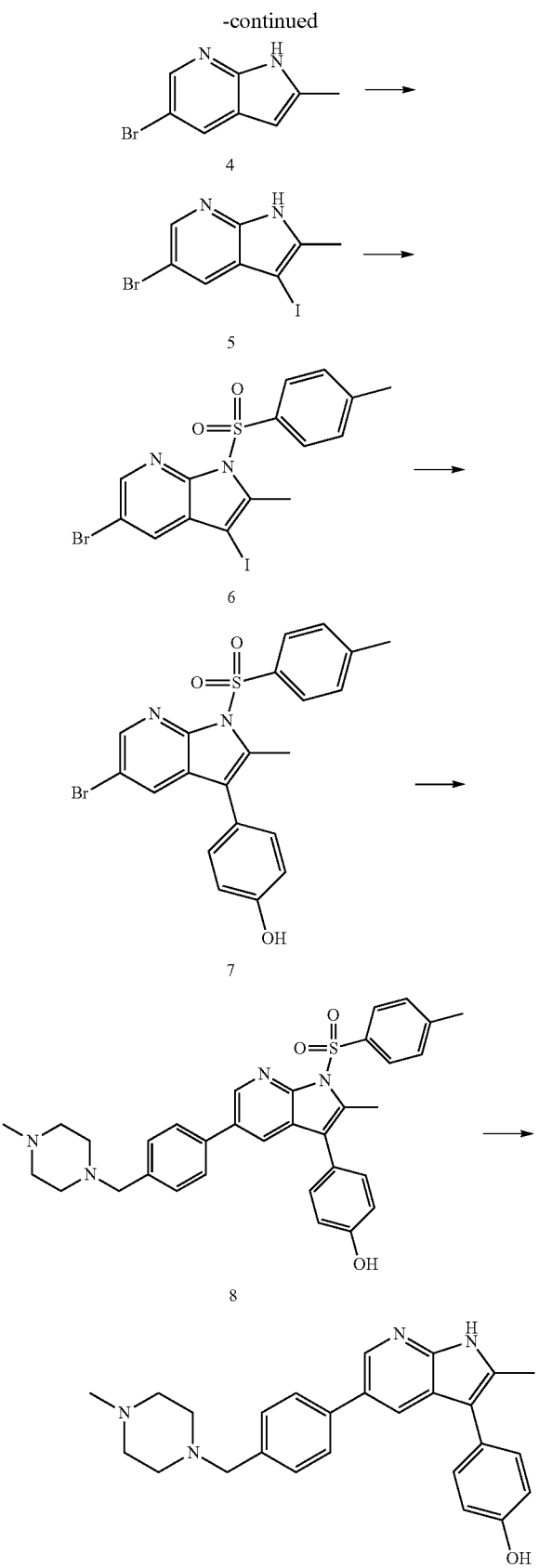

Preparation of Method A Intermediate 2: 1-Benzenesulfonyl-5-bromo-1H-pyrrolo[2,3-b]pyridine 5-Bromoazaindole (1, 2.00 g, 10.1 mmol), tetrabutylammonium bromide (0.03 eq, 0.25 mmol, 82 mg) and powdered NaOH (3 eq, 30.45 mmol, 1.22 g) are combined in DCM (100 ml) and cooled to 0° C. Phenylsulfonyl chloride (1.25 eq, 12.69 mmol, 1.62 mL) is added dropwise. After the addition is completed the mixture is stirred for 2 h at 0° C. The mixture is filtered, absorbed on Celite and purified by silica gel chromatography with a 40 to 60% gradient of EtOAc in hexane. 2.58 g (7.65 mmol, 75% yield) of 2 is obtained. $^1$H NMR (CDCl$_3$, 300 MHz): δ 8.45 (d, J=1.8 Hz, 1H), 8.17 (m, 2H), 7.98 (d, J=2.1 Hz, 1H), 7.74 (d, J=3.9 Hz, 1H), 7.60 (m, 1H), 7.50 (m, 2H), 6.55 (d, J=3.9 Hz, 1H). MS (m/z): 338 (M+H).

Preparation of Method A Intermediate 3: 1-Benzenesulfonyl-5-bromo-2-methyl-1H-pyrrolo[2,3-b]pyridine To a solution of diisopropylamine (2.8 eq, 1.66 mmol, 240 μL) in THF (2 ml) at −10° C. is added n-butyllithium (1.6 M in hexane, 2.6 eq, 1.54 mmol, 965 μl) dropwise. The mixture is allowed to stir for 30 min and then cooled to −35° C. A solution of compound 2 (1 eq., 200 mg, 0.593 mmol) in THF is added dropwise and the mixture is stirred for 30 min at −35° C. Iodomethane (3 eq, 1.78 mmol, 111 μL) is added in a dropwise fashion and the mixture is stirred for 2 h while warming up to room temperature. The reaction is quenched by addition of a saturated NH$_4$Cl solution, extracted with EtOAc and purified by silica gel chromatography (stepwise gradient of 0 to 15% EtOAc in hexane). 126 mg (0.359 mmol, 60%) of compound 3 are obtained. $^1$H NMR (CDCl$_3$, 300 MHz): δ 8.37 (d, J=2.4 Hz, 1H), 8.12 (m, 2H), 7.81 (d, J=2.4 Hz, 1H), 7.58 (m, 1H), 7.50 (m, 2H), 6.24 (d, J=1.2 Hz, 1H), 2.73 (d, J=1.2 Hz, 3H). MS (m/z): 352 (M+H).

Preparation of Method A Intermediate 4: 5-Bromo-2-methyl-1H-pyrrolo[2,3-b]pyridine Starting material 3 (88 mg, 0.251 mmol) is dissolved in MeOH (4 ml), 2 N NaOH (1 ml) is added and the mixture is refluxed for 2 h. EtOAc is added and the organic phase is washed with 1 N NaOH and water. After purification by silica gel chromatography (slow gradient from 0 to 2% MeOH in DCM), 40 mg (0.19 mmol, 76%) of 4 is obtained. $^1$H NMR (CDCl$_3$, 300 MHz): δ 10.26 (bs, 1H), 8.22 (d, J=2.1 Hz, 1H), 8.92 (d, J=2.1 Hz, 1H), 6.13 (s, 1H), 2.52 (s, 3H). MS (m/z): 210 (M+H).

Preparation of Method A Intermediate 5: 5-Bromo-3-iodo-2-methyl-1H-pyrrolo[2,3-b]pyridine A mixture of 4 (85 mg, 0.378 mmol) and N-iodosuccinimide (1.1 eq, 0.42 mmol, 95 mg) in acetone (1.5 ml) is stirred for 1 h at room temperature. The precipitate is filtered off, washed with cold acetone and dried to yield 90 mg (0.267 mmol, 71%) of the desired product.

Preparation of Method A Intermediate 6: 1-Benzenesulfonyl-5-bromo-3-iodo-2-methyl-1H-pyrrolo[2,3-b]pyridine Compound 5 (90 mg, 0.267 mmol), tetrabutylammonium bromide (0.025 eq, 0.0067 mmol, 3 mg) and powdered NaOH (3 eq, 0.8 mmol, 32 mg) are combined in DCM (3 ml)

and cooled to 0° C. Phenylsulfonyl chloride (1.25 eq, 0.334 mmol, 43 µl) is added dropwise. After the addition is completed the mixture is stirred for 15 min at 0° C. and then allowed to warm up to room temperature over 2 h. The mixture is filtered, absorbed on Celite and purified by silica gel chromatography eluting with DCM. 112 mg (0.235 mmol, 88% yield) of 6 is obtained.

Preparation of Method A Intermediate 7: 4-[5-Bromo-2-methyl-1-(toluene-4-sulfonyl)-1H-pyrrolo[2,3-b]pyridin-3-yl]-phenol To a stirred suspension of 5-bromo-3-iodo-1-tosyl-1H-pyrrolo[2,3-b]pyridine (0.30 g, 0.62 mmol) and 1H-indol-5-ylboronic acid (0.12 mg, 0.75 mmol) in CH$_3$CN (3 mL) was added 1 M Na$_2$CO$_3$ (3 mL) followed by bis(triphenylphosphine)palladium(II) dichloride (0.004 g, 0.062 mmol). The resulting mixture was stirred overnight at 60° C. After the mixture was evaporated to dryness in vacuo, it was dissolved in DMF (3 mL), absorbed onto Celite, and dried. The residue was purified via silica gel chromatography using CH$_2$Cl$_2$ as the eluent to obtain the title compound (0.26 g, 76%). $^1$H NMR (CDCl$_3$, 300 MHz): δ 8.48 (d, J=2.1 Hz, 1H), 8.27 (bs, 1H), 8.26 (d, J=2.4 Hz, 1H), 8.08 (d, J=8.1 Hz), 7.85 (s, 1H), 7.81 (m, 1H), 7.50 (d, J=8.7 Hz, 1H), 7.37 (dd, J=1.8, 8.4 Hz), 7.30 (m, 3H), 6.63 (m, 1H), 2.39 (s, 3H); MS ESI (m/z): 466.2/468.2 (M+1)$^+$, calc. 465.

Preparation of Method A: 4-{2-Methyl-5-[4-(4-methyl-piperazin-1-ylmethyl)-phenyl]-1H-pyrrolo[2,3-b]pyridin-3-yl}-phenol (Compound IT)

To a solution of 5-bromo-3-(1H-indol-5-yl)-1-tosyl-1H-pyrrolo[2,3-b]pyridine (0.220 g, 0.5 mmol) in CH$_3$CN (2.5 mL) in a Personal Chemistry microwave reaction vial was added 1-Methyl-4-[4-(4,4,5,5-tetramethyl-[1,3,2]dioxaborolan-2-yl)-benzyl]-piperazine (0.20 g, 0.65 mmol), bis(triphenylphosphine)-palladium(II) dichloride (0.003 g, 0.005 mmol), and 1 M Na$_2$CO$_3$ (1 mL). The resulting mixture was de-gassed with Ar for 10 min, after which it was heated at 150° C. for 30 min in a Personal Chemistry Optimizer. The organic layer was separated, filtered, and concentrated in vacuo. The residue was dissolved in MeOH (3 mL) and acetone (2 mL), and 2 M NaOH (1.5 mL) was added. The resulting mixture was stirred at 65° C. for 30 min, after which it was partitioned between EtOAc and 1 M NaOH. The organic layer was separated, dried over MgSO$_4$, filtered, and stripped to give a residue purified via preparatory HPLC to give the title compound as a white solid. $^1$H NMR (DMSO-d6, 300 MHz): δ 11.78 (s, 1H), 11.03 (s, 1H), 8.51 (d, J=2.1 Hz, 1H), 8.36 (d, J=1.8 Hz, 1H), 7.86 (s, 1H), 7.72 (d, J=2.4 Hz, 1H), 7.45 (s, 2H), 7.32 (m, 1H), 6.92 (s, 2H), 6.45 (m, 1H), 3.85 (s, 6H), 3.70 (s, 3H); HPLC retention time: 2.04 minutes; MS ESI (m/z): 399 (M+1)$^+$, calc. 398.51.

Example 250-257

Using similar procedure described for Example 249, the following compounds were prepared by changing boronic acids described in Table 6. Examples 250-257 were physically characterized by electro spray ionization mass spectrometry. Structure and molecular masses are also given below in Table 6.

TABLE 6

| Ex | Boronic Acid | IUPAC Name | Structure | MW | Cmpd ID |
|----|--------------|------------|-----------|-----|---------|
| 250 | 3-Hydroxyphenyl-boronic acid | 3-{2-Methyl-5-[4-(4-methyl-piperazin-1-ylmethyl)-phenyl]-1H-pyrrolo[2,3-b]pyridin-3-yl}-phenol | 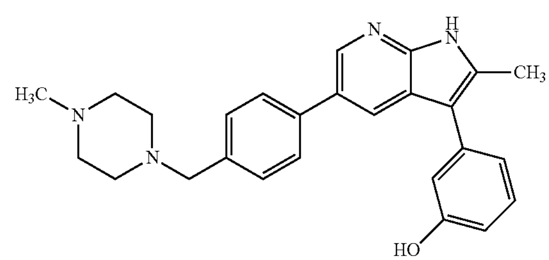 | 412.54 | IU |
| 251 | 4-Hydroxyphenyl-boronic acid | 4-{2-Methyl-5-[4-(4-methyl-piperazin-1-ylmethyl)-phenyl]-1H-pyrrolo[2,3-b]pyridin-3-yl}-phenol | 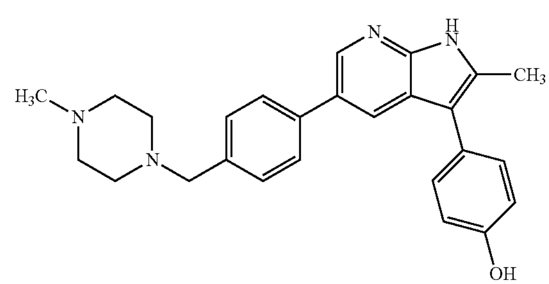 | 412.54 | IV |

TABLE 6-continued

| Ex | Boronic Acid | IUPAC Name | Structure | MW | Cmpd ID |
|---|---|---|---|---|---|
| 252 | 5-Hydroxy-2-methoxyphenyl-boronic acid | 4-Methoxy-3-{2-methyl-5-[4-(4-methyl-piperazin-1-ylmethyl)-phenyl]-1H-pyrrolo[2,3-b]pyridin-3-yl}-phenol | 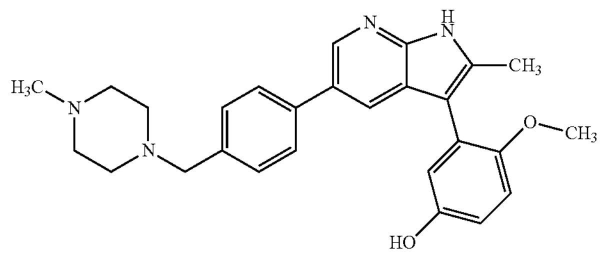 | 442.57 | IW |
| 253 | 4-Hydroxy-3-methoxyphenyl-boronic acid | 2-Methoxy-4-{2-methyl-5-[4-(4-methyl-piperazin-1-ylmethyl)-phenyl]-1H-pyrrolo[2,3-b]pyridin-3-yl}-phenol | 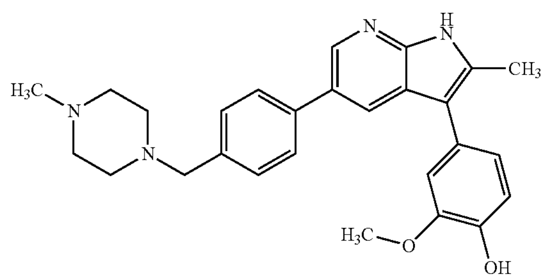 | 442.57 | IX |
| 254 | 3-Fluoro-4-hydroxyphenyl-boronic acid | 2-Fluoro-4-{2-methyl-5-[4-(4-methyl-piperazin-1-ylmethyl)-phenyl]-1H-pyrrolo[2,3-b]pyridin-3-yl}-phenol | 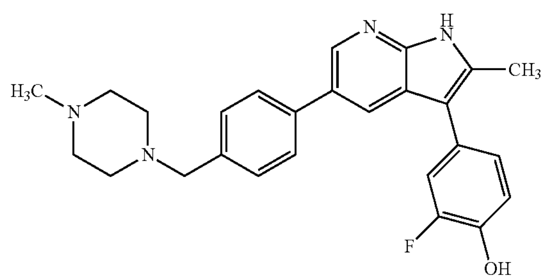 | 430.53 | IY |
| 255 | 3-Hydroxy-4-methylphenyl-boronic acid | 2-Methyl-5-{2-methyl-5-[4-(4-methyl-piperazin-1-ylmethyl)-phenyl]-1H-pyrrolo[2,3-b]pyridin-3-yl}-phenol | 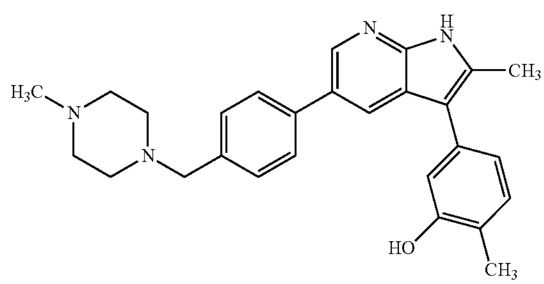 | 426.57 | IZ |
| 256 | 3-Hydroxy-4-methoxyphenyl-boronic acid | 2-Methoxy-5-{2-methyl-5-[4-(4-methyl-piperazin-1-ylmethyl)-phenyl]-1H-pyrrolo[2,3-b]pyridin-3-yl}-phenol | 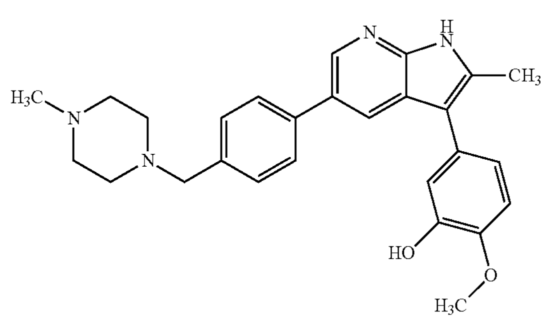 | 442.57 | JA |

TABLE 6-continued

| Ex | Boronic Acid | IUPAC Name | Structure | MW | Cmpd ID |
|---|---|---|---|---|---|
| 257 | 4-Fluoro-3-hydroxyphenyl-boronic acid | 2-Fluoro-5-{2-methyl-5-[4-(4-methyl-piperazin-1-ylmethyl)-phenyl]-1H-pyrrolo[2,3-b]pyridin-3-yl}-phenol | 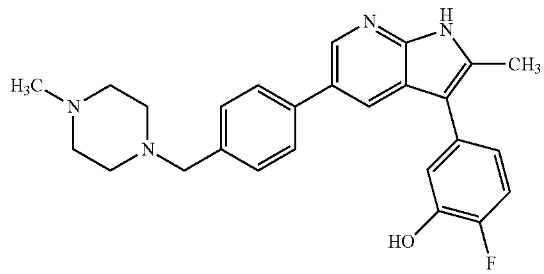 | 430.53 | JB |

Example 258

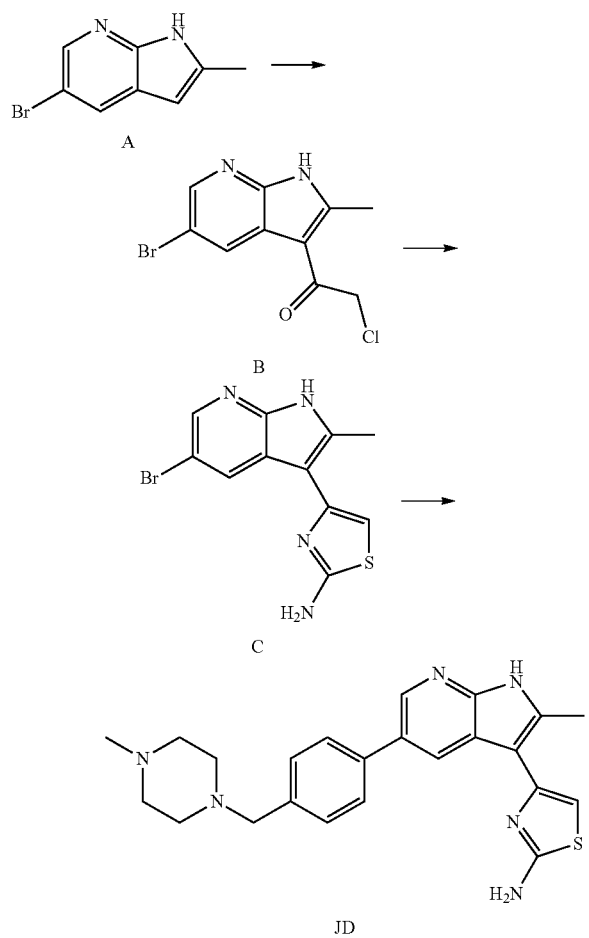

Scheme 35

Preparation of Intermediate B: 1-(5-Bromo-2-methyl-1H-pyrrolo[2,3-b]pyridin-3-yl)-2-chloro-ethanone In reference to Scheme 35, to a suspension of AlCl$_3$ (1.57 g, 11.84 mmol) in dichloromethane (50 mL) was added 5-Bromo-2-methyl-1H-pyrrolo[2,3-b]pyridine. After stirring for 30 min, chloroacetyl chloride (1.33 g, 11.84 mmol) was added and the reaction mixture was stirred for 2 hours at room temperature. On completion, solvents were evaporated and quenched with aq. NaHCO3 solution at 0° C. Resulting mixture was extracted with EtOAc. The organic layer was dried over Na2SO4 and filtered through a plug of silica gel. Solvent was evaporated to dryness to give 1-(5-Bromo-2-methyl-1H-pyrrolo[2,3-b]pyridin-3-yl)-2-chloroethanone (0.650 g, 95% yield).

Preparation of Intermediate C: 4-(5-Bromo-2-methyl-1H-pyrrolo[2,3-b]pyridin-3-yl)-thiazol-2-ylamine A solution 1-(5-Bromo-2-methyl-1H-pyrrolo[2,3-b]pyridin-3-yl)-2-chloro-ethanone (0.56 g, 1.97 mmol) and thio urea (0.16 g, 2.17 mmol) in ethanol (19 mL) was stirred at 80° C. for 2 hours. The resulting precipitate was filtered, washed with MeOH, and dried under vacuum to give 4-(5-Bromo-2-methyl-1H-pyrrolo[2,3-b]pyridin-3-yl)-thiazol-2-ylamine (0.604 g, 99% yield).

Preparation of 4-{2-Methyl-5-[4-(4-methyl-piperazin-1-ylmethyl)-phenyl]-1H-pyrrolo[2,3-b]pyridin-3-yl}-thiazol-2-ylamine (Compound JC)

In a personal chemistry microwave reaction vial 4-(5-bromo-2-methyl-1H-pyrrolo[2,3-b]pyridin-3-yl)-thiazol-2-ylamine (0.2 g, 0.64 mmol) and 1-Methyl-4-[4-(4,4,5,5-tetramethyl-[1,3,2]dioxaborolan-2-yl)-benzyl]-piperazine (0.23 g, 0.71 mmol), bis(triphenylphosphine)-palladium(II) dichloride (0.004 g, 0.006 mmol) in acetonitrile (2 mL), and 1 M Na$_2$CO$_3$ (2 mL) were added. The resulting mixture was de-gassed with N$_2$ for 10 min, after which it was heated at 175° C. for 30 min in a Personal Chemistry Optimizer. The mixture was diluted with DMF (3 mL), and concentrated in vacuo and purified on silica gel column using dichloromethane and methanol to afford 4-{2-Methyl-5-[4-(4-methyl-piperazin-1-ylmethyl)-phenyl]-1H-pyrrolo[2,3-b]pyridin-3-yl}-thiazol-2-ylamine.

Example 259

Scheme 36

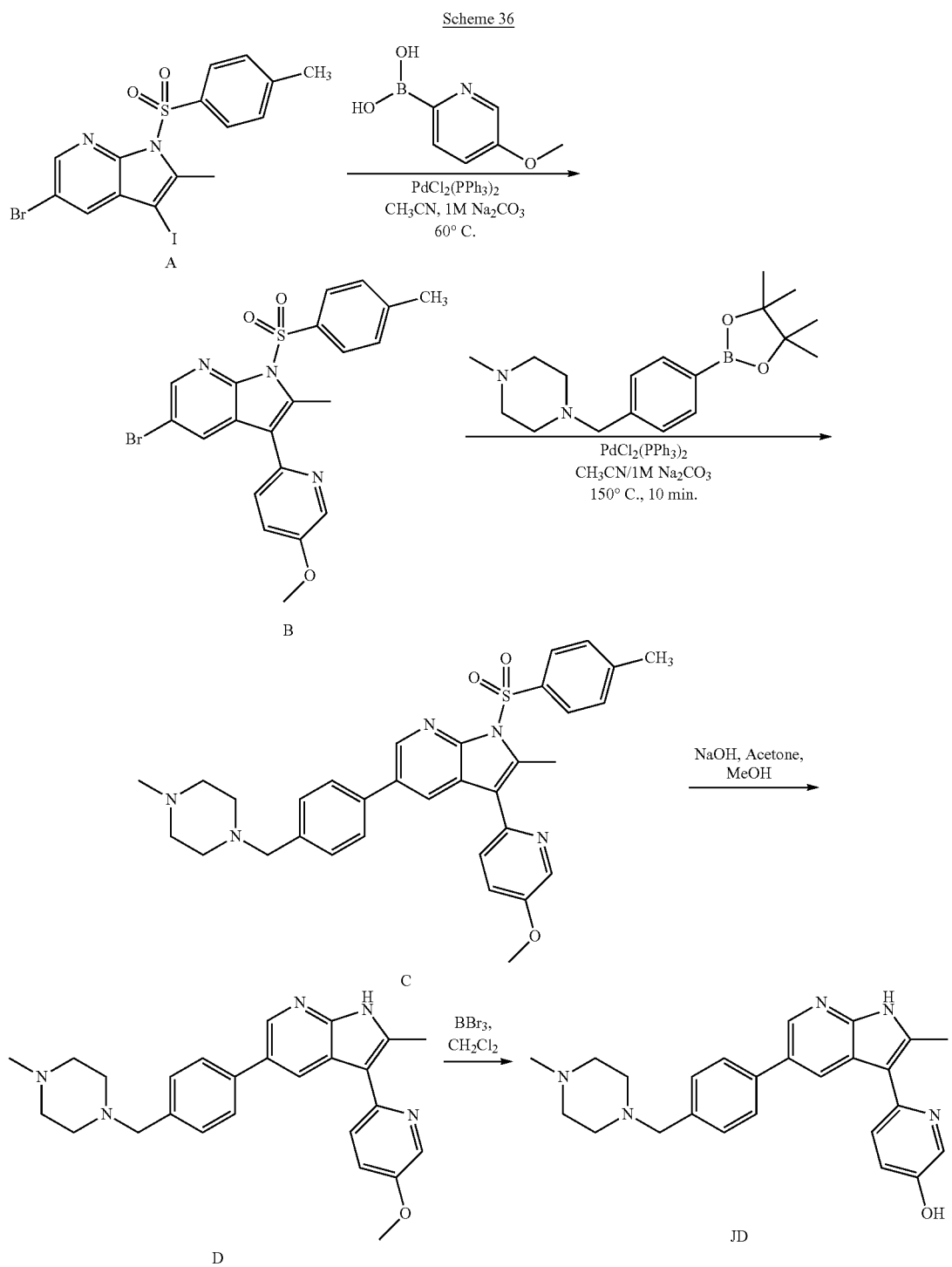

Preparation of Intermediate B: 5-Bromo-3-(5-methoxy-pyridin-2-yl)-2-methyl-1-(toluene-4-sulfonyl)-1H-pyrrolo[2,3-b]pyridine In reference to Scheme 36, to a stirred suspension of 5-bromo-3-iodo-1-tosyl-1H-pyrrolo[2,3-b]pyridine (0.25 g, 0.509 mmol) and 4-methoxy-2-pyridylboronic acid (0.094 g, 0.56 mmol) in DMF (1 mL) was added $Cs_2CO_3$ (0.663 g, 0.05 mmol), dppf (0.028 g, 0.05 mmol) followed by palladium acetate (0.011 g, 0.05 mmol). The resulting mixture was heated in personal microwave at 150° C. for 1 hour. After consumption of the starting material, the mixture was evaporated to dryness in vacuo, absorbed onto Celite, and dried. The residue was purified via silica gel chromatography using CH₂Cl₂ as the eluent to obtain 5-bromo-3-(5-methoxy-pyridin-2-yl)-2-methyl-1-(toluene-4-sulfonyl)-1H-pyrrolo[2,3-b]pyridine (0.120 g, 50%). MS ESI (m/z): 472/474 (M+1)⁺, calc. 472.36.

Preparation of 6-{2-Methyl-5-[4-(4-methyl-piperazin-1-ylmethyl)-phenyl]-1H-pyrrolo[2,3-b]pyridin-3-yl}-pyridin-3-ol (Compound JD)

To a solution of 5-bromo-3-(5-methoxy-pyridin-2-yl)-2-methyl-1-(toluene-4-sulfonyl)-1H-pyrrolo[2,3-b]pyridine (0.120 g, 0.25 mmol) in CH₃CN (2.5 mL) in a Personal Chemistry microwave reaction vial was added 1-Methyl-4-[4-(4,4,5,5-tetramethyl-[1,3,2]dioxaborolan-2-yl)-benzyl]-piperazine (0.161 g, 0.50 mmol), bis(triphenylphosphine)-palladium(II) dichloride (0.002 g, 0.002 mmol), and 1 M Na₂CO₃ (1 mL). The resulting mixture was de-gassed with Ar for 10 min, after which it was heated at 150° C. for 30 min in a Personal Chemistry Optimizer. The organic layer was separated, filtered, and concentrated in vacuo. The residue was dissolved in MeOH (3 mL) and acetone (2 mL), and 2 M NaOH (1.5 mL) was added. The resulting mixture was stirred at 65° C. for 30 min, after which it was partitioned between EtOAc and 1 M NaOH. The organic layer was separated, dried over MgSO₄, filtered, and stripped to give a residue purified on silicagel column to give brown solid. The solid was dissolved in CH₂Cl₂ (2.5 mL) and added 1M boron tiribromide solution in CH₂Cl₂ (1 mL). The resulting reaction mixture was stirred for 2 hours at room temperature and solvents evaporated and residue was purified on silica gel column to afford 6-{2-Methyl-5-[4-(4-methyl-piperazin-1-ylmethyl)-phenyl]-1H-pyrrolo[2,3-b]pyridin-3-yl}-pyridin-3-ol (Compound JD) as a white solid. MS ESI (m/z): 414 (M+1), calc. 413.51.

The following compounds can generally be made using the methods described above. It is expected that these compounds when made will have activity similar to those that have been made in the examples above.

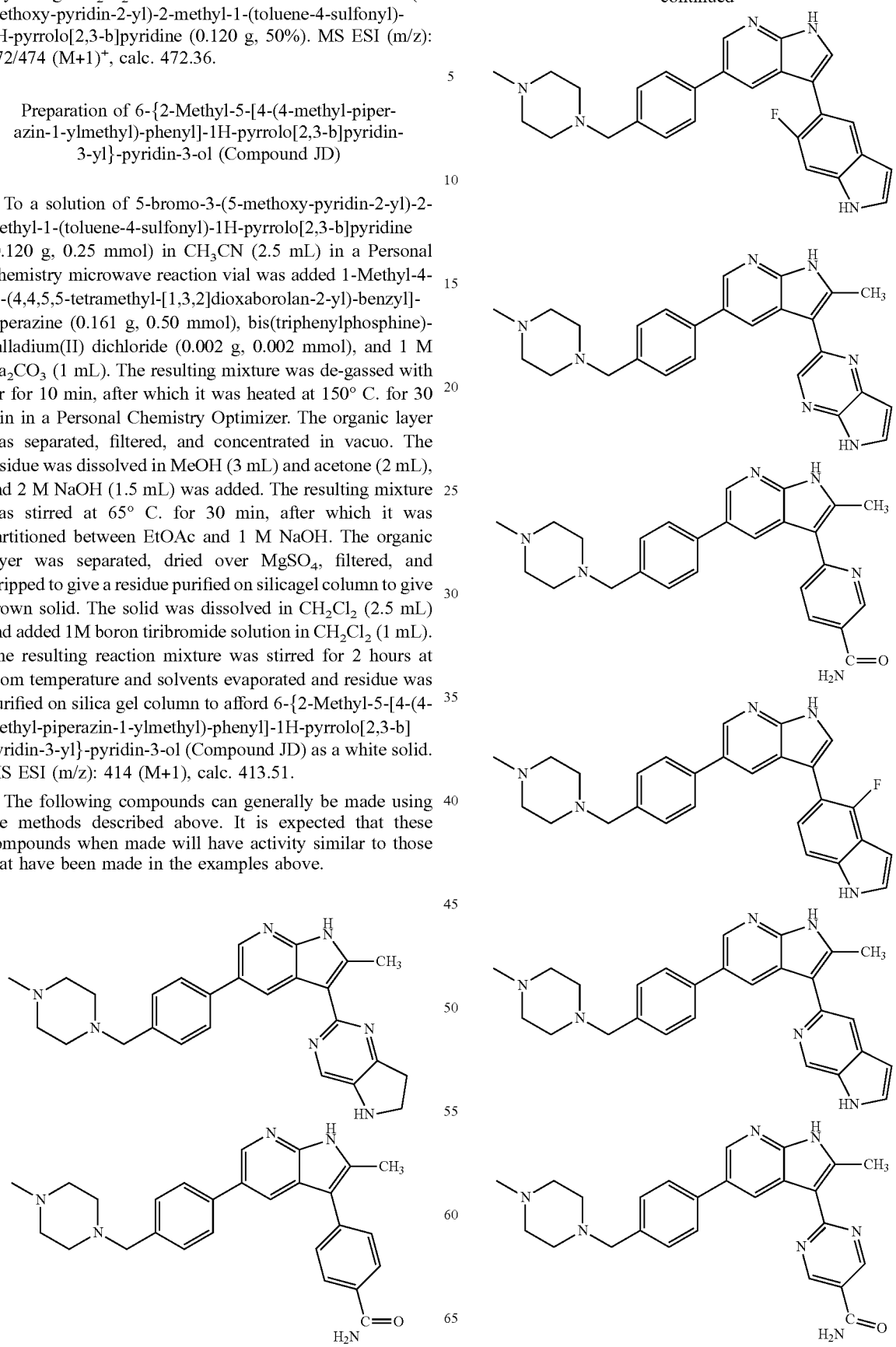

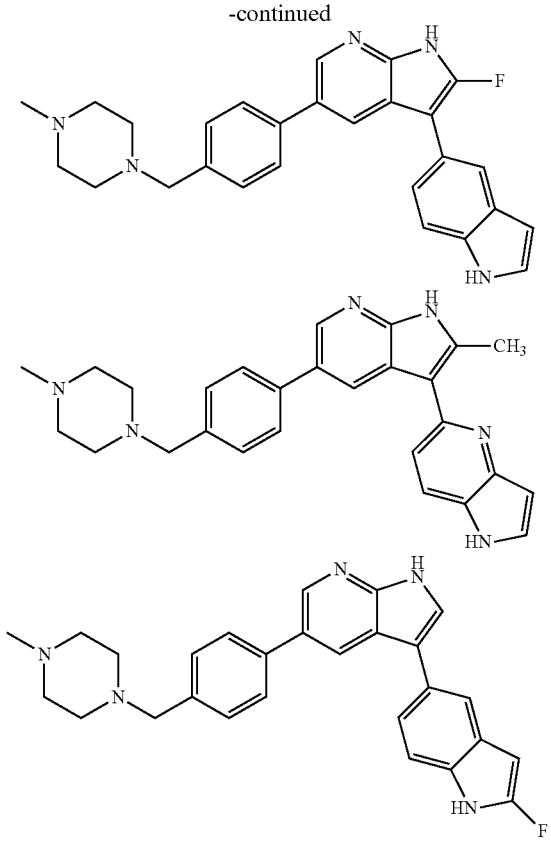

Biological Activity

The activity of the compounds in Examples 1-207 as MLK and/or inhibitors is illustrated in the following assays. The other compounds listed above, which have not yet been made and/or tested, are predicted to have activity in these assays as well.

Radiometric Filter Plate MLK3 Assay 200 ng (130 nM) MLK3 (Dundee, DU8313) was incubated with 1 µM inactive MKK7b (Dundee, DU703) in the presence of 2 µM cold ATP ($K_m$) and 0.5 µCi/assay $^{33}$P ATP and appropriate concentrations of compounds. After a twenty minute incubation, the reactions were washed through filter plates and read on a scintillation counter. Results are shown in Table 9 below, in which +++ indicates ≤0.1 µM, ++ indicates >0.1 µM and ≤1 µM, and + indicates >1 µM.

TABLE 9

| Example | Compound ID | MK3 IC$_{50}$ | MW |
|---|---|---|---|
| 1 | C | ++ | 399.45 |
| 2 | D | ++ | 369.43 |
| 3 | E | +++ | 366.5 |
| 4 | F | +++ | 325.5 |
| 5 | G | +++ | 354.5 |
| 6 | H | ++ | 340.39 |
| 7 | I | +++ | 408.5 |
| 8 | J | +++ | 324.5 |
| 9 | K | +++ | 326.36 |
| 10 | L | ++ | 394.48 |
| 11 | M | +++ | 402.5 |
| 12 | N | ++ | 348.41 |

TABLE 9-continued

| Example | Compound ID | MK3 IC$_{50}$ | MW |
|---|---|---|---|
| 13 | O | ++ | 353.43 |
| 14 | P | ++ | 309.13 |
| 15 | Q | +++ | 375.43 |
| 16 | R | +++ | 417.47 |
| 17 | S | +++ | 377.41 |
| 18 | T | +++ | 376.42 |
| 19 | U | +++ | 404.47 |
| 20 | V | + | 304.32 |
| 21 | W | ++ | 358.45 |
| 22 | X | + | 366.83 |
| 23 | Y | ++ | 301.35 |
| 24 | Z | +++ | 413.48 |
| 25 | AA | +++ | 403.44 |
| 26 | AB | +++ | 373.14 |
| 27 | AC | ++ | 358.14 |
| 28 | AD | ++ | 329.13 |
| 29 | AE | + | 338.77 |
| 30 | AF | +++ | 339.15 |
| 31 | AG | ++ | 422.54 |
| 32 | AH | +++ | 421.55 |
| 33 | AI | +++ | 366.47 |
| 34 | AJ | +++ | 467.58 |
| 35 | AK | + | 426.52 |
| 36 | AL | +++ | 400.44 |
| 37 | AM | +++ | 370.41 |
| 38 | AN | +++ | 355.4 |
| 39 | AO | +++ | 469.55 |
| 40 | AP | +++ | 417.43 |
| 41 | AQ | ++ | 431.16 |
| 42 | AR | + | 357.12 |
| 43 | AS | + | 369.16 |
| 44 | AT | + | 328.11 |
| 45 | AU | ++ | 343.11 |
| 46 | AV | + | 355.14 |
| 47 | AW | ++ | 387.13 |
| 48 | AX | + | 395.03 |
| 49 | AY | + | 375.11 |
| 50 | AZ | ++ | 372.13 |
| 51 | BA | ++ | 371.4 |
| 52 | BB | ++ | 412.45 |
| 53 | BC | ++ | 366.39 |
| 54 | BD | ++ | 343.35 |
| 55 | BE | +++ | 373.37 |
| 56 | BF | + | 366.39 |
| 57 | BG | +++ | 486.53 |
| 58 | BH | ++ | 379.33 |
| 59 | BI | +++ | 379.33 |
| 60 | BJ | +++ | 372.39 |
| 61 | BK | + | 363.33 |
| 62 | BL | +++ | 403.4 |
| 63 | BM | ++ | 385.39 |
| 64 | BN | + | 385.43 |
| 65 | BO | + | 387.4 |
| 66 | BP | + | 426.5 |
| 67 | BQ | ++ | 485.55 |
| 68 | BR | ++ | 408.42 |
| 69 | BS | + | 378.39 |
| 70 | BT | + | 334.34 |
| 71 | BU | + | 319.33 |
| 72 | BV | +++ | 431.45 |
| 73 | BW | + | 410.27 |
| 74 | BX | +++ | 370.41 |
| 75 | BY | + | 340.39 |
| 76 | BZ | ++ | 296.33 |
| 77 | CA | + | 281.32 |
| 78 | CB | ++ | 356.38 |
| 79 | CC | ++ | 326.36 |
| 80 | CD | + | 335.2 |
| 81 | CE | + | 282.3 |
| 82 | CF | + | 267.29 |
| 83 | CG | ++ | 418.42 |
| 84 | CH | ++ | 357.37 |
| 85 | CI | + | 342.36 |
| 86 | CJ | + | 351.41 |
| 87 | CK | + | 388.39 |
| 88 | CL | + | 329.32 |
| 89 | CM | + | 413.44 |

TABLE 9-continued

| Example | Compound ID | MK3 IC$_{50}$ | MW |
|---|---|---|---|
| 90 | CN | ++ | 418.42 |
| 91 | CO | ++ | 388.39 |
| 92 | CP | + | 344.34 |
| 93 | CQ | ++ | 329.32 |
| 94 | CR | + | 370.41 |
| 95 | CS | + | 356.39 |
| 96 | CT | ++ | 435.46 |
| 97 | CU | ++ | 361.38 |
| 98 | CV | + | 346.37 |
| 99 | CW | + | 373.44 |
| 100 | CX | + | 430.49 |
| 101 | CY | + | 418.46 |
| 102 | CZ | +++ | 418.42 |
| 103 | DA | ++ | 388.39 |
| 104 | DB | ++ | 413.44 |
| 105 | DC | ++ | 378.39 |
| 106 | DD | ++ | 348.36 |
| 107 | DE | ++ | 425.49 |
| 108 | DF | ++ | 439.52 |
| 109 | DG | + | 464.48 |
| 110 | DH | +++ | 418.46 |
| 111 | DI | ++ | 388.39 |
| 112 | DJ | +++ | 418.42 |
| 113 | DK | +++ | 418.42 |
| 114 | DL | ++ | 394.5 |
| 115 | DM | ++ | 364.5 |
| 116 | DN | ++ | 389.5 |
| 117 | DO | + | 296.33 |
| 118 | DP | ++ | 325.37 |
| 119 | DQ | + | 390.83 |
| 120 | DR | ++ | 328.37 |
| 121 | DS | ++ | 354.41 |
| 122 | DT | + | 413.4 |
| 123 | DU | ++ | 354.41 |
| 124 | DV | ++ | 416.44 |
| 125 | DW | + | 355.4 |
| 126 | DX | + | 401.43 |
| 127 | DY | + | 372.45 |
| 128 | DZ | ++ | 389.4 |
| 129 | EA | + | 389.4 |
| 130 | EB | + | 388.42 |
| 131 | EC | ++ | 431.44 |
| 132 | ED | + | 431.44 |
| 133 | EE | + | 413.43 |
| 134 | EF | + | 413.43 |
| 135 | EG | + | 391.42 |
| 136 | EH | + | 391.42 |
| 137 | EI | + | 390.44 |
| 138 | EJ | + | 433.46 |
| 139 | EK | ++ | 480.55 |
| 140 | EL | + | 449.55 |
| 141 | EM | +++ | 435.52 |
| 142 | EN | +++ | 421.49 |
| 143 | EO | +++ | 435.52 |
| 144 | EP | +++ | 507.63 |
| 145 | EQ | ++ | 435.52 |
| 146 | ER | +++ | 463.53 |
| 147 | ES | +++ | 435.52 |
| 148 | ET | +++ | 525.6 |
| 149 | EU | +++ | 425.48 |
| 150 | EV | ++ | 467.52 |
| 151 | EW | +++ | 525.6 |
| 152 | EX | ++ | HCl-salt: 461.94 |
| 153 | EY | ++ | 467.52 |
| 154 | EZ | ++ | 419.43 |
| 155 | FA | ++ | 425.53 |
| 156 | FB | +++ | 425.53 |
| 157 | FC | +++ | 453.54 |
| 158 | FD | +++ | 439.51 |
| 159 | FE | +++ | 431.48 |
| 160 | FF | ++ | 507.58 |
| 161 | FG | ++ | 521.61 |
| 162 | FH | +++ | 425.53 |
| 163 | FI | + | 421.54 |
| 164 | FJ | + | 417.46 |
| 165 | FK | +++ | 439.55 |
| 166 | FL | ++ | 378.4 |
| 167 | FM | ++ | 426.47 |
| 168 | FN | ++ | 507 |
| 184 | GD | +++ | 408 |
| 169 | FO | + | 400 |
| 170 | FP | + | 450 |
| 171 | FQ | ++ | 412 |
| 172 | FR | ++ | 435 |
| 173 | FS | ++ | 422 |
| 174 | FT | ++ | 437 |
| 212 | HI | ++ | 439 |
| 185 | GE | ++ | 442 |
| 175 | FU | ++ | 497 |
| 179 | FY | +++ | 407 |
| 176 | FV | ++ | 453 |
| 191 | GN | ++ | 491 |
| 192 | GO | +++ | 505 |
| 193 | GP | +++ | 479 |
| 194 | GQ | +++ | 465 |
| 195 | GR | ++ | 493 |
| 196 | GS | +++ | 477 |
| 197 | GT | +++ | 463 |
| 198 | GU | +++ | 479 |
| 199 | GV | +++ | 499 |
| 200 | GW | +++ | 485 |
| 201 | GX | +++ | 479 |
| 202 | GY | +++ | 493 |
| 203 | GZ | +++ | 489 |
| 204 | HA | +++ | 491 |
| 205 | HB | +++ | 518 |
| 207 | AD | ++ | 489 |
| 188 | GI | +++ | 463 |
| 189 | GJ | +++ | 436 |
| 190 | GL | +++ | 389 |
| 177 | FW | +++ | 449 |
| 178 | FX | ++ | 449 |
| 179 | FY | +++ | 422 |
| 180 | FZ | +++ | 433 |
| 182 | GB | NT | 440 |
| 208 | HE | NT | 436 |
| 181 | GA | +++ | 423 |
| 206 | HC | NT | 476 |

DLK and LRRK Activity

Compounds were tested for activity by Ambit Biosciences (San Diego, Calif.) against the DLK and LRRK2 kinases as described in Karaman et al., "A quantitative analysis of kinase inhibitor selectivity," *Nature Biotechnology*, 2008 Jan. 26(1): 127-132. Certain compounds disclosed herein exhibited activity in the assay as against one or both of these targets.

Dominant mutations of LRRK2 are the most common cause of inherited Parkinson's Disease (PD), a debilitating, progressive neurodegenerative disorder characterized by motor and cognitive dysfunction which affects >1 million people in North America alone. Most cases of LRRK2-related PD are clinically and pathologically indistinguishable from the idiopathic disease. LRRK2 contains both GTPase and kinase domains, as well as two protein-protein interactions domains (leucine-rich and WD40 repeats). Definitively pathogenic mutations have been identified in the GTPase and kinase domains, as well as the region between these domains. Significant efforts have been made to determine whether PD mutations alter LRRK2 kinase activity. There is consensus that G2019S significantly increases LRRK2 kinase function in assay of either auto-phosphorylation or phosphorylation of generic substrates. LRRK2 mutations appear to cause a toxic gain of function that requires intact kinase function. Inhibition of LRRK 2 represents a therapeutic strategy for the treatment of PD.

DLK In Vitro Assay

In neuronal cells, DLK specifically activates MKK7 (S. E. Merritt et al., J Biol Chem 274, 10195 (1999)). Inhibition potency of the new compounds against native DLK can be measured by using an in vitro kinase assay adapted from A. Daviau, M. Di Fruscio, R. Blouin, Cell Signal 21, 577 (2009).

DLK is immunoprecipitated from neuronally differentiated PC-12 cells (which are known to contain active DLK, see e.g., Eto et al., Neurosci Res 66, 37 (2010)). Compounds are then incubated with substrate (MKK7) plus radiolabelled ATP, in the presence or absence of selected compounds. NGF is added to PC12 cells to induce neurite outgrowth and differentiation into cells that resemble sympathetic neurons (50 ng/ml NGF will be added to cells for 6 days). The cells are lysed and DLK immunoprecipitated using specific antibodies and protein G agarose beads. DLK kinase activity is be assessed by an in vitro kinase assay using purified MKK7 (produced as a GST fusion protein in E. coli) as a specific enzyme substrate (8), in combination with radiolabelled ATP and the test compounds of interest (10, 100 nM; 1, 10 µM). DLK activity will be measured by performing SDS-PAGE and exposing the gel to a phosphorimager to quantitate the level of incorporated radioisotope. In parallel, MLK3 inhibition potency can also be analyzed, using an in vitro kinase assay with recombinant c-Jun as the substrate. Compounds are expected to exhibit DLK/MLK inhibitory activity, including (i) DLK-specific, (ii) mixed DLK/MLK3-specific and (iii) MLK3-specific inhibitory activity.

DLK Cellular Assay

Compounds can also be analyzed for DLK inhibition potency using a cell-based assay. To do this, PC12 cells are neuronally differentiated with NGF, and then exposed to either hyperglycemic (25 mM) or euglycemic (5 mM) conditions, prior to treating cells with selected DLK/MLK inhibitors or vehicle. Cell lysates are then prepared, DLK immunoprecipitated, and kinase activity assessed using the in vitro kinase assay outlined above. Exogenous DLK inhibitors are not added to the in vitro kinase reaction since they are already present as a complex with the native, cell-derived DLK in the cell lysates.

Differentiated PC12 cells have been used to model diabetic neuropathy, by exposing them to hyperglycemic (25 mM) conditions for 6 days (E. Lelkes, B. R. Unsworth, P. I. Lelkes, Neurotox Res 3, 189 (2001); F. Zhang, S. C. Challapalli, P. J. Smith, Neuropharmacology 57, 88 (2009)). Therefore, PC12 cells can be differentiated in the presence of 50 ng/ml NGF, and media supplemented with glucose to expose cells to euglycemic (5 mM) or hyperglycemic (25 mM) conditions, in the presence or absence of selected DLK/MLK inhibitors (for example, at any one or more of 0.1, 1, 10, 100, or 1000 M) or vehicle. Mannitol (5 or 25 mM) is used as an osmotic control. The cells are lysed at selected time points following exposure to hyper/eu-glycemic conditions (for example, at 1, 4, and/or 24 hours), and DLK immunoprecipitated. In vitro kinase assays can then be performed as described above, with the slight modification that exogenous DLK inhibitors will not be added to the in vitro kinase reaction. In parallel, cytotoxicity of the test compounds can also be assessed using MTT and trypan blue assays. Compounds are expected to exhibit kinase-inhibitory activity using a cell-based assay for inhibition of DLK. Exposure of cells to hyperglycemic conditions is expected to lead to enhanced DLK activity.

Results from these in vitro kinase assays can be correlated with data from functional neuroprotection experiments and small animal studies.

DLK Inhibitors and Axon Outgrowth in Cultured Adult Sensory Neurons

The adult sensory neuron culture accurately represents the neuronal cell types found in the dorsal root ganglia (DRG) of the peripheral nervous system. The process of culturing these neurons involves axotomizing the cell bodies and several studies have demonstrated that the phenotypic properties of these neurons mimic those observed in the DRG in vivo upon peripheral nerve damage (I. Gavazzi, R. D. Kumar, S. B. McMahon, J. Cohen, Eur J Neurosci 11, 3405 (1999)). The DRG neurons are comprised of a variety of neuronal sub-types that includes nociceptive neurons (NGF and GDNF sensitive), mechanoreceptive neurons (NGF, BDNF and NT-4 sensitive) and proprioceptive neurons (NT-3 sensitive) (S. Averill, S. B. McMahon, D. O. Clary, L. F. Reichardt, J. V. Priestley, Eur J Neurosci 7, 1484 (1995)). This culture system can be maintained under defined conditions in the absence of serum for up to one week before neuronal cell death begins. Upon plating the neurons rapidly initiate axon outgrowth and accurate measures of axonal outgrowth can be determined during the first 2 days in culture. During the first 2-3 days in vitro no neuronal death takes place, making interpretation of axon outgrowth a straightforward endeavor.

Cultures of adult sensory neuronsare used. Cultured adult neurons are fully differentiated and exhibit the properties of adult neurons in vivo—unlike embryonic neurons. All cultures are grown under defined conditions in the presence of Bottenstein's N2 additives. This allows, during the first 2-3 days in culture, an accurate assessment of axon outgrowth without interference from non-neuronal cells. The range of growth factors to be applied includes NGF, NT-3 and GDNF, to ensure that all the main sub-populations of neurons within this heterogeneous population will produce axonal outgrowth. The doses of the growth factors are sub-optimal, ensuring a level of axonal outgrowth that can be accurately measured but that can either be enhanced or reduced by test drugs. In order to mimic Type 1 diabetes, neuron cultures include 25 mM glucose.

First, a primary screen can be performed of the DLK inhibitors for ability to enhance axon outgrowth against sensory neurons derived from normal adult rats. The primary screen uses sensory neurons derived from normal adult rats, and assesses effectiveness in promoting axon outgrowth. This culture represents the neuronal cell types found in the DRG of the peripheral nervous system. The impact of novel DLK inhibitors on various indices of axon outgrowth proposed to be a relevant in vitro measures of axon growth and degeneration in vivo in diabetic neuropathy is examined. Assessment of levels or patterns of axon outgrowth is performed at 1 day before non-neuronal cells begin to interfere using confocal microscopy, digital images are collected of fixed cultures stained for neuron specific B-tubulin III. The images are then analyzed using SigmaScan Pro software to quantitate % neurite growth, total axon outgrowth and cell diameter.

Next, compounds identified as hits from the primary screen can be tested in a secondary screen against neurons isolated from 2-3 month STZ-diabetic rats. The assay can serve two purposes: first, to screen for drugs that enhance axon outgrowth in STZ-diabetic cultures (for methods, see above), and second, to assess the ability to prevent high [glucose]-induced axon degeneration (E. Zherebitskaya, E. Akude, D. R. Smith, P. Fernyhough, Diabetes 58, 1356

(2009)). Previous work has shown that under high [glucose] the axons exhibit oxidative stress-induced appearance of aberrant axonal swelling. Such structures can be identified by staining for amino acid adducts of 4-HNE and for accumulated mitochondria. Therefore, drug hits are analyzed quantitatively for the ability to prevent the formation of axonal swellings containing 4-HNE staining and accumulated mitochondria.

Measures of axonal outgrowth (% process-bearing neurons, total neurite length and cell diameter) are assessed using a Zeiss LSM LSM510 confocal inverted microscope and SigmaScan Pro software. Each compound is tested at 4 concentrations (e.g. 1, 10, 100, 1000 µM) in a 96-well plate format. At least 4 images at ×20 magnification are collected from the central section of each well using a digital camera (=35–40 neurons); cells from 4-8 replicate wells are counted to generate mean values. Previous studies demonstrate acceptable error levels, and permit 2-fold differences in total axonal outgrowth to be detected at a statistically significant level (P. Fernyhough, G. B. Willars, R. M. Lindsay, D. R. Tomlinson, *Brain Res* 607, 117 (1993); N. J. Gardiner et al., *Mol Cell Neurosci* 28, 229 (2005)). Statistical analyses are performed at the 5% significance level using one-way ANOVA and Dunnett's post hoc test for percentage of process-bearing neurons and total axon outgrowth. The Mann Whitney U-test is performed for comparing values for axon radii and cell diameter. Compound-treated cells are expected to show increased axonal outgrowth.

In Vivo Efficacy Assays

Compounds disclosed herein can be tested in any number of well-known and publicly available animal models of efficacy for diseases in which MLK3 or DLK inhibition can play a therapeutic role. It is within the capacity of one skilled in the art to select and tailor such a model.
Testing of Compounds for Efficacy in Established HIV-1-Encephalitic
(HIVE) Mouse Model Compounds disclosed herein can be ranked for in vivo efficacy in a mouse model relevant to NeuroAids (D. Eggert, The Journal of Immunology, in press, November 2009.) Test compounds selected can be prioritized based on MLK3 potency and favorable exposure in the brain, but this is not an absolute requirement. Four-week-old male CB-17/IcrCrl-SCIDbr (CB17/SCID) mice may be purchased from Charles River Laboratory. HIV-1ADA-infected MDM ($1.5 \times 10^5$ cells infected at an MOI of 0.1 in 5 ml) is stereotactically injected intracranially after 1 day of viral infection and referred to as HIVE mice. The test compound is then administered i.p. daily for 7 days at doses 0.5, 1.0, 1.5, 5.0, and 15.0 mg/kg/d (where, e.g., n=4 mice/treatment group). Vehicle only serves as the control. CB17/SCID mice receive intracranial (i.c.) injections of media (sham-operated) and serve as additional controls. Animals are treated with vehicle or test compound (i.e., a compound as disclosed herein) starting 1 d post-i.c. injection and for 7 d after MDM injections and test compound treatments. Dosing parameters, number per group, etc. can be varied as needed, and such variations are within the skill of one skilled in the art.
Histopathology and Image Analysis Brain tissue is collected at necropsy, fixed in 4% phosphate-buffered paraformaldehyde, and embedded in paraffin. Paraffin blocks are cut until the injection site of the human MDM is identified. HIV-1 p24 Ag (cloneKal-1; Dako, Carpinteria, Calif.) is used to test for virus-infected human MDM. For each mouse, 30-100 serial (5-mm-thick) sections are cut from the injection site and three to seven sections (10 sections apart) analyzed. Abs to vimentin intermediate filaments (clone VIM 3B4; Boehringer Mannheim, Indianapolis, Ind.) are used for detection of human cells in mouse brains. Mouse microglia are detected by Abs to Iba-1 (WAKO, Osaka, Japan), and astrocytes are detected by Abs for glial fibrillaryacidic protein ([GFAP] Dako). NeuN, MAP-2 (both from Chemicon International), and H chain (200 kDa) neurofilaments (Dako) are used for detection of neurons. All sections are counterstained with Mayer's hematoxylin. The numbers of human MDM and HIV-1 p24 Ag-positive cells are counted with a Nikon Microphot-FXA microscope. All obtained images are imported into Image-Pro Plus, v. 4.0 (Media Cybernetics, Silver Spring, Md.) for quantifying area (%) of GFAP, Iba-1, MAP-2, and NeuN positive staining. Efficacious MLK inhibitors will exhibit a dose-dependent reduction in microgliosis and restoration of normal synaptic architecture relative to control animals. Compounds disclosed herein can be tested according to this method and are expected to exhibit similar results.
Pharmacokinetic Studies Compounds disclosed herein can be evaluated in pharmacokinetic assays and models to determine absorption, distribution, metabolism, and excretion parameters. The choice and tailoring of in vitro and ex vivo assays and in vivo models will vary according to the route of administration/formulation, indication under study, properties of test compounds, etc., as well as according to such factors as costs, availability of technology and res0urces, etc. Such parameters are well known in the fields of pharmacology and drug development. It is within the capacity of one skilled in the art to design and carry out, such work, or to outsource it to a capable third party.

Several compounds disclosed herein were evaluated in a standard murine pharmacokinetic model. Compounds were selected that exhibited reasonable solubility and metabolic stability, and good predicted blood brain barrier penetration, based on low molecular weight, a low number of hydrogen bond donors, log D within a range of 2-4, and low polar surface area.

Compounds were dissolved in either 5% DMSO, 40% PEG400, and 55% saline (pH=8) or % DMSO, 40% PEG400, and 55% (20% HP-β-CD in deionized water; pH=8) to yield a nominal concentration of 2 mg/mL for intravenous administration. Compounds were administered via a single intravenous (IV) injection in CL57 BL/6 mice at 10 mg/kg in DMSO/PEG400 solution. Three mice in each group were used for blood and brain collection at each time point. Blood samples (300 µL) were collected via the retro-orbital vein predose and at 5 min, 0.25, 0.50, 1, 2, 4, 6, 8, and 24 hours postdose. Blood samples were placed into tubes containing sodium heparin and centrifuged under refrigerated conditions at 8000 rpm for 6 minutes to separate plasma from the samples. The brain of each animal was collected after the final blood collection. The whole tissue was harvested, excised and rinsed by saline, dried by filter paper, and then placed into one tube per tissue per animal. All samples were stored at −20° C. until bioanalysis.

Compound concentrations in plasma and brain homogenate were determined using a high performance liquid chromatography/mass spectrometry (HPLC/MS/MS) method (Agilent 1100 series HPLC, AB Inc. API4000 triple-quadrupole with an ESI interface and Analyst 1.4 software).

Results in the form of area under the time-versus-concentration curve (AUC) are given below in Table 10. Additional compounds disclosed herein can be tested according to this method and are expected to exhibit similar results.

TABLE 10

| Ex. | Compound ID | AUC Plasma + indicates ≥1500 − indicates <1500 | AUC Brain + indicates ≥500 − indicates <500 |
|---|---|---|---|
| 1 | C | + | + |
| 4 | F | − | − |
| 9 | K | + | + |
| 17 | S | + | − |
| 18 | T | + | − |
| 32 | AH | + | + |

HIV-1 Model

Figure 4:
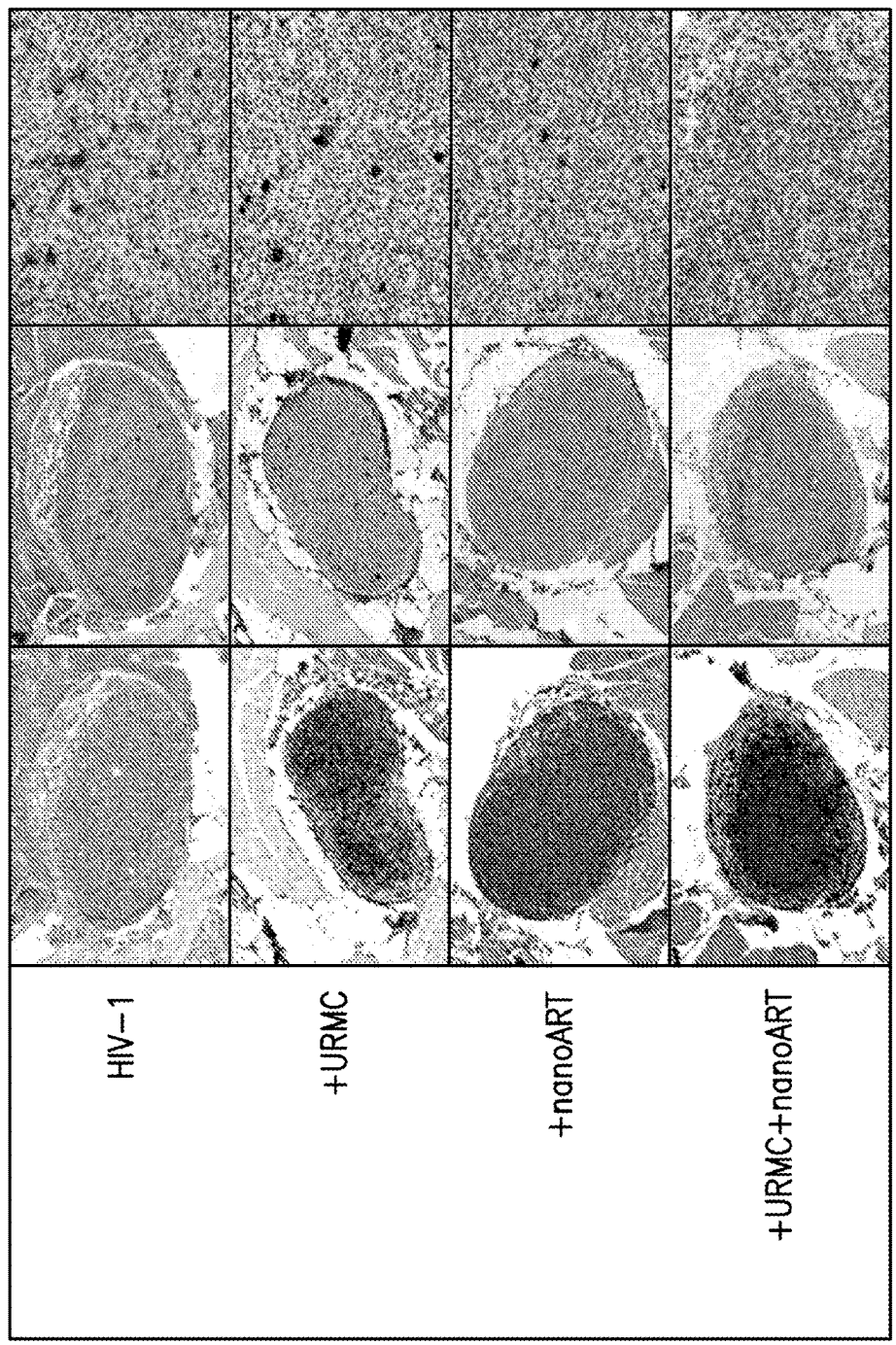
FIG. 4 is a group of photographs of HIV-1p24 staining in lymph nodes of humanized mice treated with Compound AH (denoted URMC), nanoparticles comprising atazanavir and ritonavir (denoted nanoART), or both.
Figure 5:
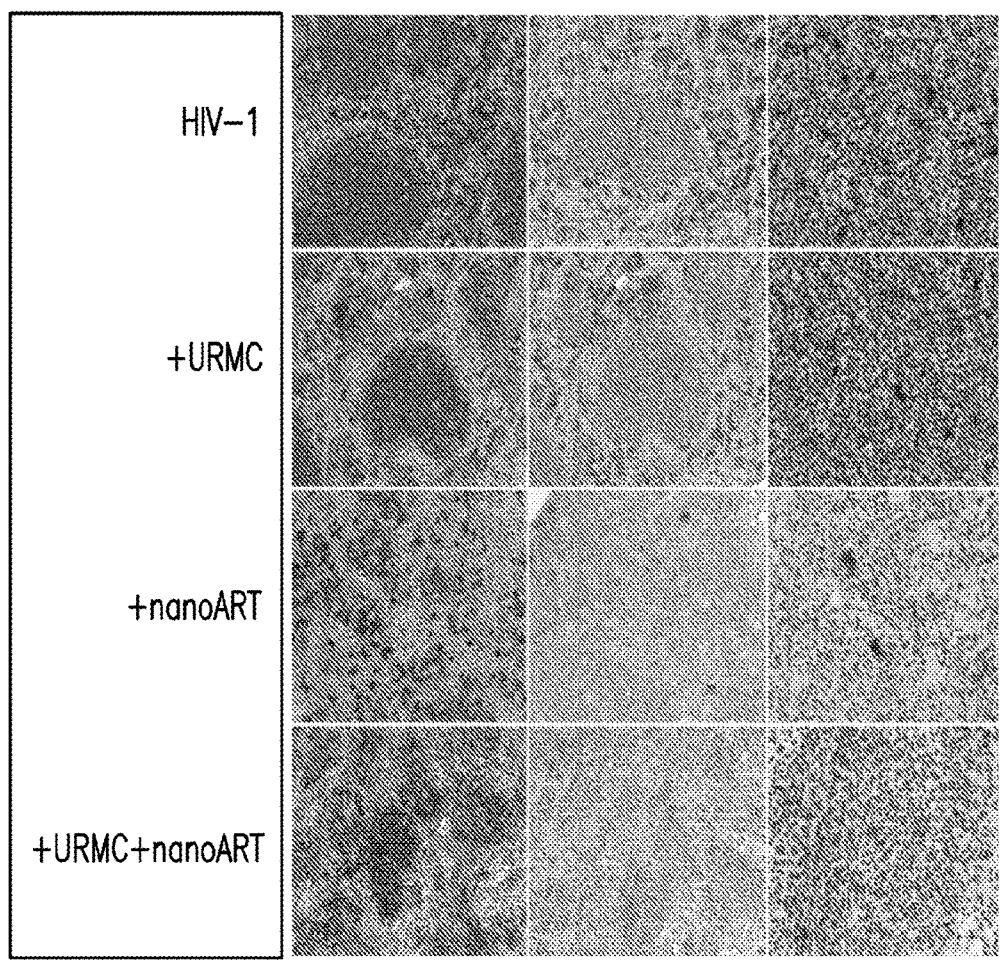
FIG. 5 is a group of photographs of HIV-1p24 staining in the spleen of humanized mice treated with Compound AH (denoted URMC), nanoparticles comprising atazanavir and ritonavir (denoted nanoART), or both.
Figure 6:
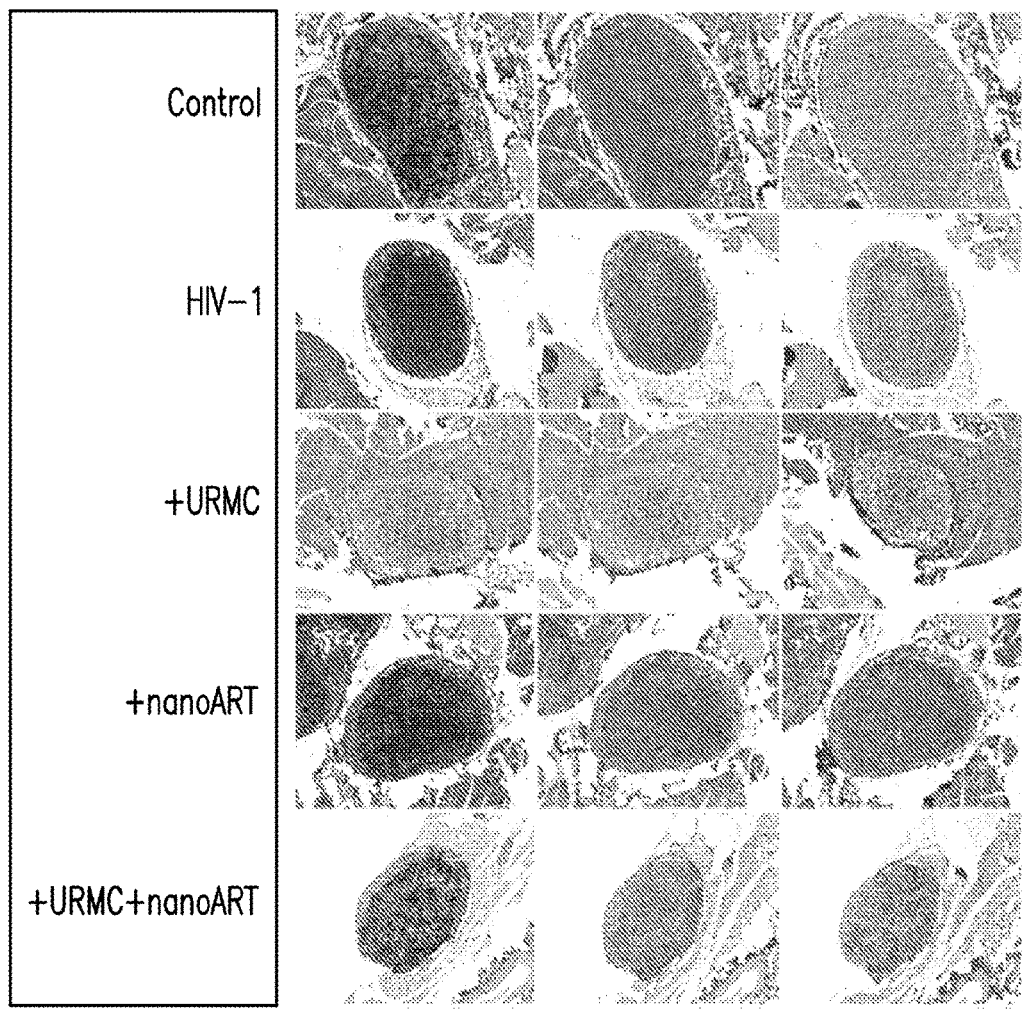
FIG. 6 is a group of photographs of B cell staining in lymph nodes of humanized mice treated with Compound AH (denoted URMC), nanoparticles comprising atazanavir and ritonavir (denoted nanoART), or both.
Figure 7A:
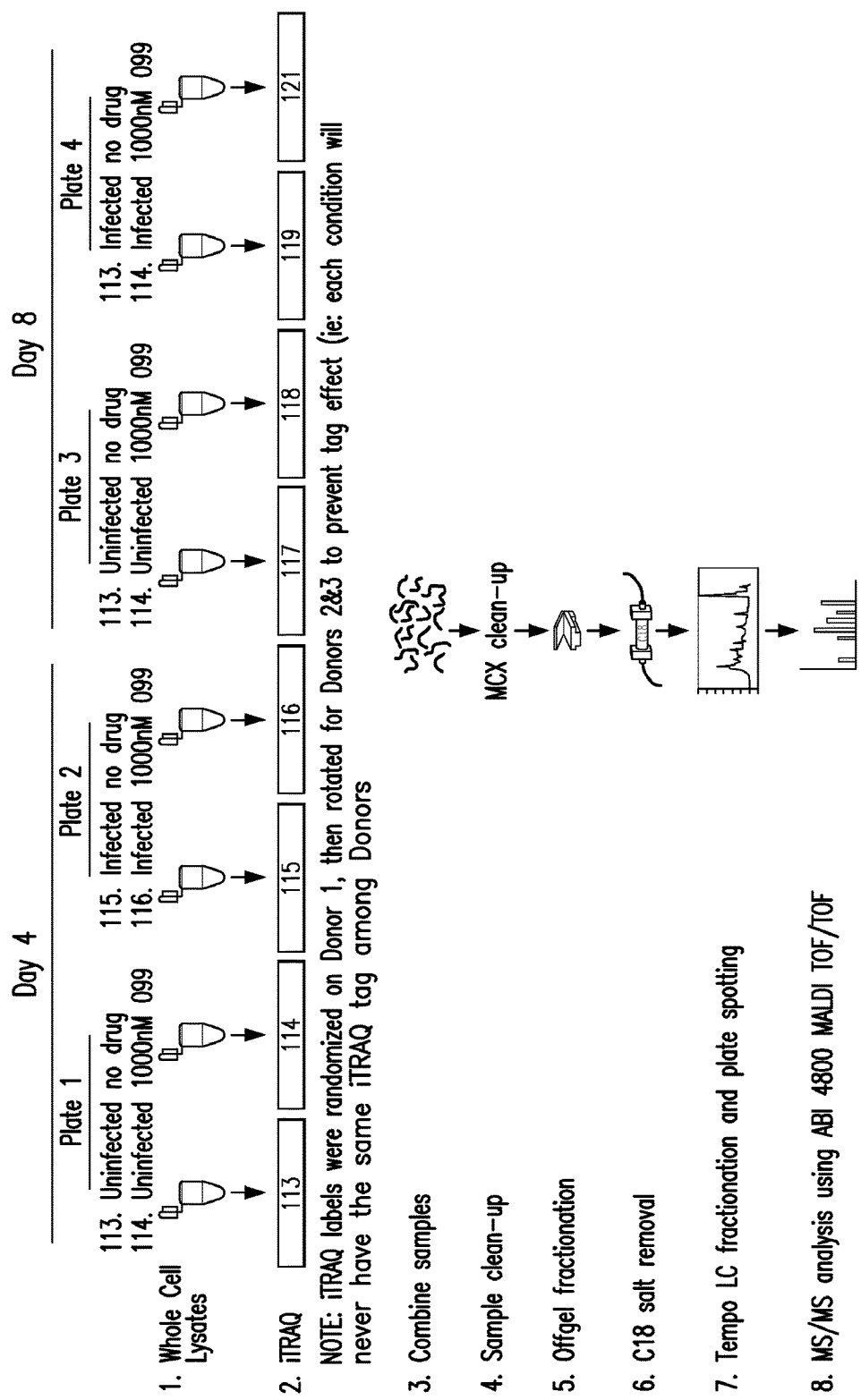
FIG. 7 (top) is a schematic of a proteomic analysis. The table (bottom) shows the number of cytosolic differentially proteins (with statistical significance) for various experimental conditions.
Figure 8:
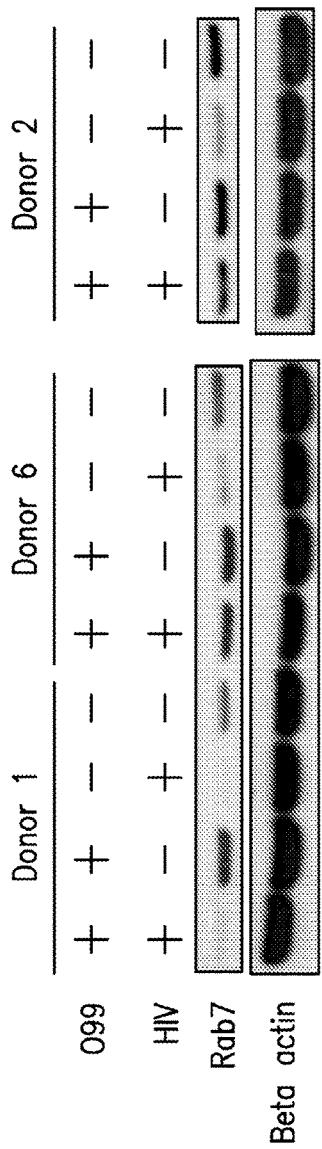
FIG. 8 is a photograph from a Western blot validation for Rab7a. Rab7A (Protein KB) is a key regulator in endolysosomal trafficking. It governs early-to-late endosomal maturation, microtubule minus-end as well as plus-end directed endosomal migration and positioning, and endosome-lysosome transport.
Figure 9:
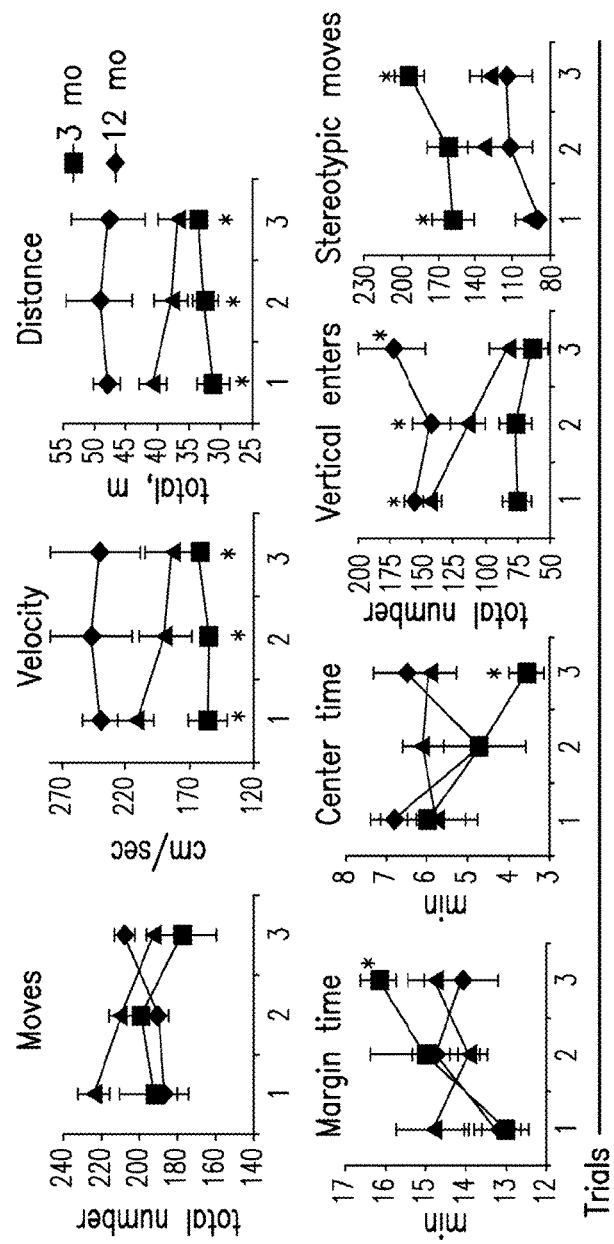
FIG. 9 shows data from humanized mice in open field tests.
Figure 10:
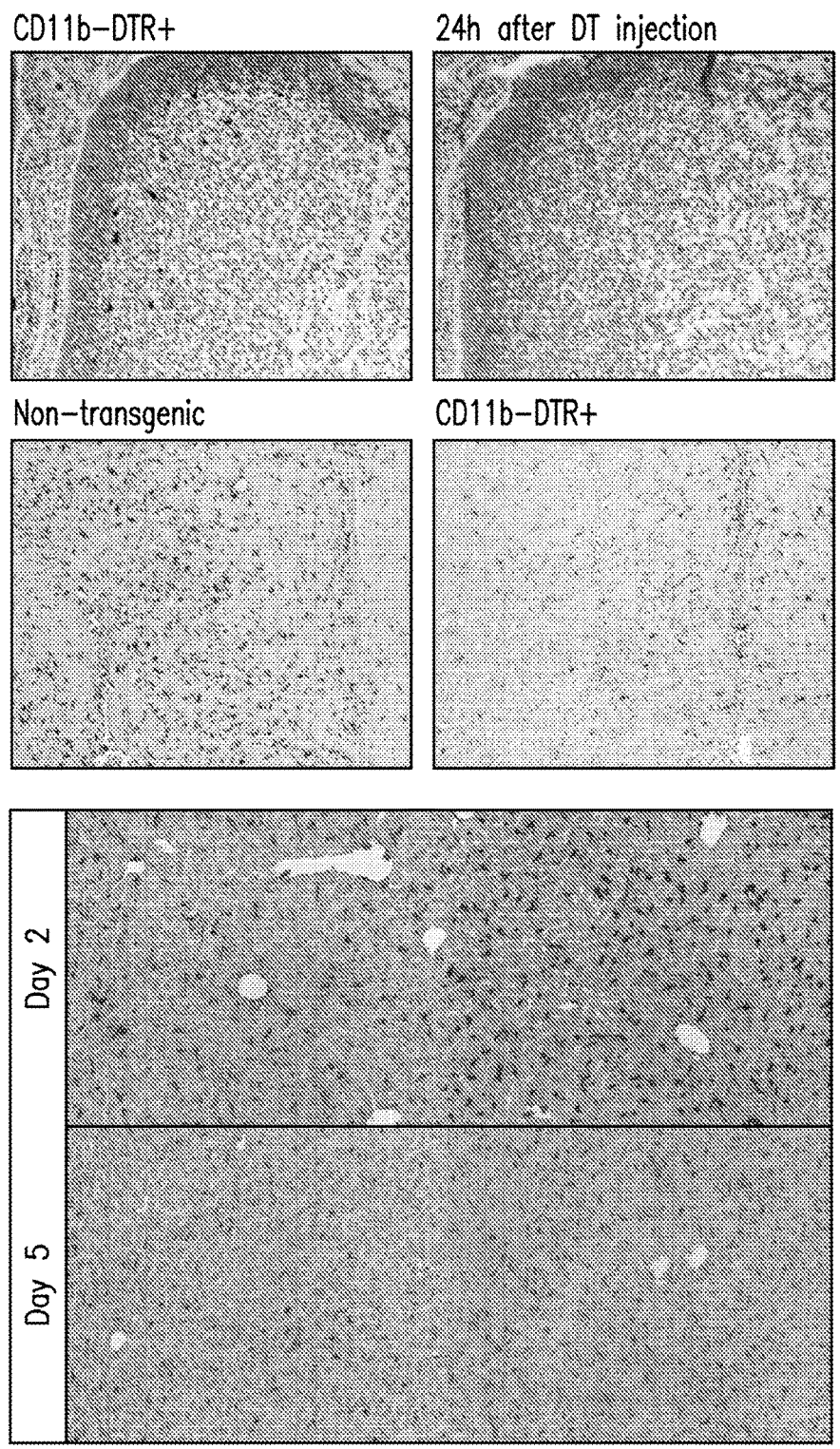
FIG. 10 is a group of photographs showing the conditional depletion of mouse microglia in CD11b-DTR/NOD mice (top four panels) and mouse liver macrophages (bottom two panels).

The MLK inhibitor Compound AH was used in test with an animal model for HIV-1 infection. Specifically, 22 week old humanized mice (NOD/scidIL-2Rγ$_c^{null}$ (NSG) mice stably engrafted with human CD34+ hematopoeitic stem cells were infected with HIV-1 ADA (Gorantla et al., *J. Virol.* 81:2700-2712, 2007). The mice were then treated with the nanoformulated antiretroviral therapy comprising atazanavir and ritonavir (nanoART) for 6 weeks by s.c. injections (6×/week). During the final two weeks, the animals also received the MLK-3 inhibitor Compound AH by once daily injection (10 mg/kg i.p.). Viral RNA load was measured over time in plasma from these mice, and productively infected cells were counted in tissues harvested from animals at sacrifice (including lymph node (FIG. 4) and spleen (FIG. 5)). Results showed that animals which received ART plus the MLK inhibitor had lower virus loads and accelerated virus clearance as compared to animals that received ART alone or animals that received the MLK-inhibitor alone. In particular, while animals treated with the MLK inhibitor alone had modest reducing in HIV-1 viral load, the combination with the ART had a profound reduction in virus with a clear protection of CD4+ T cells. These results were confirmed in lymphoid tissues where the MLK-inhibitor plus ART combination demonstrated a near clearing of the viral reservoir in spleen and lymph nodes.

Further, starting at 10 weeks post infection, when the mice were at the peak of their viral load (VL) the MLK-3 inhibitor Compound AH was administered daily and the nanoART was administered weeks for three weeks. Peripheral VL ratio of human CD4+ and CD8+ T lymphocyte, drug levels in plasma and organs and pathological changes in lymphoid and brain tissues were investigated.

Proteomic analyses of Compound AH treated human monocyte-derived macrophages with and without nanoparticles comprising atazanavir and ritonavir showed that Rab7 was regulated by compound AH in the cells and that this effect was potentiated by the antiretroviral drugs. Compound AH induced the RAS-related GTP-binding protein Rab7 in HIV-1 infected MDM. The viral loads of mice treated with combination nanoART and Compound AH for 3-weeks showed reduction in VL to an undetectable level at the end point as compared to single treatment groups. Combined treatment restored the ratio of CD4/CD8 T lymphoctyes as compared to single drug therapy at the study end. Higher plasma drug levels correspond to lowest viral load. Immunohistochemistry of spleen sections in the double treatment group showed a statistically significant decrease in HIV-1 p24+ cells as compared to untreated and single treatment groups.

Combination of MKL-inhibitors with antiretroviral therapy acted synergistically to restrict HIV-1 replication while protecting CD4+ T lymphocyte depletion. While not wishing to be bound by theory, the shuffling of endosomal compartment function through the MLK-inhibitor's effects on Rab 7 may retard viral growth.

Tat-Assays

Figure 11:
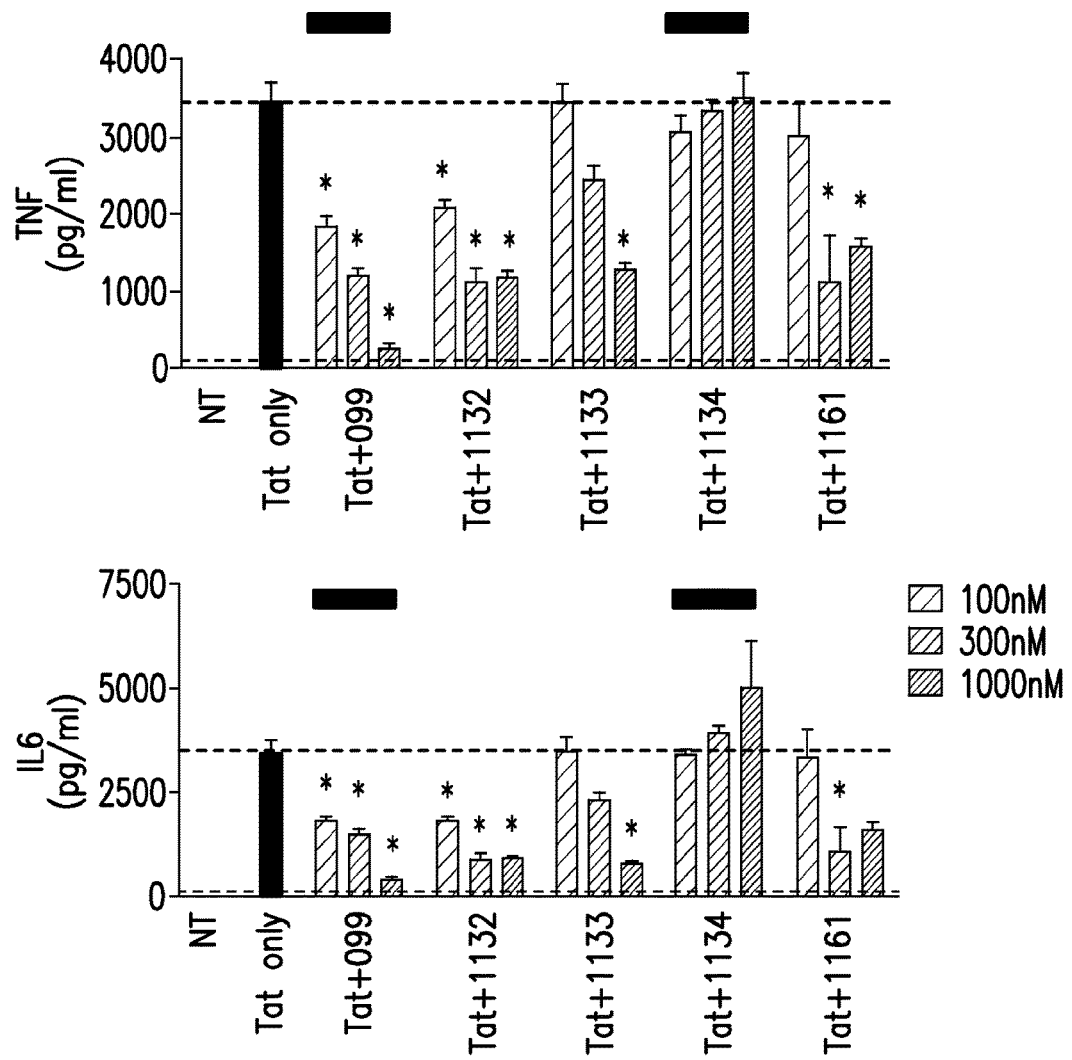
FIG. 11 shows Compound AH blocks tat-induced cytokine production by MBM.
Figure 12:
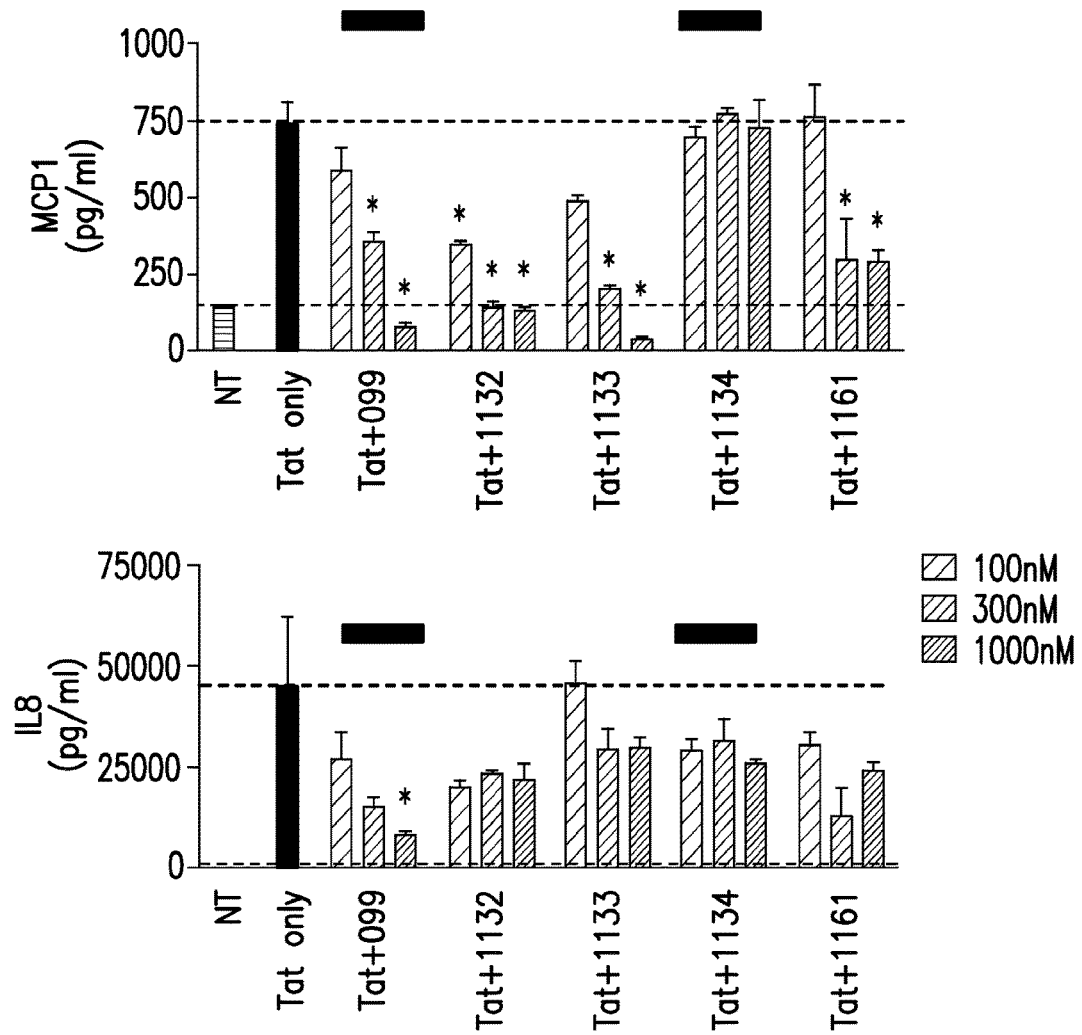
FIG. 12 shows Compound AH blocks tat-induced chemokine production by MBM.
Figure 13A:
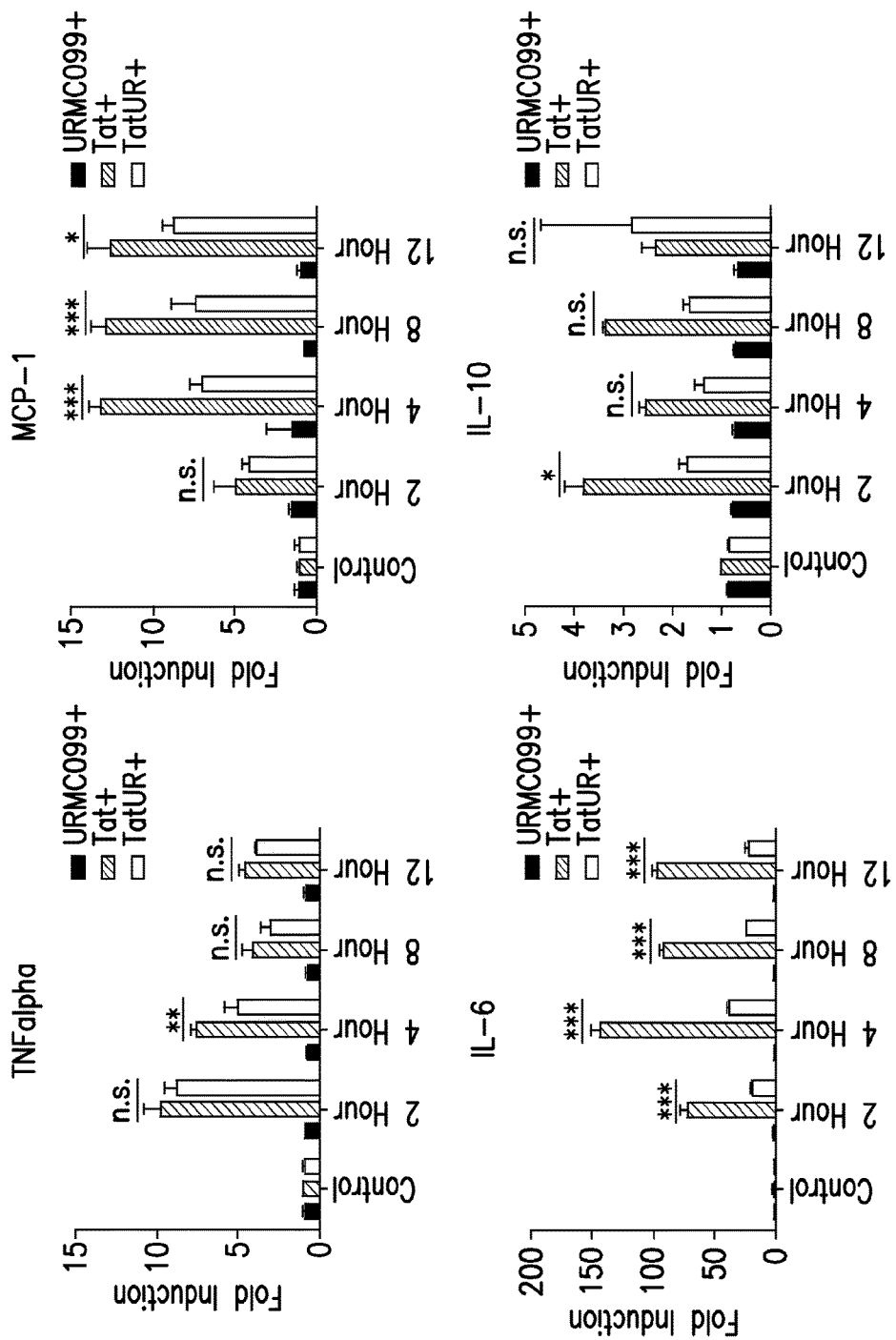
FIG. 13 are results from BV-2 cytokine relative qRT-PCT assays (top 4 panels) and Luminx (bottom 4 panels). URMC099 is Compound AH.
Figure 13B:
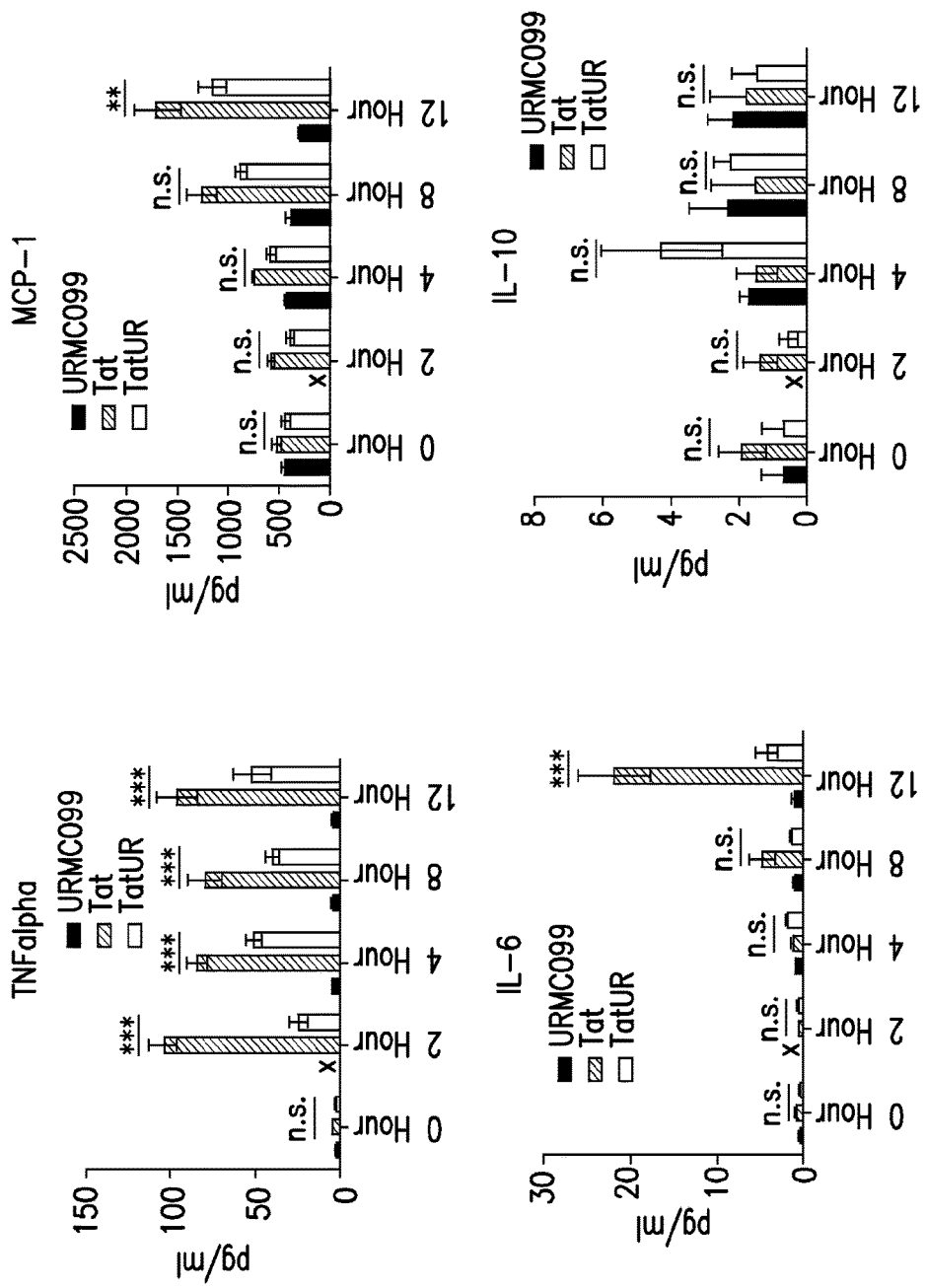
Figure 14:
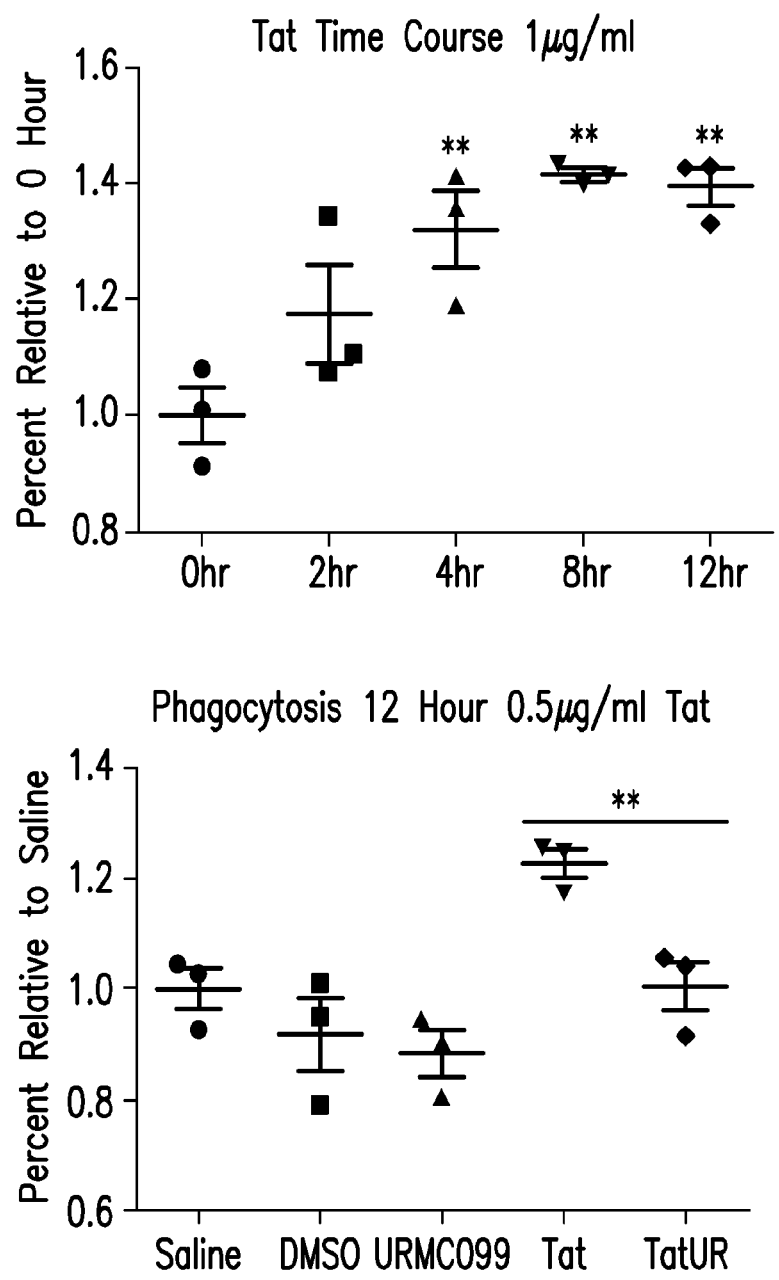
FIG. 14 are results from BV-2 phagocytosis study.
Figure 15:
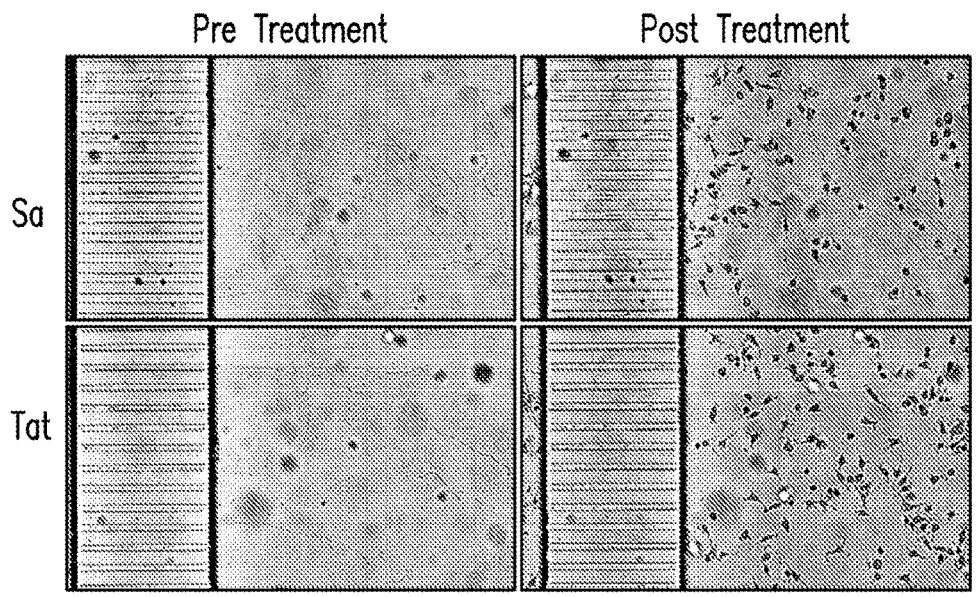
FIG. 15 is a group of photographs from a BV-2 microfluidic study.
Figure 16:
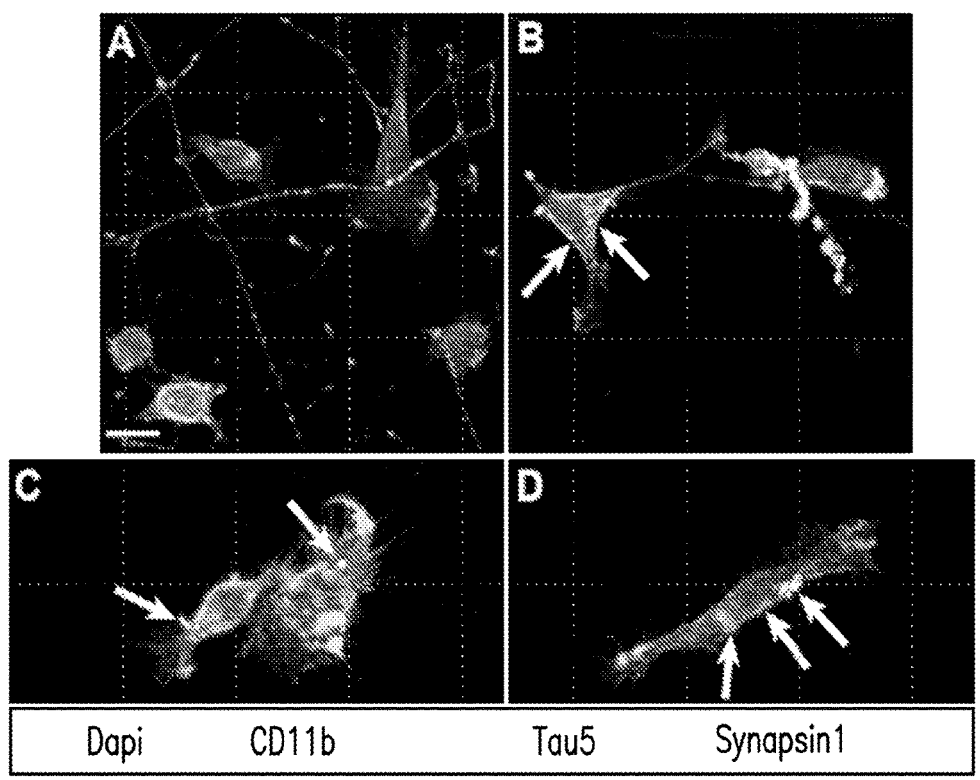
FIG. 16 is a group of photographs from a Chamber ICC study. Panel A is saline. Panels B-D are at 18 hrs with 1 µg/mL Tat. White arrows are synapsin 1 and tau 5 positive inclusions.
Figure 17:
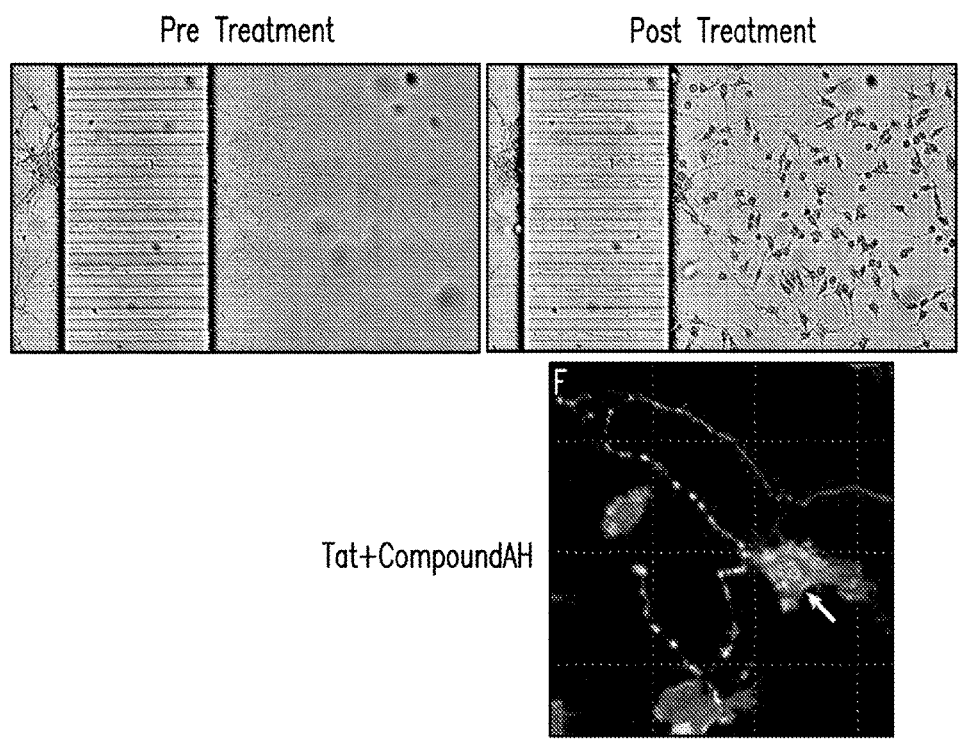
FIG. 17 is a group of photographs from microfluidic chamber study with Compound AH.
Figure 18:
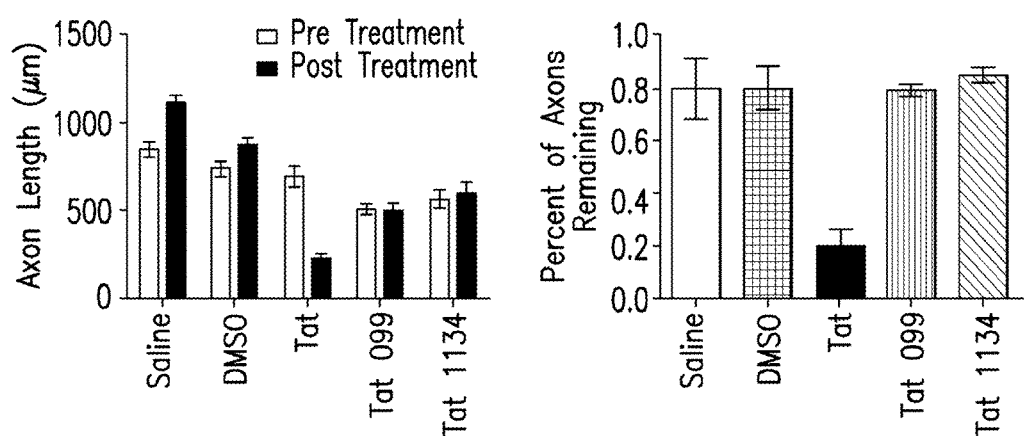
FIG. 18 is a pair of graphs showing data rom a BV-2 chamber study.
Figure 19:
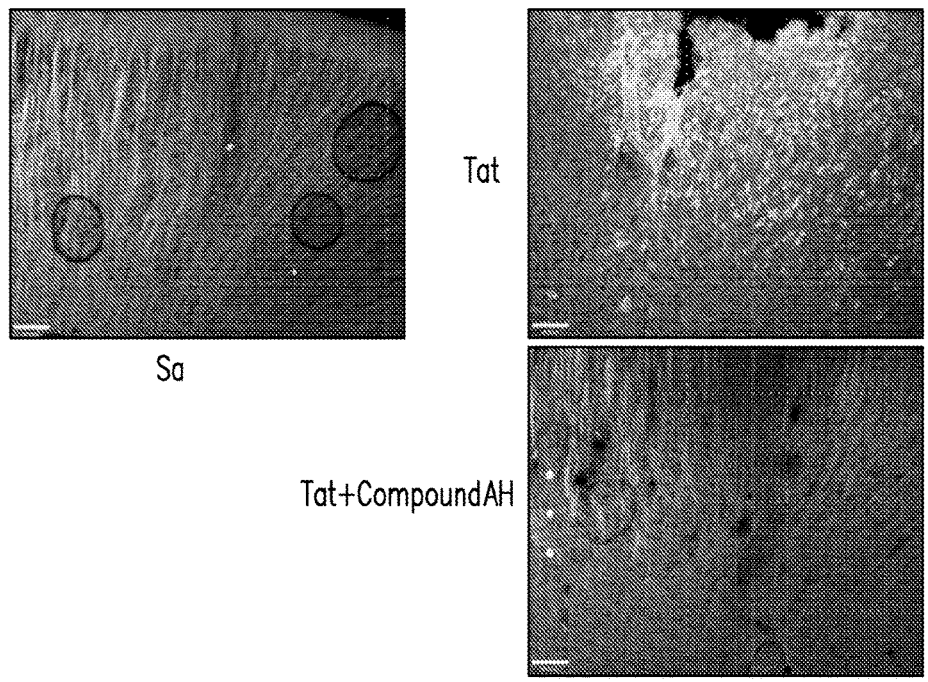
FIG. 19 is a group of photographs showing IHC synapse protection. Map2 staining 28 days post injection at the injection site. Pre/continuous treatment with Compound AH at 10 mg/kg i.p. q 12, 9 µg of Tat injected at 80 nL/min. The same Compound AH/Tat treatment paradigm was used in FIGS. 20-24.
Figure 20:
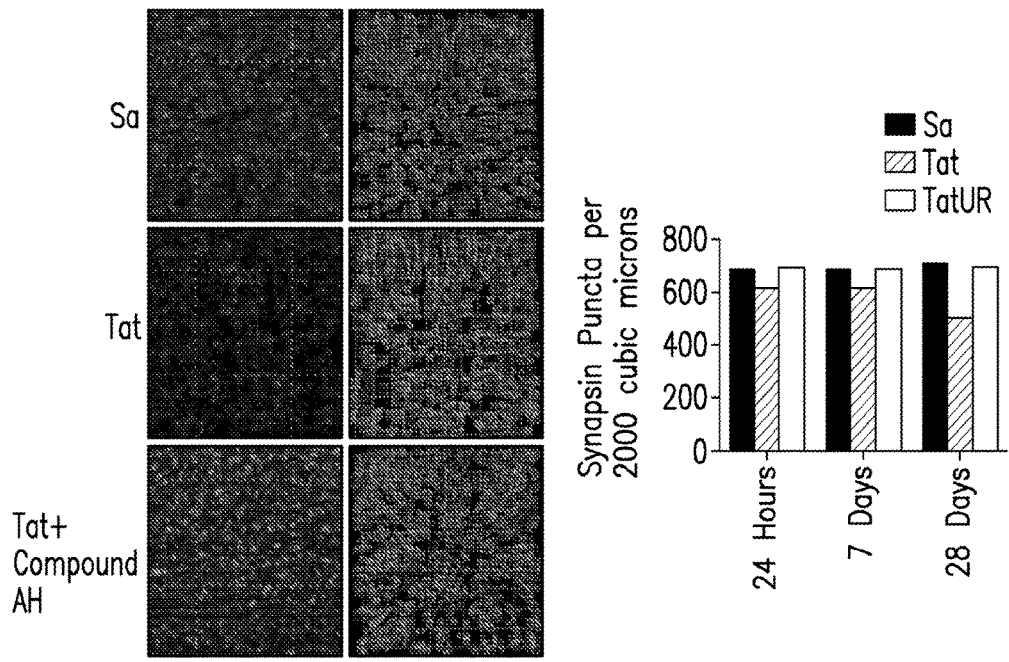
FIG. 20 shows IHC synapse protection.
Figure 21:
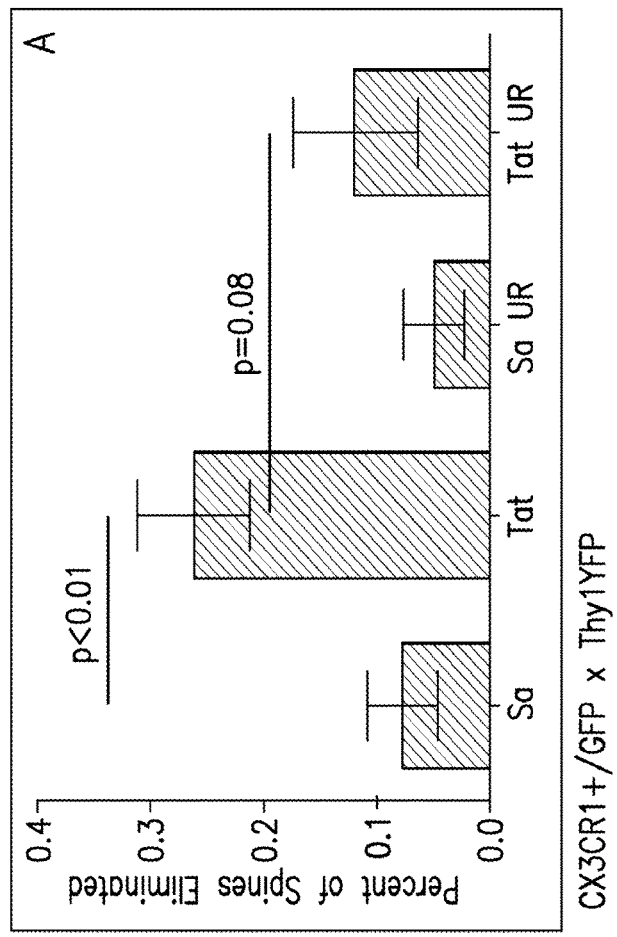
FIG. 21 shows two photon synapse protection.
Figure 21:
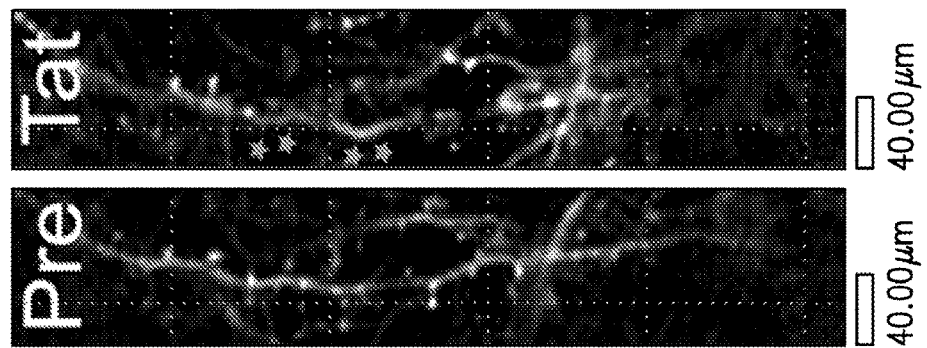
Figure 22A:
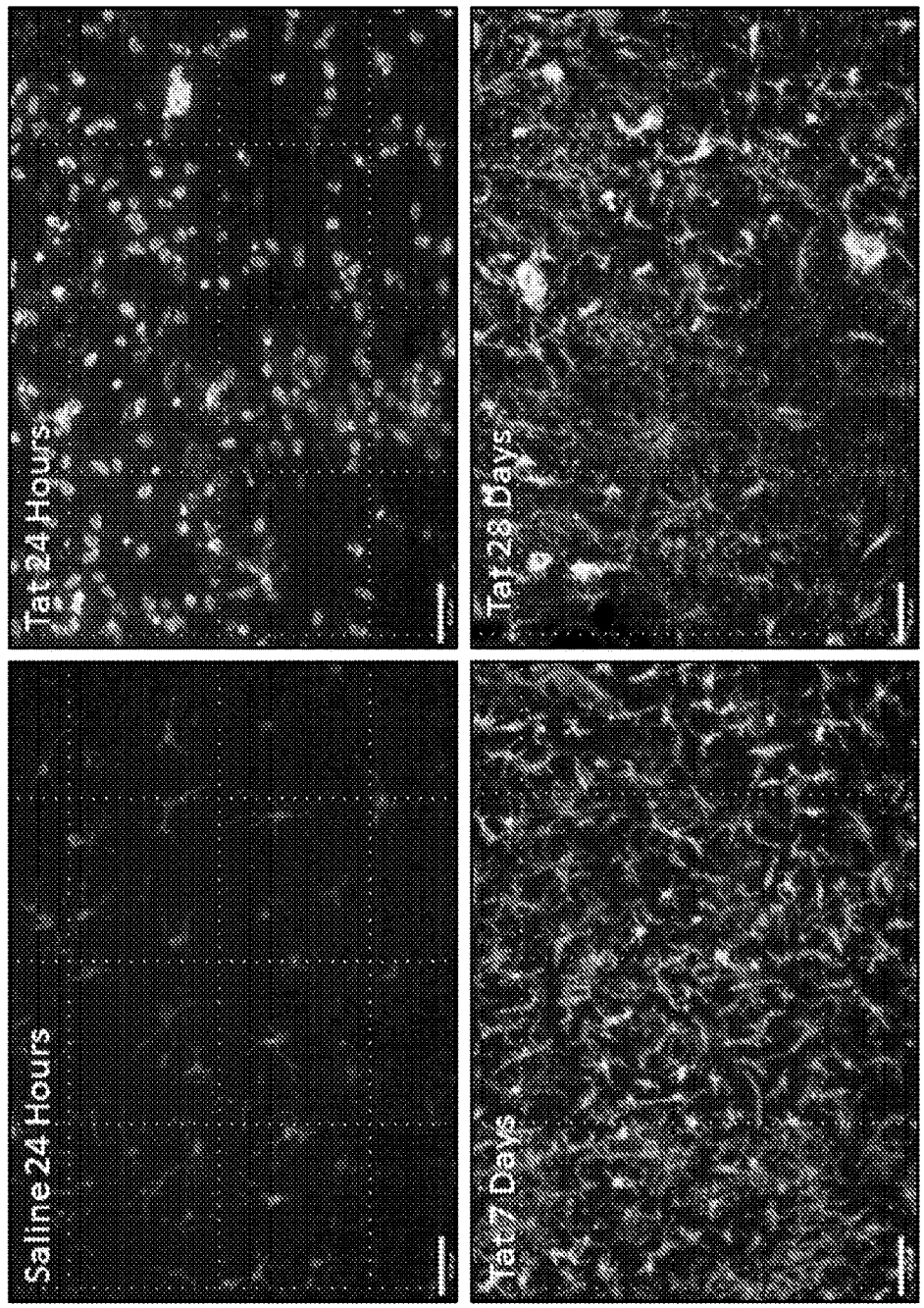
FIG. 22 shows IHC immune cells chimera.
Figure 22B:
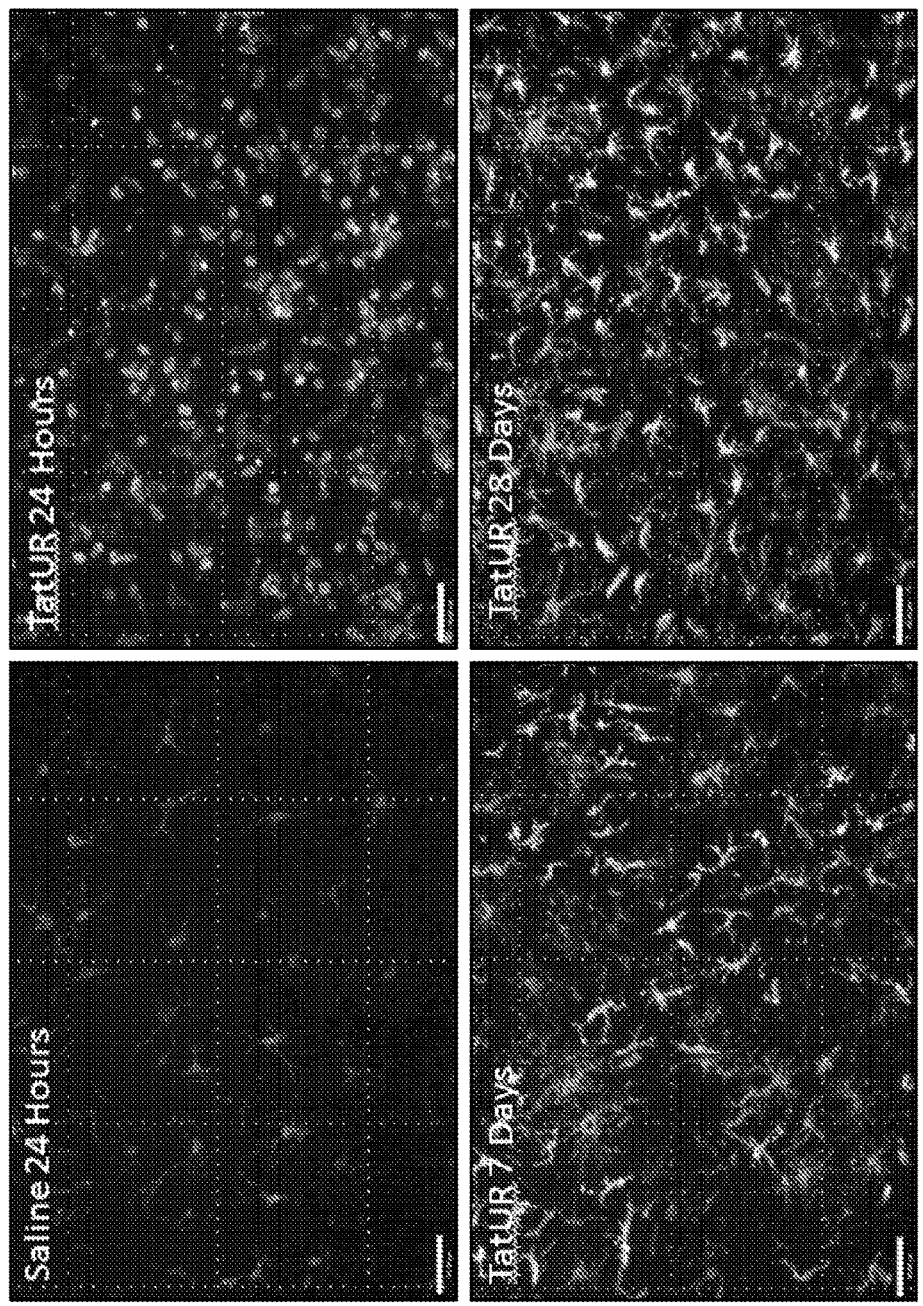
Figure 23A:
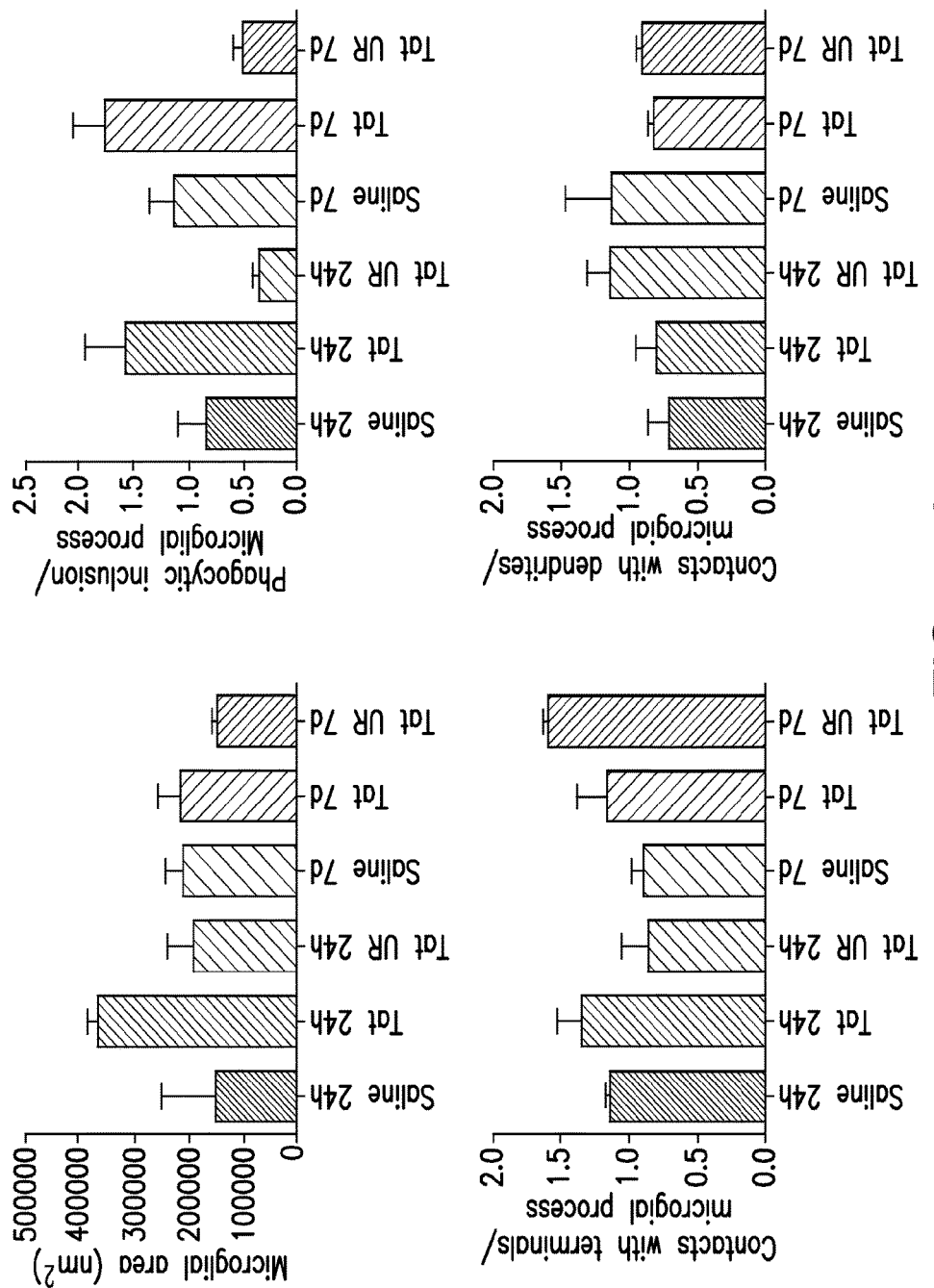
FIG. 23 is a group of graphs from quantitative EM.
Figure 23B:
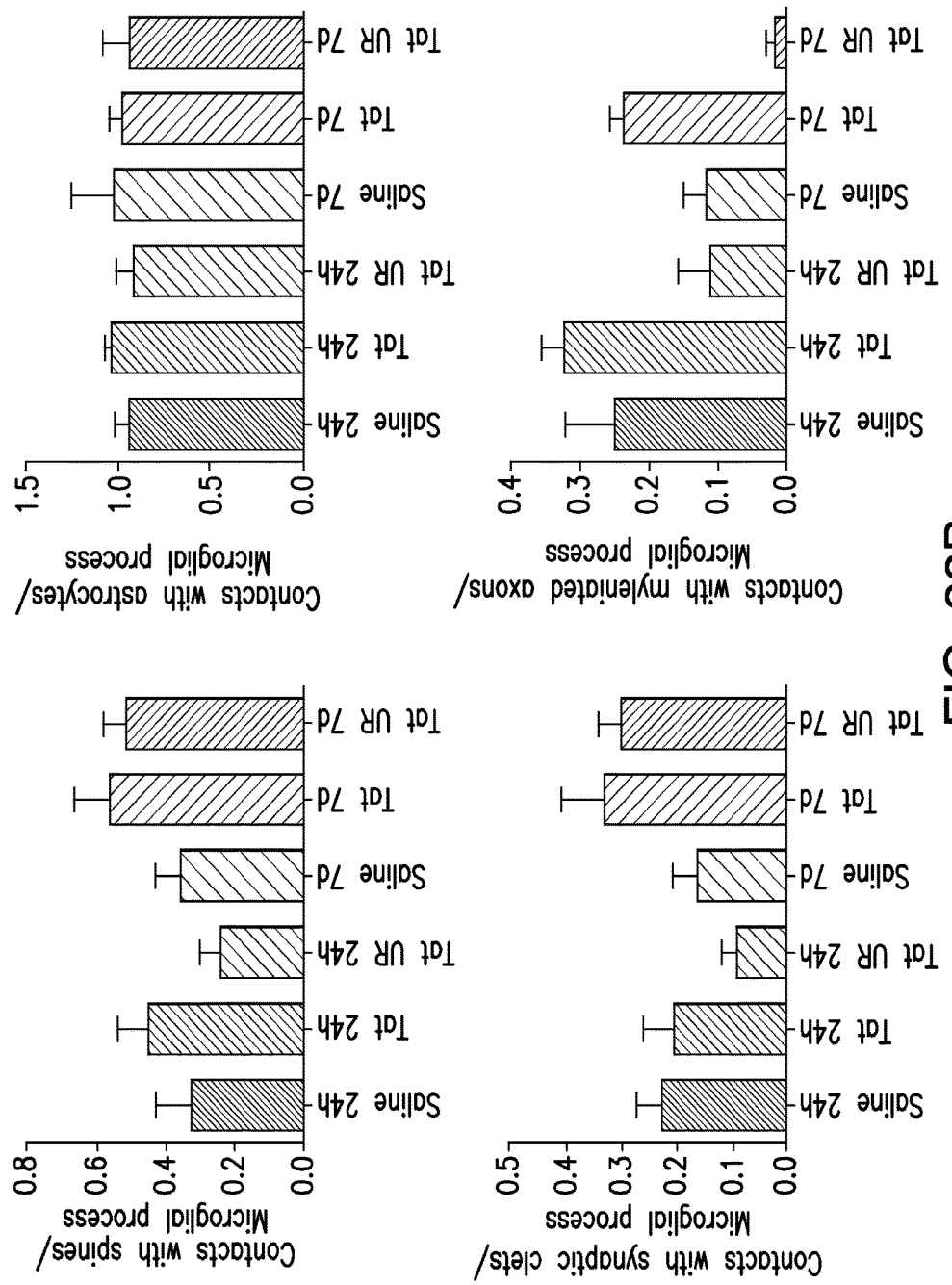
Figure 24A:
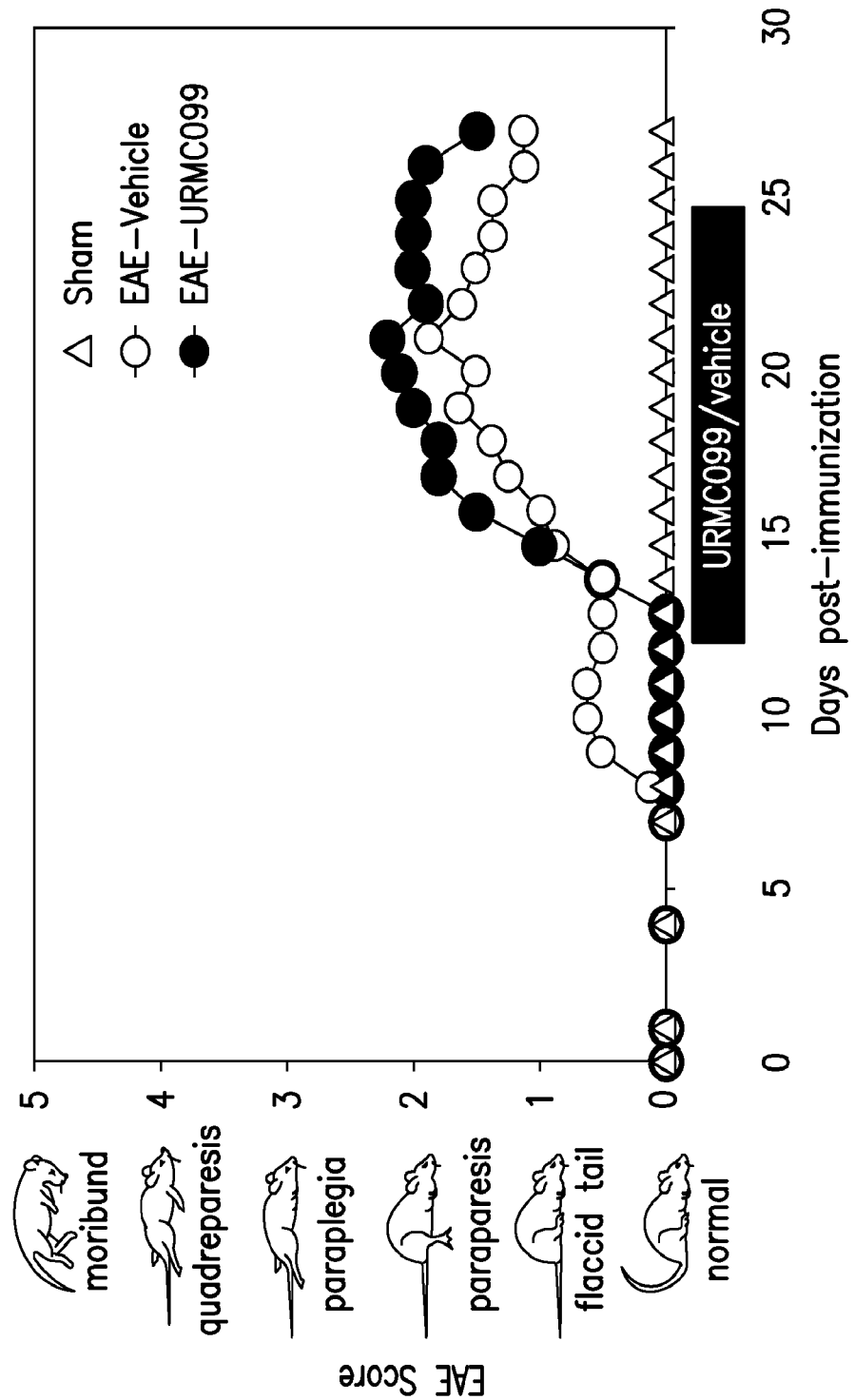
FIG. 24 shows that Compound AH (URMC099) treatment at onset of clinical disease has no effect on EAE motor deficits. Hippocampal synaptic injury in $MOG_{35-55}$ EAE mice correlates with microglial activation and may occur independent of myelin loss. This suggests that deymelination is not the sole reason for synaptic injury in inflammatory demyelinating disease, and that neuroprotective therapies are critical in addition to efforts to maintain myelination. Compound AH attenuates microglial activation and protects synaptic structure in EAE hippocampus. These results support microglial activation as a potential therapeutic target for gray matter neuroprotection in MS. Protective effects in EAE hippocampal gray matter appear dissociable from those in the spinal cord. Many interventions targeting microglial function affect EAE motor deficits and the spinal cord inflammation that those largely reflect. Compound AH has significant effects on microglia and synapses in the hippocampus but none on EAE clinical score, suggesting the possibility of selectively modulating the function of microglia in gray matter vs. white matter inflammatory lesions.
Figure 24B:
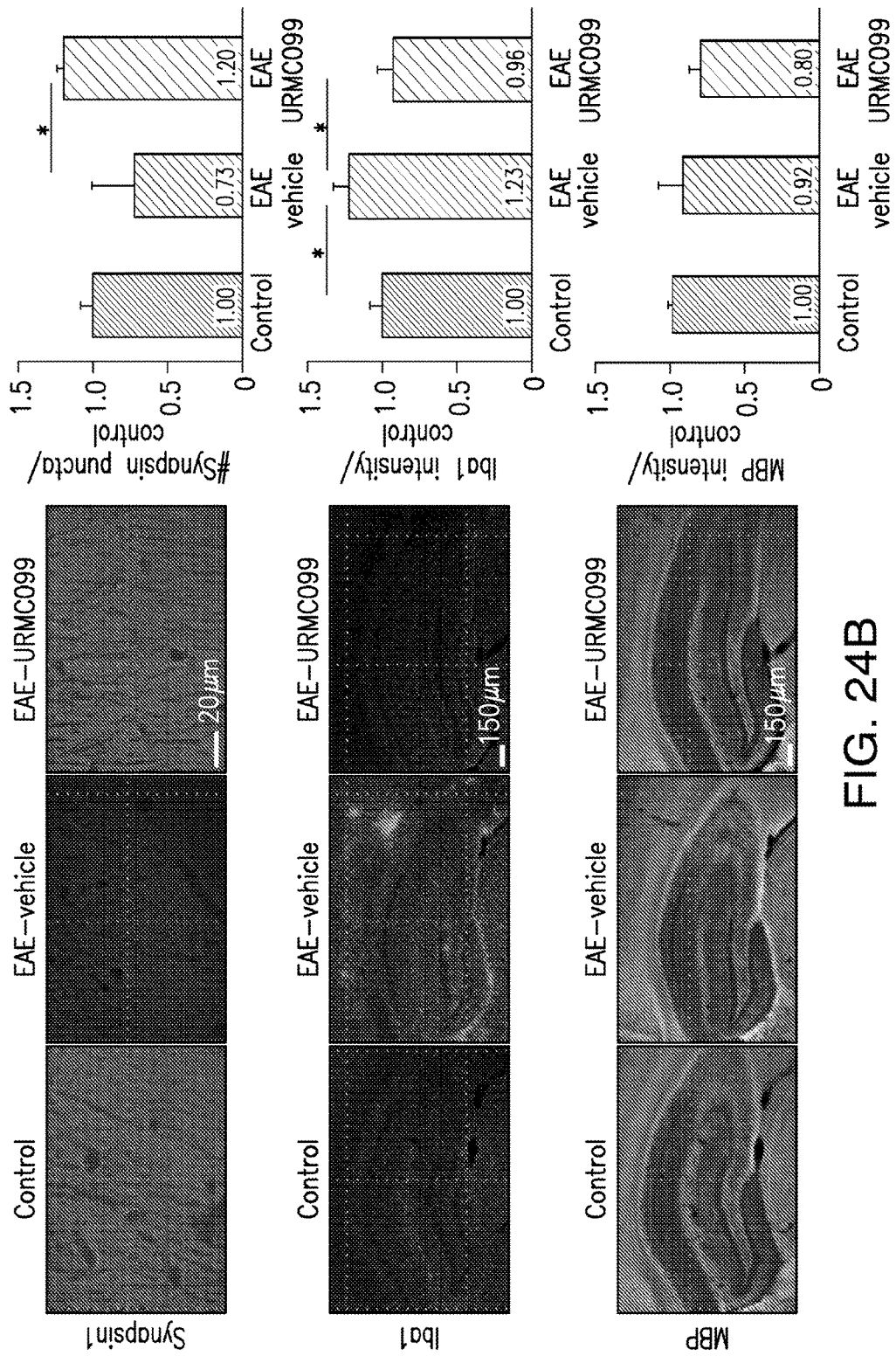

Human monocytes were isolated from freshly collected whole blood using CD14 immunomagnetic beads (Miltenyi-Biotec). Cells were then plated in 24-well plates at $5 \times 10^4$ cells/well in RPMI-1640 culture medium supplemented with 10% fetal bovine serum (FBS). The specified compounds were then added to the cultures at the indicated concentrations (100, 3000, 1000 nM); in control wells, no compound was added. 30 min later, HIV-1 Tat was added to a final concentration of 50 nM the cells were incubated for 8 hours (in control wells, nothing was added [NT]). Cell supernatants were then collected, centrifuged 15 min at 13000 rpm to remove debris, transferred to new microcentrifuge tubes and frozen at −20° C. A Luminex bead array assay was then performed, for the indicated chemokines and cytokines. Results were measured in triplicate or quadruplicate, and data are presented as mean values; error bars denote the standard deviation. Note that similar results were obtained with monocytes derived from multiple (n>5) different donors, as well as in terminally differentiated monocyte-derived macrophages (data not shown due to space limitations). *:$p<0.05$; one-way ANOVA with Bonferroni's correction (when compared to Tat only control). See FIG. 11 (tat-induced cytokine production) and FIG. 12 (tat-induced chemokine production).

The data demonstrate that Compound AH provides neuroprotection to the synapse and is anti-neuroinflammatory. (FIGS. 10-24). The compound is a selectively non-selective inhibitor for a subset of kinases that have pathogenetic roles for activation of immune effector cells with damage to target cells (neurons, myocytes, pancreatic acinar cells) in both central and peripheral degenerative diseases with autoimmune components.

Rab Studies

Figure 25:
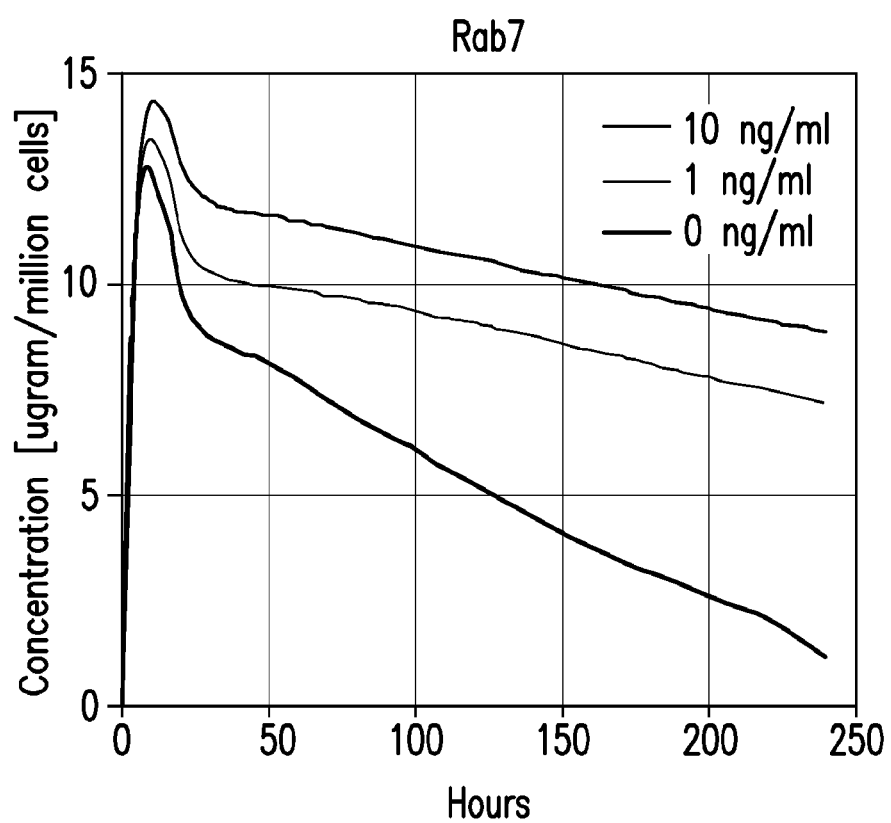
FIG. 25 is a graph showing that Compound AH is able to sustain the presence of atazanavir/ritonavir nanoART in late endosomes. Concentrations of 1 and 10 ng/mL of Compound AH increases drug levels for more than 10 days in these compartments. This is significant and reproducible. It also explains the longer half of the nano particles comprising atazanavir/ritonavir and the more potent antiretroviral responses as assembly of progeny HIV occurs in late endosomes. Thus more of the drug is present in there for longer time periods, boosting efficacy and leading to reduction of residual virus.

In Rab studies, a general increase in drug levels was seen in all Rab compartments from Compound AH induction. However, the compartment where clear up regulation was seen in both proteomic and Western blot tests was Rab 7, which is the late endosomal compartment (FIG. 25). The Rab 7 compartment increased marked in size and expression (protein content) as a result of HIV infection. As virus is assembled inside the Rab 7 late endosomal compartment in macrophases, this compartment gets bigger and significantly so. That is also where anti-HIV proteases work and where their sites of actions lie. These data confirm that combination therapy with an MLK inhibitor and nanoparticles comprising drugs, e.g., anti-retrovirals, has particular advantages, namely, the ability to bring drug crystals in stable intracellular compartments where they act as depots and extend the drug's half life. Moreover, these data show that an MLK inhibitor like Compound AH can bring a drug precisely to the late endosomal compartment, which is extremely beneficial for anti-virals, which is the site of action for where viral eradication occurs. Compound AH used to nanoparticulate ATV/r shrinks the compartment ot what is seen with uninfected cells, a result not seen with free ATV or Compound AH alone. This signals that the combination has eliminated or nearly so, the ability of virus to assemble in this compartment.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

What is claimed is:

1. A method of treating an individual infected with HIV, comprising: administering to the individual a composition comprising effective amounts of both a mixed lineage kinase inhibitor and an antiretroviral drug, wherein the antiretroviral drug comprises one or more antiretroviral compounds chosen from lamivudine, ziduvudine, emtricitabine, abacavir, abacavir sulfate, zidovudine, tenofovir, didanosine, stavudine, delavirdine, efavirenz, nevirapine, etravirine, maraviroc, rilpivirine, raltegravir, atazanavir, efavirenz, indinavir, and ritonavir, in a crystalline nanoparticle; and
wherein the mixed lineage kinase inhibitor has structural Formula XIX:

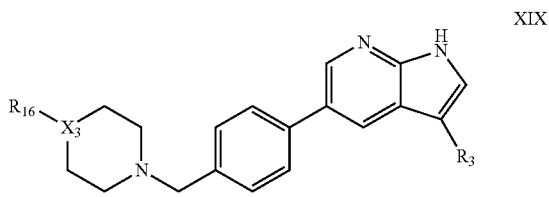

wherein
$X_3$ is chosen from C, N, and O;
$R_3$ is chosen from lower cycloalkyl, phenyl, and lower heteroaryl, any of which is optionally substituted with one or more substituents chosen from halogen, hydroxy, lower amino, lower amido, lower carboxyl, $C_1$-$C_3$ alkoxy, $C_1$-$C_3$ alkyl, (O), (S), cyano, haloalkyl, phenyl, cycloalkyl, heteroaryl, and cycloheteroalkyl;
$R_{16}$ is chosen from lower alkyl, lower carboxyl, carbonyl, alkoxyethanone, carbamate, sulfonyl, heteroaryl, cycloalkyl, heteroarylalkyl, aryl, arylalkyl, and heterocycloalkylcarbonyl, any of which can be optionally substituted, and when $X_3$ is O, $R_{16}$ is null.

2. The method of claim 1, wherein the nanoparticle further comprises one or more surfactants.

3. The method of claim 2, wherein the nanoparticle is rod shaped with a z-average diameter from about 100 nm to 1 µm.

4. The method of claim 2, wherein the surfactant comprises an amphiphilic block copolymer comprising at least one block of polyoxyethylene and at least one block of polyoxypropylene.

5. The method of claim 2, wherein the surfactant is one or more of the following: poloxyamer 188, poloxamer 407, polyvinyl alcohol, 1,2-distearoyl-phosphatidyl ethanolamine-methyl-polyethyleneglycol conjugate 2000 (mPEG$_{2000}$DSPE), sodium dodecyl sulfate, and 1,2-dioleoyloxy-3-trimethylammonium propane.

6. The method of claim 2, wherein the surfactant is coupled to a targeting ligand.

7. The method of claim 6, wherein the targeting ligand is folate.

8. The method of claim 2, wherein the nanoparticle is at least about 95% by weight of the antiretroviral compound.

9. The method of claim 1, wherein $R_3$ is chosen from benzothiazolyl, pyrrolopyridinyl, cyclopropyl, cyclopentyl, phenyl, pyridinyl, pyrimidinyl, and indolyl, any of which is optionally substituted with one or more substituents chosen from fluorine, chlorine, hydroxy, $NH_2$, $NH(CH_3)$, $N(CH_3)_2$, $C(O)NH_2$, $C(O)NHCH_3$, morpholino, piperazinyl, methylpiperazinyl, acetamido, methylacetamido, methylpropionamido, phenylacetamidomethylene, benzamidomethylene, phenylpropanamidomethylene, methoxy, and methyl.

10. The method of claim 1, wherein $R_3$ is phenyl optionally substituted with one or more substituents chosen from hydroxyl, lower alkyl, lower alkoxy, lower haloalkyl, lowerhaloalkoxy, halogen, lower amino, lower carboxyl, and cyano.

11. The method of claim 1, wherein $R_3$ is chosen from indolyl, indazolyl, indolinonyl, benzothiophenyl, quinolinyl, isoquinolinyl, pyrrolopyrazinyl, and pyrrolopyridinyl, any of which is optionally substituted with one or more substituents chosen from hydroxy, lower alkyl, lower alkoxy, lower haloalkyl, lowerhaloalkoxy, halogen, lower amino, and lower carboxyl.

12. The method of claim 1, wherein the mixed lineage kinase inhibitor is Compound AH

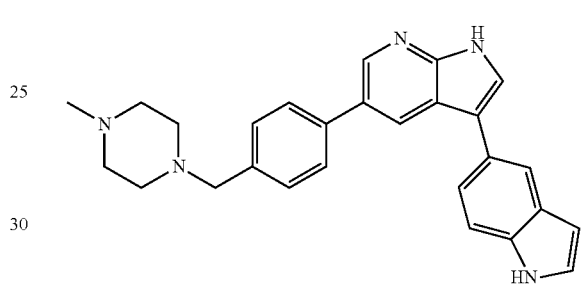

13. A composition, comprising: an antiretroviral drug, a mixed lineage kinase inhibitor, and a surfactant, wherein the antiretroviral drug comprises one or more antiretroviral compounds chosen from lamivudine, ziduvudine, emtricitabine, abacavir, abacavir sulfate, zidovudine, tenofovir, didanosine, stavudine, delavirdine, efavirenz, nevirapine, etravirine, maraviroc, rilpivirine, raltegravir, atazanavir, efavirenz, indinavir, and ritonavir, in a crystalline nanoparticle, and wherein the mixed lineage kinase inhibitor has structural Formula XIX:

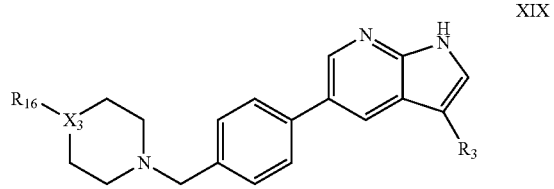

wherein
$X_3$ is chosen from C, N, and 0;
$R_3$ is chosen from lower cycloalkyl, phenyl, and lower heteroaryl, any of which is optionally substituted with one or more substituents chosen from halogen, hydroxy, lower amino, lower amido, lower carboxyl, $C_1$-$C_3$ alkoxy, $C_1$-$C_3$ alkyl, (O), (S), cyano, haloalkyl, phenyl, cycloalkyl, heteroaryl, and cycloheteroalkyl;
$R_{16}$ is chosen from lower alkyl, lower carboxyl, carbonyl, alkoxyethanone, carbamate, sulfonyl, heteroaryl, cycloalkyl, heteroarylalkyl, aryl, arylalkyl, and heterocycloalkylcarbonyl, any of which can be optionally substituted, and when $X_3$ is O, $R_{16}$ is null.

14. The composition of claim 13, wherein the nanoparticle is coated with folate.

15. The composition of claim 13, wherein the nanoparticle is rod shaped with a z-average diameter from about 100 nm to 1 μm.

16. The composition of claim 13, wherein the surfactant comprises an amphiphilic block copolymer comprising at least one block of polyoxyethylene and at least one block of polyoxypropylene.

17. The composition of claim 13, wherein the surfactant is one or more of the following: poloxyamer 188, poloxamer 407, polyvinyl alcohol, 1,2-distearoyl-phosphatidyl ethanolamine-methyl-polyethyleneglycol conjugate 2000 (mPEG$_{2000}$DSPE), sodium dodecyl sulfate, and 1,2-dioleoyloxy-3-trimethylammonium propane.

18. The composition of claim 13, wherein the surfactant is coupled to a targeting ligand.

19. The composition of claim 13, wherein the nanoparticle is at least about 95% by weight of the antiretroviral compound.

20. The composition of claim 13, wherein the mixed lineage kinase inhibitor is Compound AH

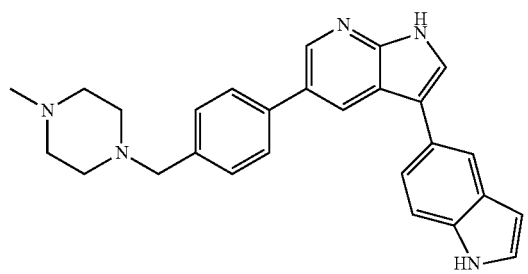

21. The method of claim 1, wherein the mixed lineage kinase inhibitor and the one or more antiretroviral compounds are in the crystalline nanoparticle.

22. The composition of claim 13, wherein the mixed lineage kinase inhibitor and the one or more antiretroviral compounds are in the crystalline nanoparticle.

* * * * *